US012440571B2

(12) United States Patent
Jin et al.

(10) Patent No.: US 12,440,571 B2
(45) Date of Patent: Oct. 14, 2025

(54) IMMUNE AGONISTS

(71) Applicants: SHENZHEN UNIVERSITY, Guangdong (CN); SHENZHEN CONJUGENIX PHARMACEUTICAL TECHNOLOGY COMPANY LIMITED, Guangdong (CN)

(72) Inventors: Guangyi Jin, Guangdong (CN); Zhulin Wang, Guangdong (CN); Ji Zhou, Guangdong (CN); Mian Qin, Guangdong (CN); Sumei Ren, Guangdong (CN); Yajuan Cheng, Guangdong (CN); Shuxian Tan, Guangdong (CN)

(73) Assignees: SHENZHEN UNIVERSITY, Guangdong (CN); SHENZHEN CONJUGENIX PHARMACEUTICAL TECHNOLOGY COMPANY LIMITED, Guangdong (CN)

( * ) Notice: Subject to any disclaimer, the term of this patent is extended or adjusted under 35 U.S.C. 154(b) by 417 days.

(21) Appl. No.: 17/632,420

(22) PCT Filed: Dec. 7, 2020

(86) PCT No.: PCT/CN2020/134260

§ 371 (c)(1),
(2) Date: Feb. 2, 2022

(87) PCT Pub. No.: WO2021/208459

PCT Pub. Date: Oct. 21, 2021

(65) Prior Publication Data

US 2023/0108709 A1 Apr. 6, 2023

(30) Foreign Application Priority Data

Apr. 15, 2020 (CN) ......................... 202010299076.4
Jun. 24, 2020 (CN) ......................... 202010595158.3

(51) Int. Cl.

| | |
|---|---|
| ***A61K 47/55*** | (2017.01) |
| ***A61K 47/62*** | (2017.01) |
| ***A61P 37/04*** | (2006.01) |
| ***C07D 487/04*** | (2006.01) |
| ***C07D 519/00*** | (2006.01) |
| ***C07F 9/6561*** | (2006.01) |
| ***C07F 9/6584*** | (2006.01) |

(52) U.S. Cl.

CPC .............. *A61K 47/55* (2017.08); *A61K 47/62* (2017.08); *A61P 37/04* (2018.01); *C07D 487/04* (2013.01); *C07D 519/00* (2013.01); *C07F 9/65616* (2013.01); *C07F 9/65846* (2013.01)

(58) Field of Classification Search

CPC ........ A61K 47/55; A61K 47/62; A61K 47/64; A61K 38/00; A61P 37/04; A61P 31/12; A61P 35/00; C07D 487/04; C07D 519/00; C07D 473/18; C07F 9/65616; C07F 9/65846; C07F 9/65583; C07F 9/6581; C07K 5/0202; C07K 7/06

See application file for complete search history.

(56) References Cited

FOREIGN PATENT DOCUMENTS

| | | | | | |
|---|---|---|---|---|---|
| CN | 102439011 | A | | 5/2012 | |
| CN | 102993265 | A | | 3/2013 | |
| CN | 103254304 | A | | 8/2013 | |
| CN | 106267188 | A | | 1/2017 | |
| CN | 108379591 | A | * | 8/2018 | ......... A61K 39/3955 |
| CN | 111704614 | A | * | 9/2020 | ............. A61K 47/55 |
| WO | 2011134669 | A1 | | 11/2011 | |

OTHER PUBLICATIONS

Blasius, Amanda L. et. al,: Intracellular Toll-like Receptors, Immunity Review, Mar. 12, 2010.

Chi, Huju et. al.: Anti-tumor Activity of Toll-Like Receptor 7 Agonists, Frountiers in Pharmacology, May 31, 2017.

International Search Report PCTCN2020/134260, Prepared by the China National Intellectual Property Administration, mailing date Feb. 25, 2021, including English Translation, 6 pages.

* cited by examiner

*Primary Examiner* — Joseph K Mckane
*Assistant Examiner* — Meghan C Heasley
(74) *Attorney, Agent, or Firm* — Brooks Kushman P. C.

(57) ABSTRACT

The present application provides a novel series of small molecular immune agonists of Toll-like receptor 7, having a structure represented by Formula I. The present application further provides use of the immune agonist for activating and amplifying immune cells and lymphocytes, and for preparing an immunomodulatory drug, an immune anti-tumor small molecule drug, and an immune anti-tumor macromolecular drug.

15 Claims, 19 Drawing Sheets

Specification includes a Sequence Listing.

| | Chidamide | GY146 | GY101 | MIX |
|---|---|---|---|---|
| IC50 | 21.93 | ~ 42.90 | | 9.860 |

SEQUENCE LISTING

```
<160> NUMBER OF SEQ ID NOS: 1

<210> SEQ ID NO 1
<211> LENGTH: 54
<212> TYPE: PRT
<213> ORGANISM: Artificial Sequence
<220> FEATURE:
<223> OTHER INFORMATION: Peptide-54 (54 amino acids, FZD7 epitope),
```

-continued

```
      fully synthetic

<400> SEQUENCE: 1

Ala Pro Val Cys Thr Val Leu Asp Gln Ala Ile Pro Pro Cys Arg Ser
1               5                   10                  15

Leu Cys Glu Arg Ala Arg Gln Gly Cys Glu Ala Leu Met Asn Lys Phe
            20                  25                  30

Gly Phe Gln Trp Pro Glu Arg Leu Arg Cys Glu Asn Phe Pro Val His
        35                  40                  45

Gly Ala Gly Glu Ile Cys
    50
```

IMMUNE AGONISTS

CROSS-REFERENCE TO RELATED APPLICATION

This application is the U.S. national phase of PCT Application No. PCT/CN2020/134260 filed on Dec. 7, 2020, which claims priority to Chinese Patent Application No. 202010299076.4 titled "novel series of immune agonists", filed with the Chinese Patent Office on Apr. 15, 2020, and Chinese Patent Application No. 202010595158.3 titled "novel series of immune agonists", filed with the Chinese Patent Office on Jun. 24, 2020, the contents of which are incorporated herein by reference.

SEQUENCE LISTING

The text file PUS2122147-1_ST25 of size 1 KB created Feb. 2, 2022, filed herewith, is hereby incorporated by reference.

TECHNICAL FIELD

The present application relates to a series of novel small molecule immune agonists for a Toll-like receptor 7 (TLR7) and use thereof, and relates to the interdisciplinary field of medicinal chemistry and immunology.

BACKGROUND

Toll-like receptor 7 (TLR7) belongs to a natural immune system of animals and plays an important role in the defense and treatment of microbial infections and tumor treatment[1,2].

TLR7 can be activated by synthetic small chemical molecules as ligands, and at the same time induce immune cells to produce immune cell factors IL-6, TNF-α, IFN-γ, and the like. Representative small molecule agonists for TLR7 include: Imiquimod (https://www.drugs.com/cdi/imiquimod-cream-aldara.html, FDA approved for clinical antiviral and cancer treatment), and Resiquimod (R848) (https://pubchem.ncbi.nlm.nih.gov/compound/Resiquimod, for applied researches on various innate immunity).

The main side effect of TLR7 agonists is the potential toxicity associated with systemic medication. Excessively active TLR7 agonists may trigger a fatal and severe cytokine storm, which therefore limits their clinical applicability; while the weakly active TLR7 agonist is unable to achieve the required immunotherapy effect. In order to overcome such a defect, it is necessary to develop novel TLR7 agonists to achieve normal immune activation and targeted immune activation.

In the present application, based on the discovery of an alkynyl derivative of purine as a TLR7 agonist, a series of novel TLR7 agonists are synthesized, some of which have incorporated with targeting effects to achieve local immune activation, such as tumor localization microenvironment, and at the same time has the effect of inhibiting tumor cells, as well as protecting and amplifying immune cells.

Technical Problems

It is one of the objectives of embodiments of the present application to provide a series of novel immune agonists, aiming to provide a series of novel small molecule immune agonists for a Toll-like receptor 7, the use thereof in activating and amplifying immune cells and lymphocytes, in preparing immunomodulatory drugs, small molecule immune anti-tumor drugs, and macromolecular immune anti-tumor drugs.

Technical Solutions

In order to solve the above technical problems, the following technical solutions are adopted by embodiments of the present application:

In a first aspect, the present application provides an immune agonist compound having a structure represented by Formula I:

Formula I

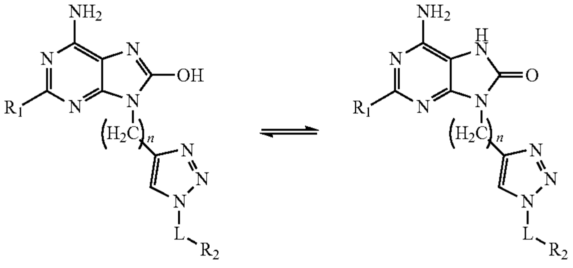

in which, $R_1$ represents any one of the following alkoxy groups and alkylamino groups:

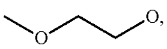,
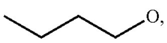,
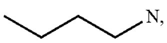,
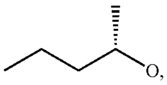,
and
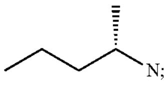;

L represents a connection chain comprising a PEG chain (a polyethylene glycol chain

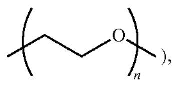), an alkyl chain, and a heterocyclic chain;

n represents an integer between 1 and 20 (including 1);

$R_2$ represents a functional group or a functional carrier, for example, a carboxyl group (COOH), a phosphate group

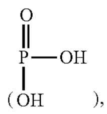), an amino group ($NH_2$), an isothiocyano group (NCS), an isocyanate group (NCO), a thiourea group, an azide group, an unsaturated double bond, an unsaturated triple bond, and the like; and a targeted drug or a precursor thereof, a protein, a polypeptide, an antibody, a virus, a bacteria, and a cell; and $R_2$ may also represent a biocompatible material and a carrier capable of binding and/or supporting the Formula I.

Preferably, a target protein of the targeted drug is at least one selected from the group consisting of: EGFR and a tyrosine kinase thereof, VEGFR and a tyrosine kinase thereof, VEGF, FGFR, HER2, HER3, HER4, NTRK, ROS1, ALK, BRD4, HDAC, KRAS, BRAF, BTK, PARP, BRCA, MEK, MET, NYC, TOPK, EZH2, BCMA, PI3K, PDGFR, FLT3, TOX, PD-L1, PD-1, CTLA-4, LAG3, TIM3, Siglec-15, TIGIT, TROP2, OX40, mTOR, BCL2, CD40, CD47, CD122, CD160, CD3, CD19, CD20, CD38, MUC1, MUC16, CDK4/6, TGF-β, HIF-1α/2α, PSGL-1, SURVIVIN, Frizzled-7, SLC4A7, CCR4, CCR5, CXCR4, CXCR5, CCL12, CXCL1, CXCL8, CXCL10, carbonic anhydrase IX, subunit proteins of various viruses and bacteria, and T and/or B cell epitope peptides of these subunit proteins. Or alternatively, the targeted drug is an antibacterial drug, a precursor of the antibacterial drug, an antiviral drug, and a precursor of the antiviral drug. For example, TQB3804; AMG510; Mavorixafor; TAK-220; TAK-779; Osimertinib; Ibrutinib; Zanubrutinib; JQ1; Norfloxacin; various subtypes, conservative or variant proteins and epitope peptides thereof in SARS-CoV and SARS-CoV-2; RNA polymerase inhibitors; and the like.

In a specific embodiment, the immune agonist compound comprises a series of GY compounds as follows: GY101, GY102, GY103, GY104, GY105, GY106, GY107, GY108, GY109, GY110, GY111, GY112, GY113, GY114, GY116, GY117, GY118, GY119, GY126, GY127, GY131, GY132, GY133, GY134, GY135, GY136, GY137, GY138, GY139, GY140, GY141, GY142, GY143, GY144, GY145, GY146, GY147, GY148, GY149, GY150, GY153, GY155, GY156, GY157, GY158, GY159, GY160, GY161, GY162, GY163, GY164, GY165, GY167, GY168, GY169, GY170, GY171, GY172, GY173, GY174, GY178, GY179, GY180, GY181, GY182, GY183, GY184, GY185, GY186, GY187, GY189, GY190, GY191, GY192, GY193, GY196, GY197, GY198, GY199, GY200, GY201, GY202, GY203, Peptide-54-GY106, GY106-PD-1, and GY-106-PD-L1.

In a specific embodiment, the immune agonist compound is GY115, GY120, GY121, GY122, GY151, GY152, GY166, GY175, or GY176, with each being an alkynyl-containing compound derived from GY100.

In a specific embodiment, the immune agonist compound is GY123.

In a second aspect, the present application further provides use of the immune agonist compound according to the first aspect, an enantiomer thereof, a salt thereof, and a crystal form thereof in preparation of an immunomodulatory drug and/or an immunotargeted drug, and/or in activating and/or amplifying immune cells and lymphocytes.

In a third aspect, the present application further provides use of a conjugate of the immune agonist compound according to the first aspect, an enantiomer thereof, a salt thereof, and a crystal form thereof with at least one of an antibody, a protein, a polypeptide, and a cell in preparation of a vaccine and/or an immunotargeted drug.

In a fourth aspect, the present application further provides use of the immune agonist compound according to the first aspect, an enantiomer thereof, a salt thereof, and a crystal form thereof in preparation of an anti-tumor drug, an antiviral drug, or a drug for targeted protein clearance.

In a fifth aspect, the present application further provides use of the immune agonist compound according to the first aspect, an enantiomer thereof, a salt thereof, and a crystal form thereof in preparation of various pharmaceutical preparations. The pharmaceutical preparations comprise various solid preparations, liquid preparations, spray preparations, and covalents or complexes or crystal hydrates thereof formed together with various carriers.

In a sixth aspect, the present application further provides use of the compound GY100 in preparation of an immunomodulatory drug and/or an immunotargeted drug.

In a sixth aspect, the present application further provides an immune agonist compound, being selected from the group consisting of SZU-194, SZU-195, SZU-213, SZU-215, SZU-251, SZU-107 and SZU-254.

In a seventh aspect, the present application further provides use of the immune agonist compound provided by the sixth aspect in preparation of an immunomodulatory drug and/or an immunotargeted drug.

In an eighth aspect, the present application further provides an anti-tumor or anti-virus method, comprising administering the immune agonist compound having a structure represented by Formula I to a subject.

BENEFICIAL EFFECTS

In the present application, a potent TLR7 agonist, that is, an alkynyl derivative of purine GY100, is accidentally discovered. Based on this discovery, a series of immune agonists containing a five-membered heterocycle having three nitrogens are synthesized. Through further exploration and optimization, a series of novel immune agonists are obtained. These novel immune agonists not only have good immune activation effects, but also can be coupled with other targeted compounds and drugs to produce a new generation of dual-function immune targeted agonists. On the basis of maintaining or strengthening the original targeting effect, this series of novel immune agonists are also incorporated with immune activation effect, and can amplify the number of immune cells as well. These series of novel multifunctional immune targeted compounds are directed to new directions for immunotargeted drugs. It has been known that the major side effect of many classic anticancer drugs or the targeted drugs is immunosuppression, and viral infections reduce lymphocytes. The multifunctional immune targeted compounds of the present application have the above-mentioned beneficial effects, and have important values in anti-tumor and anti-viral aspects.

DETAILED DESCRIPTION OF THE EMBODIMENTS

Figure 1:
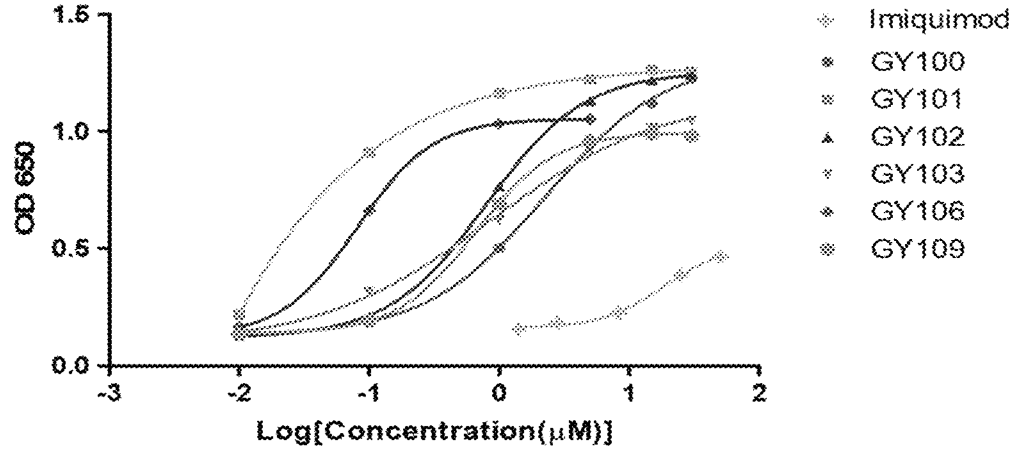
FIG. 1 shows effects of a series of GY compounds GY100, GY 101, GY 102, GY 103, GY 106, GY 109, and Imiquimod on activation of an TLR7 reporter cell line pathway (Imiquimod is a standard TLR7 agonist approved by the FDA for clinical use, and an OD value represents a SEAP induced expression).
Figure 2:
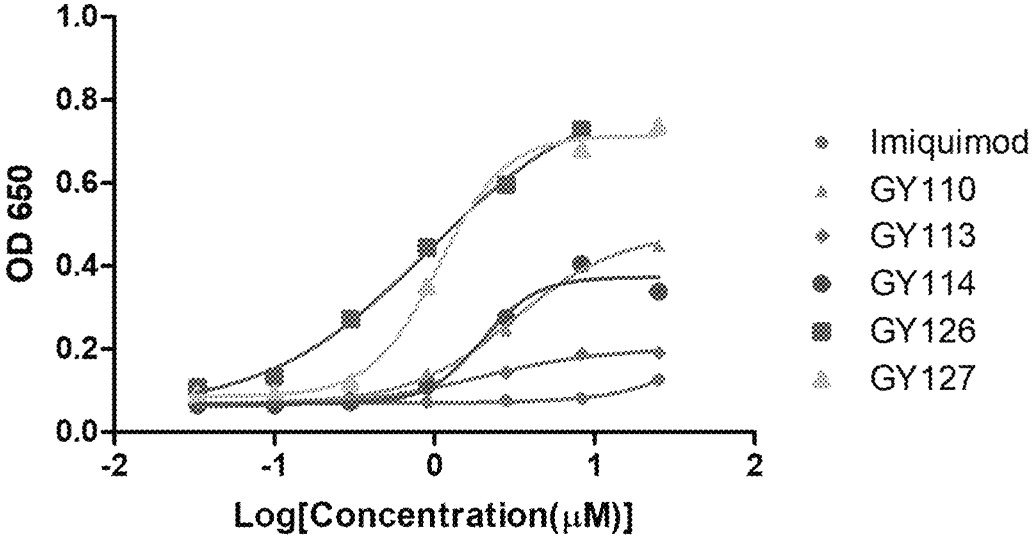
FIG. 2 shows effects of a series of GY compounds GY110, GY 113, GY 114, GY 126, GY 127, and Imiquimod on activation of an TLR7 reporter cell line pathway (Imiquimod is a standard TLR7 agonist approved by the FDA for clinical use, and an OD value represents a SEAP induced expression).
Figure 3A:
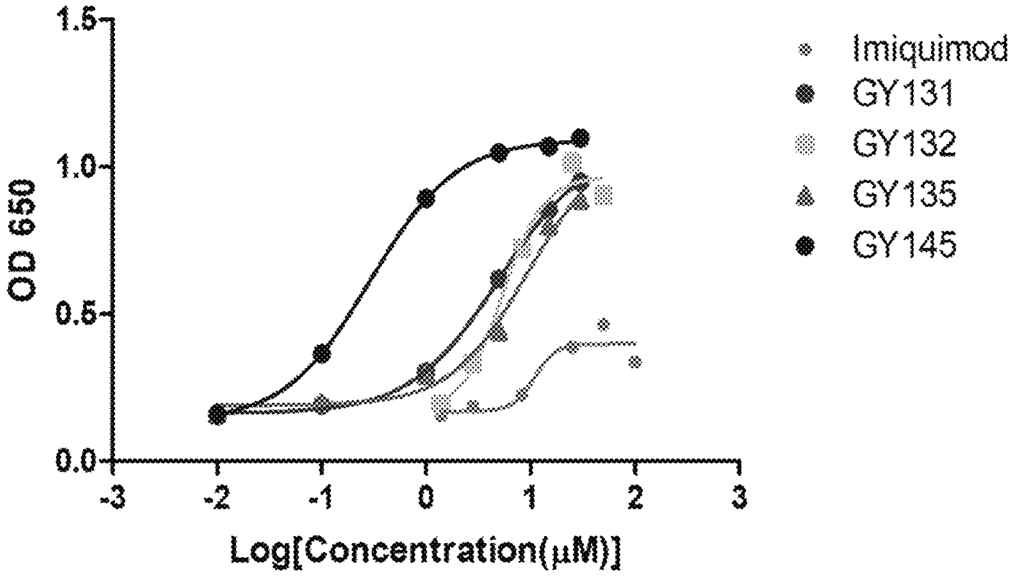
FIG. 3A shows effects of a series of GY compounds GY131, GY132, 135, 145, and Imiquimod on activation of an TLR7 reporter cell line pathway (Imiquimod is a standard TLR7 agonist approved by the FDA for clinical use, and an OD value represents a SEAP induced expression)
Figure 3B:
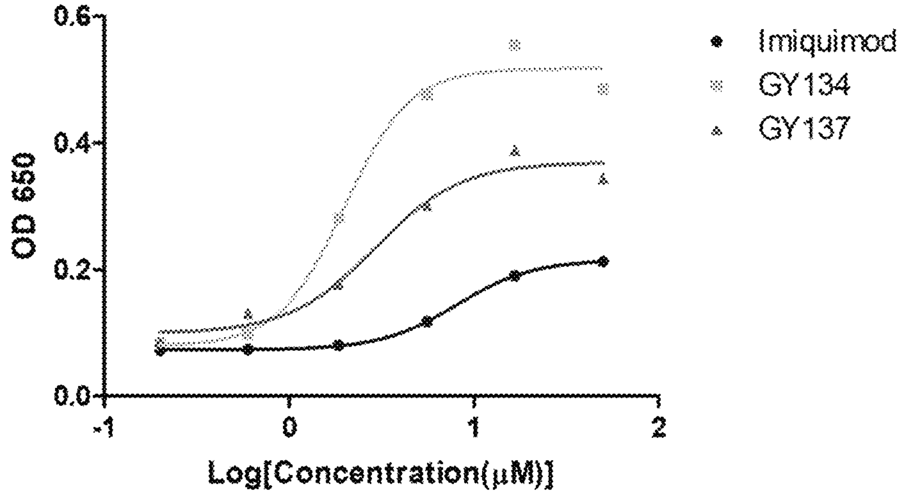
FIG. 3B shows effects of a series of GY compounds GY134, GY137, and Imiquimod on activation of an TLR7 reporter cell line pathway (Imiquimod is a standard TLR7 agonist approved by the FDA for clinical use, and an OD value represents a SEAP induced expression).
Figure 4:
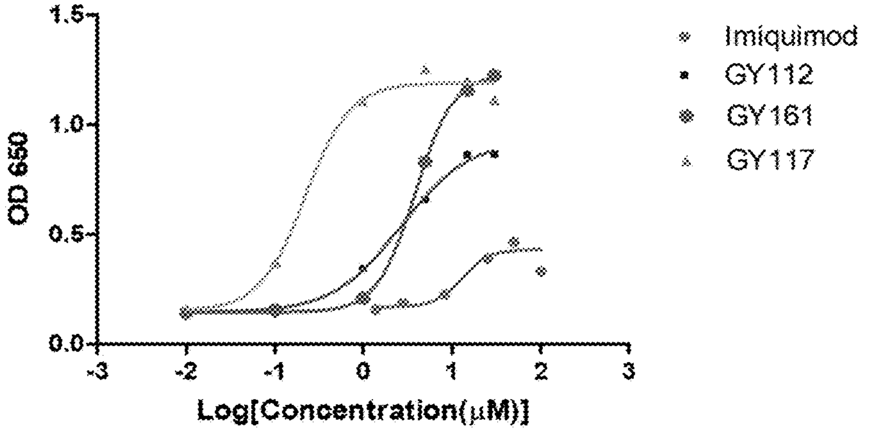
FIG. 4 shows effects of a series of GY compounds GY112, GY161, GY117, and Imiquimod on activation of an TLR7 reporter cell line pathway (Imiquimod is a standard TLR7 agonist approved by the FDA for clinical use, and an OD value represents a SEAP induced expression).
Figure 5:
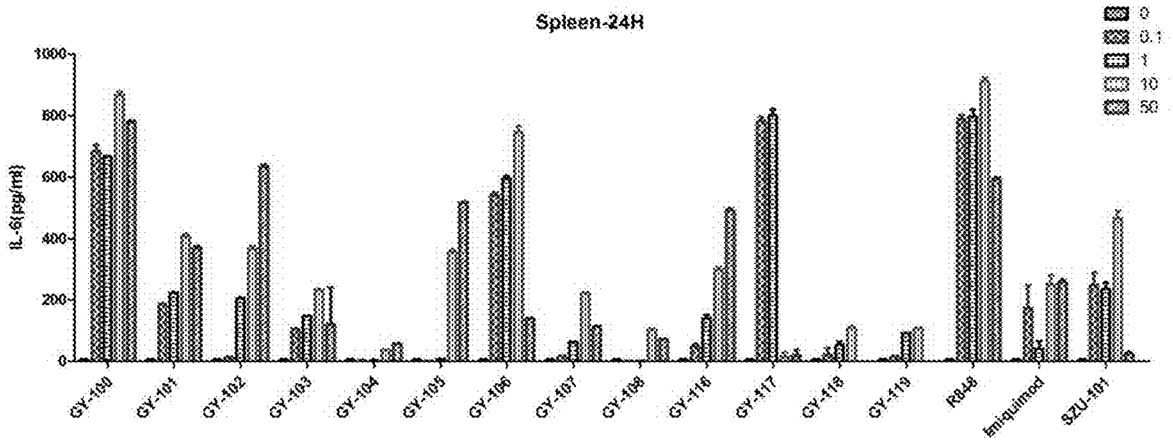
FIG. 5 shows the IL-6 cytokine production effect of a series of GY compounds on spleen cells.
Figure 6:
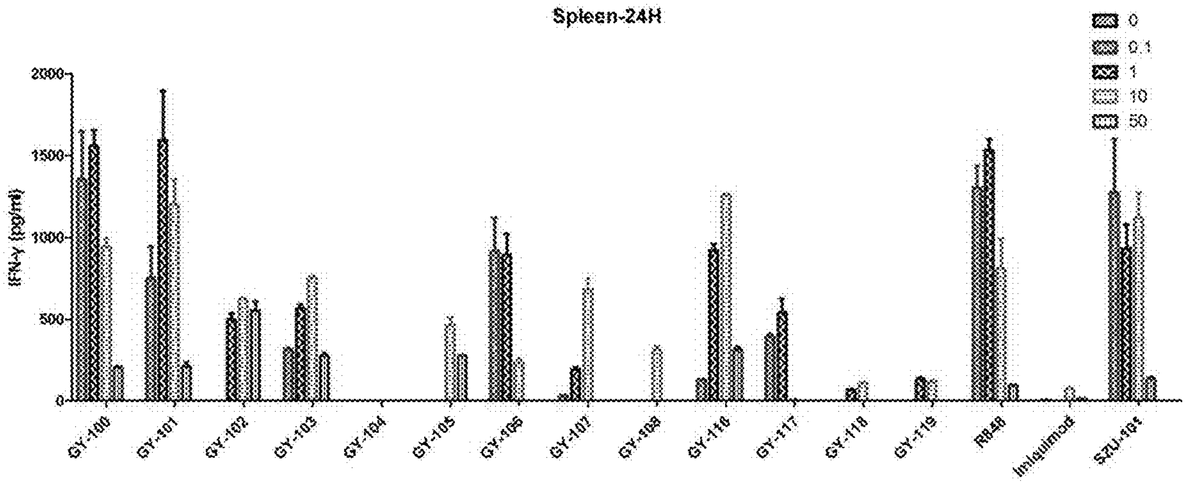
FIG. 6 shows the IFN-γ cytokine production effect of a series of GY compounds on spleen cells.
Figure 7:
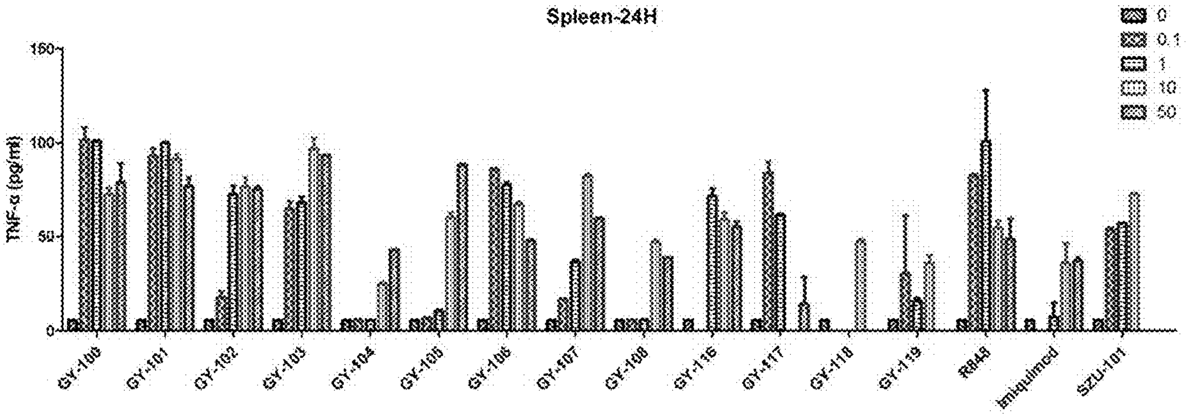
FIG. 7 shows the TNF-α cytokine production effect of a series of GY compounds on spleen cells.
Figure 8:
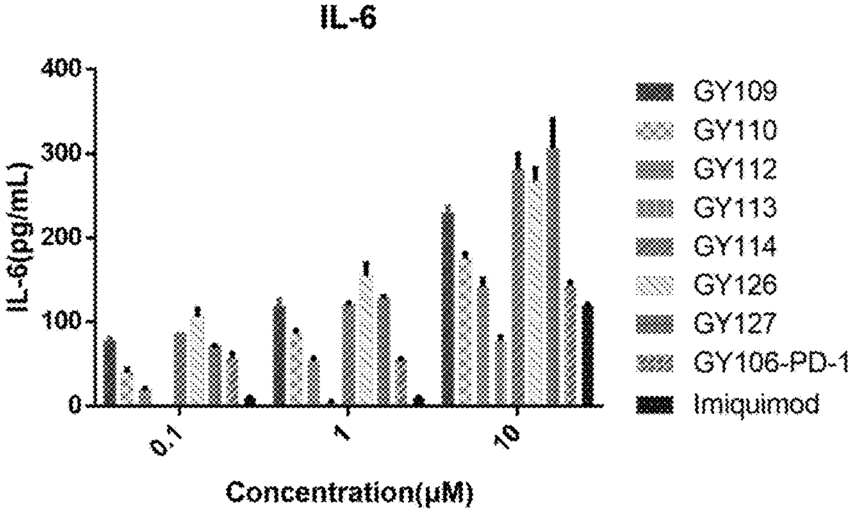
FIG. 8 shows the IL-6 cytokine production effect of a series of GY compounds on spleen cells.
Figure 9:
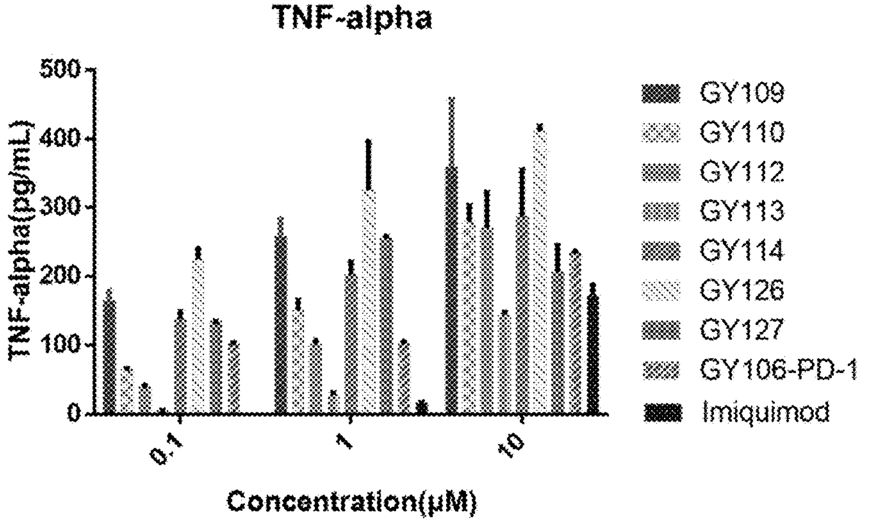
FIG. 9 shows the TNF-α cytokine production effect of a series of GY compounds on spleen cells.
Figure 10:
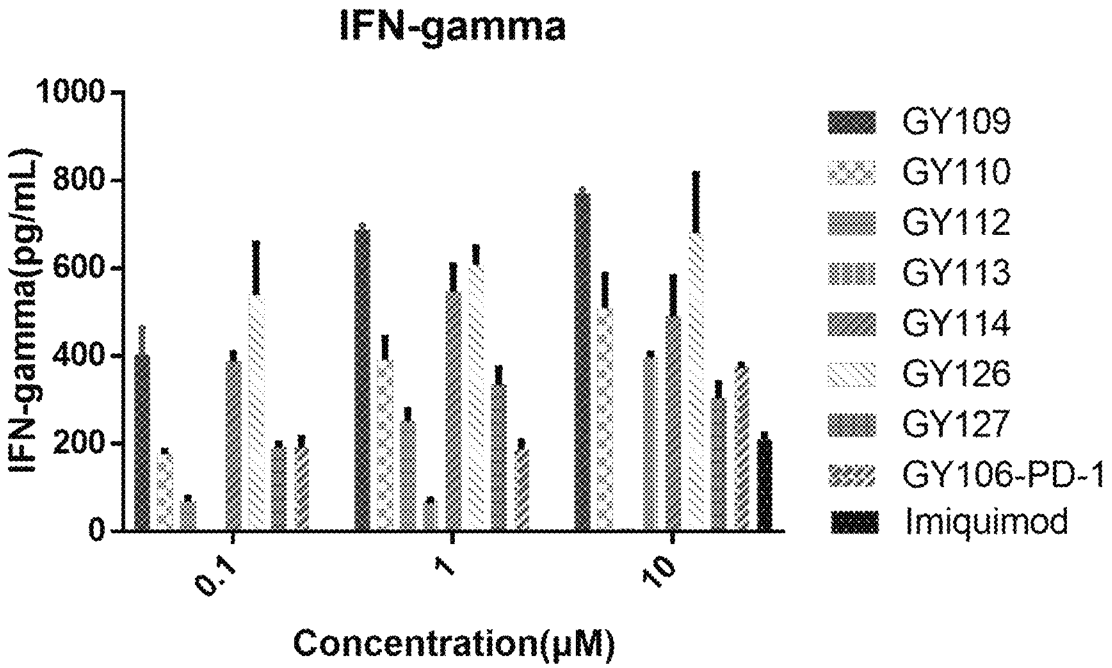
FIG. 10 shows the IFN-γ cytokine production effect of a series of GY compounds on spleen cells.
Figure 11:
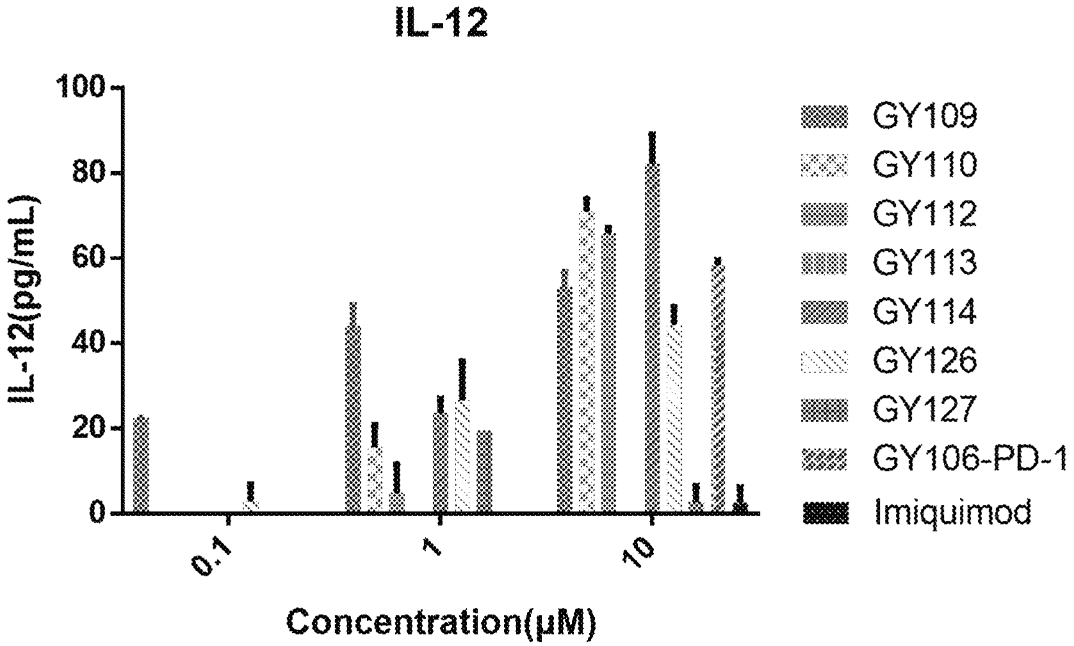
FIG. 11 shows the IL-12 cytokine production effect of a series of GY compounds on spleen cells.
Figure 12:
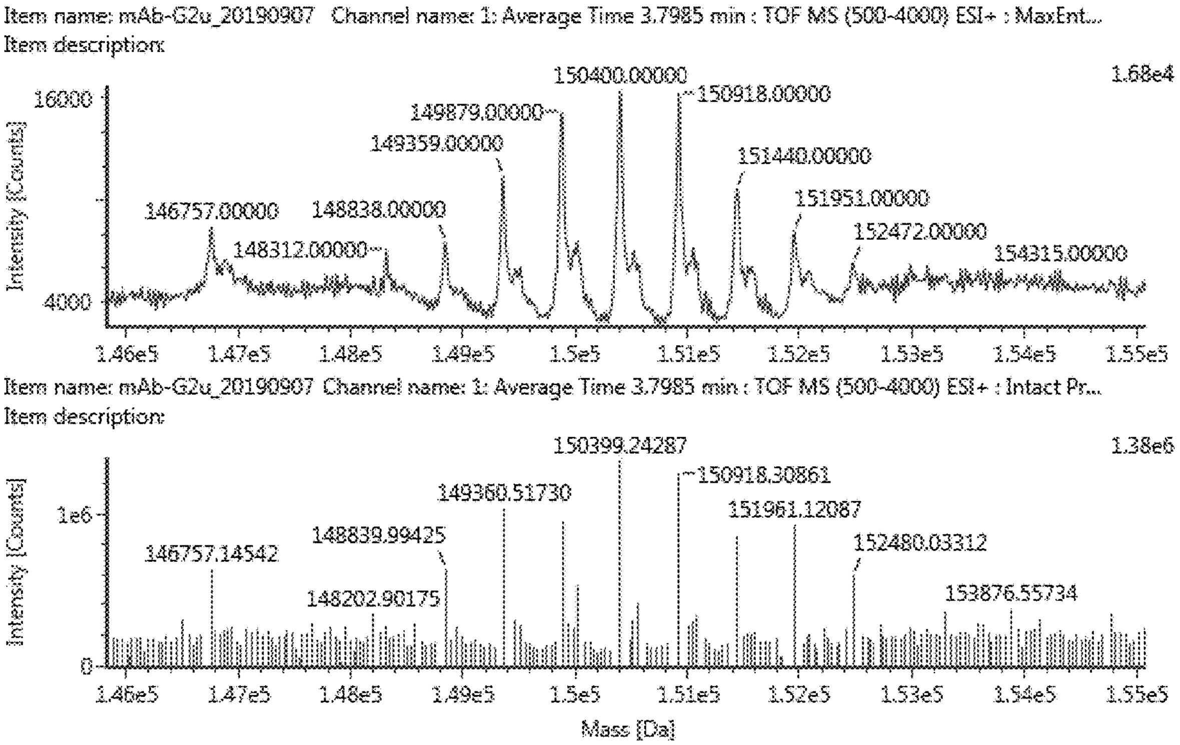
FIG. 12 shows the degree of coupling of GY106-PD-1 (drug/antibody ratio: DAR value; a molecular weight of the original naked anti-PD-1 is 146755). Mass spectrometry confirmed that GY106-PD-1 had an average of 7 GY106 coupled thereto.
Figure 13:
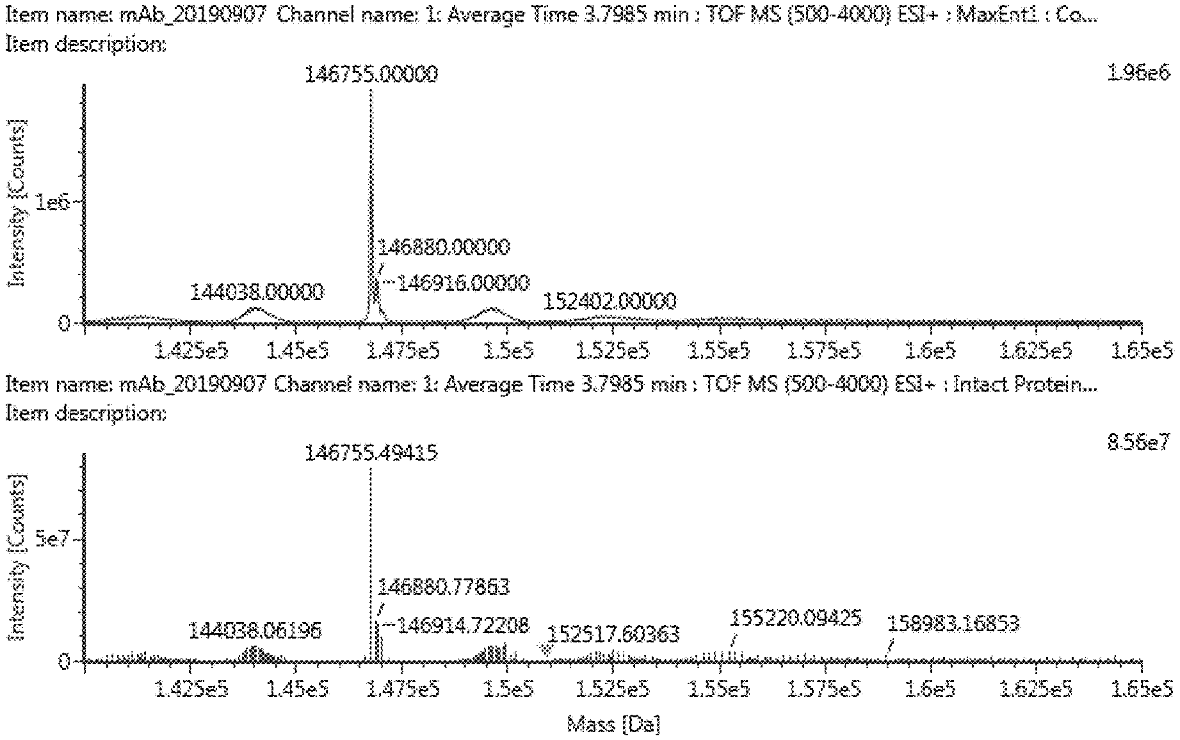
FIG. 13 shows determination of a mass spectrometric molecular weight of an original PD-1 antibody.

The present application provides an immune agonist compound having a structure represented by Formula I:

Formula I

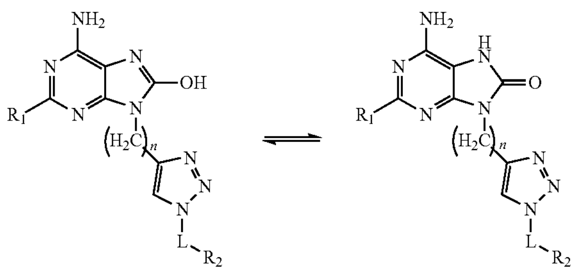

in which, $R_1$ represents any one of the following alkoxy groups and alkylamino groups:

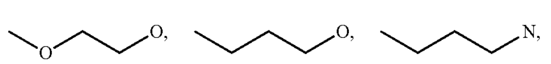

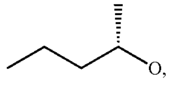

and

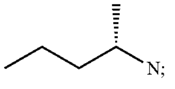

L represents a connection chain comprising a PEG chain (a polyethylene glycol chain

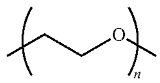

), an alkyl chain, and a heterocyclic chain;

n represents an integer between 1 and 20 (including 1);

$R_2$ represents a functional group or a functional carrier, for example, a carboxyl group (COOH), a phosphate group

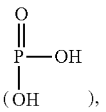

an amino group ($NH_2$), an isothiocyano group (NCS), an isocyanate group (NCO), a thiourea group, an azide group, and the like; and a targeted drug or a precursor thereof, a protein, a polypeptide, an antibody, a virus, a bacteria, and a cell;

Preferably, a target protein of the targeted drug is at least one selected from the group consisting of: EGFR and a tyrosine kinase thereof, VEGFR and a tyrosine kinase thereof, VEGF, FGFR, HER2, HER3, HER4, NTRK, ROS1, ALK, BRD4, HDAC, KRAS, BRAF, BTK, PARP, BRCA, MEK, MET, NYC, TOPK, EZH2, BCMA, PI3K, PDGFR, FLT3, TOX, PD-L1, PD-1, CTLA-4, LAG3, TIM3, Siglec-15, TIGIT, TROP2, OX40, mTOR, BCL2, CD40, CD47, CD122, CD160, CD3, CD19, CD20, CD38, MUC1, MUC16, CDK4/6, TGFβ, HIF-1α/2α, PSGL-1, SURVIVIN, Frizzled-7, SLC4A7, CCR4, CCR5, CXCR4, CXCR5, CCL12, CXCL1, CXCL8, CXCL10, carbonic anhydrase IX, a virus subunit protein and a T and/or B cell epitope peptide thereof, and a T and/or B cell epitope peptide of a bacterial subunit protein. Or alternatively, the targeted drug is an antibacterial drug, a precursor of the antibacterial drug, an antiviral drug, and a precursor of the antiviral drug. For example, TQB3804; AMG510; Mavorixafor; TAK-220; TAK-779; Osimertinib; Ibrutinib; Zanubrutinib; JQ1; Norfloxacin; various subtypes, conservative or variant proteins and epitope peptides thereof in SARS-CoV and SARS-CoV-2; RNA polymerase inhibitors; and the like.

In a specific embodiment, immune agonist compound comprises a series of GY compounds as follows: GY101, GY102, GY103, GY104, GY105, GY106, GY107, GY108, GY109, GY110, GY111, GY112, GY113, GY114, GY116, GY117, GY118, GY119, GY126, GY127, GY131, GY132, GY133, GY134, GY135, GY136, GY137, GY138, GY139, GY140, GY141, GY142, GY143, GY144, GY145, GY146, GY147, GY148, GY149, GY150, GY153, GY155, GY156, GY157, GY158, GY159, GY160, GY161, GY162, GY163, GY164, GY165, GY167, GY168, GY169, GY170, GY171, GY172, GY173, GY174, GY178, GY179, GY180, GY181, GY182, GY183, GY184, GY185, GY186, GY187, Peptide-54-GY106, GY106-PD-1, and GY-106-PD-L1.

In a specific embodiment, the immune agonist compound is GY115, GY120, GY121, GY122, GY151, GY152, GY166, GY175, or GY176, with each being an alkynyl-containing compound derived from GY100.

In a specific embodiment, the immune agonist compound is GY123.

Specifically, the representative compound of Formula I has the following structural formulas as listed in Table 1 (in which, $R_2$ is a functional group or a precursor thereof). Representative compounds containing alkynyl groups are also included in Table 1.

TABLE 1

| Number | Structure | Molecular weight |
|---|---|---|
| GY101 | 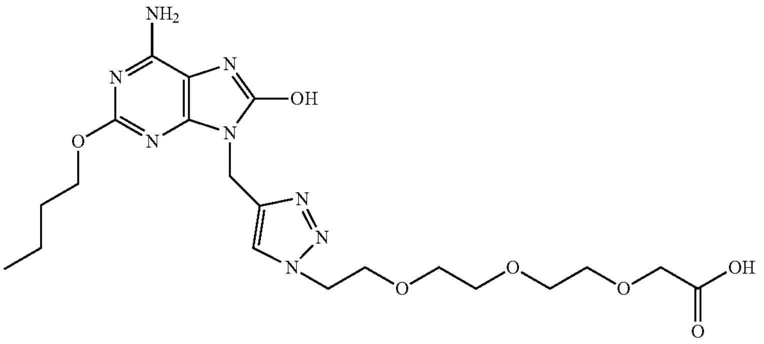 [SMILES: CCCCOc1nc(N)c2nc(O)n(Cc3cn(CCOCCOCCOCC(=O)O)nn3)c2n1] | 494.22 |
| GY102 | 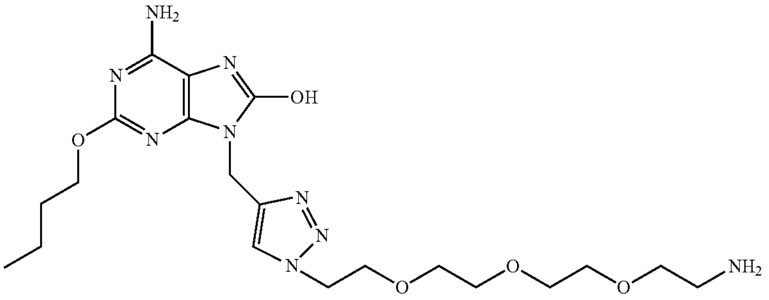 [SMILES: CCCCOc1nc(N)c2nc(O)n(Cc3cn(CCOCCOCCOCCN)nn3)c2n1] | 479.26 |

TABLE 1-continued
| Number | Structure | Molecular weight |
|---|---|---|
| GY103 | 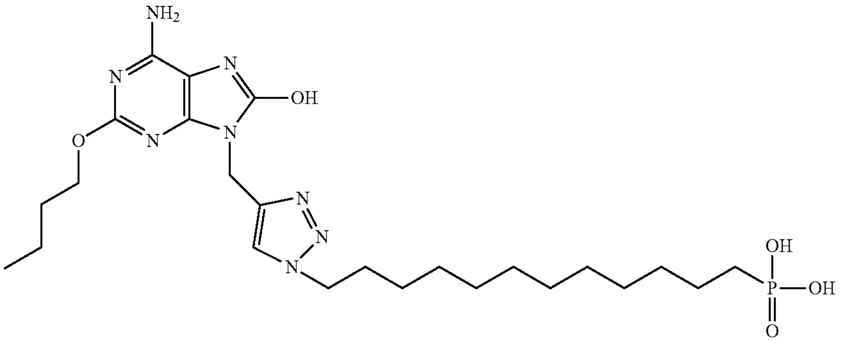 [SMILES: CCCCOc1nc(N)c2nc(O)n(Cc3cn(CCCCCCCCCCCCP(=O)(O)O)nn3)c2n1] | 552.29 |
| GY104 | 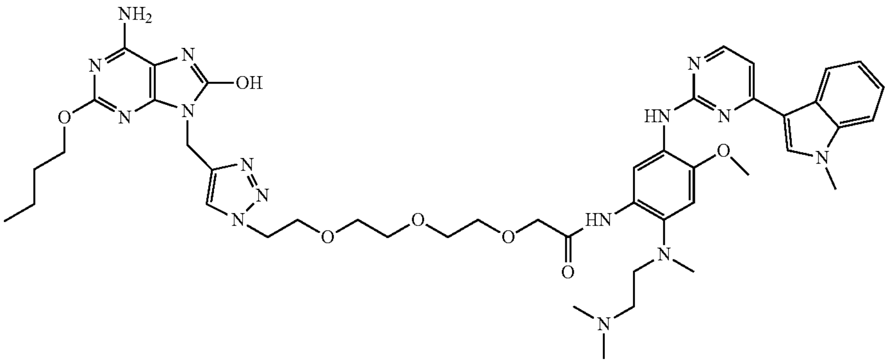 Derivative coupled with Osimertinib | 921.47 |
| GY105 | 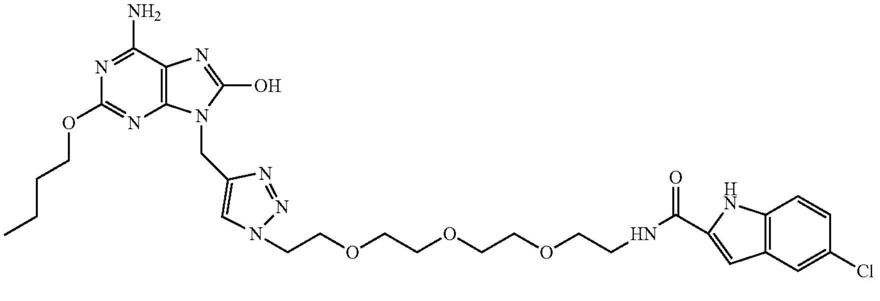 [SMILES: CCCCOc1nc(N)c2nc(O)n(Cc3cn(CCOCCOCCOCCNC(=O)c4cc5cc(Cl)ccc5[nH]4)nn3)c2n1] | 656.26 |
| GY106 | 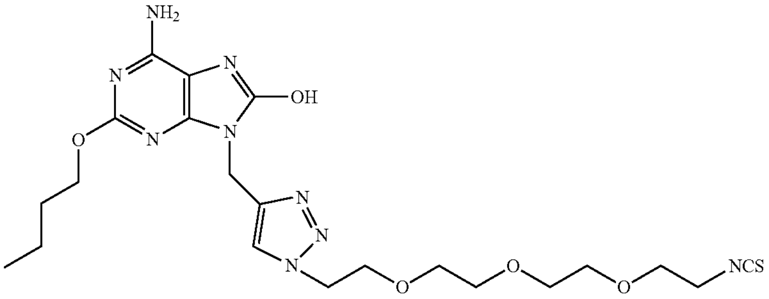 | 521.22 |

TABLE 1-continued
| Number | Structure | Molecular weight |
| --- | --- | --- |
| GY107 | 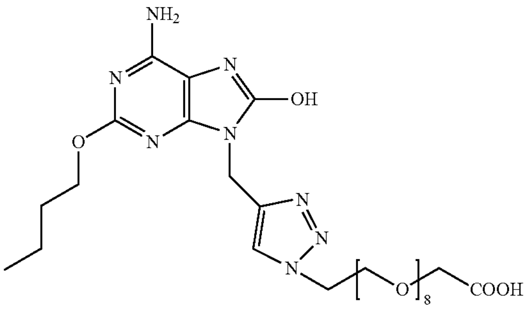 | 728 |
| GY108 | 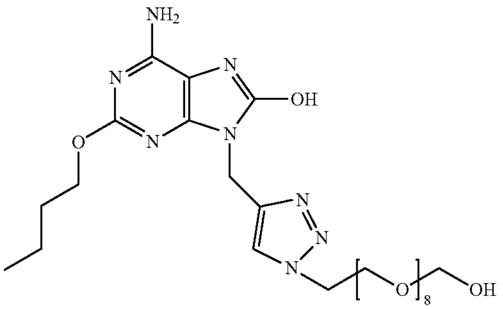 | 655 |
| GY109 | 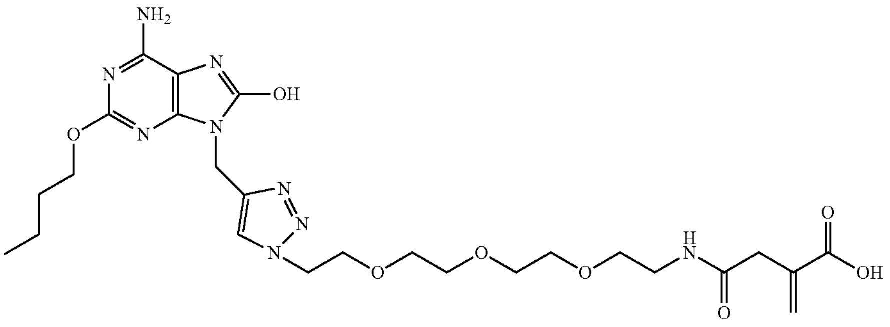 [SMILES: C=C(CC(=O)NCCOCCOCCOCCn1cc(Cn2c(O)nc3c(N)nc(OCCCC)nc32)nn1)C(=O)O] | 591.28 |
| GY110 | 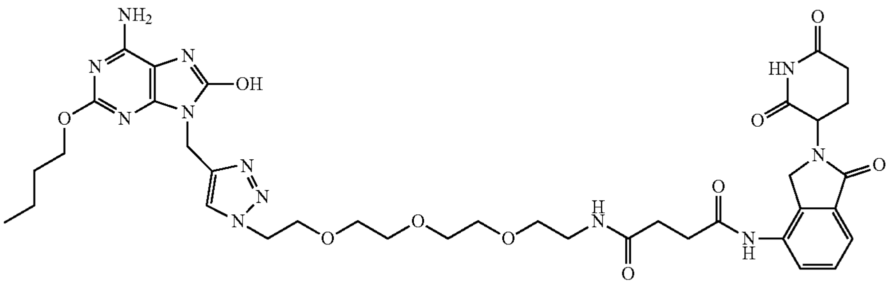 [SMILES: CCCCOc1nc(N)c2nc(O)n(Cc3cn(CCOCCOCCOCCNC(=O)CCC(=O)Nc4cccc5c4CN(C4CCC(=O)NC4=O)C5=O)nn3)c2n1] | 820 |
| GY111 | 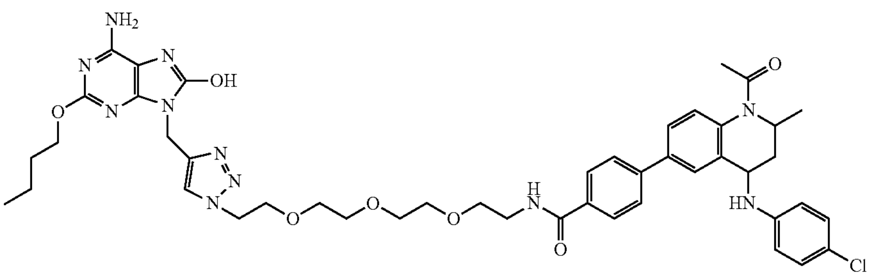 [SMILES: CCCCOc1nc(N)c2nc(O)n(Cc3cn(CCOCCOCCOCCNC(=O)c4ccc(-c5ccc6c(c5)C(Nc5ccc(Cl)cc5)CC(C)N6C(C)=O)cc4)nn3)c2n1] | 895 |

TABLE 1-continued
| Number | Structure | Molecular weight |
|---|---|---|
| GY112 | 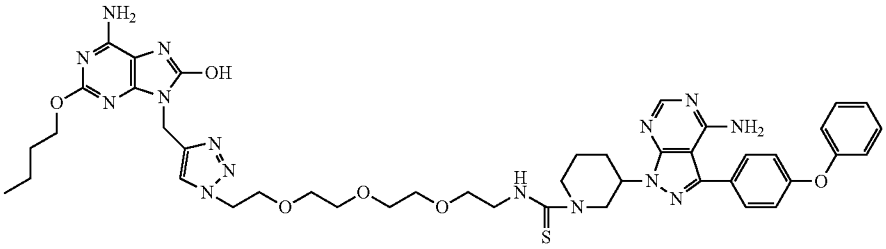 Derivative coupled with Ibrutinib | 907 |
| GY113 | 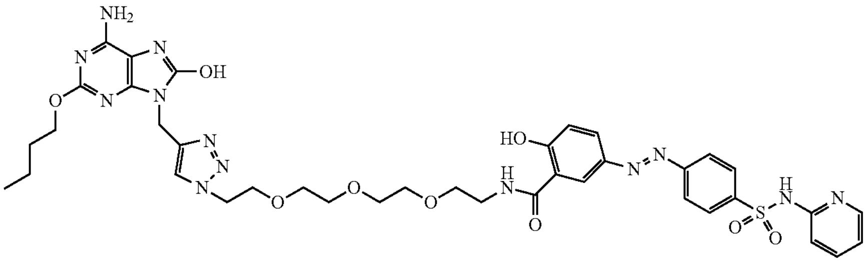 [SMILES: CCCCOc1nc(N)c2nc(O)n(Cc3cn(CCOCCOCCOCCNC(=O)c4cc(/N=N/c5ccc(S(=O)(=O)Nc6ccccn6)cc5)ccc4O)nn3)c2n1] | 859 |
| GY114 | 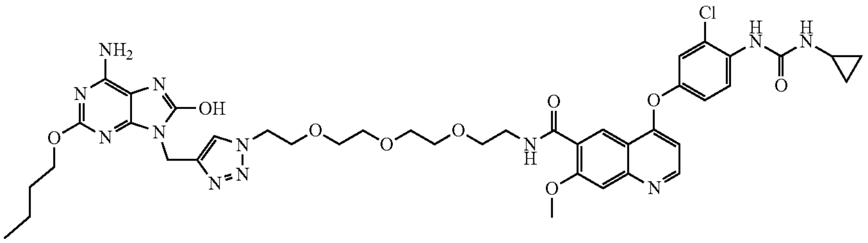 Derivative coupled with Lenvatinib | 889 |
| GY115 | 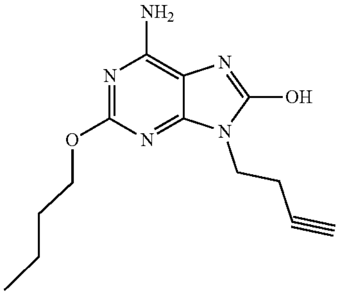 [SMILES: C#CCCn1c(O)nc2c(N)nc(OCCCC)nc21] | 275 |
| GY116 | 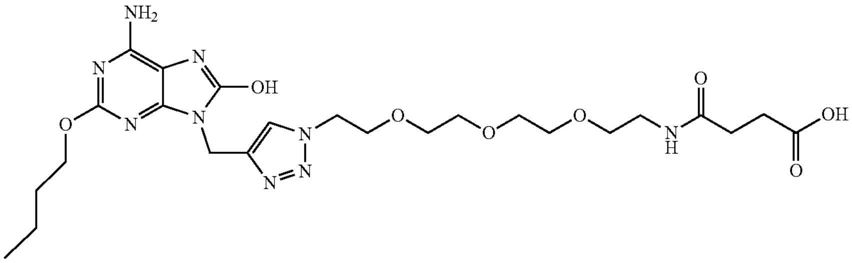 [SMILES: CCCCOc1nc(N)c2nc(O)n(Cc3cn(CCOCCOCCOCCNC(=O)CCC(=O)O)nn3)c2n1] | 580 |

TABLE 1-continued
| Number | Structure | Molecular weight |
|---|---|---|
| GY117 | 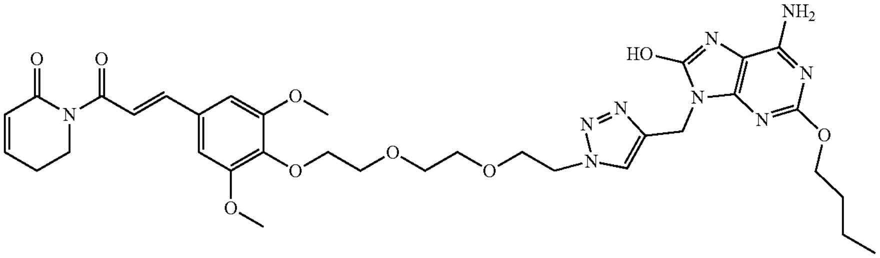 Derivative coupled with Piperlongumine | 722 |
| GY118 | 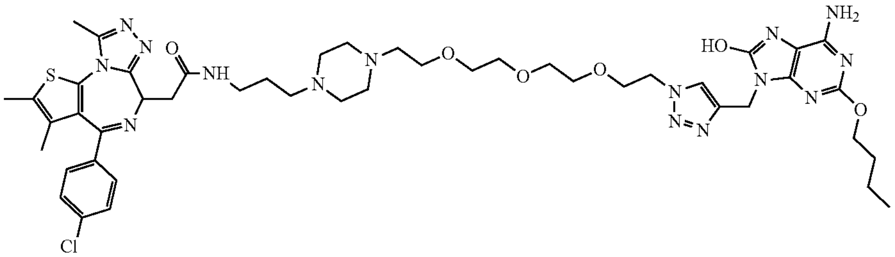 Derivative coupled with JQ1 | 988 |
| GY119 | 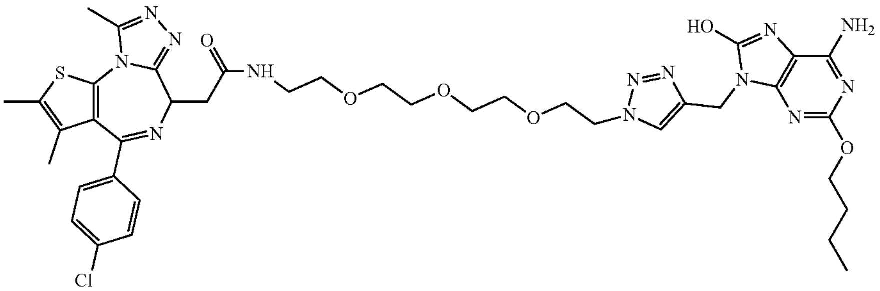 Derivative coupled with JQ1 | 862 |
| GY120 | 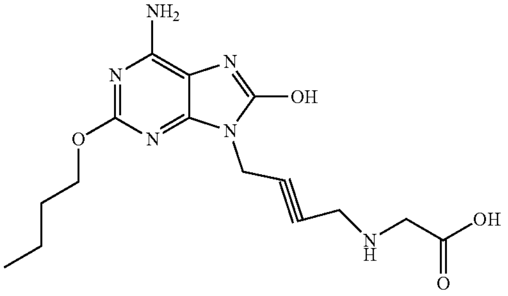 [SMILES: CCCCOc1nc(N)c2nc(O)n(CC#CCNCC(=O)O)c2n1] | 348 |
| GY-121 | 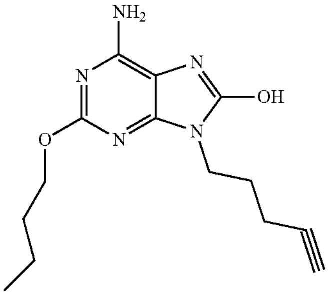 [SMILES: C#CCCCn1c(O)nc2c(N)nc(OCCCC)nc21] | 289 |

TABLE 1-continued
| Number | Structure | Molecular weight |
|---|---|---|
| GY-122 | 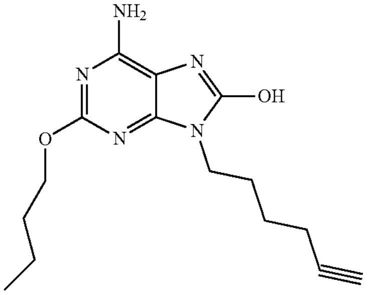 [SMILES: C#CCCCCn1c(O)nc2c(N)nc(OCCCC)nc21] | 303 |
| GY-123 | 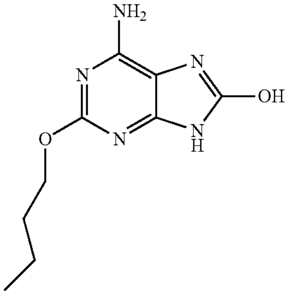 [SMILES: CCCCOc1nc(N)c2nc(O)[nH]c2n1] | 223 |
| GY126 | 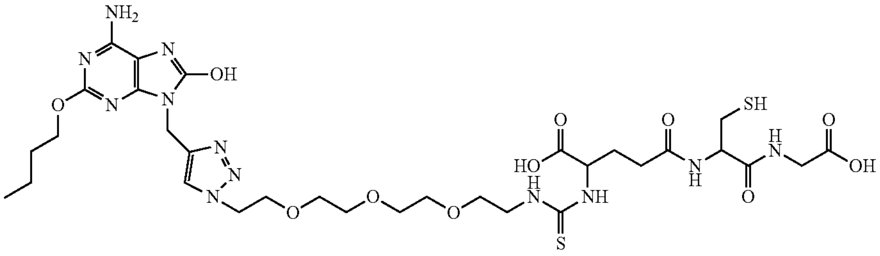 [SMILES: CCCCOc1nc(N)c2nc(O)n(Cc3cn(CCOCCOCCOCCNC(=S)NC(CCC(=O)NC(CS)C(=O)NCC(=O)O)C(=O)O)nn3)c2n1] | 828 |
| GY127 | 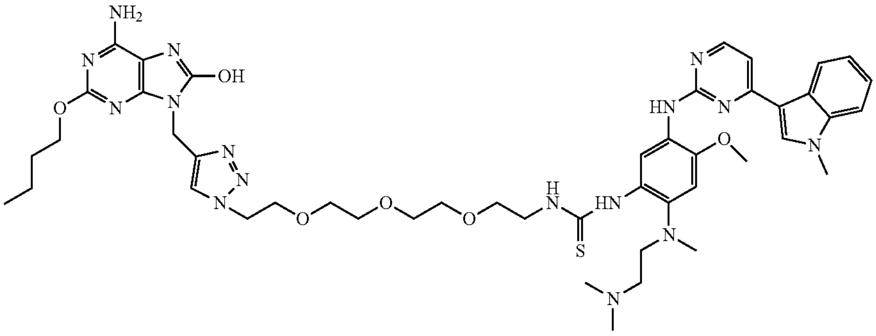 | 967 |
Derivative coupled with AZD9291

TABLE 1-continued
| Number | Structure | Molecular weight |
|---|---|---|
| GY131 | 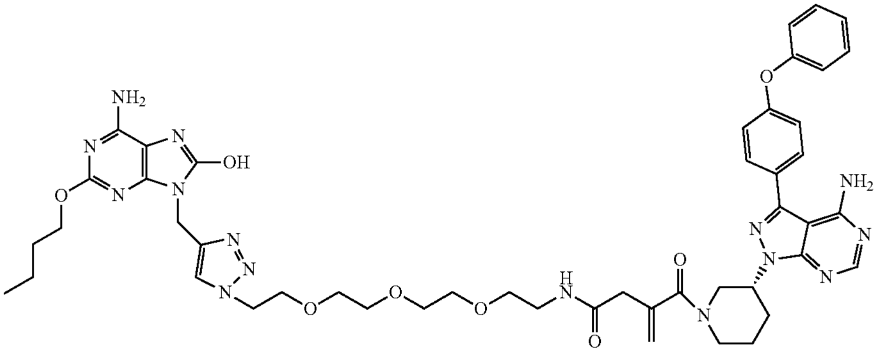 Derivative coupled with Ibrutinib | 959 |
| GY132 | 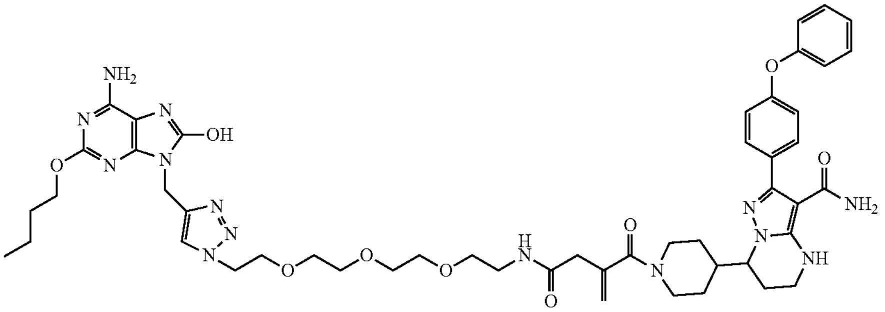 Derivative coupled with Zanubrutinib of S-configuration | 990 |
| GY133 | 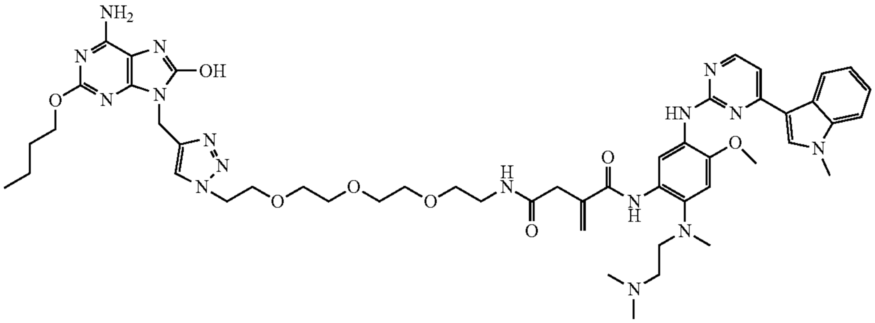 Derivative coupled with AZD9291 | 1018.52 |
| GY134 | 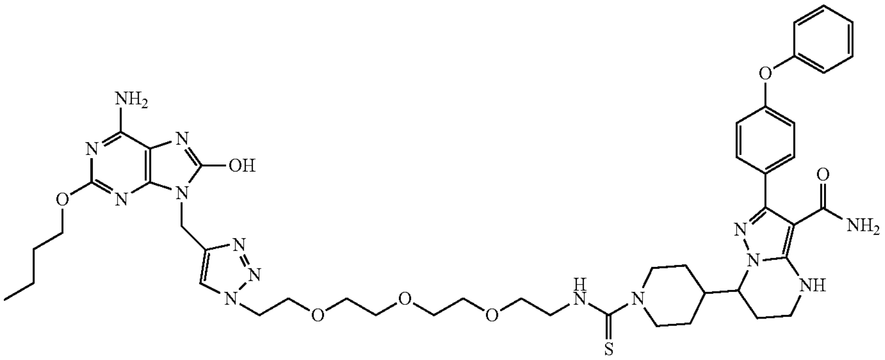 Derivative coupled with Zanubrutinib of R-configuration | 938 |

TABLE 1-continued
| Number | Structure | Molecular weight |
|---|---|---|
| GY135 | 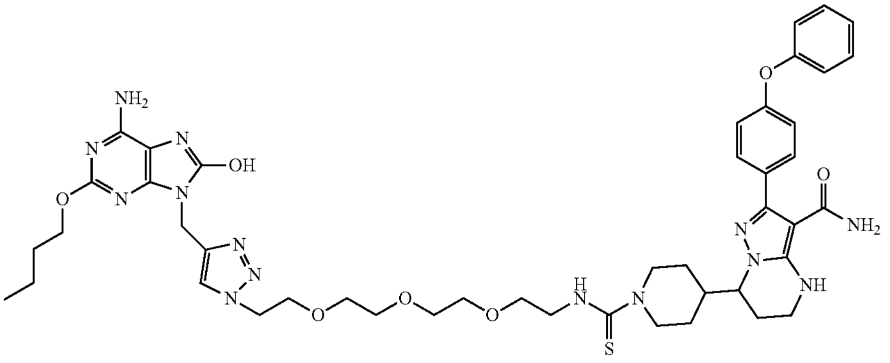 Derivative coupled with Zanubrutinib of S-configuration | 938 |
| GY136 | 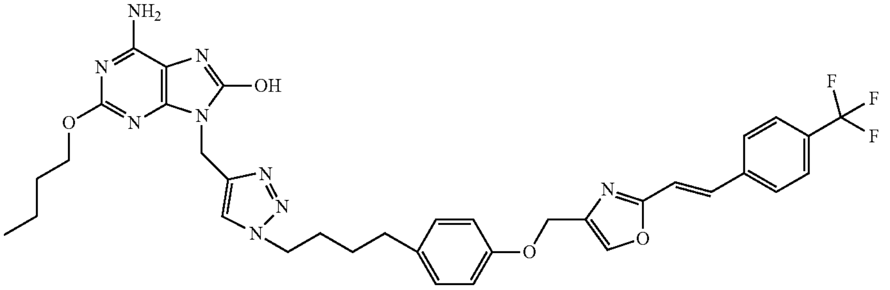 Derivative coupled with Mubritinib | 703 |
| GY137 | 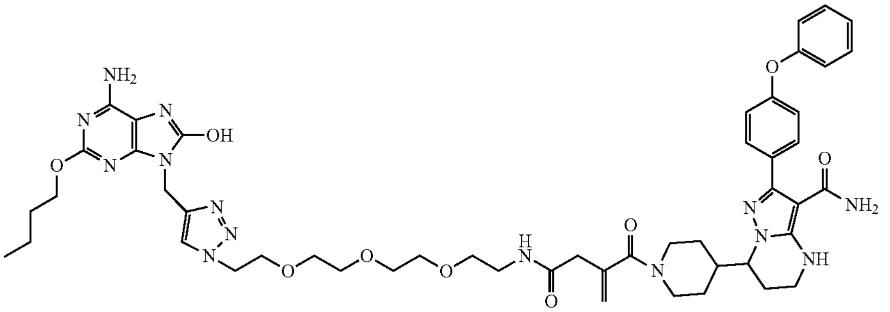 Derivative coupled with Zanubrutinib of R-configuration | 990 |
| GY138 | 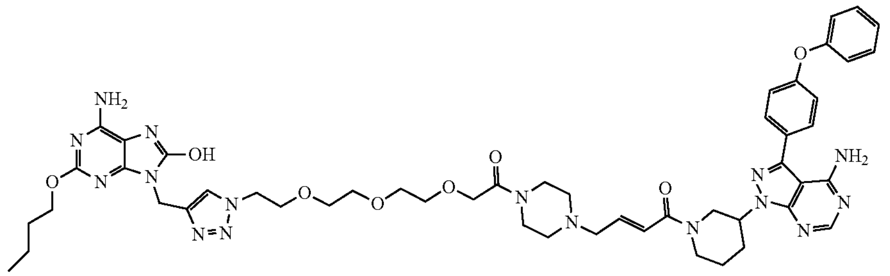 Derivative coupled with Ibrutinib | 1015 |

TABLE 1-continued
| Number | Structure | Molecular weight |
|---|---|---|
| GY139 | 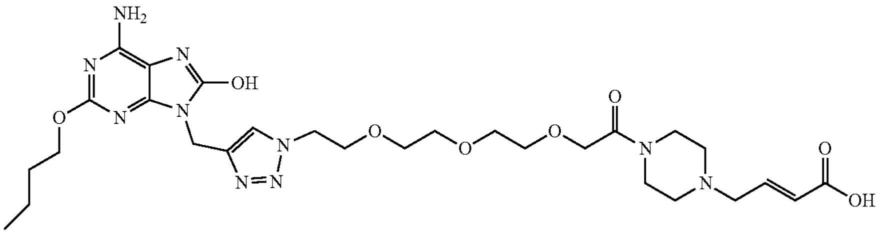 [SMILES: CCCCOc1nc(N)c2nc(O)n(Cc3cn(CCOCCOCCOCC(=O)N4CCN(C/C=C/C(=O)O)CC4)nn3)c2n1] | 646 |
| GY140 | 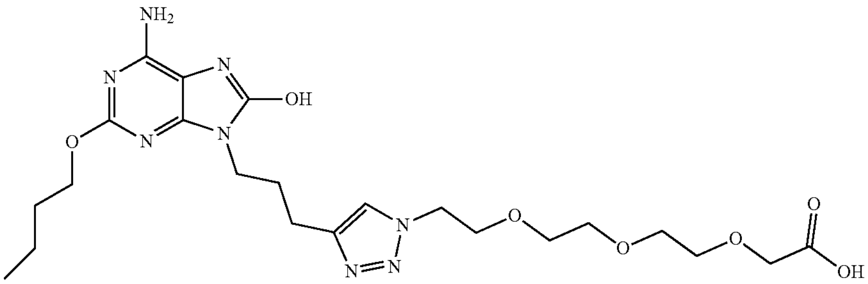 [SMILES: CCCCOc1nc(N)c2nc(O)n(CCCc3cn(CCOCCOCCOCC(=O)O)nn3)c2n1] | 523 |
| GY141 | 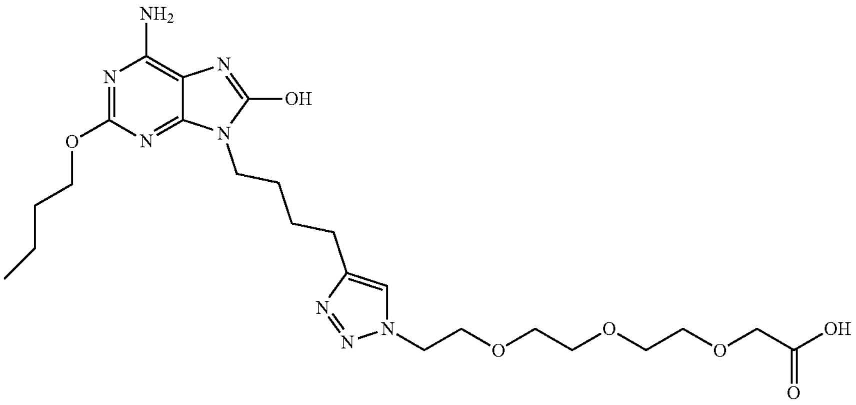 [SMILES: CCCCOc1nc(N)c2nc(O)n(CCCCc3cn(CCOCCOCCOCC(=O)O)nn3)c2n1] | 537 |
| GY142 | 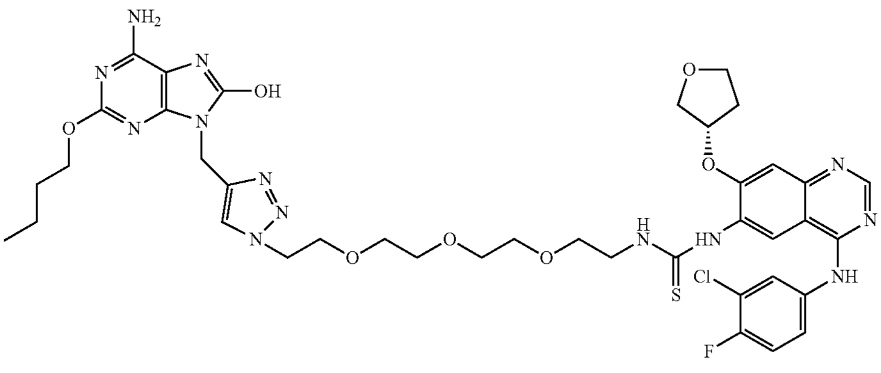 | 895 |
Derivative coupled with Afatinib TABLE 1-continued
| Number | Structure | Molecular weight |
|---|---|---|
| GY143 | 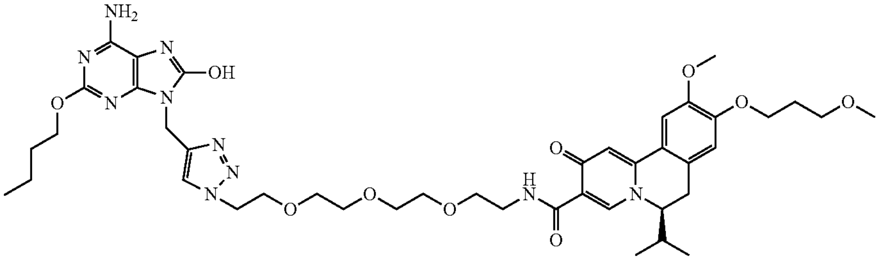 Derivative coupled with RG7834 | 862 |
| GY144 | 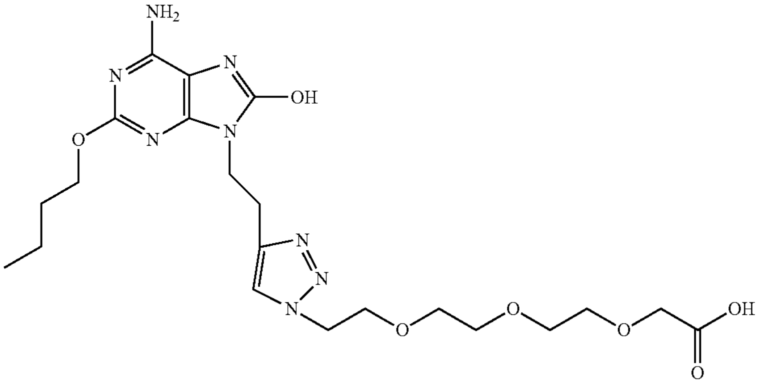 [SMILES: CCCCOc1nc(N)c2nc(O)n(CCc3cn(CCOCCOCCOCC(=O)O)nn3)c2n1] | 509 |
| GY145 | 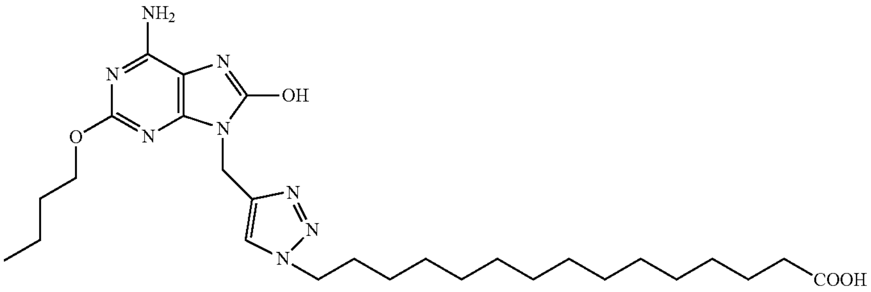 [SMILES: CCCCOc1nc(N)c2nc(O)n(Cc3cn(CCCCCCCCCCCCCCC(=O)O)nn3)c2n1] | 544.35 |
| GY146 | 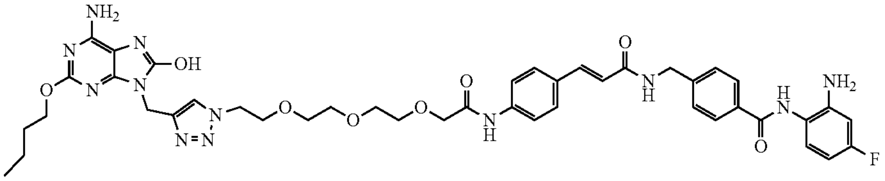 [SMILES: CCCCOc1nc(N)c2nc(O)n(Cc3cn(CCOCCOCCOCC(=O)Nc4ccc(/C=C/C(=O)NCc5ccc(C(=O)Nc6ccc(F)cc6N)cc5)cc4)nn3)c2n1] | 881.1 |
| GY147 | 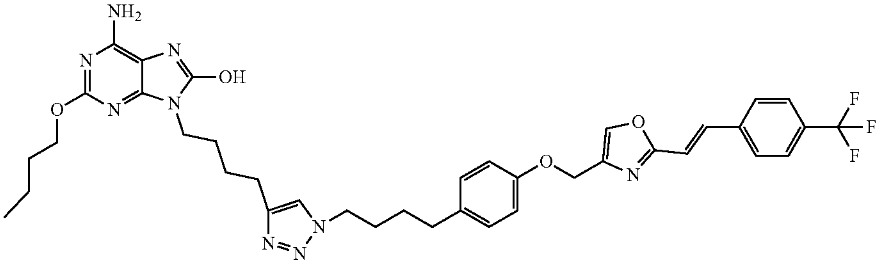 Derivative coupled with Mubritinib | 745 |

TABLE 1-continued
| Number | Structure | Molecular weight |
| --- | --- | --- |
| GY148 | 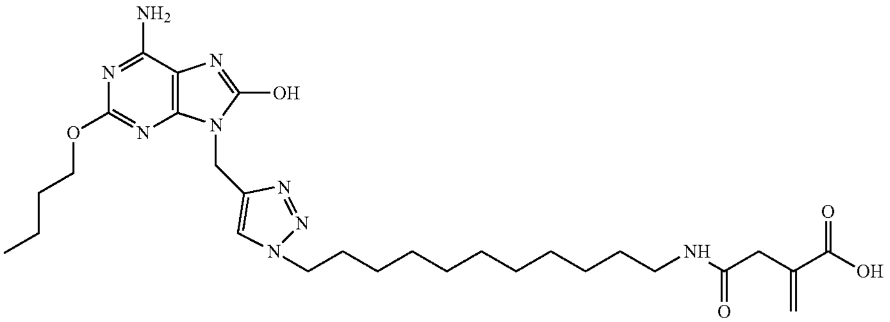 [SMILES: C=C(CC(=O)NCCCCCCCCCCCn1cc(Cn2c(O)nc3c(N)nc(OCCCC)nc32)nn1)C(=O)O] | 585.34 |
| GY149 | 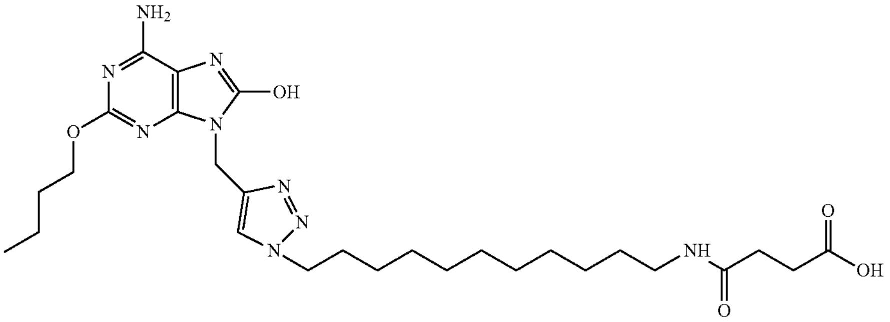 [SMILES: CCCCOc1nc(N)c2nc(O)n(Cc3cn(CCCCCCCCCCCNC(=O)CCC(=O)O)nn3)c2n1] | 573.34 |
| GY150 | 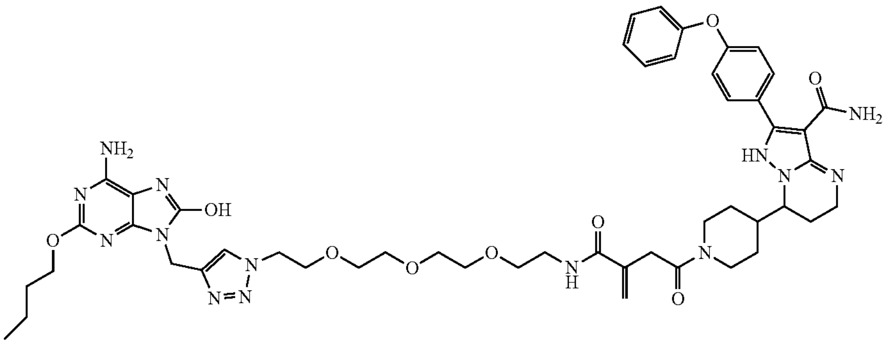 Derivative coupled with Zanubrutinib of R-configuration | 992 |
| GY151 | 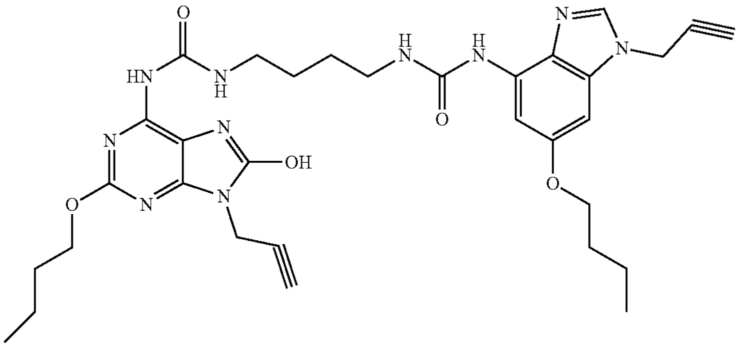 [SMILES: C#CCn1cnc2c(NC(=O)NCCCCNC(=O)Nc3nc(OCCCC)nc4c3nc(O)n4CC#C)cc(OCCCC)cc21] | 664 |

TABLE 1-continued
| Number | Structure | Molecular weight |
|---|---|---|
| GY152 | 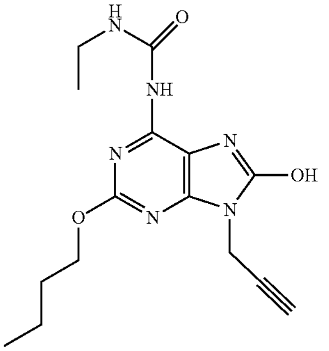 [SMILES: C#CCn1c(O)nc2c(NC(=O)NCC)nc(OCCCC)nc21] | 332 |
| GY153 | 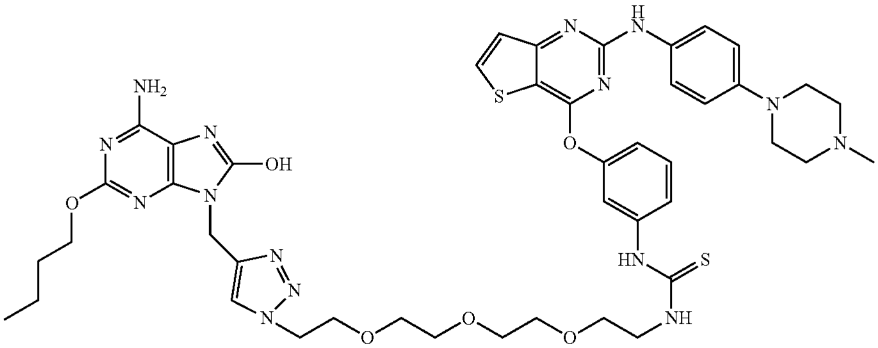 Derivative coupled with Olmutinib | 953 |
| GY155 | 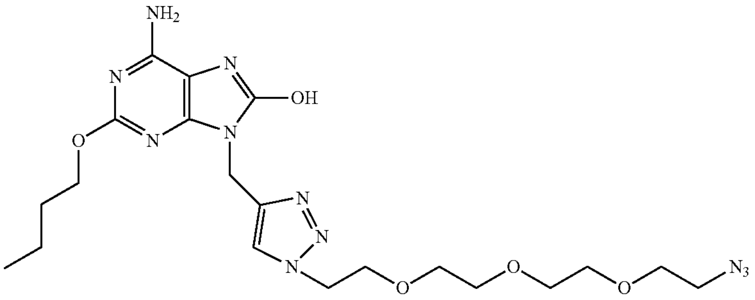 [SMILES: CCCCOc1nc(N)c2nc(O)n(Cc3cn(CCOCCOCCOCCN=[N+]=[N-])nn3)c2n1] | 505 |
| GY156 | 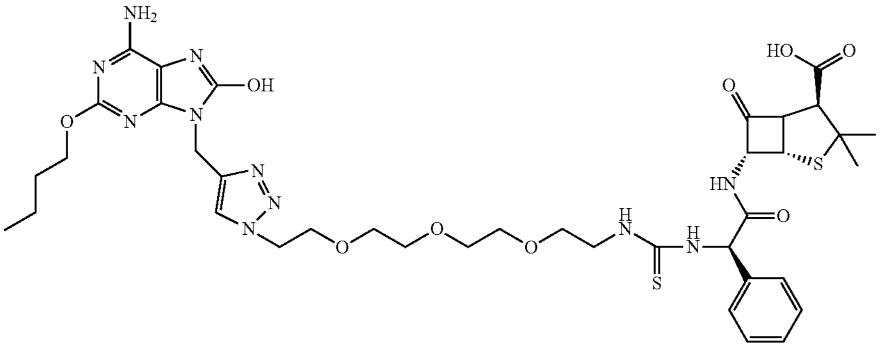 Derivative coupled with penicillin | 870 |

TABLE 1-continued
| Number | Structure | Molecular weight |
|---|---|---|
| GY157 | 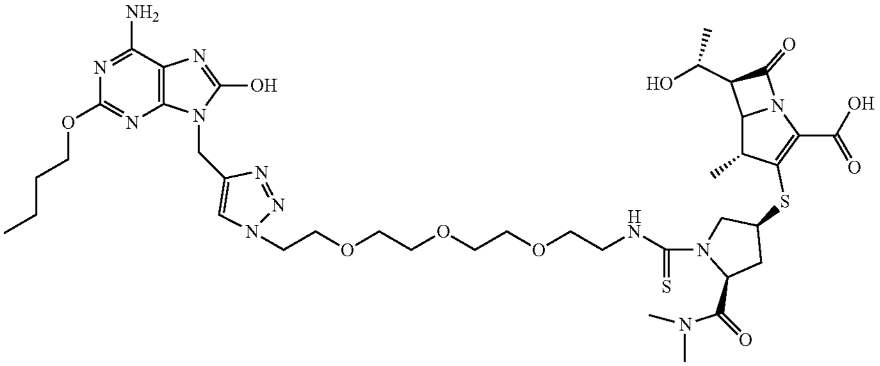 Derivative coupled with Meropenem | 904 |
| GY158 | 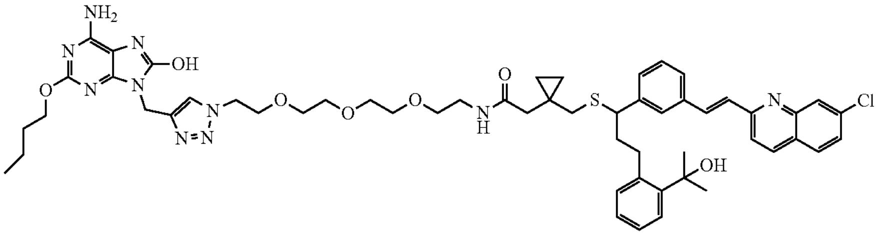 Derivative coupled with Monroust | 1047 |
| GY159 | 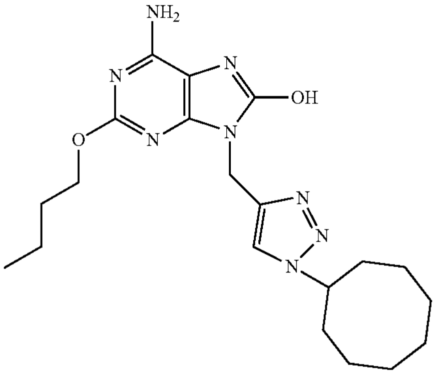 [SMILES: CCCCOc1nc(N)c2nc(O)n(Cc3cn(C4CCCCCCC4)nn3)c2n1] | 414 |
| GY160 | 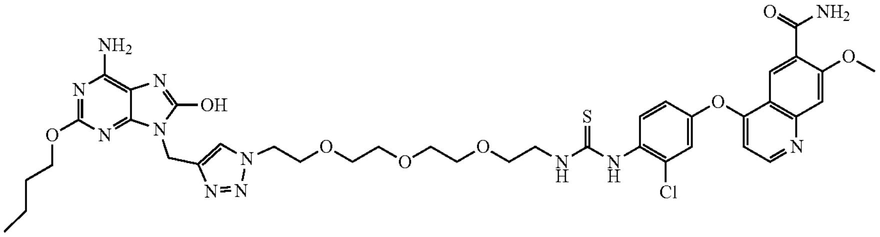 Conjugate of Lenvatinib intermediate | 864 |

TABLE 1-continued
| Number | Structure | Molecular weight |
|---|---|---|
| GY161 | 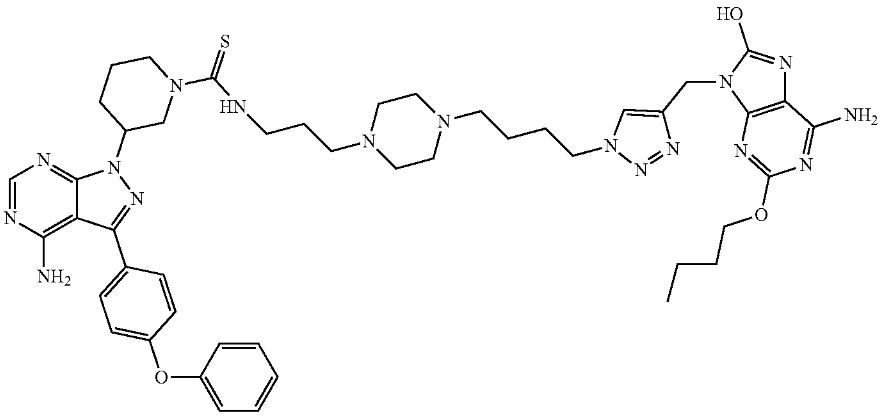 Conjugate of Ibrutinib intermediate | 930 |
| GY162 | 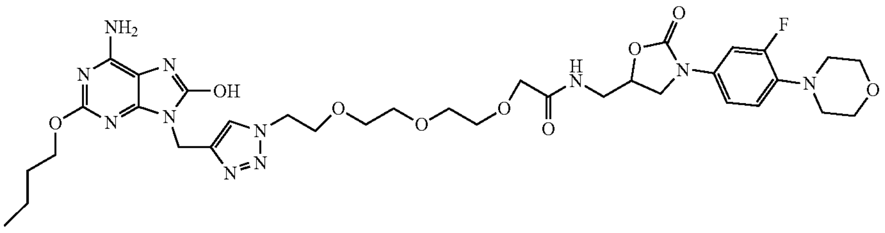 Conjugate of Linezolid intermediate | 771 |
| GY163 | 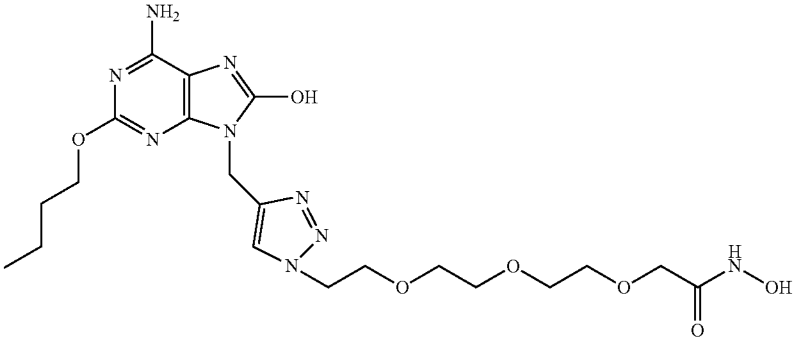 [SMILES: CCCCOc1nc(N)c2nc(O)n(Cc3cn(CCOCCOCCOCC(=O)NO)nn3)c2n1] | 509 |
| GY164 | 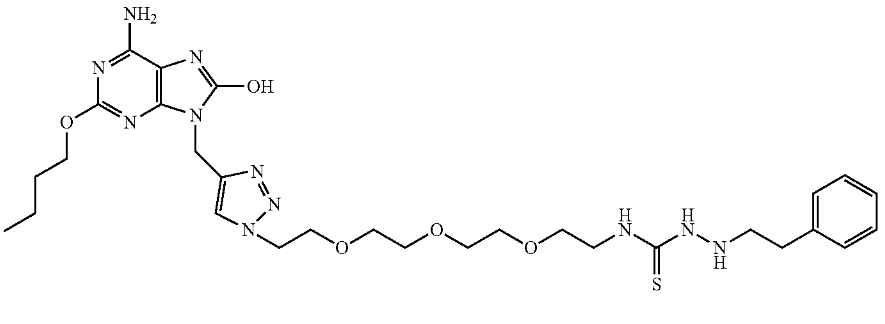 [SMILES: CCCCOc1nc(N)c2nc(O)n(Cc3cn(CCOCCOCCOCCNC(=S)NNCCc4ccccc4)nn3)c2n1] | 657 |

TABLE 1-continued
| Number | Structure | Molecular weight |
|---|---|---|
| GY165 | 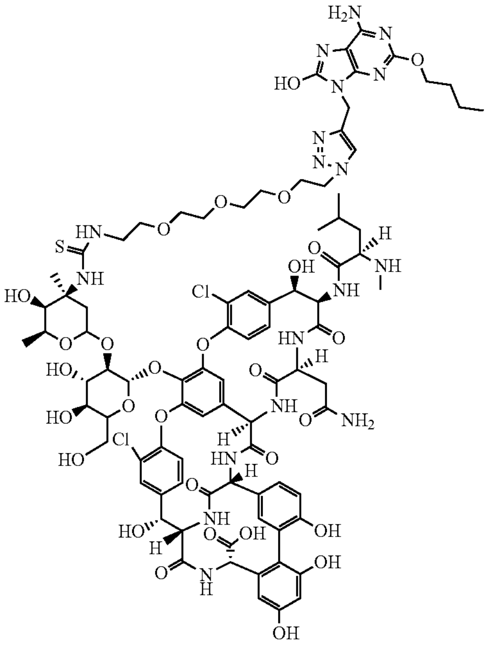 [SMILES: CCCCOc1nc(N)c2nc(O)n(Cc3cn(CCOCCOCCOCCNC(=S)N[C@@]4(C)CC(O[C@H]5[C@H](Oc6c7cc8cc6Oc6ccc(cc6Cl)[C@@H](O)[C@@H](NC(=O)[C@@H](CC(C)C)NC)C(=O)N[C@@H](CC(N)=O)C(=O)N[C@H]8C(=O)N[C@H]6C(=O)N[C@H](C(=O)N[C@H](C(=O)O)c8cc(O)cc(O)c8-c8cc6ccc8O)[C@H](O)c6ccc(c(Cl)c6)O7)OC(CO)[C@@H](O)[C@@H]5O)O[C@@H](C)[C@H]4O)nn3)c2n1] Conjugate of vancomycin | 1970 |
| GY166 | 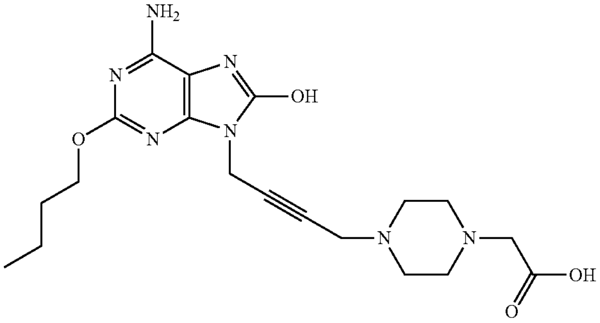 [SMILES: CCCCOc1nc(N)c2nc(O)n(CC#CCN3CCN(CC(=O)O)CC3)c2n1] | 417 |
| GY167 | 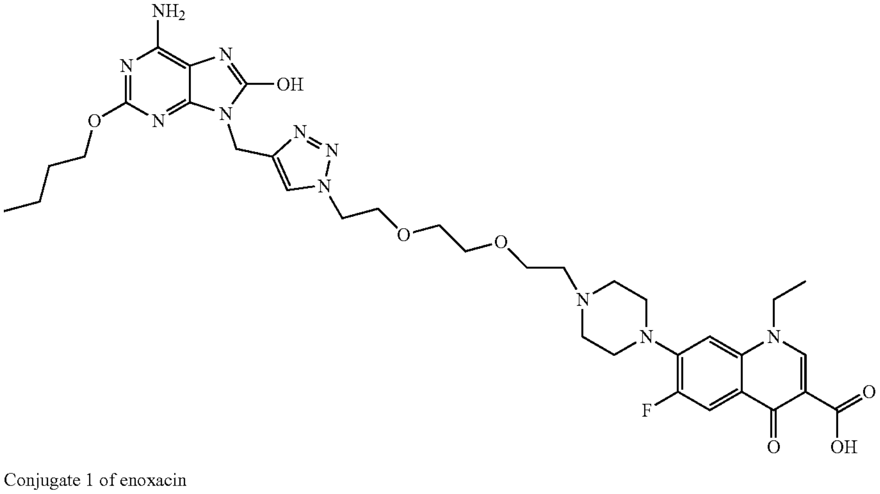 [SMILES: CCCCOc1nc(N)c2nc(O)n(Cc3cn(CCOCCOCCN4CCN(c5cc6c(cc5F)c(=O)c(C(=O)O)cn6CC)CC4)nn3)c2n1] Conjugate 1 of enoxacin | 737 |

TABLE 1-continued
| Number | Structure | Molecular weight |
|---|---|---|
| GY168 | 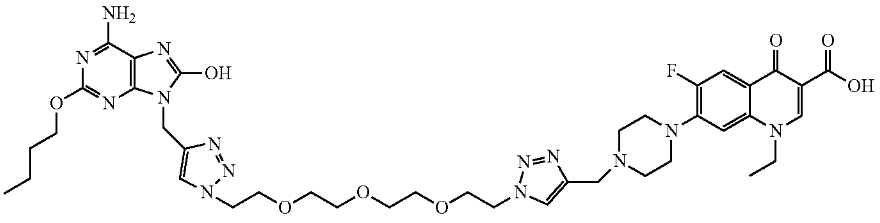 Conjugate 2 of enoxacin | 863 |
| GY169 | 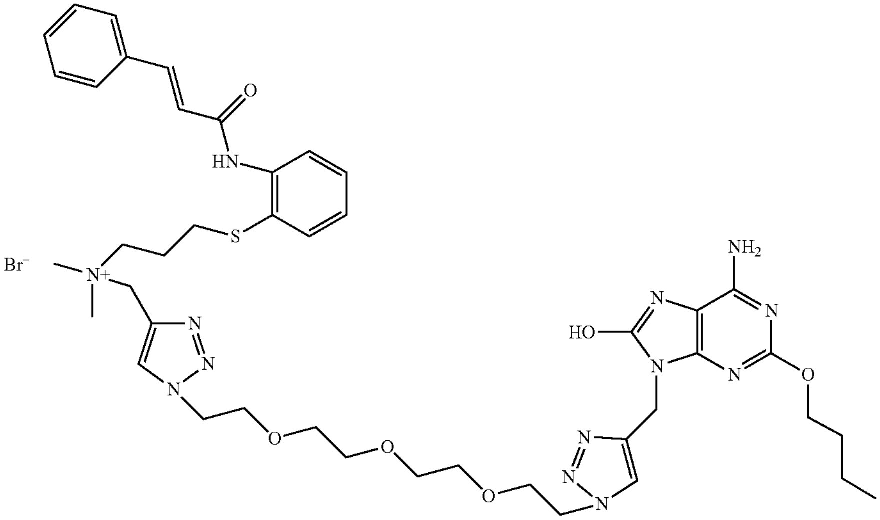 Quaternary ammonium salt product of Cinanserin | 965 |
| GY170 | 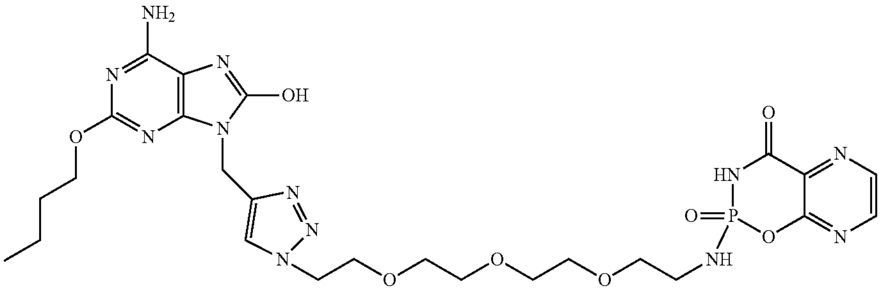 [SMILES: CCCCOc1nc(N)c2nc(O)n(Cc3cn(CCOCCOCCOCCNP4(=O)NC(=O)c5nccnc5O4)nn3)c2n1] | 662 |
| GY171 | 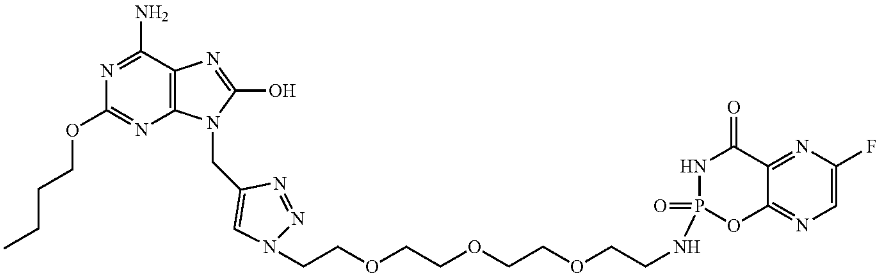 [SMILES: CCCCOc1nc(N)c2nc(O)n(Cc3cn(CCOCCOCCOCCNP4(=O)NC(=O)c5nc(F)cnc5O4)nn3)c2n1] | 681 |

TABLE 1-continued
| Number | Structure | Molecular weight |
|---|---|---|
| GY172 | 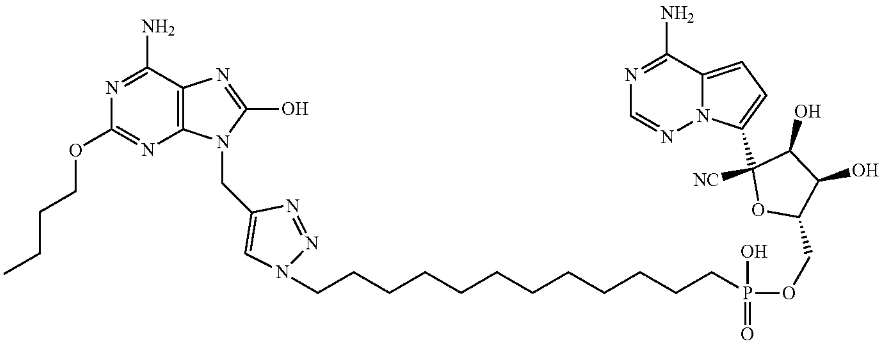 | 825 |
| GY173 | 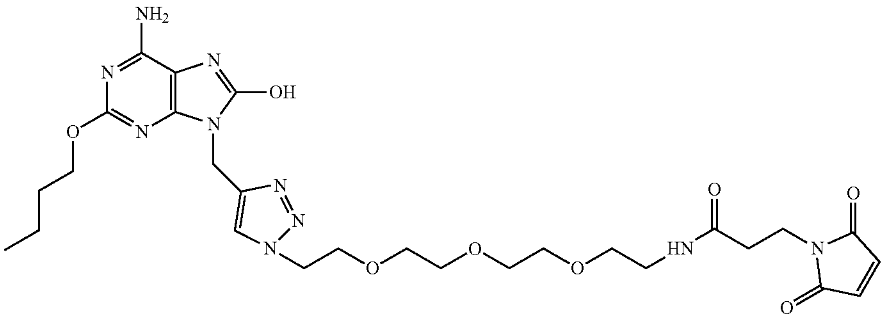 [SMILES: CCCCOc1nc(N)c2nc(O)n(Cc3cn(CCOCCOCCOCCNC(=O)CCN4C(=O)C=CC4=O)nn3)c2n1] | 630 |
| GY174 | 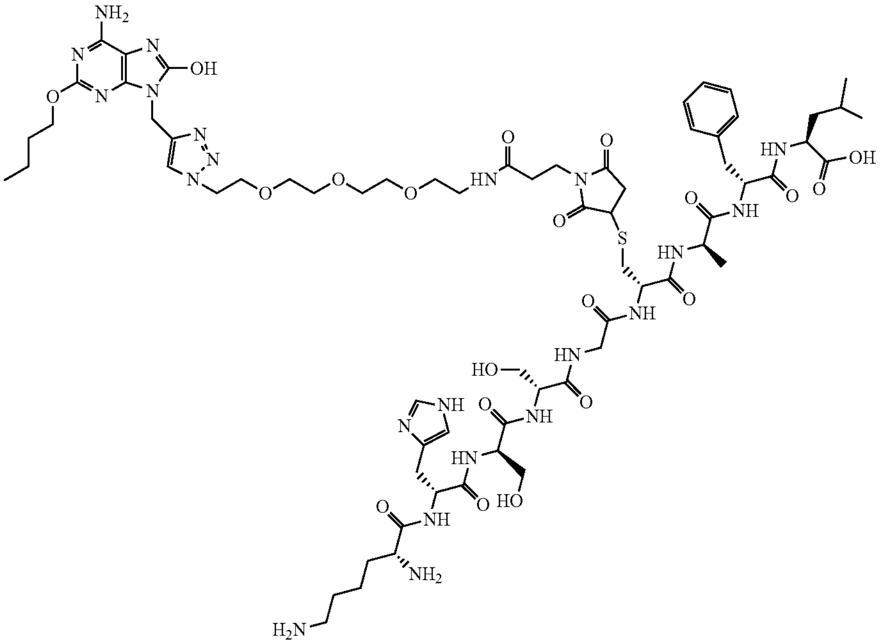 [SMILES: CCCCOc1nc(N)c2nc(O)n(Cc3cn(CCOCCOCCOCCNC(=O)CCN4C(=O)CC(SC[C@@H](NC(=O)CNC(=O)[C@@H](CO)NC(=O)[C@@H](CO)NC(=O)[C@@H](Cc5c[nH]cn5)NC(=O)[C@H](N)CCCCN)C(=O)N[C@H](C)C(=O)N[C@H](Cc5ccccc5)C(=O)N[C@@H](CC(C)C)C(=O)O)C4=O)nn3)c2n1] | 1578 |

TABLE 1-continued
| Number | Structure | Molecular weight |
|---|---|---|
| GY175 | 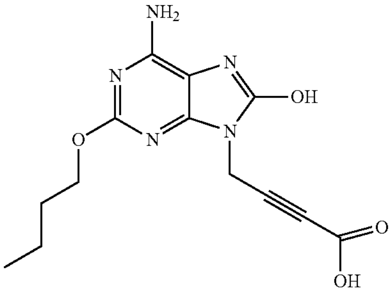 [SMILES: CCCCOc1nc(N)c2nc(O)n(CC#CC(=O)O)c2n1] | 305 |
| GY176 | 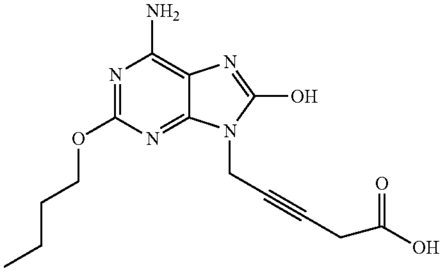 [SMILES: CCCCOc1nc(N)c2nc(O)n(CC#CCC(=O)O)c2n1] | 319 |
| GY178 | 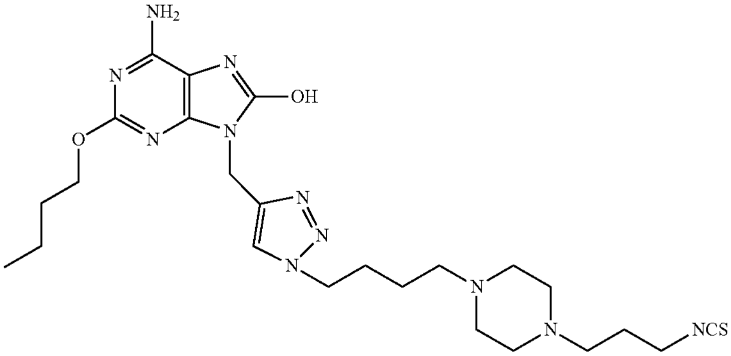 | 544 |
| GY179 | 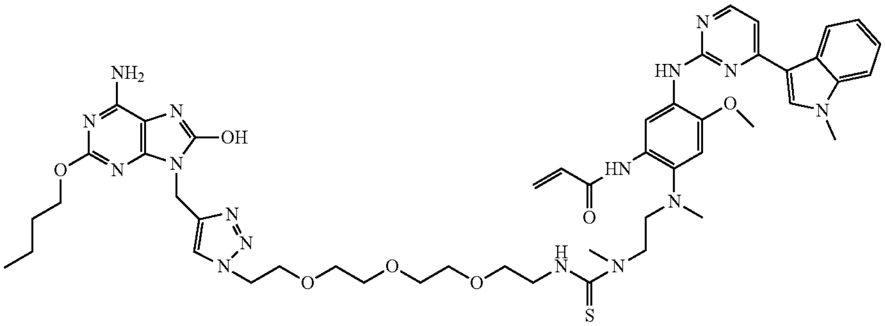 [SMILES: C=CC(=O)Nc1cc(Nc2nccc(-c3cn(C)c4ccccc34)n2)c(OC)cc1N(C)CCN(C)C(=S)NCCOCCOCCOCCn1cc(Cn2c(O)nc3c(N)nc(OCCCC)nc32)nn1] | 1006 |
| GY180 | 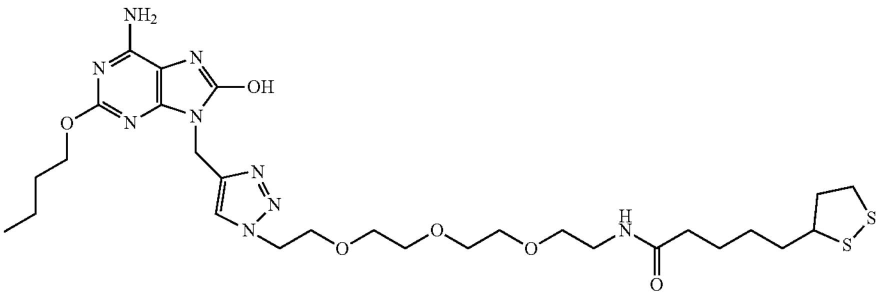 [SMILES: CCCCOc1nc(N)c2nc(O)n(Cc3cn(CCOCCOCCOCCNC(=O)CCCCC4CCSS4)nn3)c2n1] | 667 |

TABLE 1-continued
| Number | Structure | Molecular weight |
|---|---|---|
| GY181 | 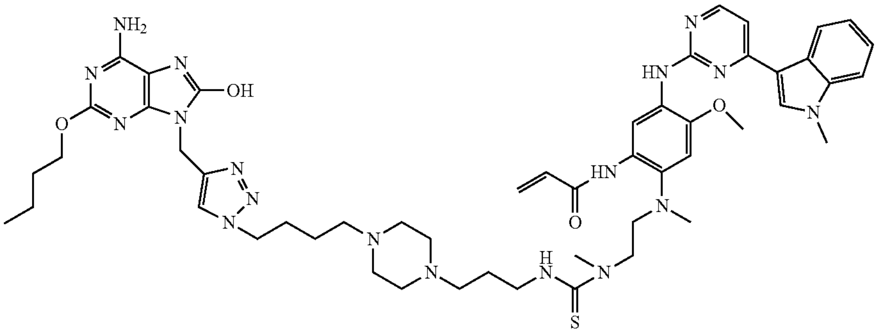 [SMILES: C=CC(=O)Nc1cc(Nc2nccc(-c3cn(C)c4ccccc34)n2)c(OC)cc1N(C)CCN(C)C(=S)NCCCN1CCN(CCCCn2cc(Cn3c(O)nc4c(N)nc(OCCCC)nc43)nn2)CC1] | 1028 |
| GY182 | 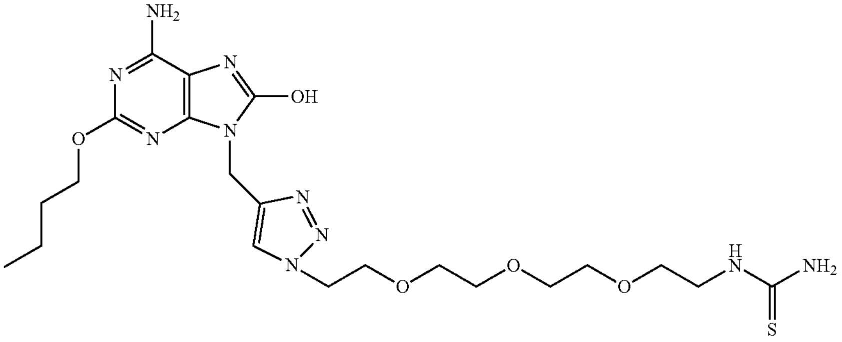 [SMILES: CCCCOc1nc(N)c2nc(O)n(Cc3cn(CCOCCOCCOCCNC(N)=S)nn3)c2n1] | 538 |
| GY183 | 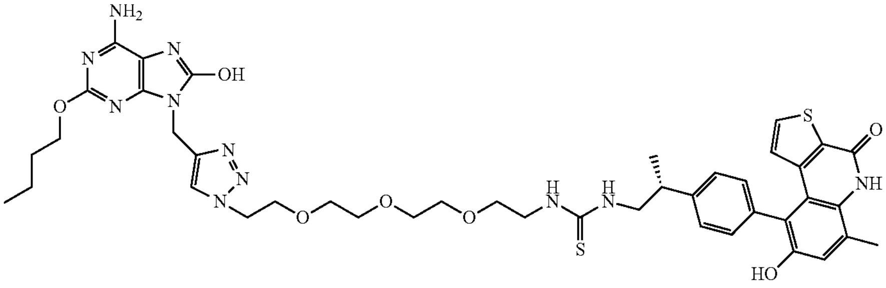 [SMILES: CCCCOc1nc(N)c2nc(O)n(Cc3cn(CCOCCOCCOCCNC(=S)NC[C@H](C)c4ccc(-c5c(O)cc(C)c6[nH]c(=O)c7sccc7c56)cc4)nn3)c2n1] | 885 |
| GY184 | 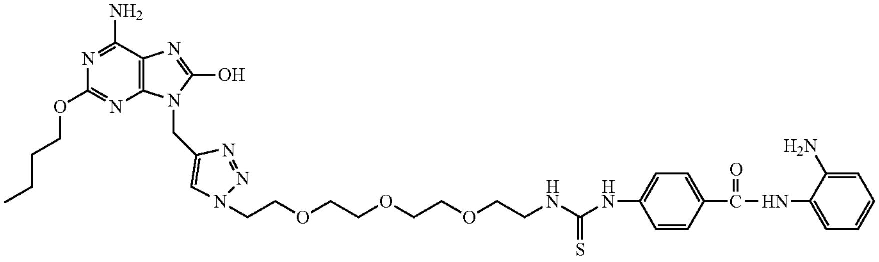 [SMILES: CCCCOc1nc(N)c2nc(O)n(Cc3cn(CCOCCOCCOCCNC(=S)Nc4ccc(C(=O)Nc5ccccc5N)cc4)nn3)c2n1] | 748 |
| GY185 | 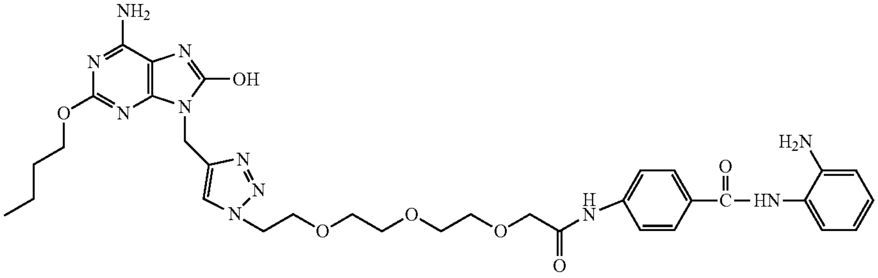 [SMILES: CCCCOc1nc(N)c2nc(O)n(Cc3cn(CCOCCOCCOCC(=O)Nc4ccc(C(=O)Nc5ccccc5N)cc4)nn3)c2n1] | 703 |

TABLE 1-continued
| Number | Structure | Molecular weight |
| --- | --- | --- |
| GY186 | 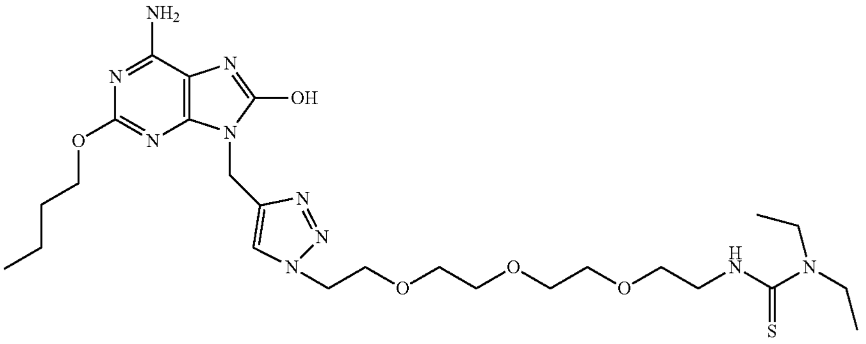 [SMILES: CCCCOc1nc(N)c2nc(O)n(Cc3cn(CCOCCOCCOCCNC(=S)N(CC)CC)nn3)c2n1] | 594 |
| GY187 | 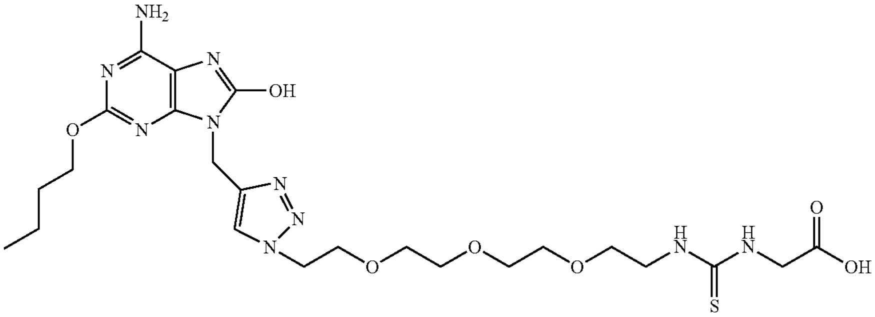 [SMILES: CCCCOc1nc(N)c2nc(O)n(Cc3cn(CCOCCOCCOCCNC(=S)NCC(=O)O)nn3)c2n1] | 596 |
| GY189 | 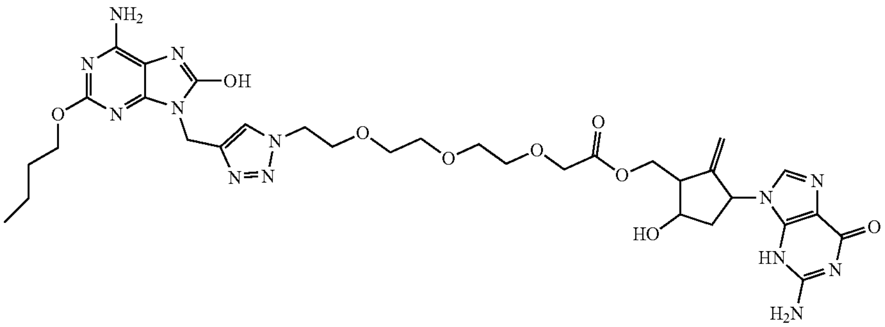 [SMILES: C=C1C(COC(=O)COCCOCCOCCn2cc(Cn3c(O)nc4c(N)nc(OCCCC)nc43)nn2)C(O)CC1n1cnc2c(=O)nc(N)[nH]c21] | 755.1 |
| GY190 | 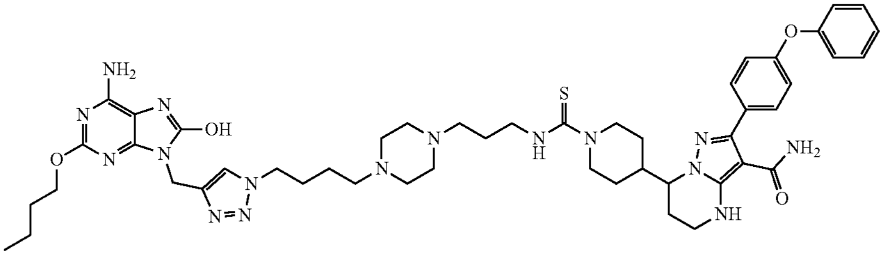 [SMILES: CCCCOc1nc(N)c2nc(O)n(Cc3cn(CCCCN4CCN(CCCNC(=S)N5CCC(C6CCNc7c(C(N)=O)c(-c8ccc(Oc9ccccc9)cc8)nn76)CC5)CC4)nn3)c2n1] | 961.2 |
| GY191 | 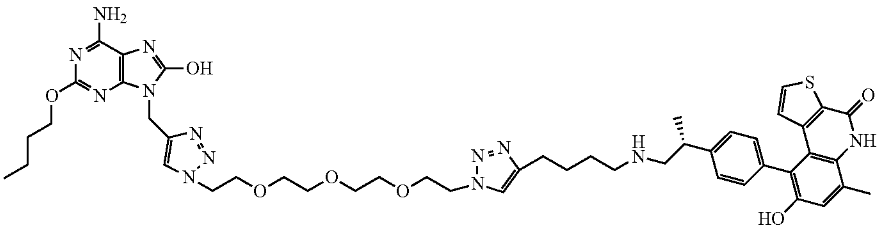 [SMILES: CCCCOc1nc(N)c2nc(O)n(Cc3cn(CCOCCOCCOCCn4cc(CCCCNC[C@H](C)c5ccc(-c6c(O)cc(C)c7[nH]c(=O)c8sccc8c67)cc5)nn4)nn3)c2n1] | 949.4 |

TABLE 1-continued
| Number | Structure | Molecular weight |
| --- | --- | --- |
| GY192 | 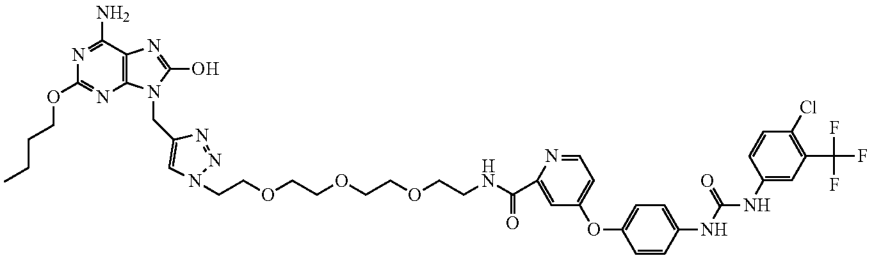 [SMILES: CCCCOc1nc(N)c2nc(O)n(Cc3cn(CCOCCOCCOCCNC(=O)c4cc(Oc5ccc(NC(=O)Nc6ccc(Cl)c(C(F)(F)F)c6)cc5)ccn4)nn3)c2n1] | 912.3 |
| GY193 | 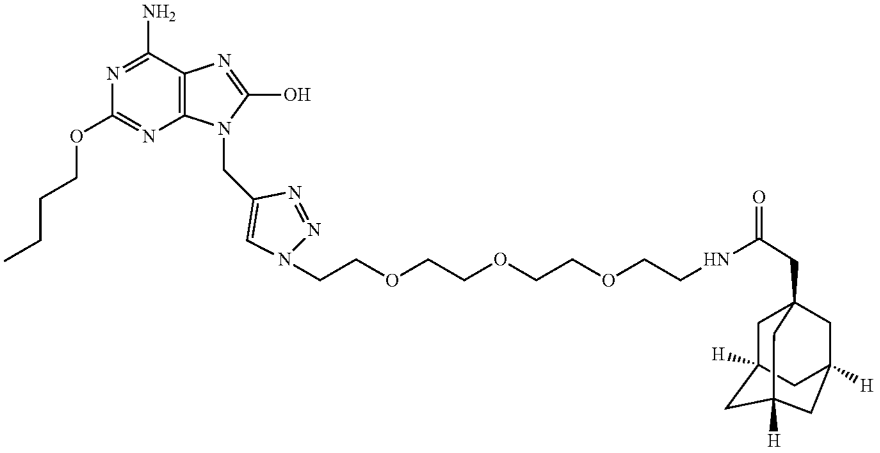 [SMILES: CCCCOc1nc(N)c2nc(O)n(Cc3cn(CCOCCOCCOCCNC(=O)C[C@]45C[C@H]6C[C@H](C[C@H](C6)C4)C5)nn3)c2n1] | 656 |
| GY196 | 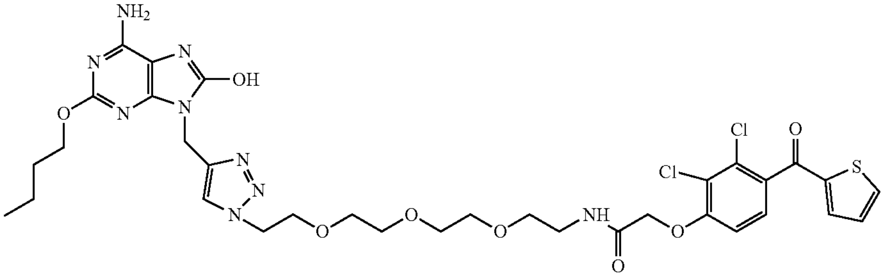 [SMILES: CCCCOc1nc(N)c2nc(O)n(Cc3cn(CCOCCOCCOCCNC(=O)COc4ccc(C(=O)c5cccs5)c(Cl)c4Cl)nn3)c2n1] | 792.7 |
| GY197 | 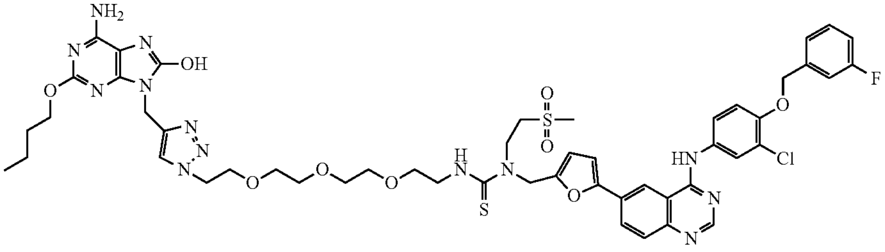 [SMILES: CCCCOc1nc(N)c2nc(O)n(Cc3cn(CCOCCOCCOCCNC(=S)N(CCS(C)(=O)=O)Cc4ccc(-c5ccc6ncnc(Nc7ccc(OCc8cccc(F)c8)c(Cl)c7)c6c5)o4)nn3)c2n1] | 1102.6 |

TABLE 1-continued
| Number | Structure | Molecular weight |
|---|---|---|
| GY198 | 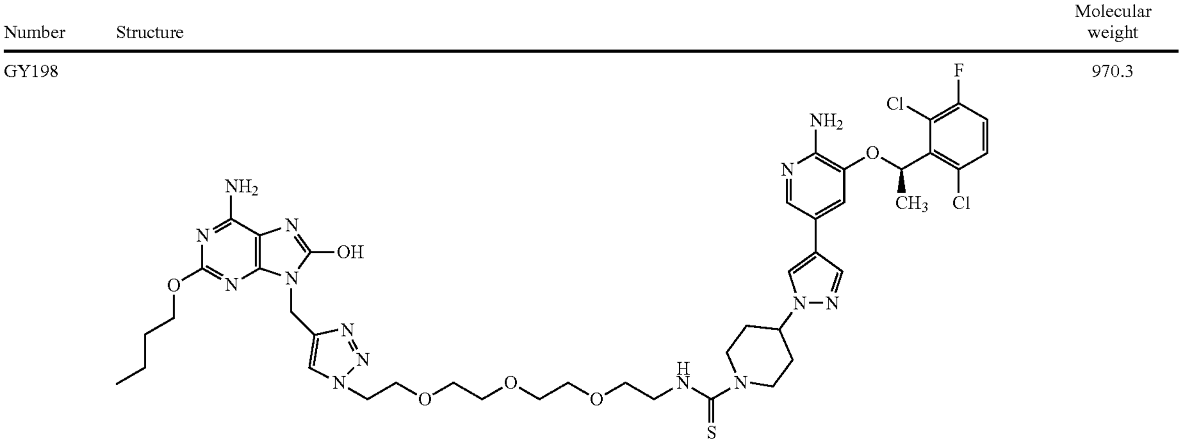 | 970.3 |
| GY199 | 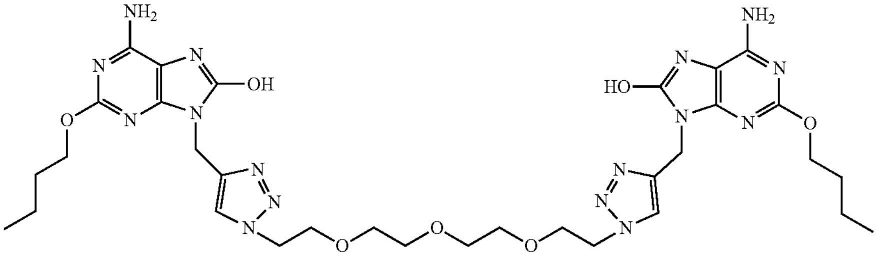 [SMILES: CCCCOc1nc(N)c2nc(O)n(Cc3cn(CCOCCOCCOCCn4cc(Cn5c(O)nc6c(N)nc(OCCCC)nc65)nn4)nn3)c2n1] | 766.8 |
| GY200 | 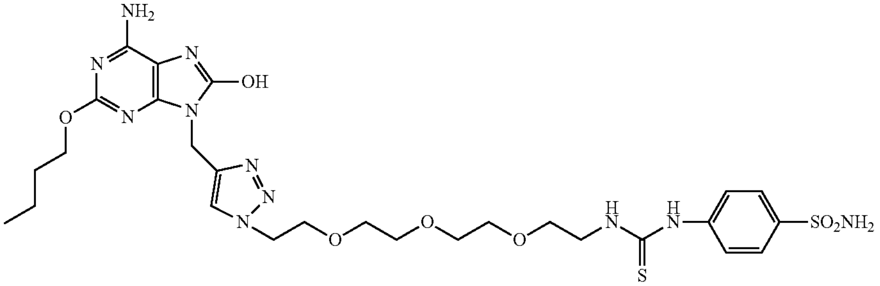 [SMILES: CCCCOc1nc(N)c2nc(O)n(Cc3cn(CCOCCOCCOCCNC(=S)Nc4ccc(S(N)(=O)=O)cc4)nn3)c2n1] | 693.2 |
| GY201 | 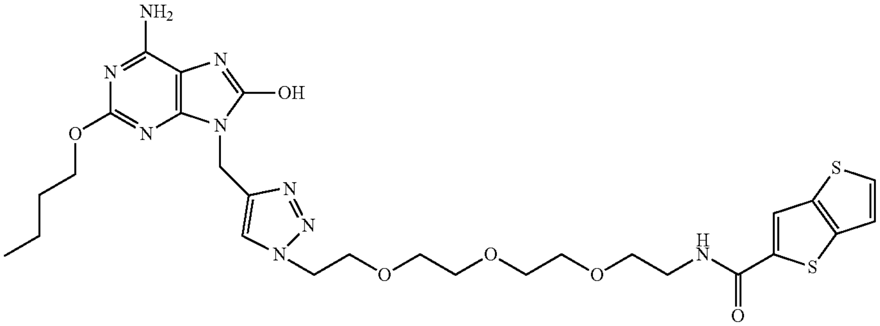 [SMILES: CCCCOc1nc(N)c2nc(O)n(Cc3cn(CCOCCOCCOCCNC(=O)c4cc5sccc5s4)nn3)c2n1] | 645.7 |
| GY202 | 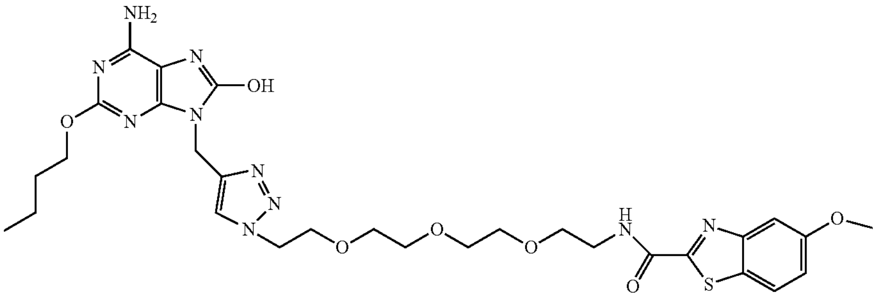 [SMILES: CCCCOc1nc(N)c2nc(O)n(Cc3cn(CCOCCOCCOCCNC(=O)c4nc5cc(OC)ccc5s4)nn3)c2n1] | 670.7 |

TABLE 1-continued

| Number | Structure | Molecular weight |
|---|---|---|
| GY203 | 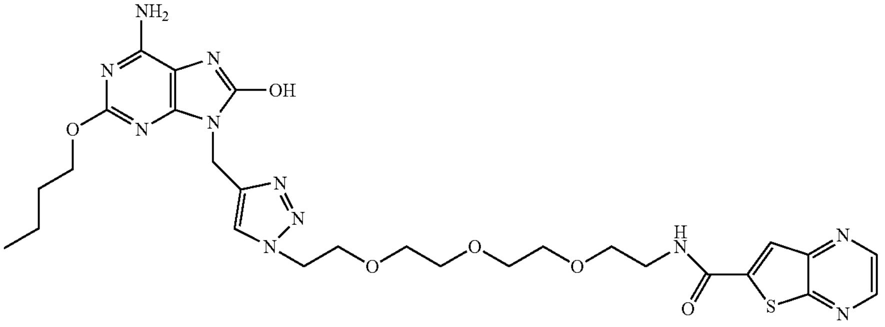 [SMILES: CCCCOc1nc(N)c2nc(O)n(Cc3cn(CCOCCOCCOCCNC(=O)c4cc5nccnc5s4)nn3)c2n1] | 641.7 |

Among them, $R_2$ corresponds to a precursor of AZD9291 (Osimertinib) in GY104; $R_2$ corresponds to lenalidomide in GY110; $R_2$ corresponds to GSK1324726A in GY111; $R_2$ corresponds to of represents Ibrutinib GY112; $R_2$ corresponds to of represents sulfasalazine GY113; $R_2$ corresponds to represents Lenvatinib GY114; $R_2$ corresponds to represents piperlongumine GY117; $R_2$ corresponds to JQ1 in both GY118 and GY119; $R_2$ corresponds to glutathione in GY126; $R_2$ corresponds to a precursor of AZD9291 (Osimertinib) in GY127; and $R_2$ corresponds to an intermediate or a precursor of Zanubrutinib in GY132.

The compounds as listed in Table 1 are specific compounds representing Formula I, it should be noted that compounds satisfying Formula I are not limited to those listed in Table 1.

Preparation Examples

The synthesis scheme of the compound provided by embodiments of the present application is as follows:

HPLC Conditions

- Mobile phase: 45% acetonitrile and 55% water (1% formic acid), isocratic elution, flow rate 5 mL/min;
- Ultraviolet: 254 nm;
- Instrument model: Agilent 1260 infinity I; and
- Column model: YMC-Pack ODS-A, 250×20 mm, S-5 μm.12 nm.
- LC-MS conditions:
- Mobile phase:

| Time (min) | Concentration of acetonitrile (%) | Water (1‰ formic acid) (%) | Flow rate (mL/min) |
|---|---|---|---|
| 0 | 5 | 95 | 0.5 |
| 5 | 90 | 10 | 0.5 |
| 7 | 90 | 10 | 0.5 |
| 10 | 5 | 5 | 0.5 |
| 12 | 5 | 5 | 0.5 |

- Ultraviolet: 254 nm
- Material identification mass spectrometer model: Angilent
- Liquid phase: Angilent 1260 infinity I;
- Mass spectrum: Angilent G6125B;
- Column model: YMC-Pack ODS-A, 150×4.6 mm, S-5 μm.12 nm; and
- Antibody and peptide detection instrument model: XevoG2XSQTOF mass spectrometer, manufactured by Waters Company.

Preparation of Compounds

GY100

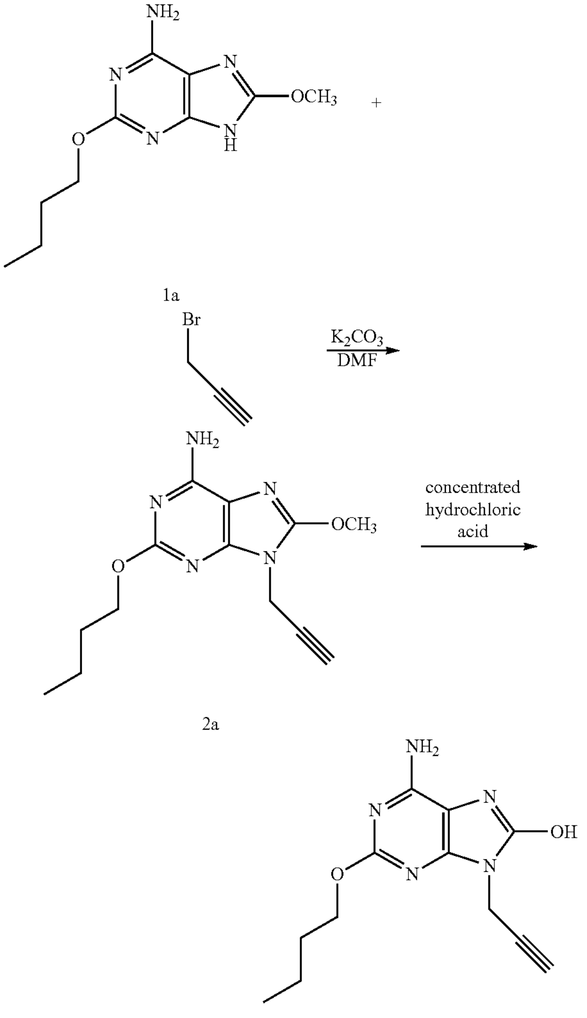

1a

2a

GY100

1 g of compound 1a, 552 mg of bromopropyne, and 1.75 g of $K_2CO_3$ were dissolved in 10 mL of anhydrous dimethylformamide (DMF) and reacted overnight at room temperature. The reaction was monitored by a liquid chromatography mass spectrometry (LC-MS). When the reaction was completed, a resulting reaction solution was added into water to separate out a precipitate. The precipitate was filtered and dried to obtain a crude product B, and the crude product B was then directly performed with a next reaction.

800 mg of compound 2a was added with 5 mL of a concentrated hydrochloric acid, stirred at room temperature for 3 hrs for reaction. After the reaction was completed, a pH value was adjusted to about 4 with 2M NaOH, a solid was precipitated, and performed with suction filtration, and dried. After being purified by HPLC, 630 mg of compound GY100 was obtained in the form of a white solid with a yield of 57.3 wt. %. ESI-MS: m/z=262.1 $[M+H]^+$.

The compound GY100 is a starting material for the synthesis of the compound represented by Formula I. Experiments have confirmed that GY100 is a highly active TLR7 agonist. Taken GY100 being a starting material as an example, the reaction formula (Reaction formula 1) for synthesizing the typical compound represented by Formula I is as follows, in which, $N_3$ in $N_3$-L-$R_2$ represents an azide group, L and $R_2$ represent the same meaning as defined in Formula I.

Reaction Formula 1

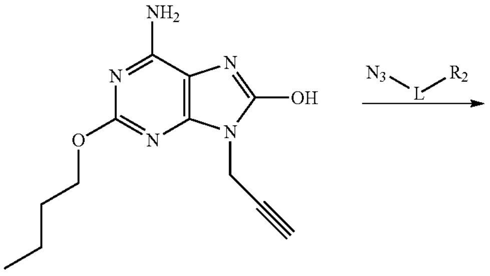

GY100

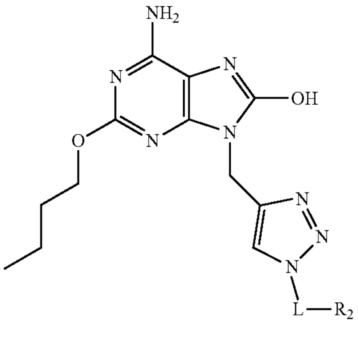

GY101

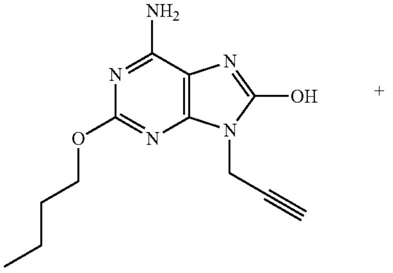

GY100

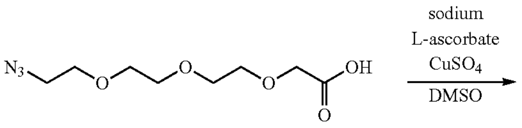

3a

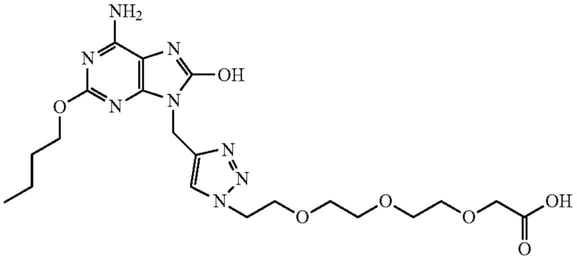

GY101

100 mg of compound GY100, 98 mg of compound 3a, 8 mg of sodium L-ascorbate, and 8 mg of $CuSO_4$ were dissolved in 100 µL of water+400 µL of DMSO, and reacted at room temperature for 5 hrs. The reaction was monitored by an LC-MS. When the reaction was completed, a resulting reaction product was purified by a high performance liquid chromatography (HPLC), and 97 mg of compound GY101 in the form of a white solid having a yield of 51.4 wt. % was obtained. ESI-MS: m/z=495.1 $[M+H]^+$.

GY102

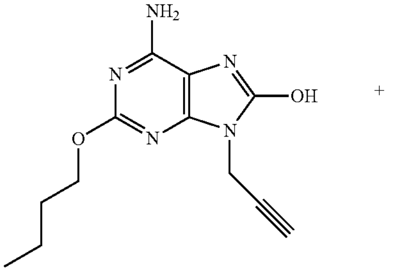

GY100

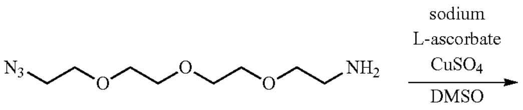

4a

-continued

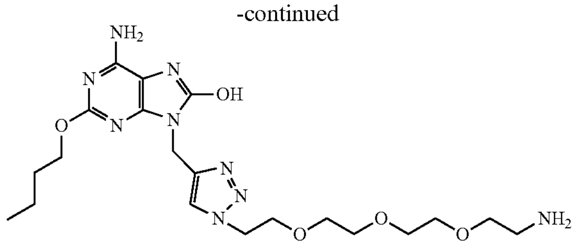

GY102

100 mg of compound GY100, 91.5 mg of compound 4a, 8 mg of sodium L-ascorbate, and 8 mg of $CuSO_4$ were dissolved in 100 μL of water+400 μL of DMSO, and reacted at room temperature for 5 hrs. The reaction was monitored by an LC-MS. When the reaction was completed, a resulting reaction product was purified by an HPLC, and 110 mg of compound GY102 in the form of a light yellow oily liquid having a yield of 60.1 wt. % was obtained. ESI-MS: m/z=480.1 $[M+H]^+$.

GY103

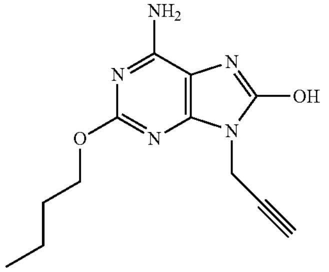

GY100

+

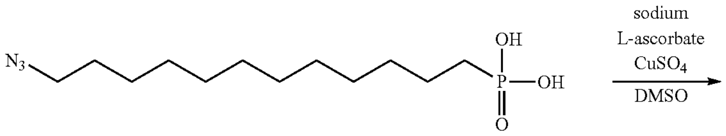

5a

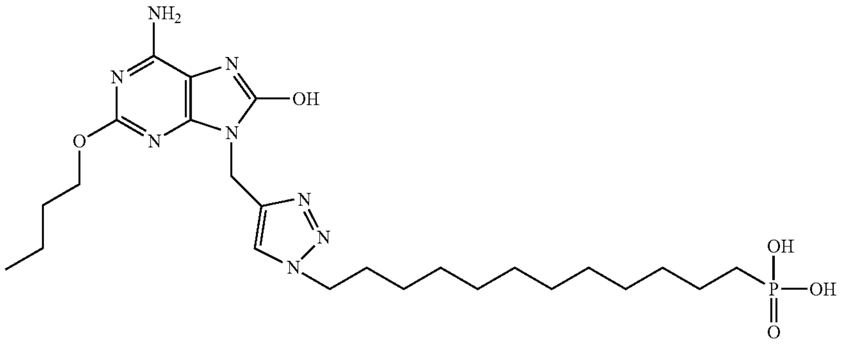

GY103

100 mg of compound GY100, 122 mg of compound 5a, 8 mg of sodium L-ascorbate, and 8 mg of $CuSO_4$ were dissolved in 100 μL of water+400 μL of DMSO, and reacted at room temperature for 5 hrs. The reaction was monitored by an LC-MS. When the reaction was completed, a resulting reaction product was purified by an HPLC, and 65 mg of compound GY103 in the form of a white solid having a yield of 30.8 wt. % was obtained. ESI-MS: m/z=553.2 $[M+H]^+$.

GY104

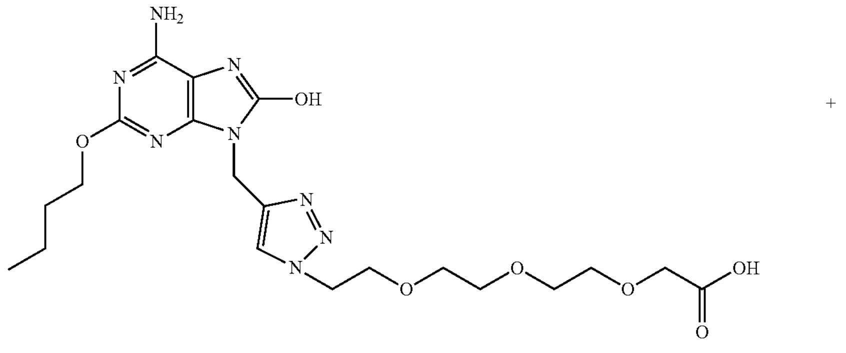

GY101

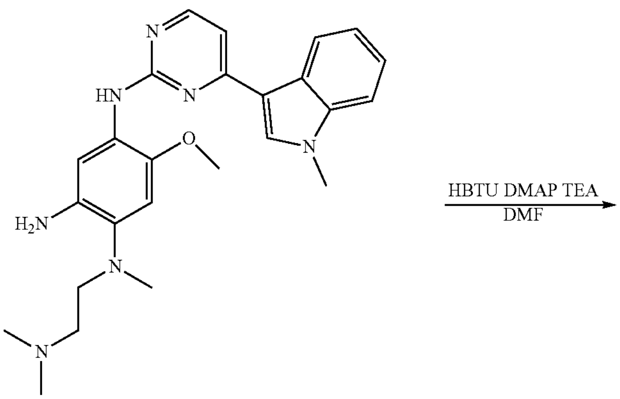

6a

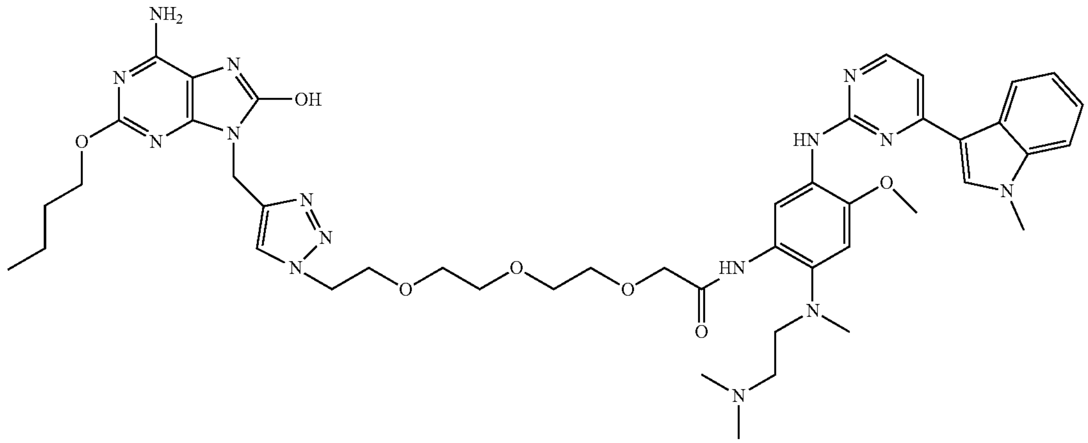

GY104

50 mg of compound GY101, 49.5 mg of compound 6a, 46 mg of HBTU, a small amount of DMAP, and 42.5 μL of TEA were dissolved in 500 μL of DMF, and reacted overnight at room temperature. The reaction was monitored by an LC-MS. When the reaction was completed, a resulting reaction product was purified by an HPLC, and 15.5 mg of compound GY104 in the form of a yellow solid having a yield of 16.7 wt. % was obtained. ESI-MS: m/z=923.1 $[M+H]^+$.

GY105

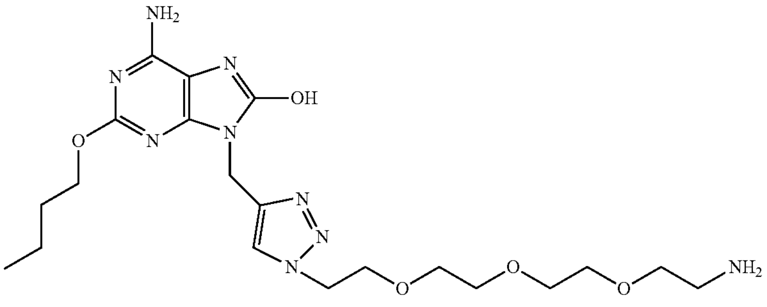

GY102

+

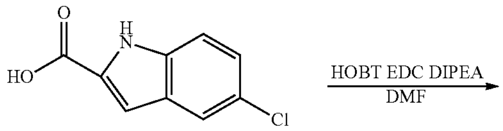

7a

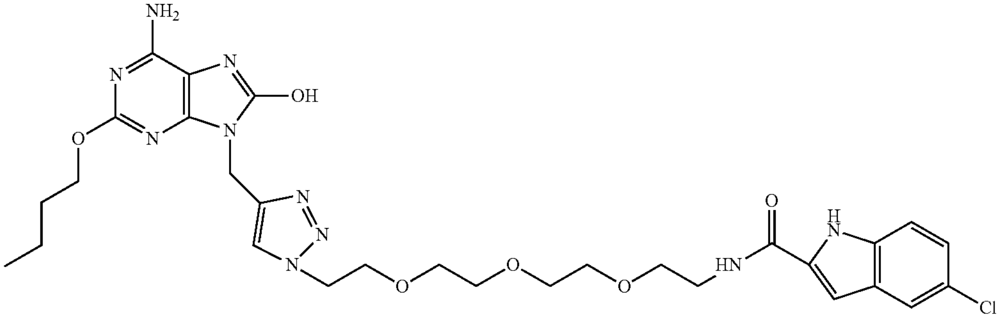

GY105

50 mg of compound GY102, 22.5 mg of compound 7a, 21.5 mg of HOBT, 31 mg of EDC, and 52.5 μL of DIPEA were dissolved in 500 μL of DMF, and reacted overnight at room temperature. The reaction was monitored by an LC-MS. When the reaction was completed, a resulting reaction product was purified by an HPLC, and 15 mg of compound GY105 in the form of a white solid having a yield of 21.9 wt. % was obtained. ESI-MS: m/z=657.1 $[M+H]^+$.

GY106

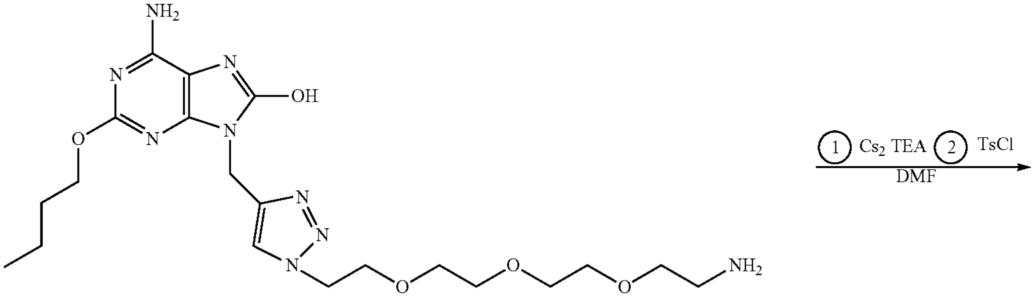

GY102

-continued

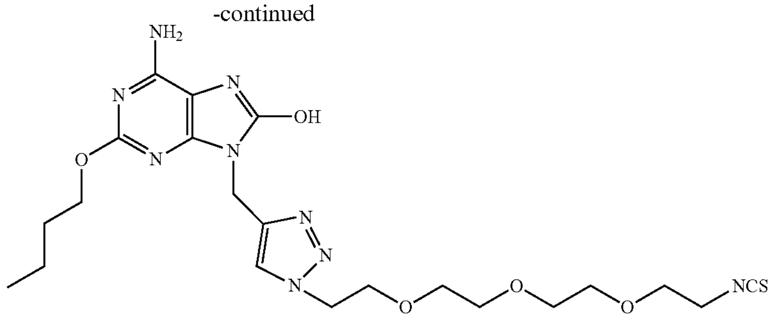

GY106

200 mg of compound GY102, 95.2 mg $CS_2$, and 174 μL of TEA were dissolved in 1 mL of DMF, and reacted overnight at room temperature. A resulting mixture was added with 87.2 mg TsCl, and reacted at room temperature for 5 hrs. The reaction was monitored by an LC-MS. When the reaction was completed, a resulting reaction product was purified by an HPLC, such that 96 mg of compound GY106 in the form of a white solid having a yield of 44 wt. % was obtained. ESI-MS: m/z=522.1 $[M+H]^+$.

GY107

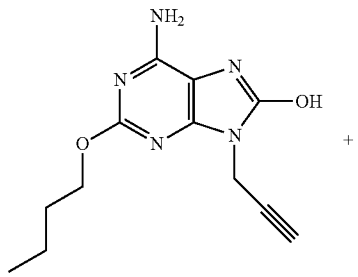

GY106

+

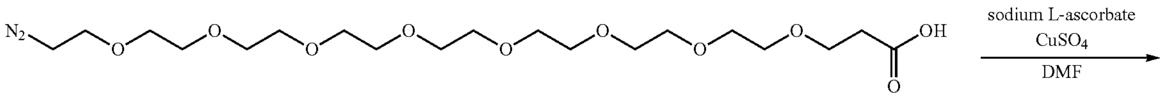

8a

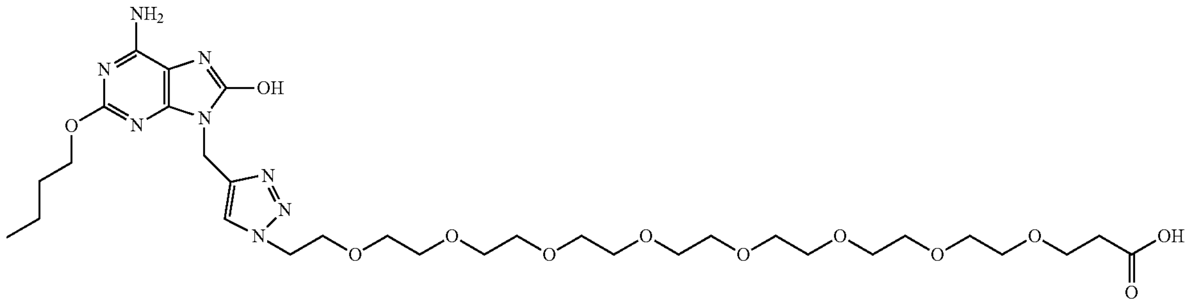

GY107

20 mg of compound GY100, 40 mg of compound 8a, 4 mg of sodium L-ascorbate, and 4 mg of $CuSO_4$ were dissolved in 100 μL of water+400 μL of DMSO, and reacted at room temperature for 5 hrs. The reaction was monitored by an LC-MS. When the reaction was completed, a resulting reaction production was purified by an HPLC, such that 20.9 mg of compound GY107 in the form of a white solid having a yield of 37.7 wt. % was obtained. ESI-MS: m/z=729.2 $[M+H]^+$.

GY108

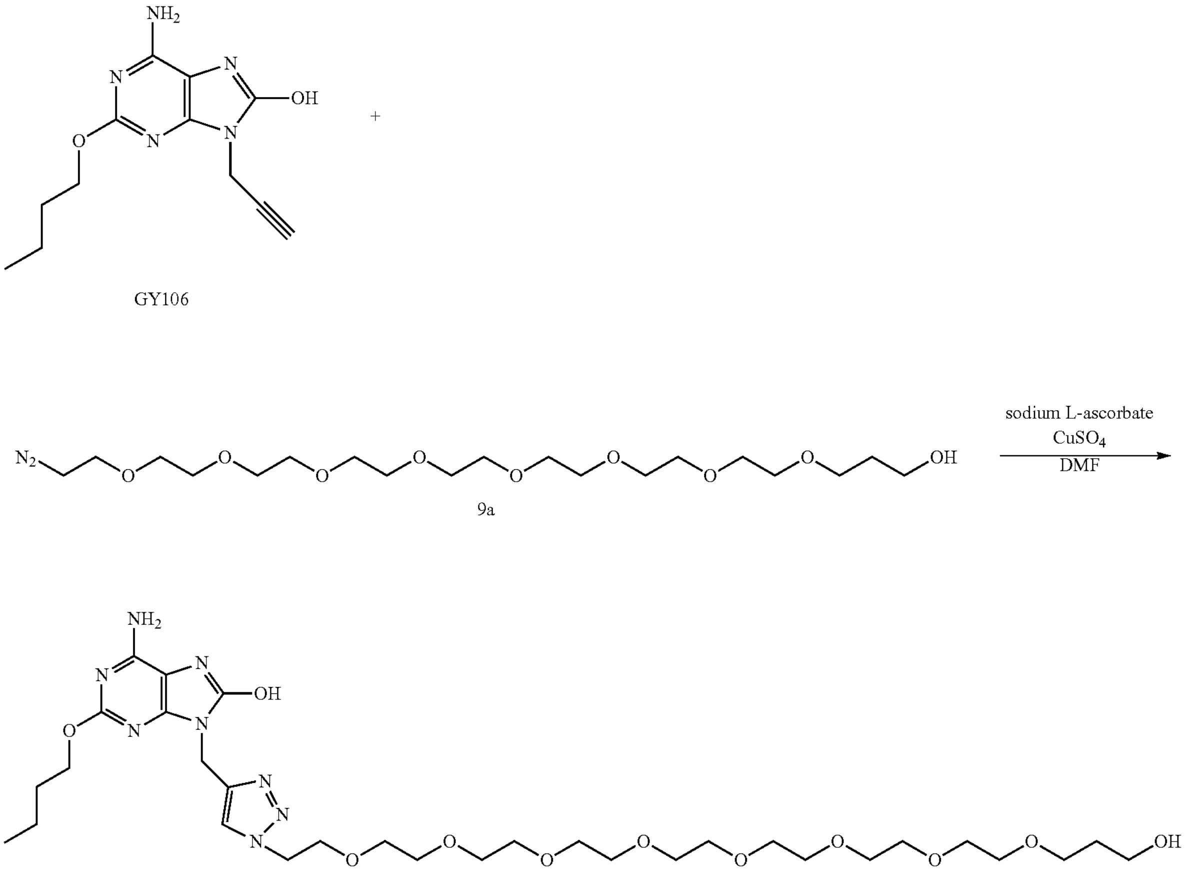

GY106

9a

GY108

20 mg of compound GY100, 33 mg of compound 9a, 4 mg of sodium L-ascorbate, and 4 mg of $CuSO_4$ were dissolved in 100 μL of water+400 μL of DMSO, and reacted at room temperature for 5 hrs. The reaction was monitored by an LC-MS. When the reaction was completed, a resulting reaction product was purified by an HPLC, such that 18.4 mg of compound GY108 in the form of a white solid having a yield of 36.8 wt. % was obtained. ESI-MS: m/z=657.2 $[M+H]^+$.

GY109

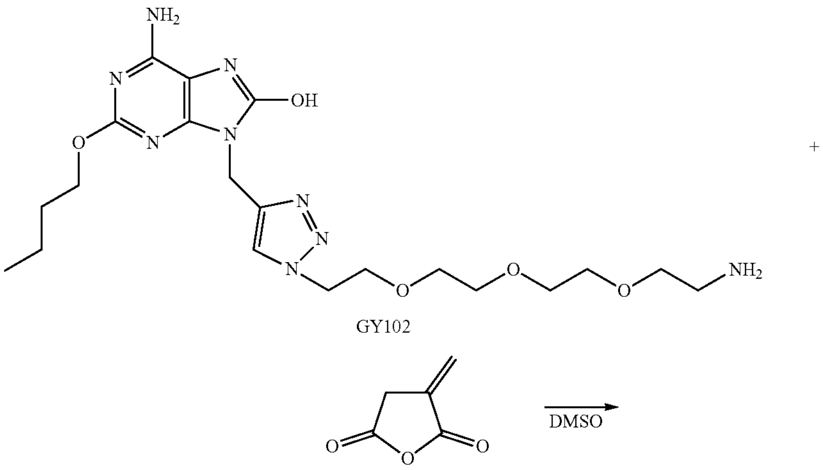

GY102

-continued
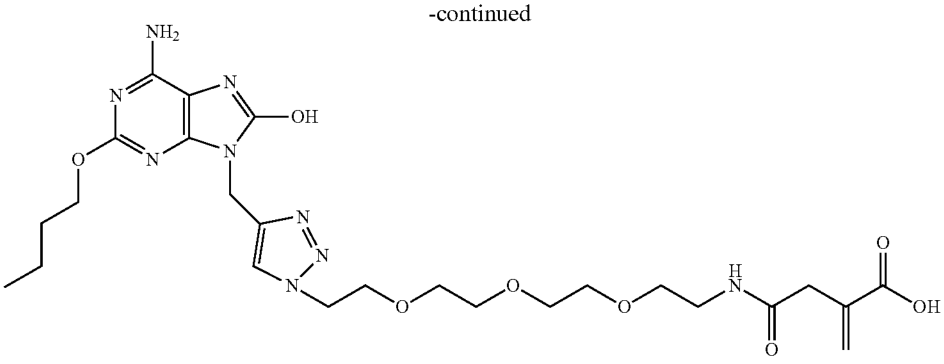
GY109
128.5 mg of compound GY102 and 30 mg of itaconic anhydride were dissolved in 500 μL of DMSO, and reacted at room temperature for 6 hrs. The reaction was monitored by an LC-MS. When the reaction was completed, a resulting reaction product was purified by an HPLC, such that 97 mg of compound GY109 in the form of a white solid having a yield of 61.4 wt. % was obtained. ESI-MS: m/z=592.1 $[M+H]^+$.
GY110
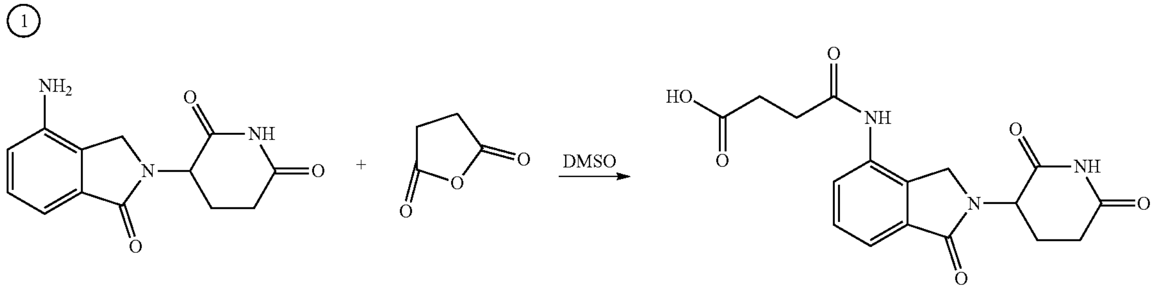
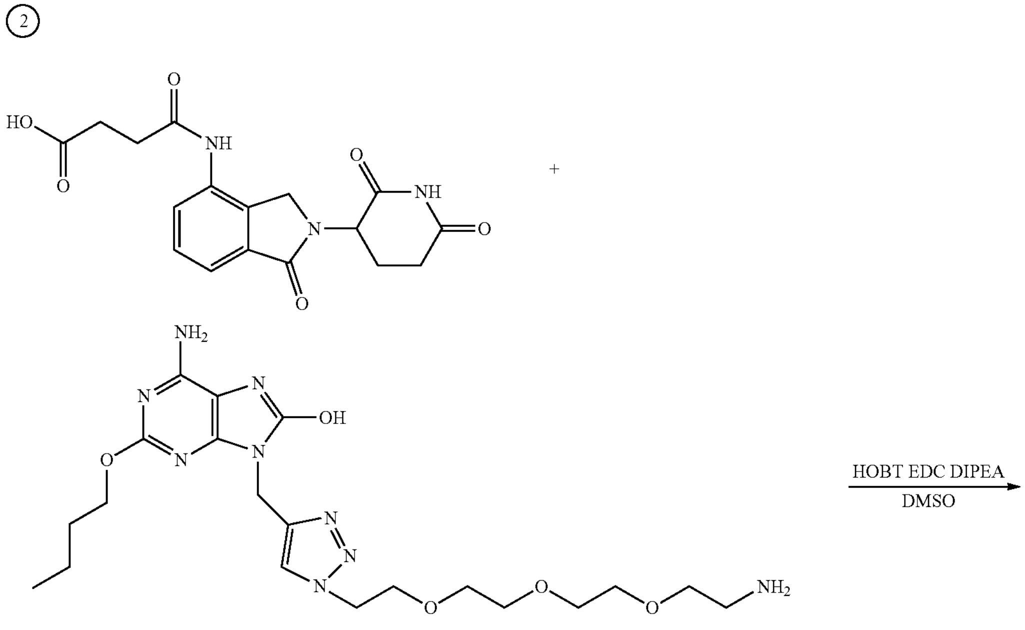
GY102

-continued

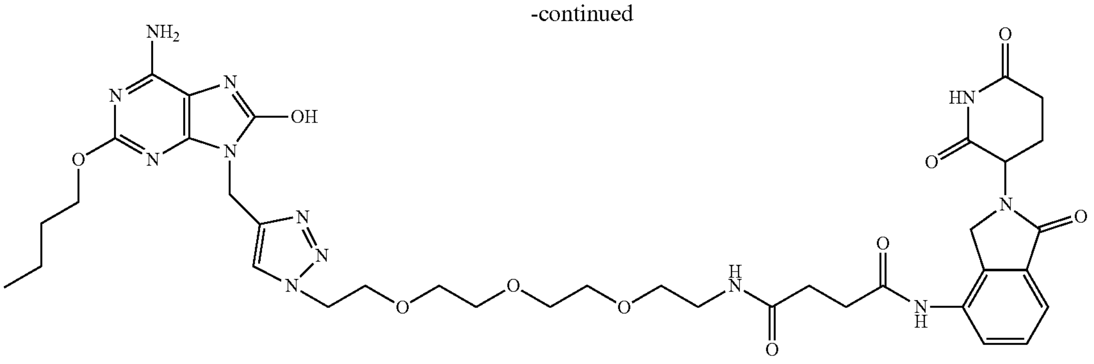

GY110

30 mg of lenalidomide and 12.7 mg of succinic anhydride were dissolved in 500 μL of DMSO, and reacted overnight at room temperature. The reaction was monitored by an LC-MS. When the reaction was completed, a next step reaction was directly performed.

49.8 mg of compound GY102, 17 mg of HOBT, 24.6 mg of HEDC, and 21 μL of DIPEA were dissolved in a reaction solution from the last reaction, stirred at room temperature for 7 hrs, and the reaction was monitored by the LC-MS. When the reaction was completed, a resulting reaction product was purified by an HPLC, such that 11.2 mg of compound GY110 in the form of a white solid having a yield of 11.8 wt. % was obtained. ESI-MS: m/z=821.1 $[M+H]^+$.

GY111

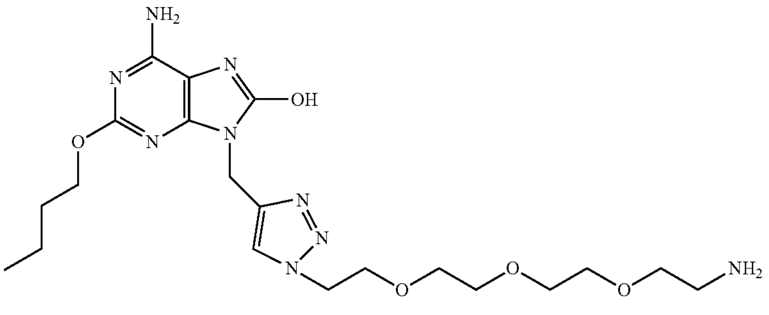

GY102

+

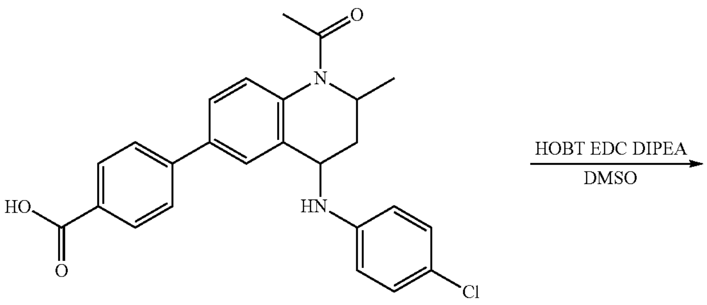

10a

-continued

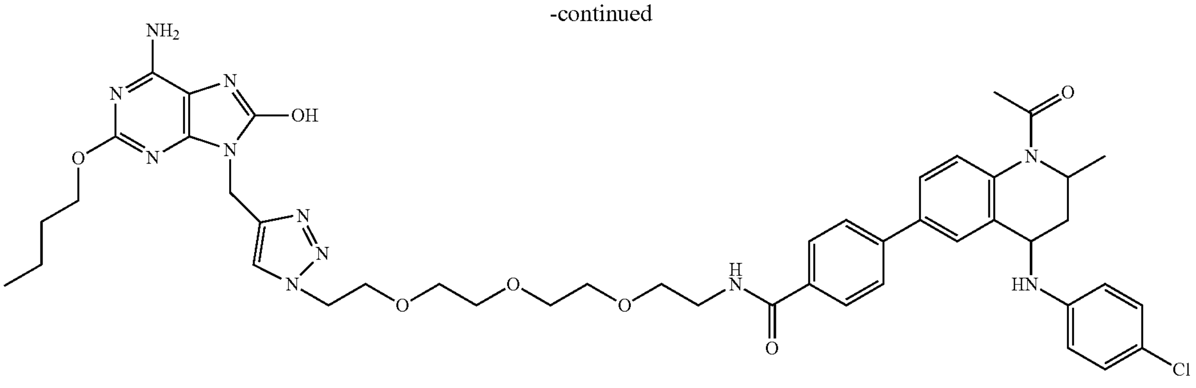

GY111

20 mg of compound GY102, 17 mg of compound 10a, 8 mg of HOBT, 12 mg of EDC, and 10 μL of DIPEA were dissolved in 300 μL of DMSO, and reacted overnight at room temperature. The reaction was monitored by an LC-MS. When the reaction was completed, a resulting reaction product was purified by an HPLC, and 8.2 mg of compound GY111 in the form of a white solid having a yield of 21.9 wt. % was obtained. ESI-MS: m/z=896.1 $[M+H]^+$.

GY112

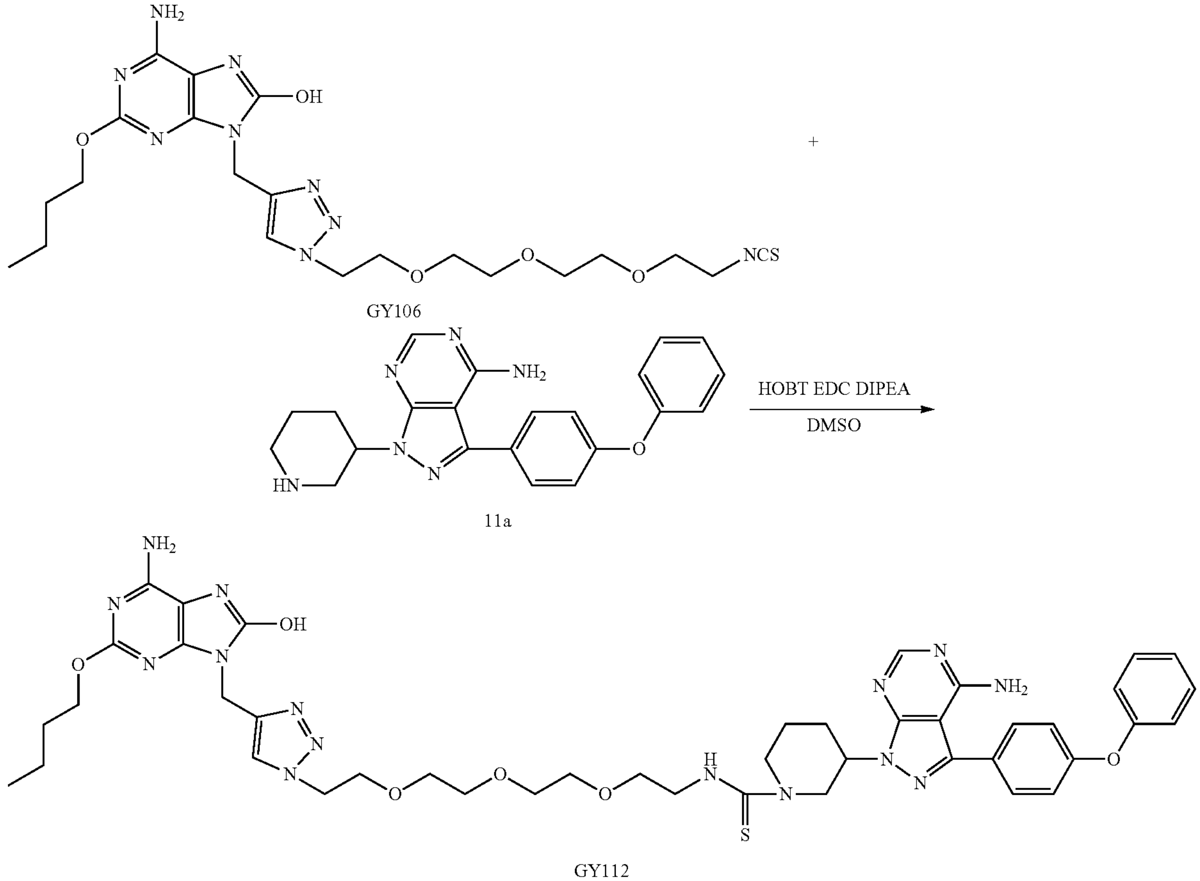

GY106

11a

GY112

25 mg of a compound GY106, 20 mg of compound 11a (intermediate of Ibrutinib in an R-configuration), and 19 μL of TEA were dissolved in 500 μL of DMSO, and reacted overnight at room temperature. The reaction was monitored by an LC-MS. When the reaction was completed, a resulting reaction product was purified by an HPLC, such that 20 mg of compound GY112 in the form of a white solid having a yield of 46 wt. % was obtained. ESI-MS: m/z=909.1 $[M+H]^+$.

GY113

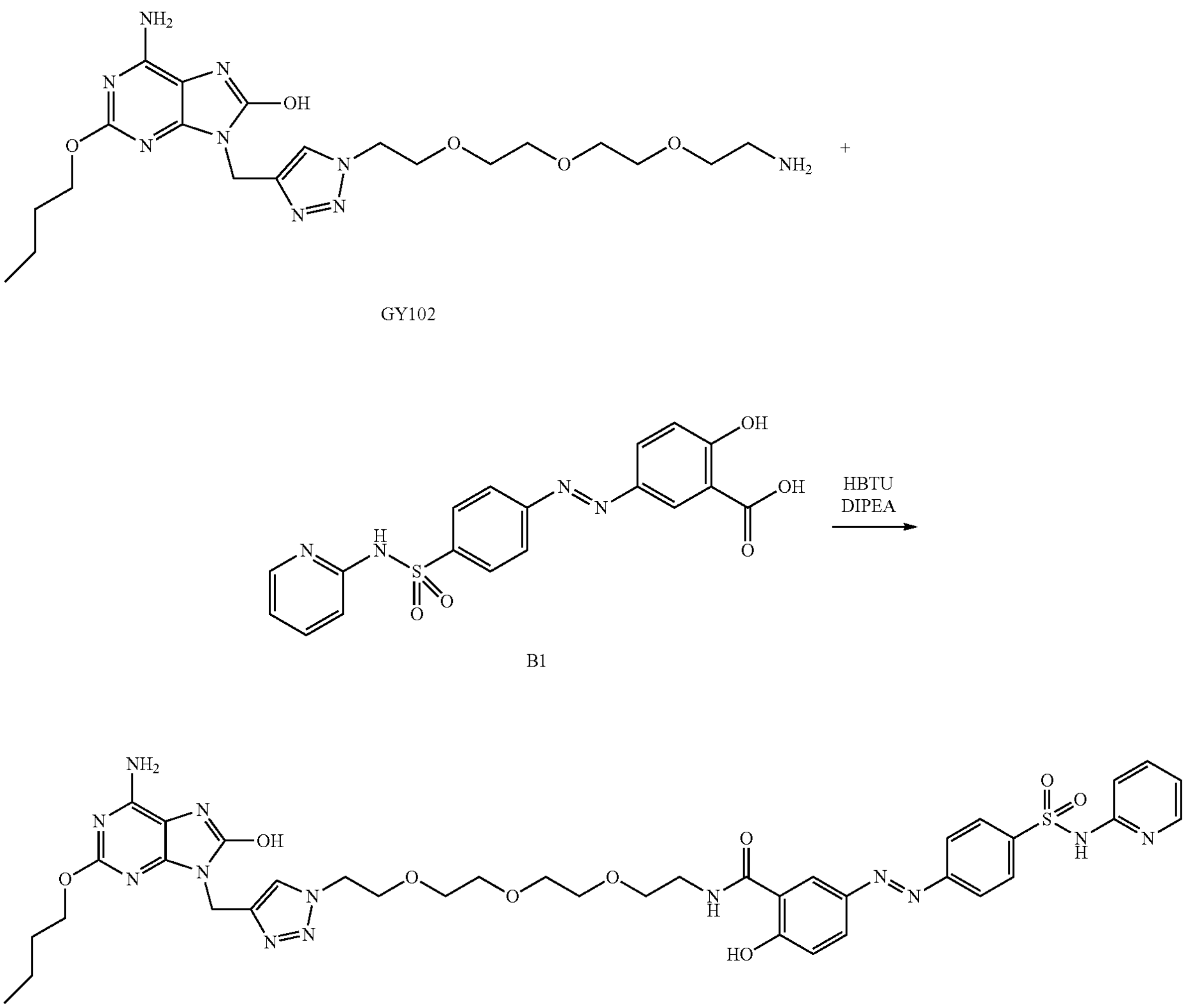

GY102

B1

GY113

39.8 mg of compound B1, 57.6 mg of compound GY102, 45.48 mg of HBTU, and 38.7 mg of DIPEA were dissolved in 1 mL of DMSO, and reacted at room temperature for 4 hrs. The reaction was monitored by a TLC. When the reaction was completed, a resulting reaction product was purified by an HPLC, lyophilized, and 30.9 mg of compound GY113 in the form of a white solid having a yield of 36 wt. % was obtained. ESI-MS=860.1 $[M+H]^+$.

GY114

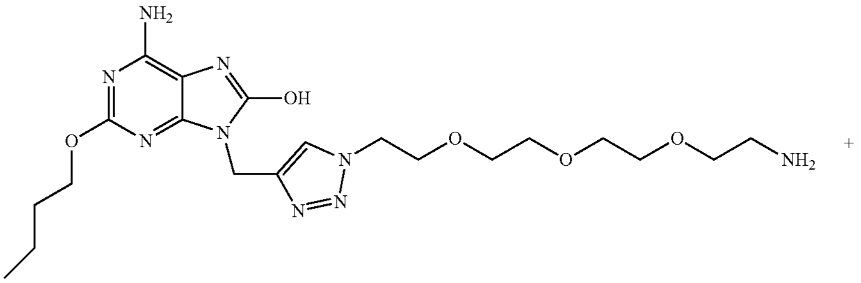

GY102

-continued

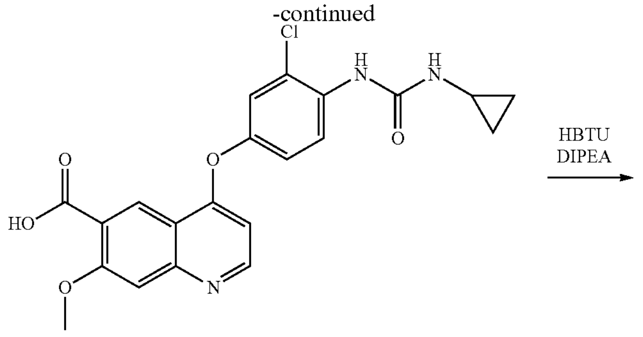

B2

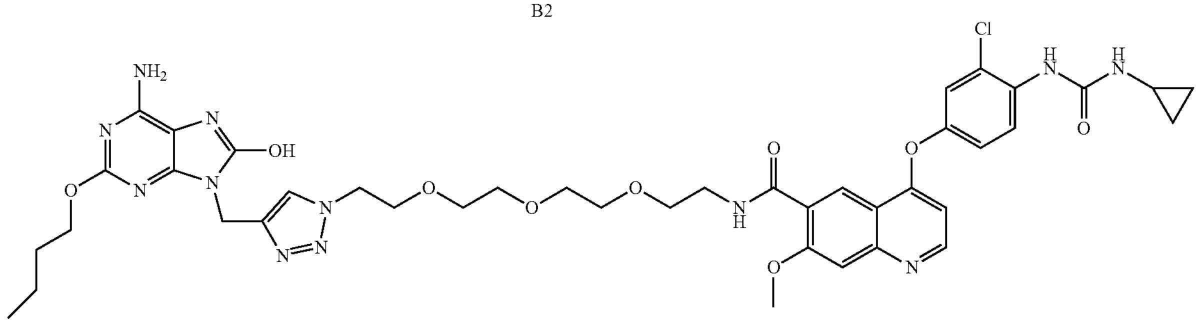

GY114

23.5 mg of compound B2 (Lenvatinib acid), 31.6 mg of compound GY102, and 27.2 mg of HBTU, 23.2 mg of DIPEA were dissolved in 1 mL of DMSO, and reacted at room temperature for 4 hrs. The reaction was monitored by a TLC. When the reaction was completed, a resulting reaction product was purified by an HPLC, lyophilized, and 12.3 mg of compound GY114 in the form of a white solid having a yield of 23 wt. % was obtained. ESI-MS=889.1 $[M+H]^+$.

GY115

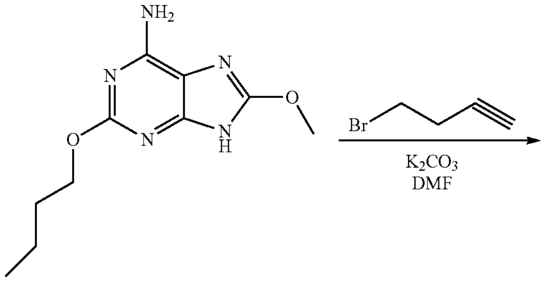

B3

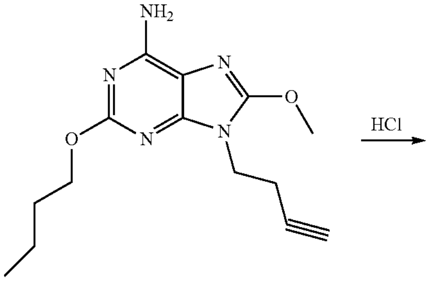

B4

-continued

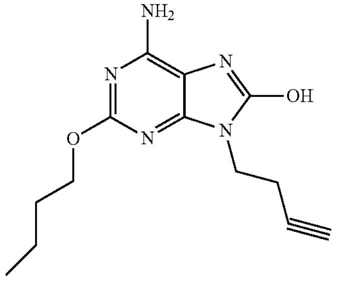

GY115

75 mg of compound B3, 46.5 mg of bromobutyne, 52.4 mg of $K_2CO_3$ were added to 1 mL of DMF, and reacted at room temperature for 4 hrs. The reaction was monitored by a TLC. When the reaction was completed, water was added to a resulting reaction mixture to separate out a precipitate, which was filtered and dried, a crude compound B4 was obtained for a next step reaction.

The crude compound B4 was dissolved in 1 mL of concentrated hydrochloric acid, and stirred at room temperature for 1 hr. After the reaction, a resulting reaction product was performed with rotary evaporation, and NaOH aqueous solution was added to adjust a pH value thereof, until a solid was precipitated. The solid was filtered and dried to obtain a crude compound GY115, which was purified by an HPLC, and lyophilized to obtain 21 mg of compound GY115 in the form of a white solid, a yield was 4 wt. %. ESI-MS=276.1 $[M+H]^+$.

GY116

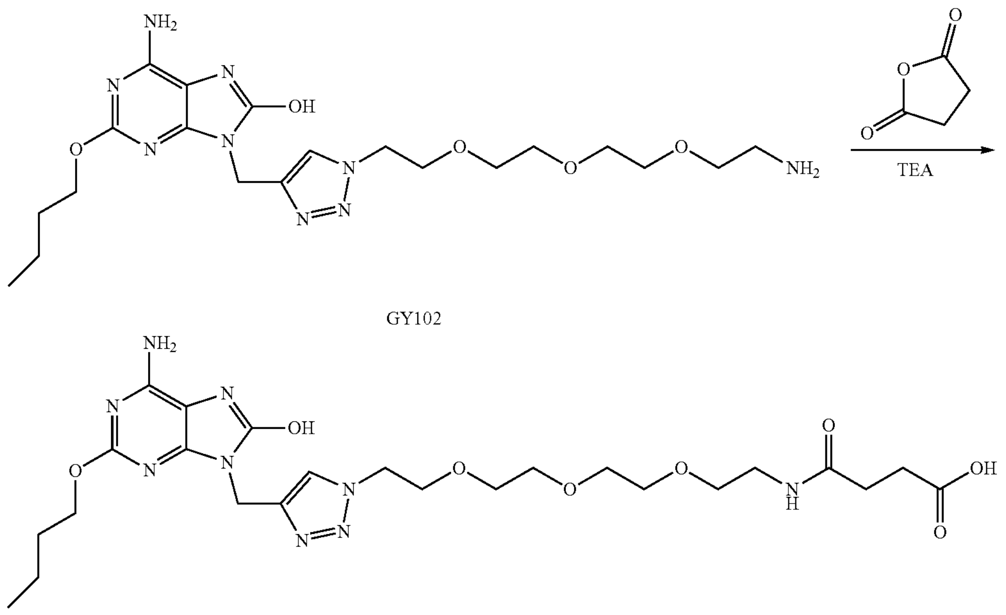

GY102

GY116

28.8 mg of compound GY102, 6.6 mg of succinic anhydride, and 6.6 mg of triethylamine were dissolved in 1 mL of DMSO, and reacted at room temperature for 2 hrs. The reaction was monitored by TLC. When the reaction was completed, a resulting reaction product was purified by an HPLC, lyophilized, and 10.3 mg of compound GY116 in the form of a white solid having a yield of 29.5 wt. % was obtained. ESI-MS=580.1 $[M+H]^+$.

GY117

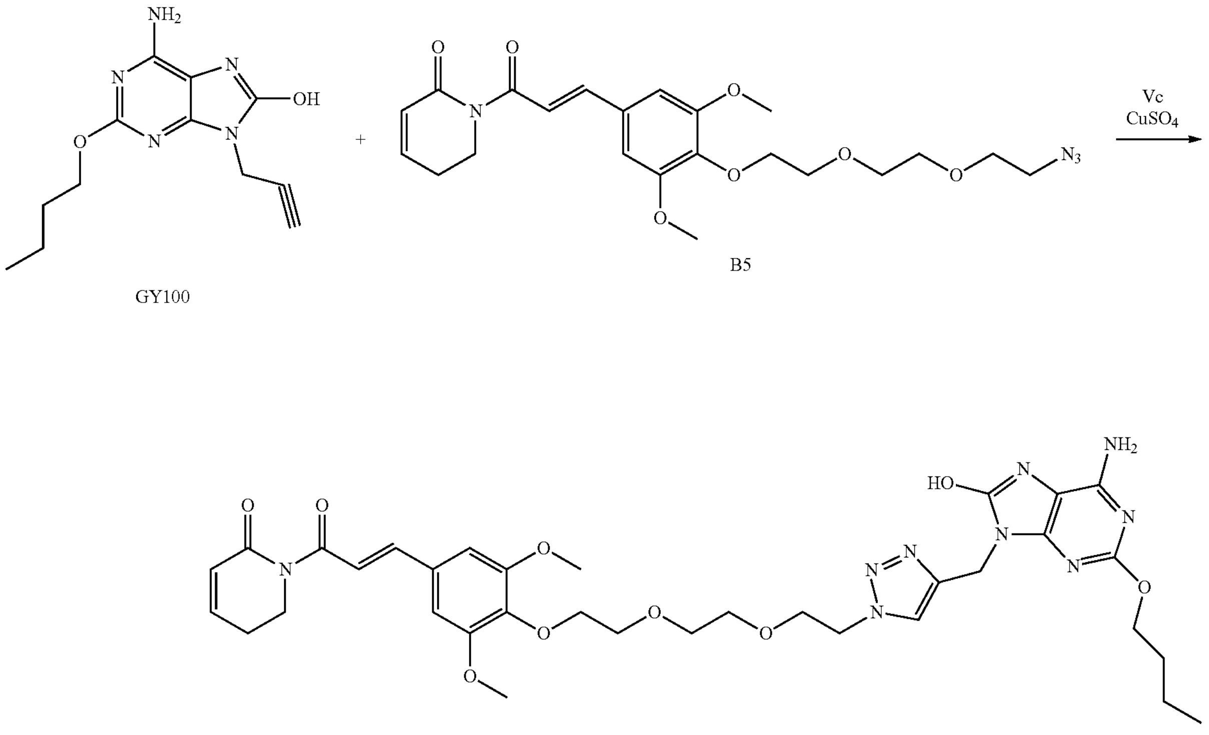

GY100

B5

GY117

33.1 mg of compound B5, 15.7 mg of GY100, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, lyophilized, and 9.7 mg of compound GY117 in the form of a white solid having a yield of 22.4 wt. % was obtained. ESI-MS=722.1 $[M+H]^+$.

GY118

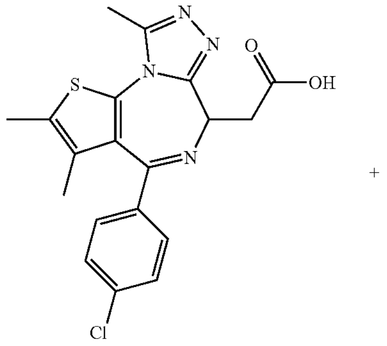

JQ1

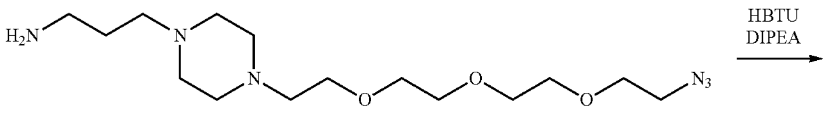

B6

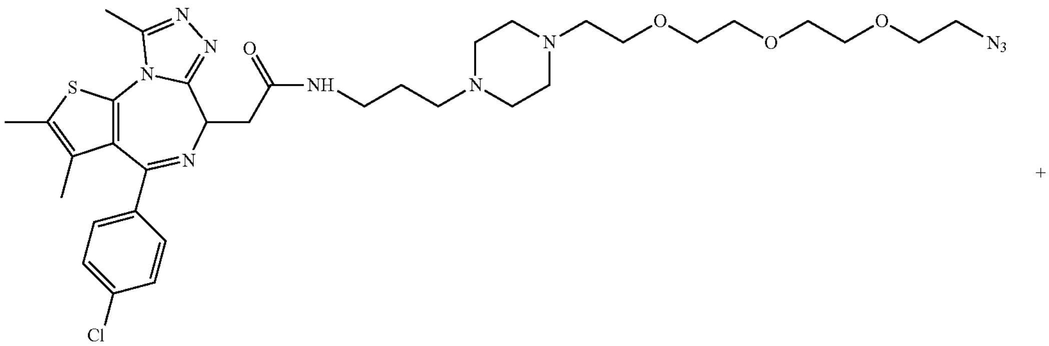

B7

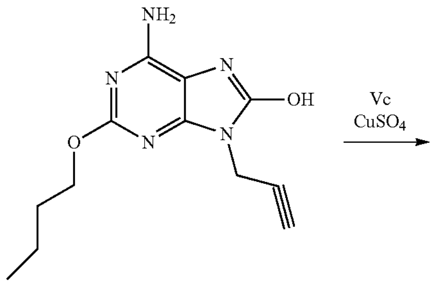

GY100

-continued

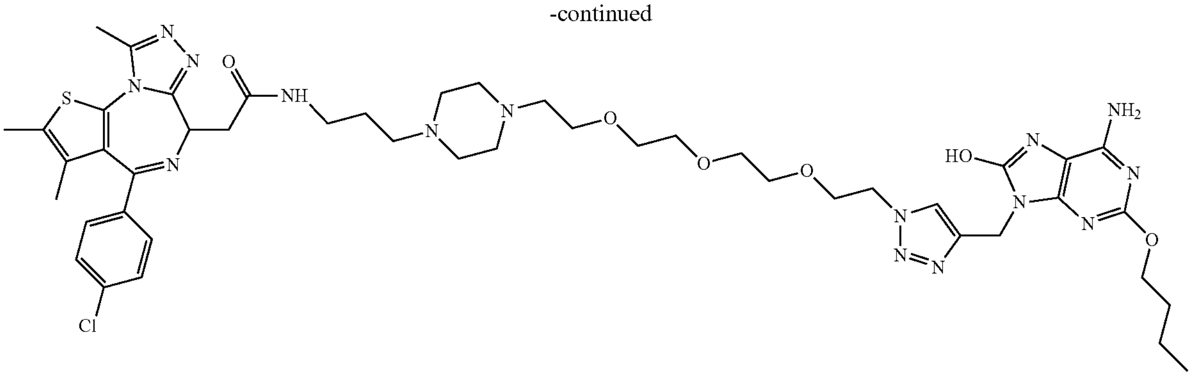

GY118

40 mg of JQ1 acid, 41.3 mg of compound B6, 45.5 mg of HBTU, and 38.7 mg of DIPEA were dissolved in 1 mL of DMSO, and reacted at room temperature for 4 hrs. The reaction was monitored by a TLC. When the reaction was completed, water was added to a resulting reaction mixture to separate out a precipitate, which was filtered and dried to obtain a crude compound B7.

24 mg of the crude compound B7, 8.6 mg of compound GY100, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, lyophilized, and 5.3 mg of compound GY118 in the form of a white solid having a yield of 16.2 wt. % was obtained. ESI-MS=988.1 $[M+H]^+$.

GY119

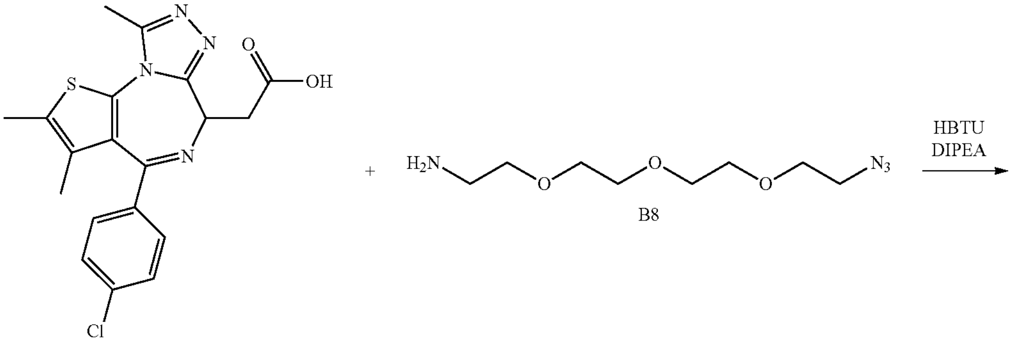

JQ1

B8

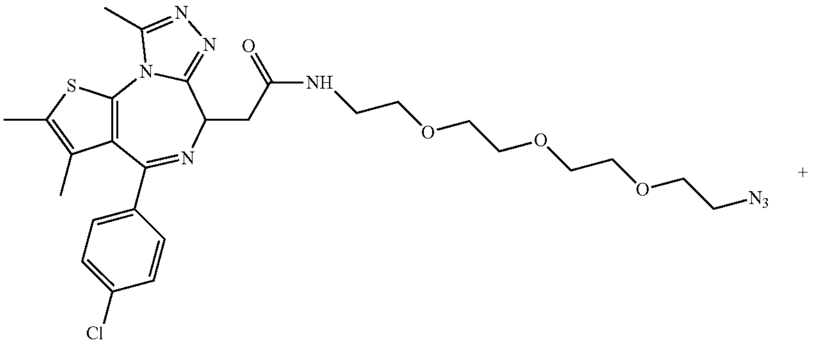

B9

-continued

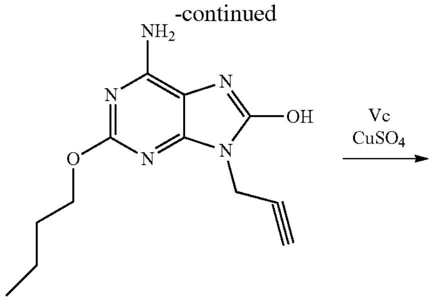

GY100

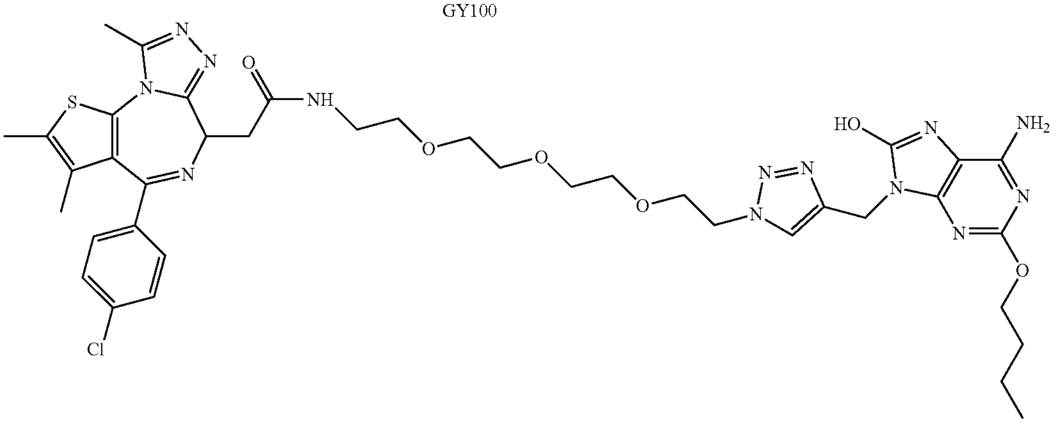

GY119

40 mg of JQ1 acid, 41.3 mg of compound B8, 45.5 mg of HBTU, and 38.7 mg of DIPEA were dissolved in 1 mL of DMSO, and reacted at room temperature for 4 hrs. The reaction was monitored by a TLC. When the reaction was completed, water was added to a resulting reaction mixture to separate out a precipitate, which was filtered and dried to obtain a crude compound B9.

30 mg of the crude compound B9, 13.1 mg of compound GY100, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, lyophilized, and 7.6 mg of compound GY119 in the form of a white solid having a yield of 17.6 wt. % was obtained. ESI-MS=862.1 $[M+H]^+$.

GY120

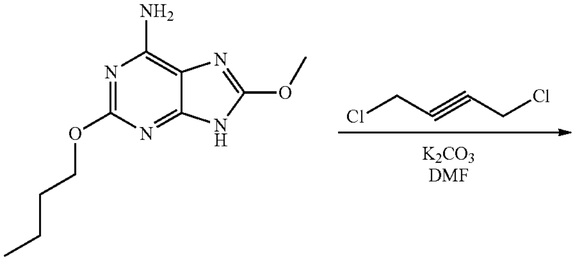

b3

-continued

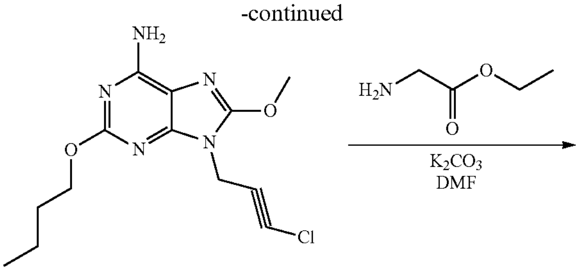

b10

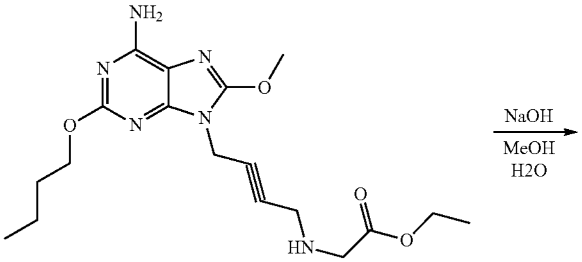

b11

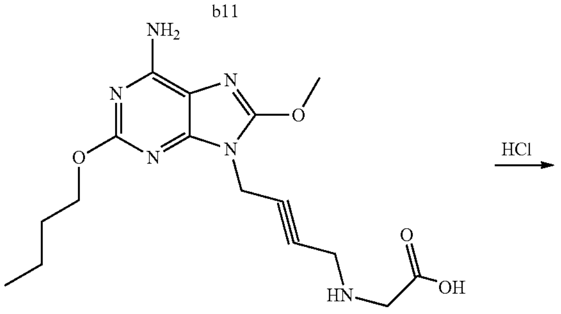

b12

-continued

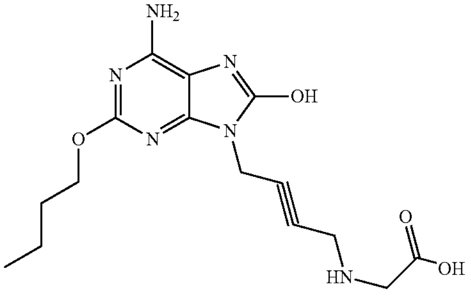

GY-120

94.8 mg of compound b3, 61.5 mg of 1,4-dichlorobutyne, 69 mg of $K_2CO_3$ were added to 2 mL of DMF, and reacted at room temperature for 4 hrs. The reaction was monitored by a TLC. When the reaction was completed, 138 mg of glycine and 138 mg of $K_2CO_3$ were added to the reaction system. When the reaction was completed, water was added to a resulting reaction system to precipitate a white solid, which was filtered and dried to obtain a crude compound b11.

The obtained crude compound b11 was dissolved in methanol, an aqueous solution of sodium hydroxide was added, and a resulting mixture was stirred at room temperature for 2 hrs. After the reaction, rotary vaporization was performed to remove methanol, pH value was adjusted to precipitate a white solid, which was filtered and dried to obtain a crude compound b12.

The crude compound b12 was dissolved in 1 mL of concentrated hydrochloric acid, stirred at room temperature for 1 hr. After the reaction, rotary evaporation was performed under a reduced pressure, and the pH was adjusted with an aqueous solution of NaOH to precipitate a solid, which was filtered and dried to obtain a crude compound GY120. The crude compound GY120 was purified by an HPLC and lyophilized to obtain 23 mg of compound GY120 in the form of a white solid, and a yield thereof was 16.5 wt. %. ESI-MS=349.1 $[M+H]^+$.

GY121

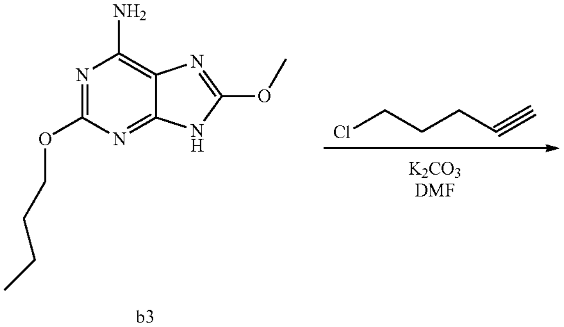

b3

-continued

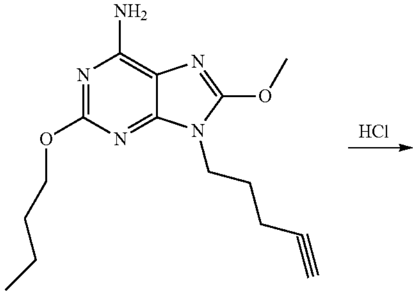

b13

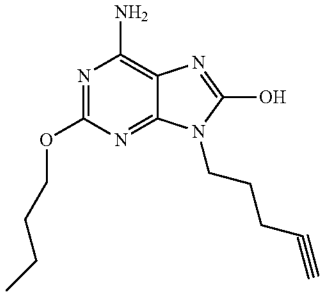

GY-121

71 mg of compound b3, 34 mg of 5-chloropentyne, 49.7 mg of $K_2CO_3$ were added to 1 mL of DMF, and reacted at room temperature for 4 hrs. The reaction was monitored by a TLC. When the reaction was completed, water was added to a resulting reaction mixture to separate out a precipitate, which was filtered and dried to obtain a crude compound b13, for perform a next step reaction.

The crude compound b13 was dissolved in 1 mL of concentrated hydrochloric acid, stirred at room temperature for 1 hr. After the reaction, rotary evaporation was performed under a reduced pressure, and the pH was adjusted with an aqueous solution of NaOH to precipitate a solid, which was filtered and dried to obtain a crude compound GY121. The crude compound GY121 was purified by an HPLC and lyophilized to obtain 17.8 mg of compound GY121 in the form of a white solid, and yield thereof was 20.4 wt. %, ESI-MS=290.2 $[M+H]^+$.

GY122

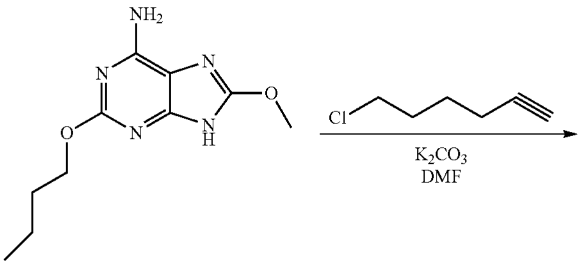

B3

-continued

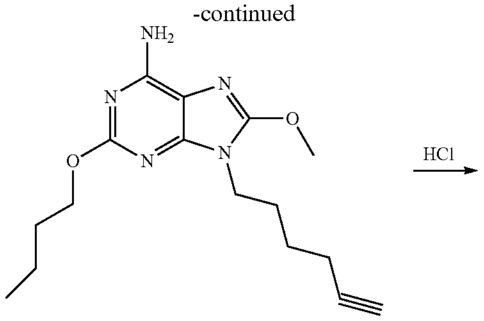

B13

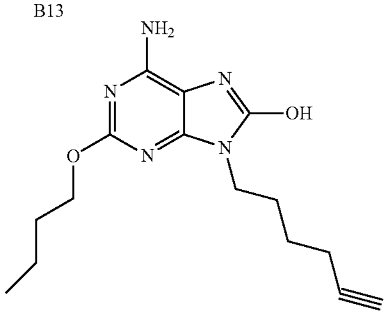

GY122

71 mg of compound B3, 38.2 mg of 6-chlorohexyne, 49.7 mg of $K_2CO_3$ were added to 1 mL of DMF, and reacted at room temperature for 4 hrs. The reaction was monitored by a TLC. When the reaction was completed, water was added to a resulting reaction mixture to separate out a precipitate, which was filtered and dried to obtain a crude compound B13, for use in a next step reaction.

The crude compound B13 was dissolved in 1 mL of concentrated hydrochloric acid, stirred at room temperature for 1 hr. After the reaction, rotary evaporation was performed under reduced pressure, and the pH was adjusted with an aqueous solution of NaOH to precipitate a solid, which was filtered and dried to obtain a crude compound GY122. The crude compound GY122 was purified by an HPLC and then lyophilized, to obtain 19 mg of compound GY122 in the form of a white solid. A yield thereof was 20.9 wt. %. ESI-MS=304.1 $[M+H]^+$.

GY123

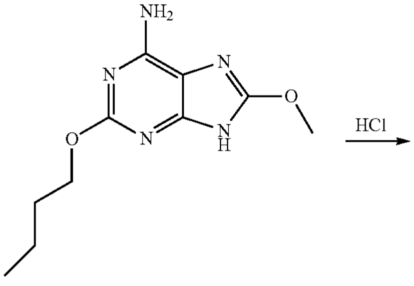

B3

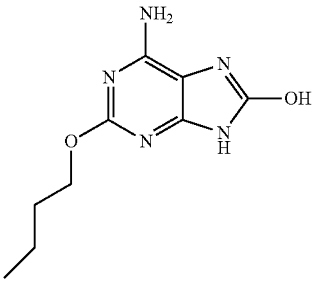

GY123

47.4 mg of compound B3 was dissolved in 1 mL of concentrated hydrochloric acid, stirred at room temperature for 1 hr. After the reaction, rotary evaporation was performed under reduced pressure, and the pH was adjusted with an aqueous solution of NaOH to precipitate a solid, which was filtered and dried to obtain a crude compound GY123. The crude compound GY123 was then purified by an HPLC, and lyophilized to obtain 15.6 mg of compound GY123 in the form of a white solid. A yield thereof was 34.9 wt. %. ESI-MS=224.0 $[M+H]^+$.

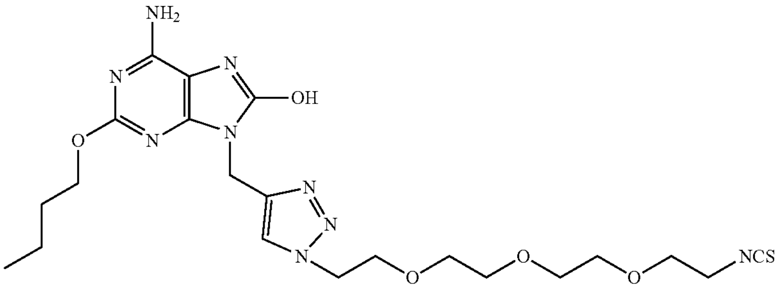

GY106

+

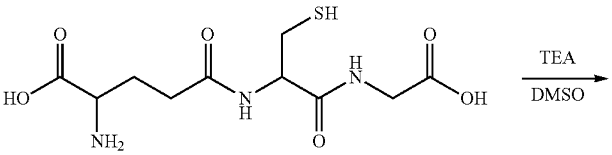

-continued

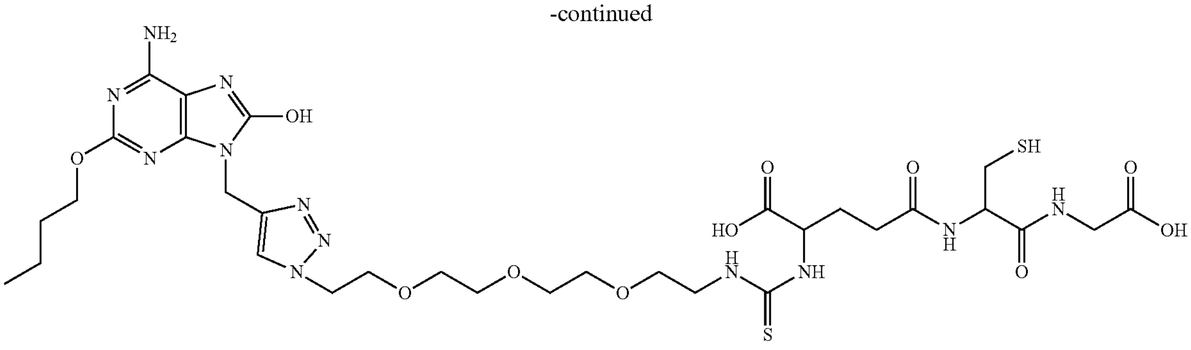

GY126

20 mg of compound GY106, 13 mg of glutathione (reduced type), and 5 μL of TEA were dissolved in 500 μL of DMSO, and reacted overnight at room temperature. The reaction was monitored by an LC-MS. When the reaction was completed, a resulting reaction product was purified by an HPLC, to obtain 12.4 mg of compound GY126 in the form of a white solid, and a yield thereof was 39 wt. %. ESI-MS: m/z=829.1 $[M+H]^+$.

GY127

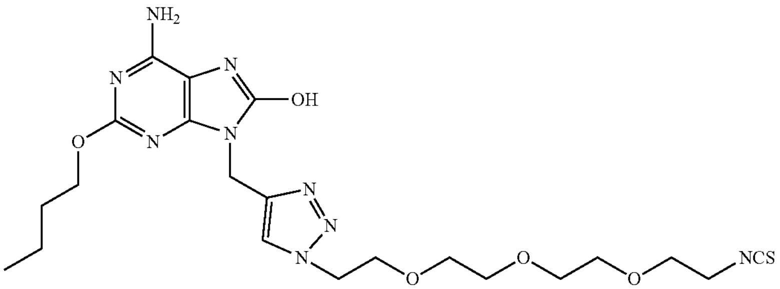

GY106

+

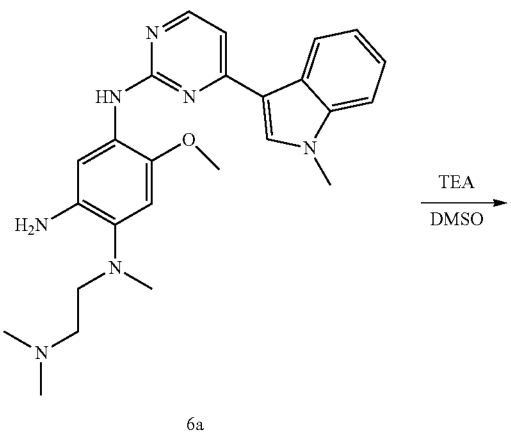

6a

-continued

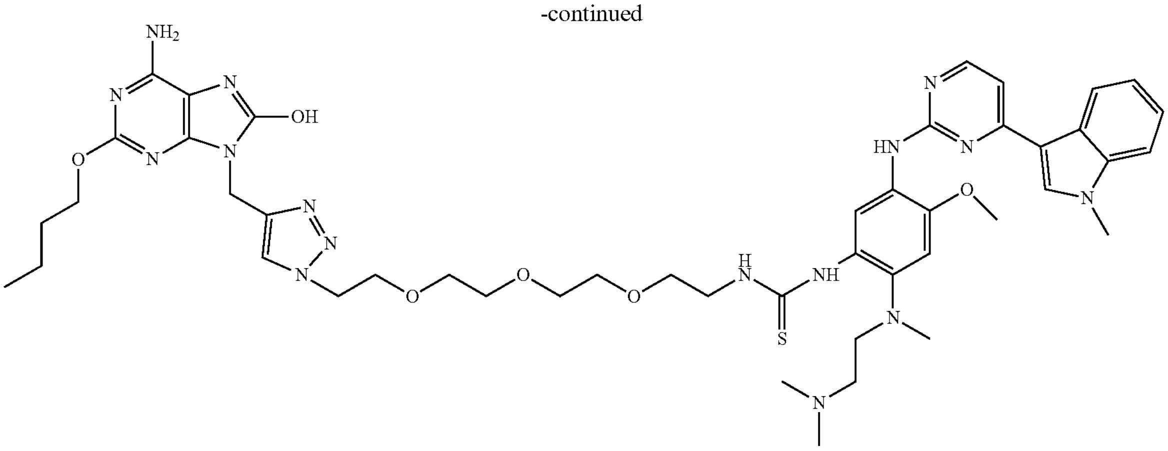

GY127

13 mg of compound GY106, 12 mg of compound 6a, and 6.4 μL of TEA were dissolved in 500 μL of DMSO, and reacted overnight at room temperature. The reaction was monitored by an LC-MS. When the reaction was completed, a resulting reaction product was purified by an HPLC, such that 8 mg of compound GY127 in the form of a white solid having a yield of 33.2 wt. % was obtained. ESI-MS: m/z=968.2 $[M+H]^+$.

GY131

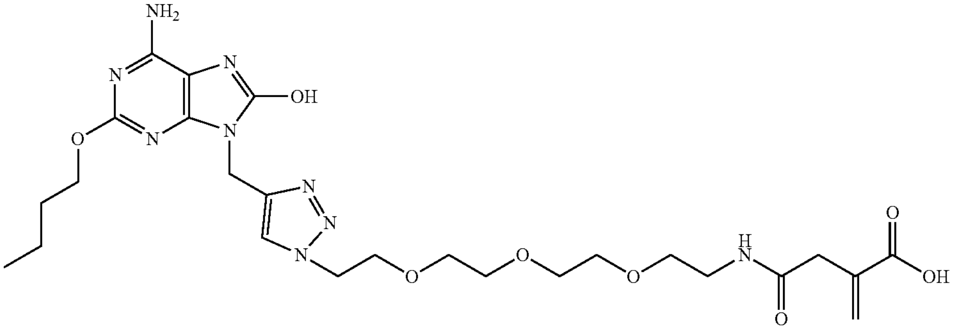

GY109

+

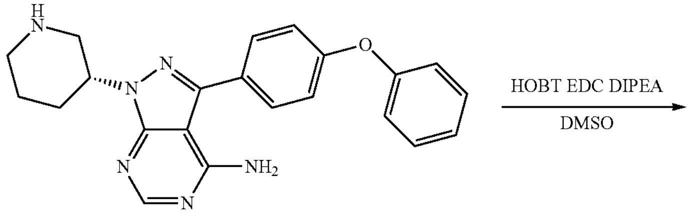

ibrutinib-intermediate

-continued

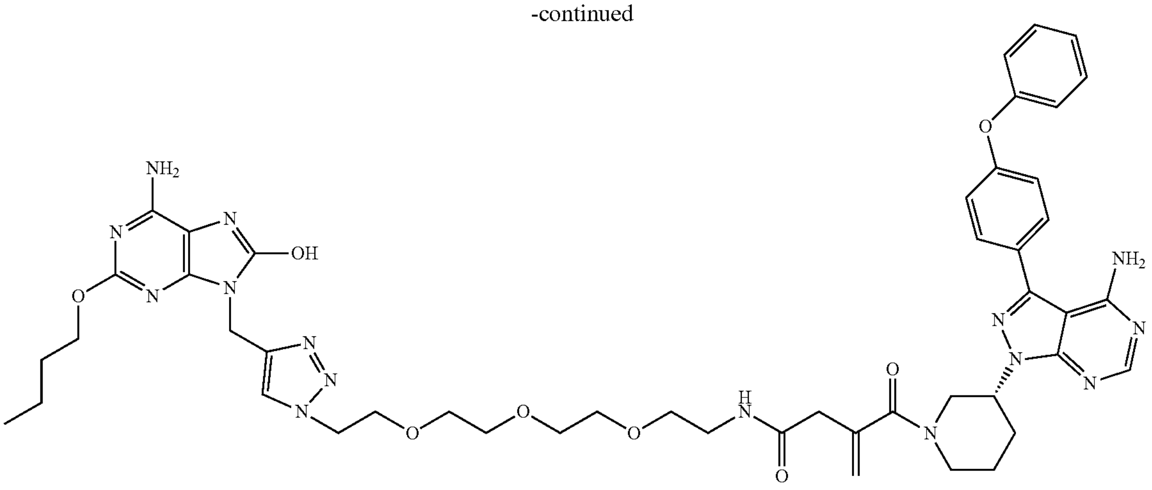

GY131

20 mg of compound GY109, 15.6 mg of an Ibrutinib-intermediate, 6.3 mg of HOBT, 9 mg of EDCI, and 15 μL of DIPEA were dissolved in 500 μL of DMSO, and reacted overnight at room temperature. The reaction was monitored by an LC-MS. When the reaction was completed, a resulting reaction product was purified by an HPLC, such that 14.3 mg of compound GY131 in the form of a light yellow solid having a yield of 44.1 wt. % was obtained. ESI-MS: m/z=961.2 [M+H]$^+$.

GY132

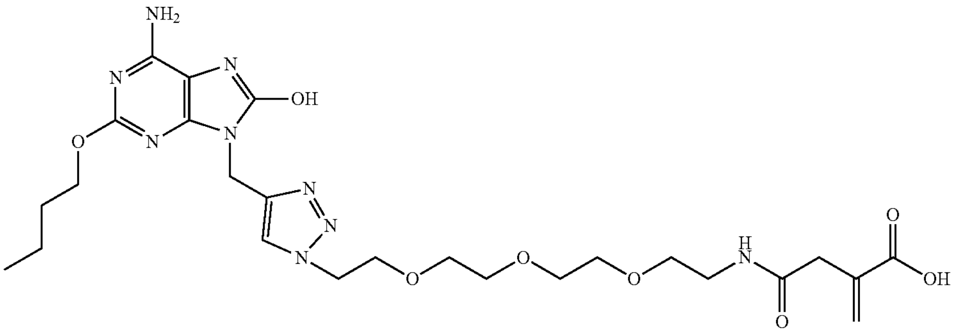

GY109

+

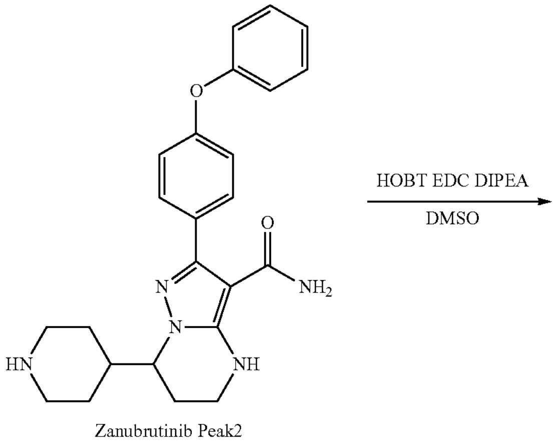

Zanubrutinib Peak2

-continued

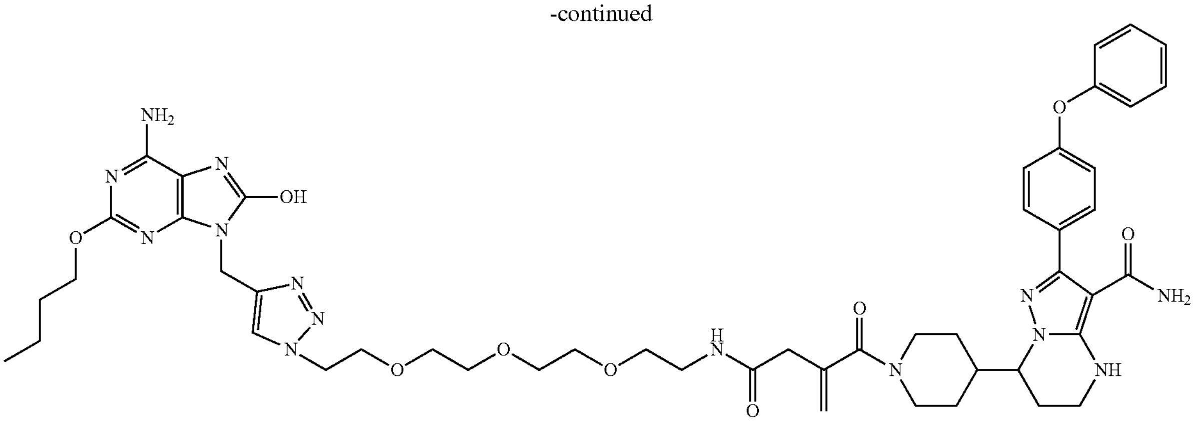

GY132

20 mg of compound GY109, 12.8 mg of Zanubrutinib Peak2 (Zanubrutinib intermediate in an S-configuration), 6.3 mg of HOBT, 9 mg of EDC, and 15 μL of DIPEA were dissolved in 500 μL of DMSO, and reacted overnight at room temperature. The reaction was monitored by an LC-MS. When the reaction was completed, a resulting reaction product was purified by an HPLC, such that 5.8 mg of compound GY132 in the form of a beige solid having a yield of 19.3 wt. % was obtained. ESI-MS: m/z=992.2 $[M+H]^+$.

GY133

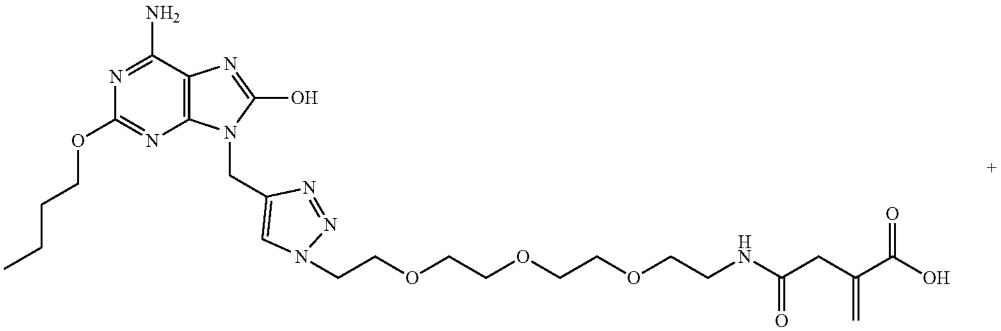

GY109

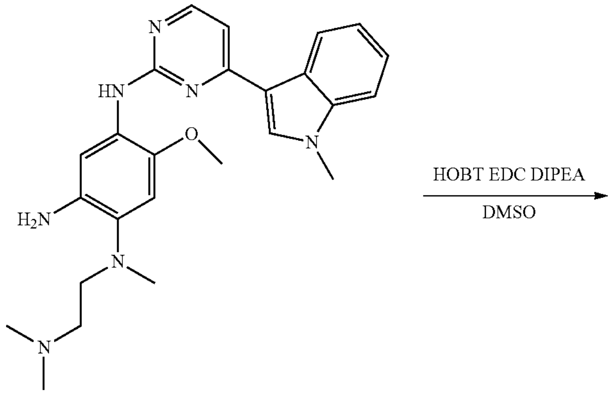

AZO-9291 intermediate

-continued

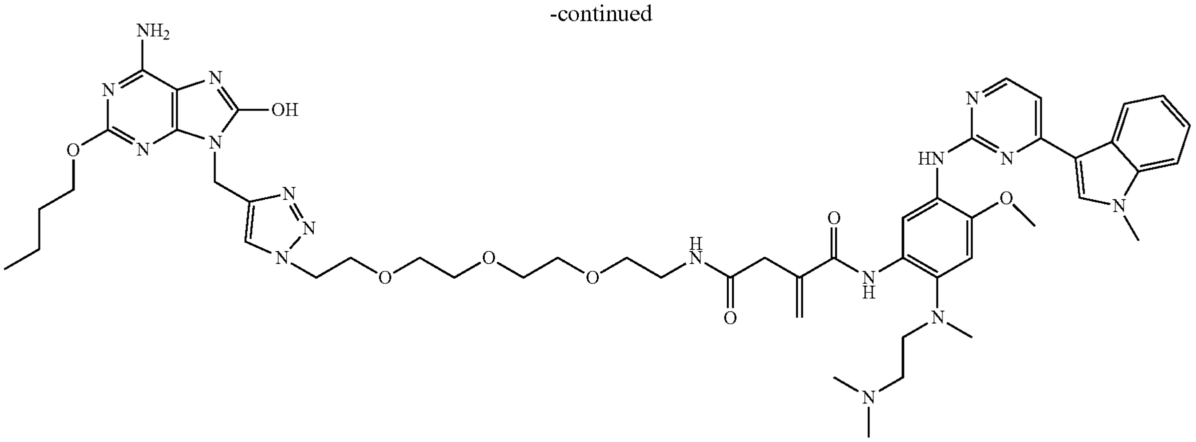

GY133

36 mg of compound GY109, 30 mg of an AZD-9291 intermediate, 14 mg of HOBT, 20 mg of EDC, and 36 μL of DIPEA were dissolved in 500 μL of DMSO, and reacted overnight at room temperature. The reaction was monitored by an LC-MS. When the reaction was completed, a resulting reaction product was purified by an HPLC, such that 7.5 mg of compound GY133 in the form of a beige solid having a yield of 12.1 wt. % was obtained. ESI-MS: m/z=1019.3 $[M+H]^+$.

GY134

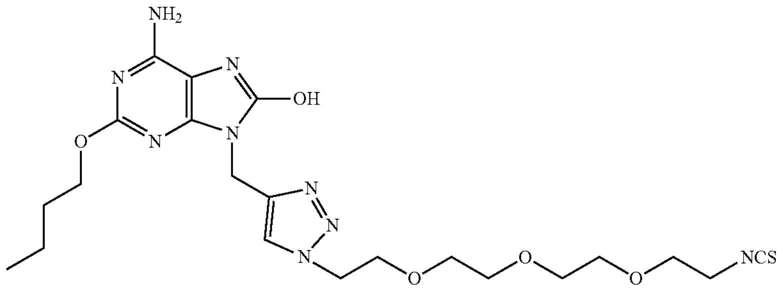

GY106

+

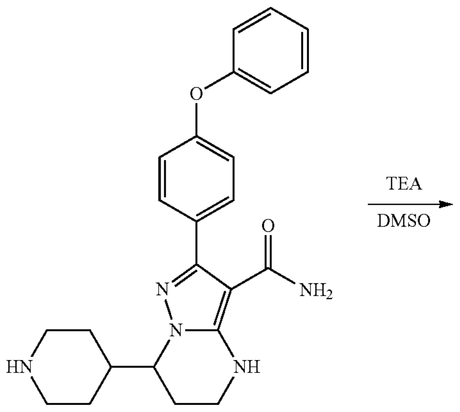

Zanubrutinib Peak1

-continued

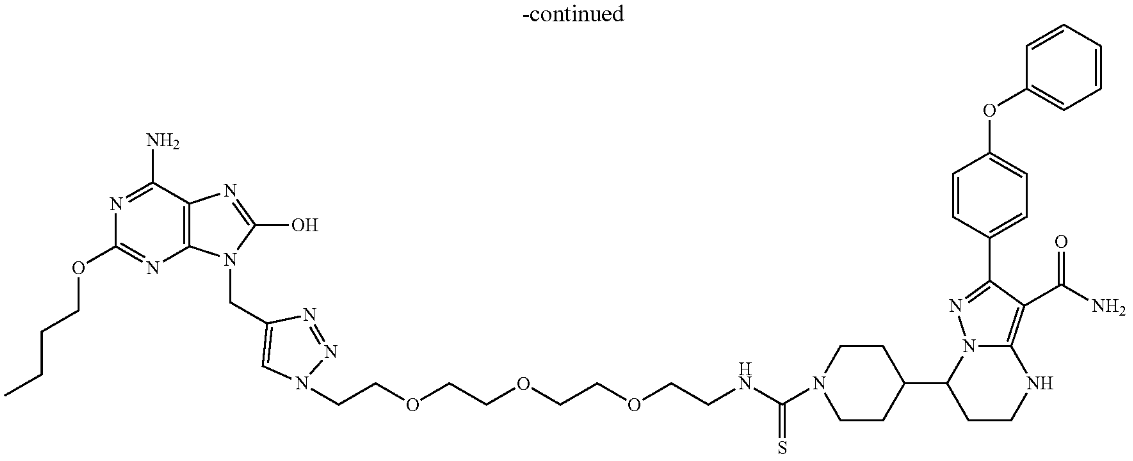

GY134

28 mg of compound GY106, 20 mg of Zanubrutinib Peak1 (Zanubrutinib intermediate in an R-configuration), and 19 μL of TEA were dissolved in 500 μL of DMSO, and reacted overnight at room temperature. The reaction was monitored by an LC-MS. When the reaction was completed, a resulting reaction product was purified by an HPLC, such that 7.3 mg of compound GY134 in the form of an of f-white solid having a yield of 16.2 wt. % was obtained. ESI-MS: m/z=939.1 $[M+H]^+$.

GY135

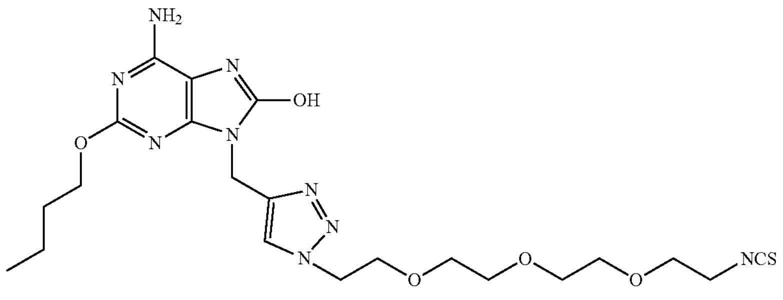

GY106

+

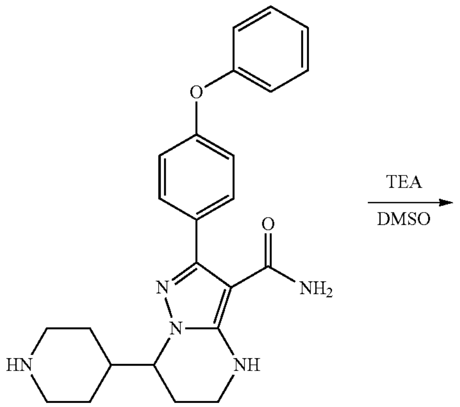

Zanubrutinib Peak2

-continued

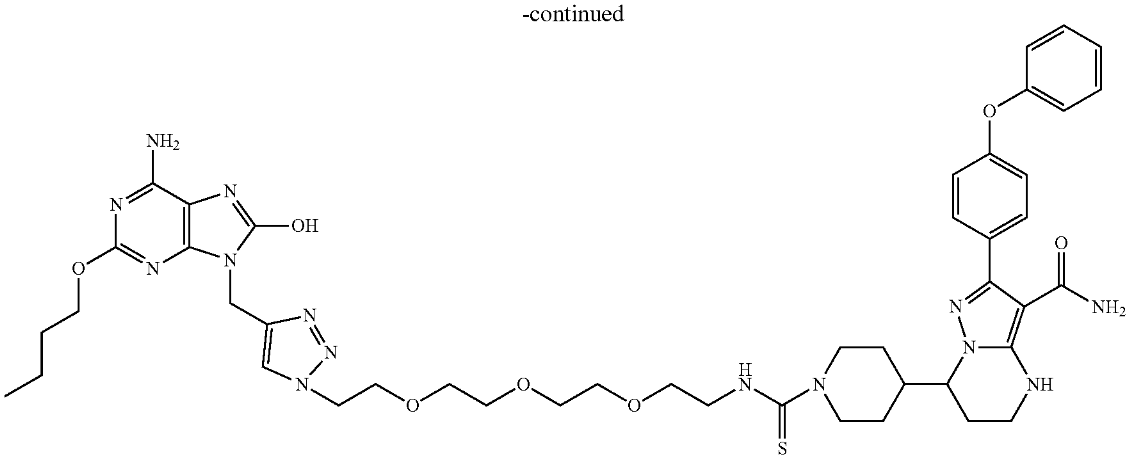

GY135

28 mg of compound GY106, 20 mg of Zanubrutinib Peak1 (Zanubrutinib intermediate in an S-configuration), and 19 μL of TEA were dissolved in 500 μL of DMSO, and reacted overnight at room temperature. The reaction was monitored by an LC-MS. When the reaction was completed, a resulting reaction product was purified by an HPLC, such that 5.8 mg of GY135 in the form of an of f-white solid having a yield of 12.9 wt. % was obtained. ESI-MS: m/z=939.1 [M+H]$^+$.

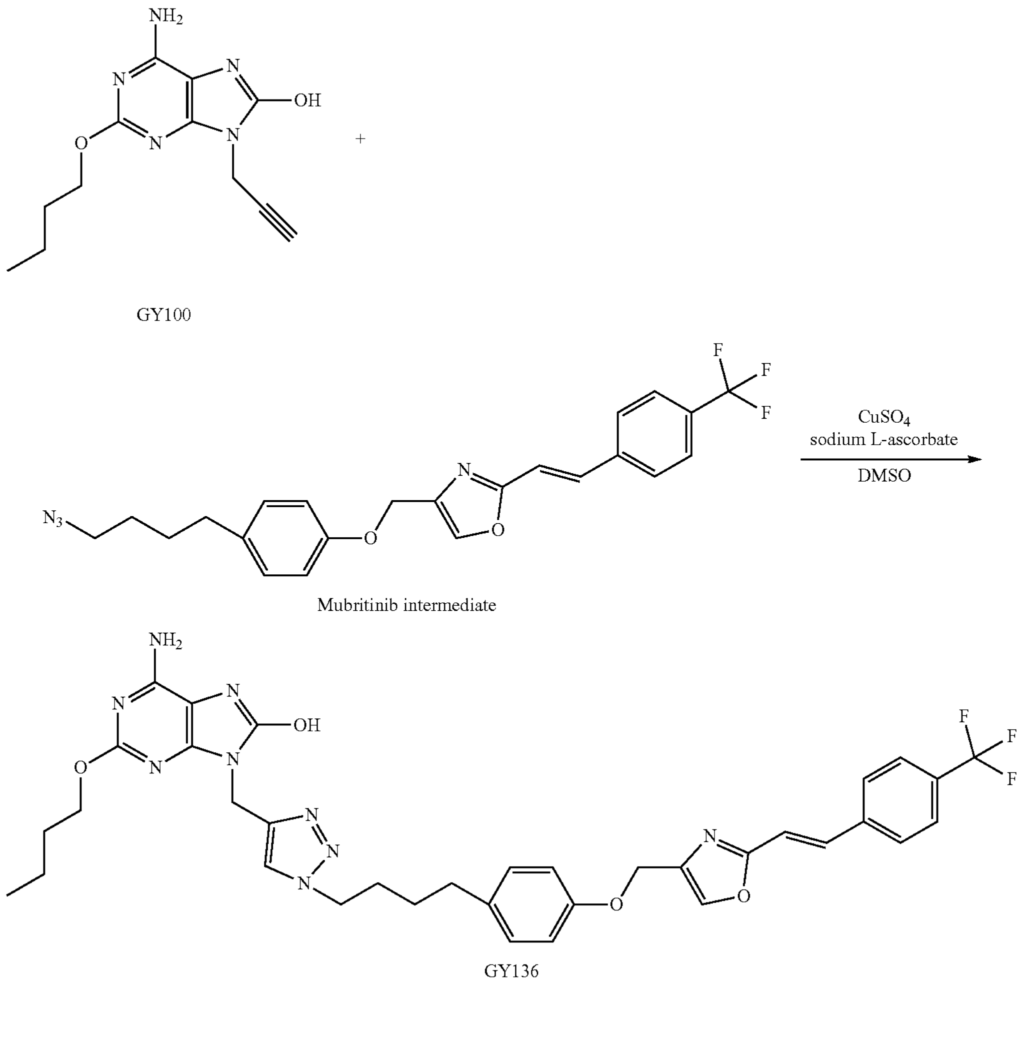

GY100

Mubritinib intermediate

GY136

20 mg of compound GY100, 30 mg of Mubritinib intermediate, 4 mg of sodium L-ascorbate, and 4 mg of $CuSO_4$ were dissolved in 100 μL of water+400 μL of DMSO, and reacted at room temperature for 5 hrs. The reaction was monitored by an LC-MS. When the reaction was completed, a resulting reaction product was purified by an HPLC, such that 10 mg of compound GY136 in the form of a white solid having a yield of 18.6 wt. % was obtained. ESI-MS: m/z=704.3 $[M+H]^+$.

GY137

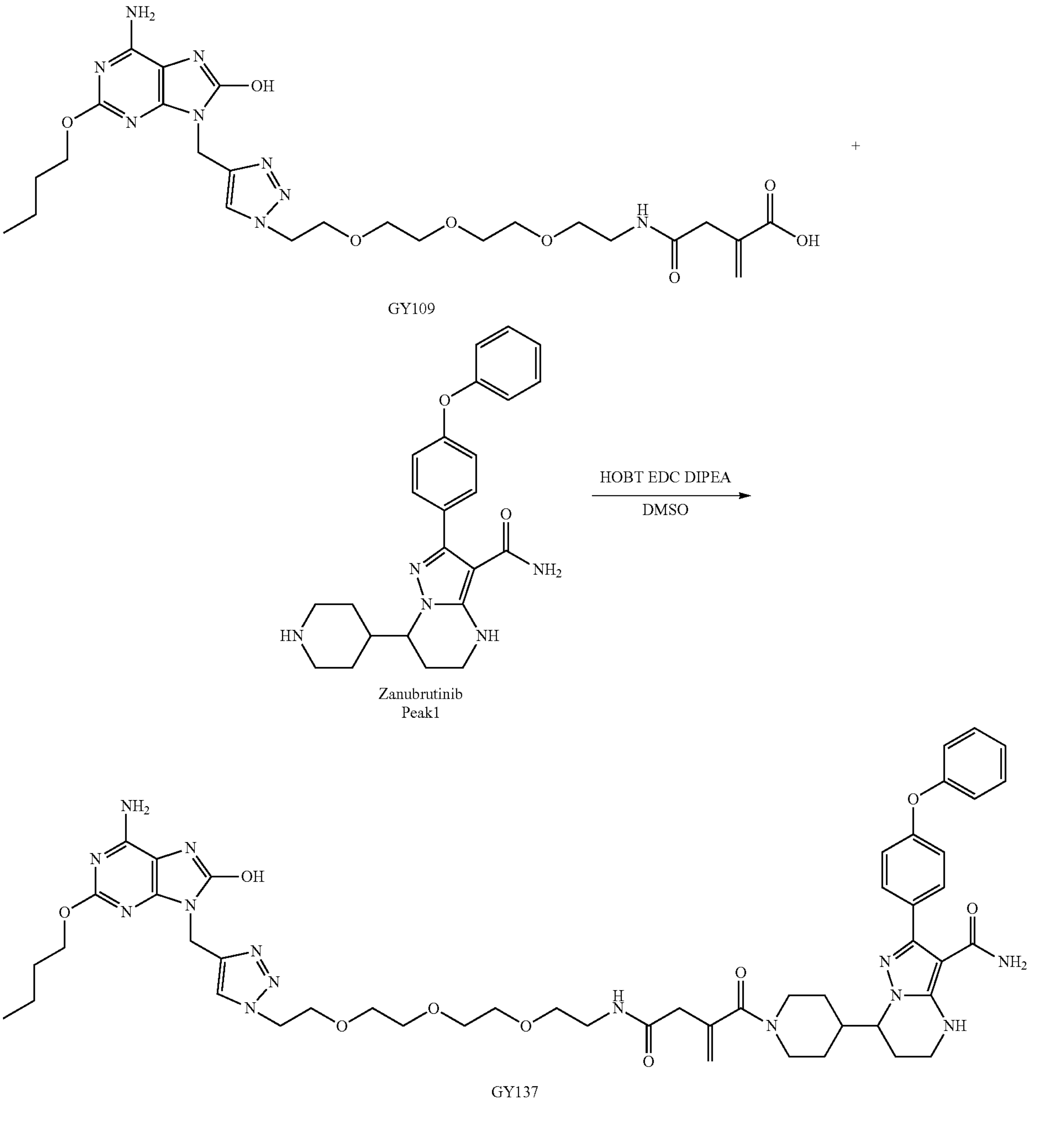

GY109

Zanubrutinib Peak1

GY137

20 mg of compound GY109, 12.8 mg of Zanubrutinib Peak1 (Zanubrutinib intermediate in an R-configuration), 6.3 mg of HOBT, 9 mg of EDC, and 15 μL of DIPEA were dissolved in 500 μL of DMSO, and reacted overnight at room temperature. The reaction was monitored by an LC-MS. When the reaction was completed, a resulting reaction product was purified by an HPLC, such that 7.2 mg of compound GY137 in the form of a beige solid having a yield of 24 wt. % was obtained. ESI-MS: m/z=992.2 $[M+H]^+$.

GY138

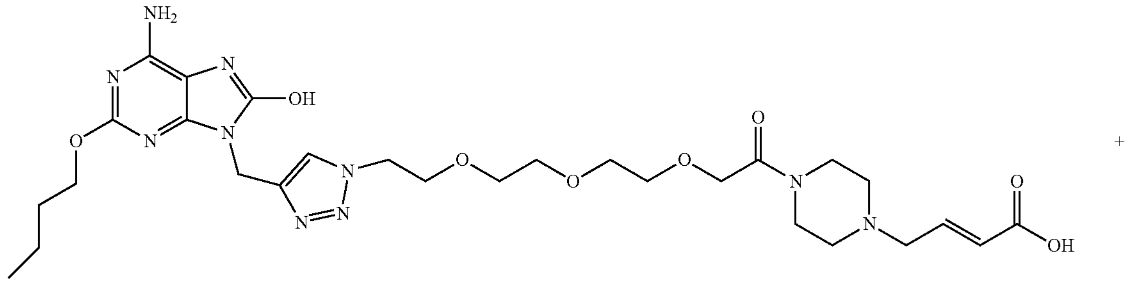

GY139

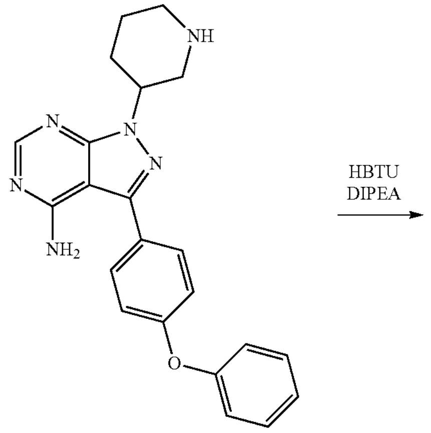

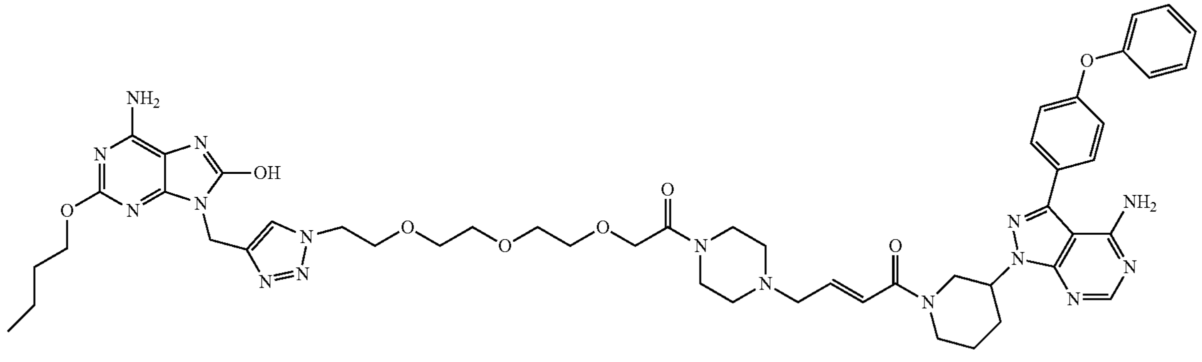

GY138

16.5 mg of compound GY139, 10 mg of Ibrutinib intermediate (in an R-configuration), 10.2 mg of HBTU, and 6.5 mg of DIPEA were dissolved in 1 mL of DMSO, and reacted at room temperature for 4 hrs. The reaction was monitored by a TLC. When the reaction was completed, a resulting reaction product was purified by an HPLC, and lyophilized, such that 5.6 mg of compound GY138 in the form of a white solid having a yield of 22.1 wt. % was obtained. ESI-MS=1016.1 [M+H]$^+$.

GY139

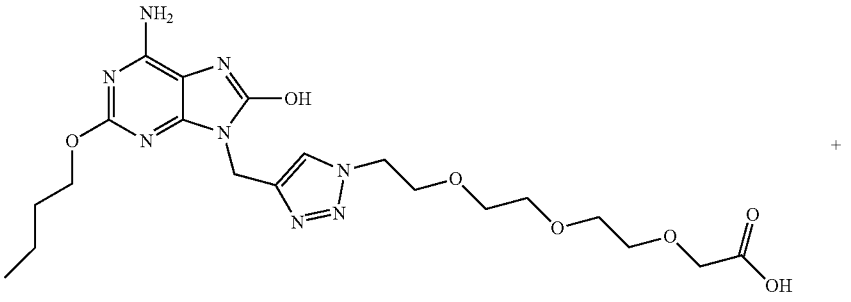

GY101

-continued

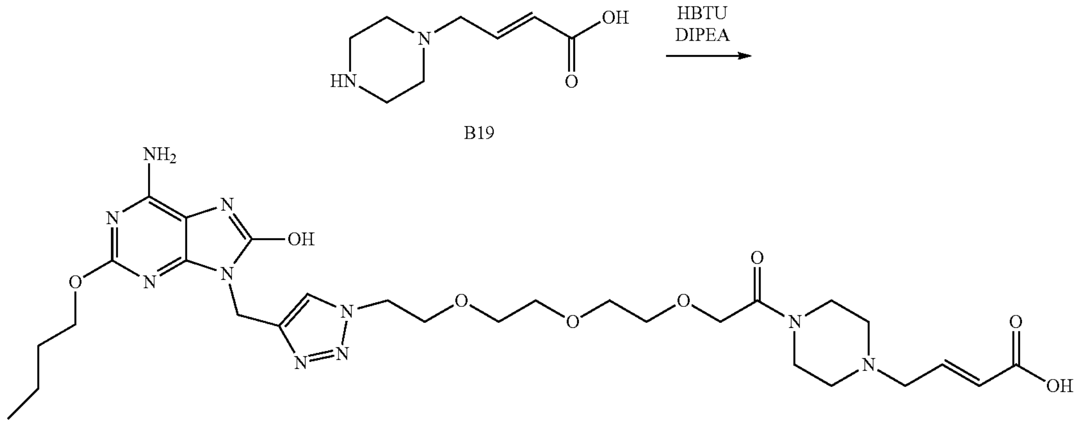

B19

GY139

49.5 mg of compound GY101, 17.1 mg of compound B19, 45.5 mg of HBTU, and 38.7 mg of DIPEA were dissolved in 1 mL of DMSO, and reacted at room temperature for 4 hrs. The reaction was monitored by a TLC. When the reaction was completed, a resulting reaction product was purified by an HPLC, and lyophilized, such that 22.5 mg of compound GY139 in the form of a white solid having a yield of 34.7 wt. % was obtained. ESI-MS=647.1 $[M+H]^+$.

GY140

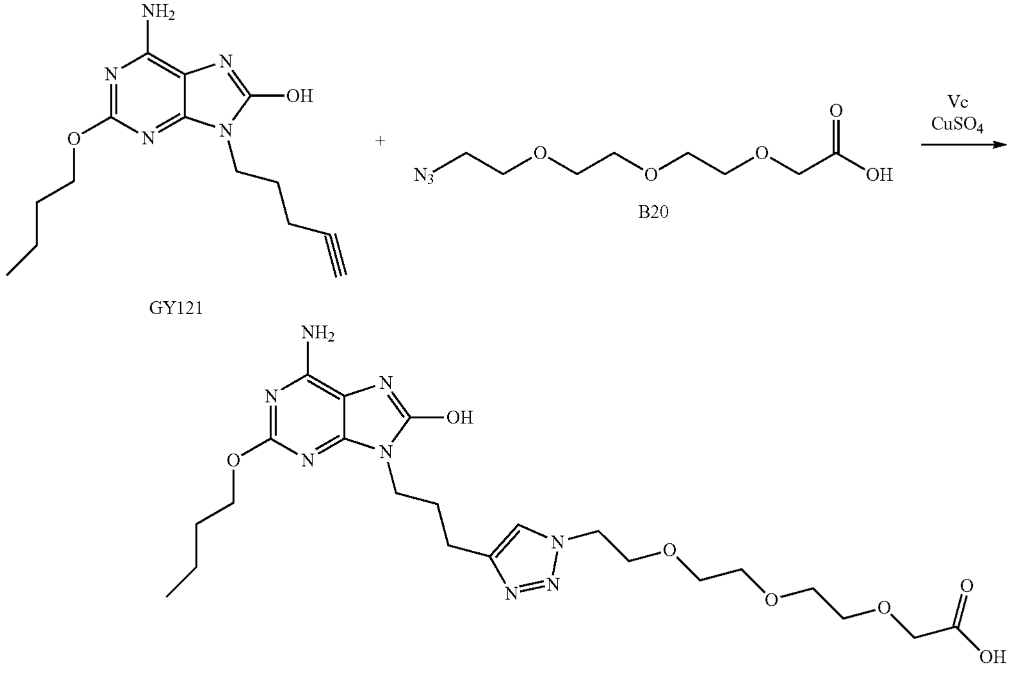

GY121

B20

GY140

28.9 mg of a crude compound GY121, 23.3 mg of B20, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, and lyophilized, such that 15.6 mg of compound GY140 in the form of a white solid having a yield of 29.8 wt. % was obtained. ESI-MS=523.1 $[M+H]^+$.

GY141

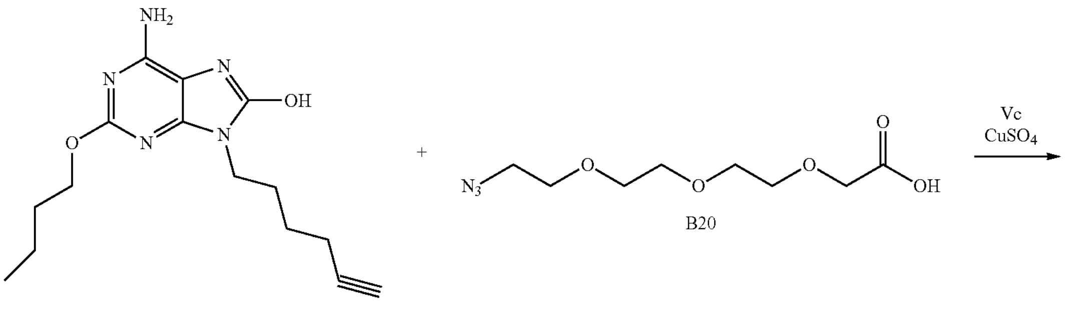

GY122

B20

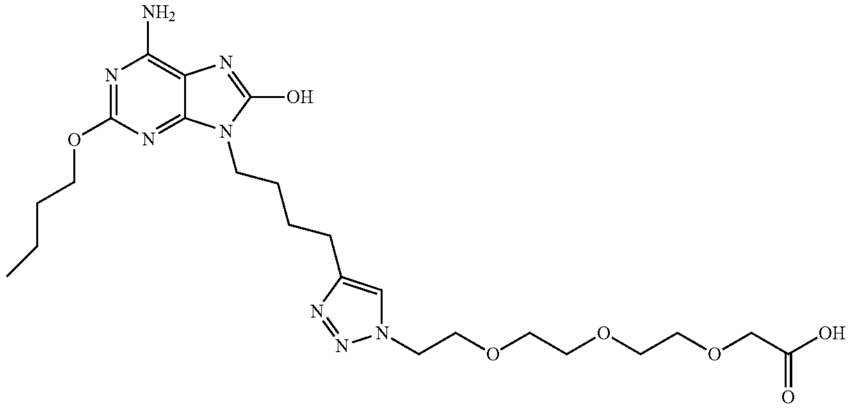

GY141

30.3 mg of a crude compound GY122, 23.3 mg of B20, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, and lyophilized, such that 19.6 mg of compound GY141 in the form of a white solid having a yield of 36.5 wt. % was obtained, ESI-MS=537.1 $[M+H]^+$.

GY142

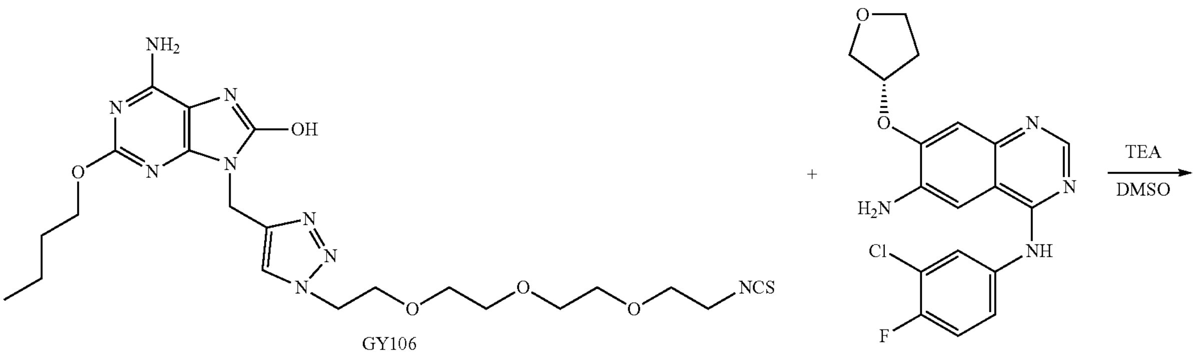

GY106 afatinib intermediate

-continued

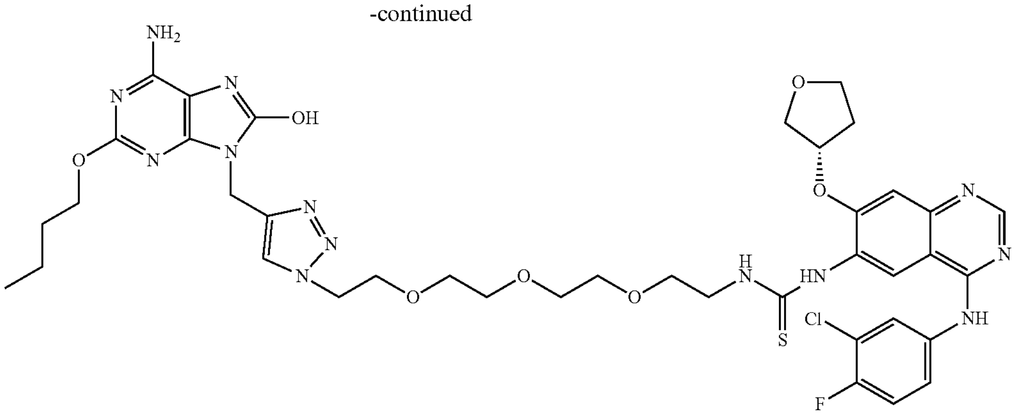

GY142

61.5 mg of compound GY106, 40 mg of an afatinib intermediate, and 20 μL of TEA were dissolved in 500 μL of DMSO, and stirred at 60° C. for 1 day. The reaction was monitored by an LC-MS. When the reaction was completed, a resulting reaction product was purified by an HPLC, such that 10 mg of compound GY142 in the form of a yellow solid having a yield of 12.9 wt. % was obtained. ESI-MS: m/z=896.0 $[M+H]^+$.

GY143

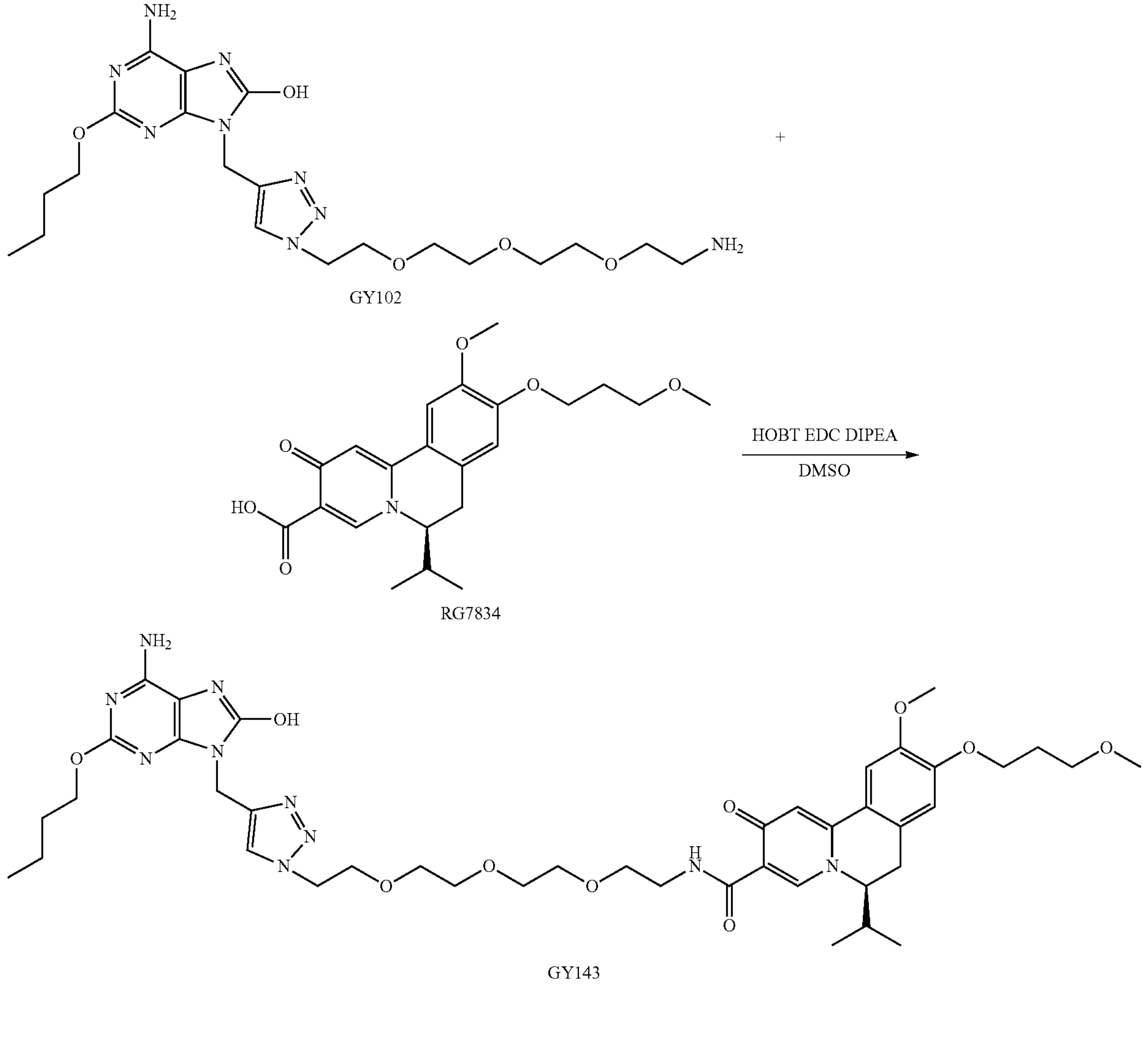

GY102

RG7834

GY143

26.5 mg of compound GY102, 20 mg of RG7834, 10 mg of HOBT, 14.7 mg of EDC, and 27 μL of DIPEA were dissolved in 500 μL of DMSO, and reacted overnight at room temperature. The reaction was monitored by an LC-MS. When the reaction was completed, a resulting reaction product was purified by an HPLC, such that 5.6 mg of compound GY143 in the form of a white solid having a yield of 13 wt. % was obtained. ESI-MS: m/z=863.2 $[M+H]^+$.

GY144

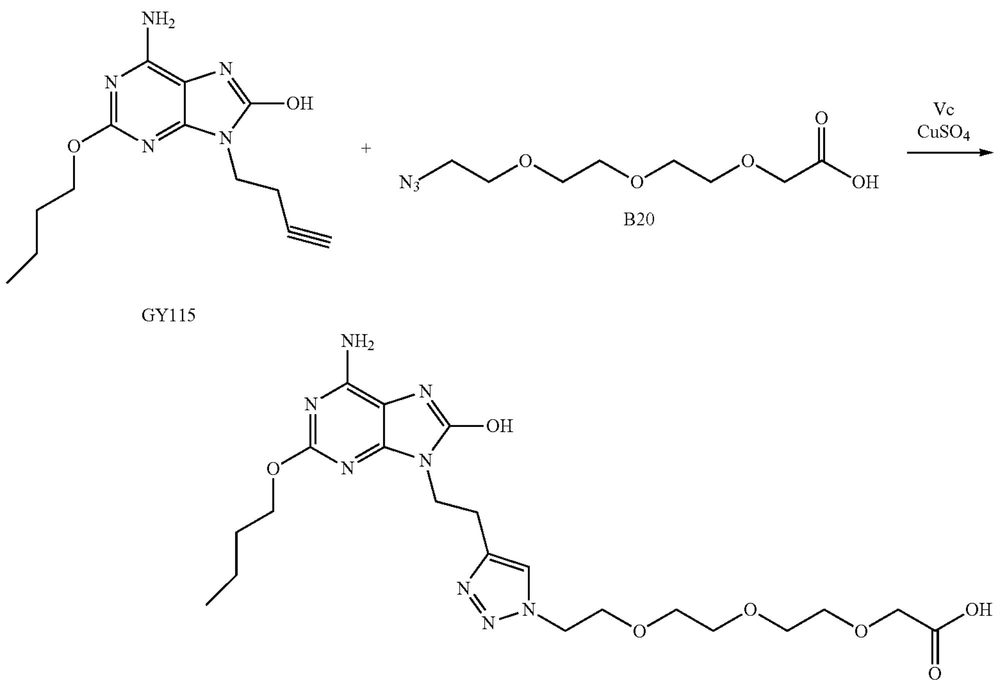

GY115

B20

GY144

27.5 mg of a crude compound GY115, 23.3 mg of B20, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, lyophilized, and 12.3 mg of compound GY144 in the form of a white solid having a yield of 24.1 wt. % was obtained. ESI-MS=509.1 $[M+H]^+$.

GY145

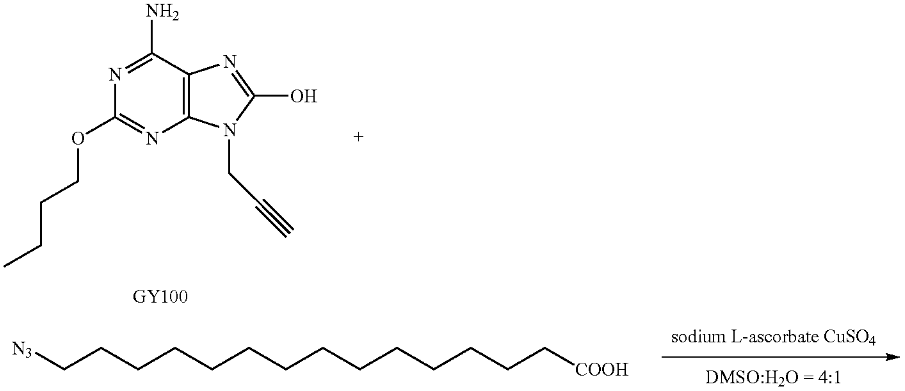

GY100

15-Azido-pentadecanoic acid

-continued

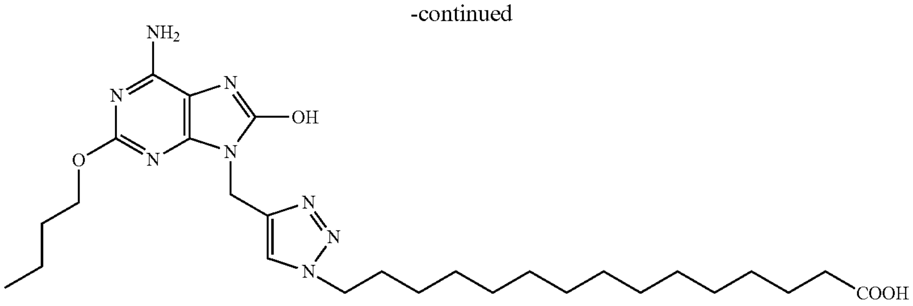

GY145

50 mg of compound GY100, 50 mg of 15-azido-pentadecanoic acid, 10 mg of sodium L-ascorbate, and 10 mg of $CuSO_4$ were dissolved in 200 μL of water+800 μL of DMSO, and reacted at room temperature for 5 hrs. The reaction was monitored by an LC-MS. When the reaction was completed, a resulting reaction product was purified by an HPLC, such that 15 mg of compound GY145 in the form of an of f-white solid having a yield of 15.6 wt. % was obtained. ESI-MS: m/z=545.2[M+H]$^+$.

GY146

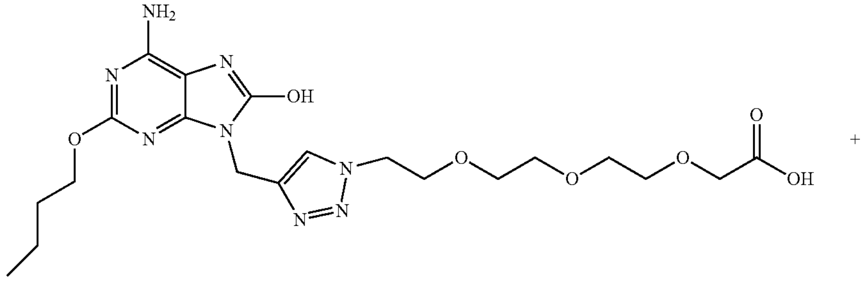

GY101

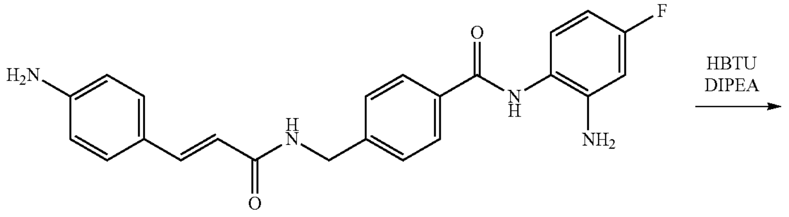

B21

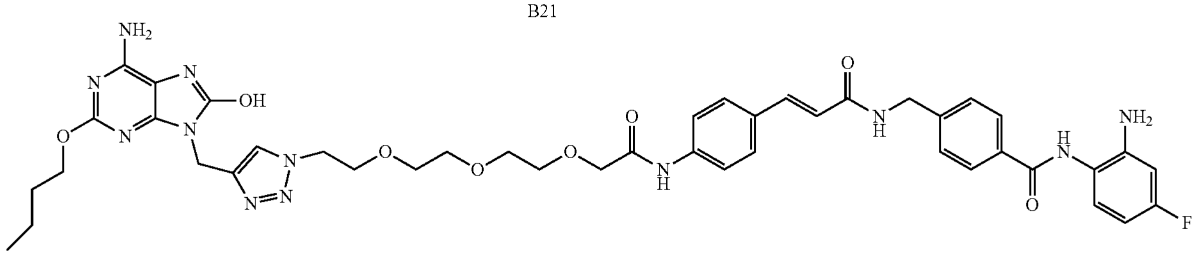

GY146

24.5 mg of compound GY101, 20.5 mg of B21, 22.7 mg of HBTU, and 19.3 mg of DIPEA were dissolved in 1 mL of DMSO, and reacted at room temperature for 4 hrs. The reaction was monitored by a TLC. When the reaction was completed, a resulting reaction product was purified by an HPLC, lyophilized, and 12.5 mg of compound GY146 in the form of a white solid having a yield of 28.2 wt. % was obtained. ESI-MS=881.2 [M+H]$^+$.

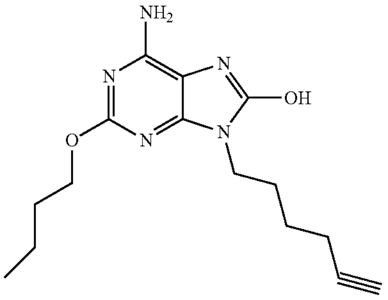

GY122

+

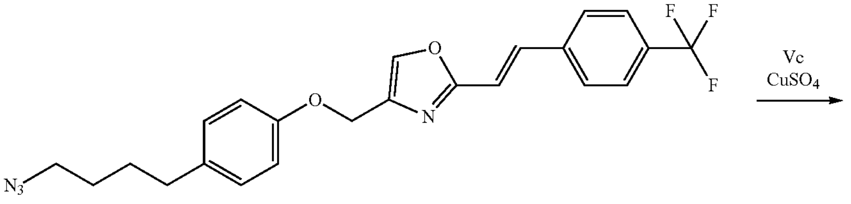

B22

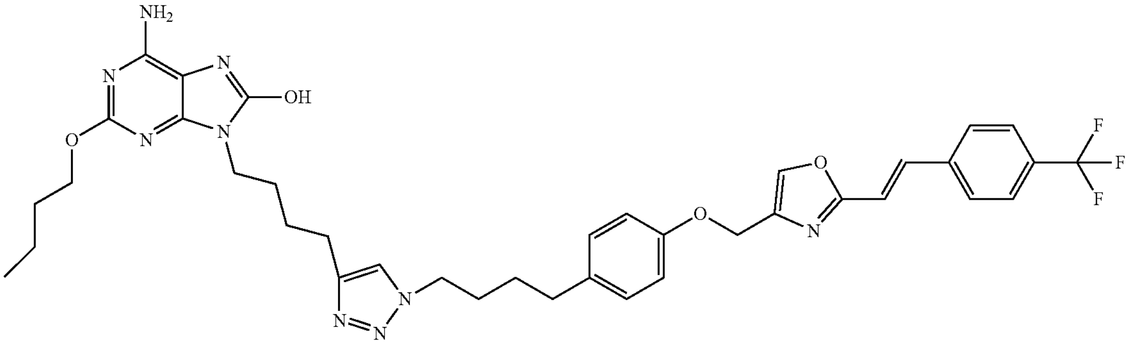

GY147

15.2 mg of compound GY122, 22.1 mg of compound B22, and a catalytic amount of $CuSO_4$ and sodium L-ascorbate were dissolved in 1 mL of a mixed solution of DMSO and $H_2O$ (DMSO: $H_2O$=4:1), and reacted at room temperature for 2 hrs. The reaction was monitored by TLC. When the reaction was completed, a resulting reaction product was purified by an HPLC, and lyophilized, such that 17.9 mg of compound GY147 in the form of a white solid having a yield of 48.1 wt. % was obtained. ESI-MS=746.3 $[M+H]^+$.

GY148

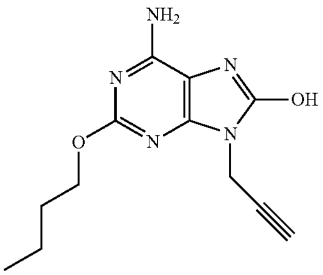

GY100

+

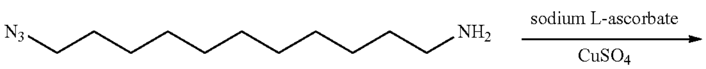

11-Azido-1-undecanamine

-continued

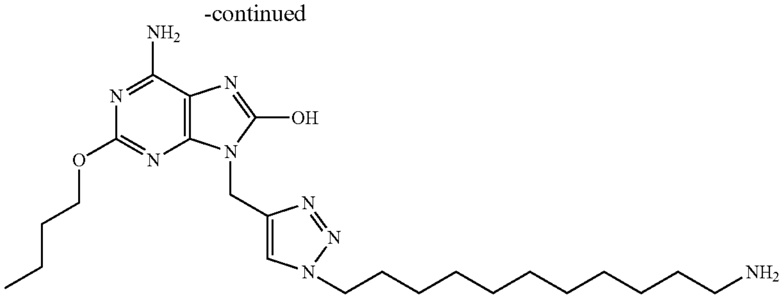

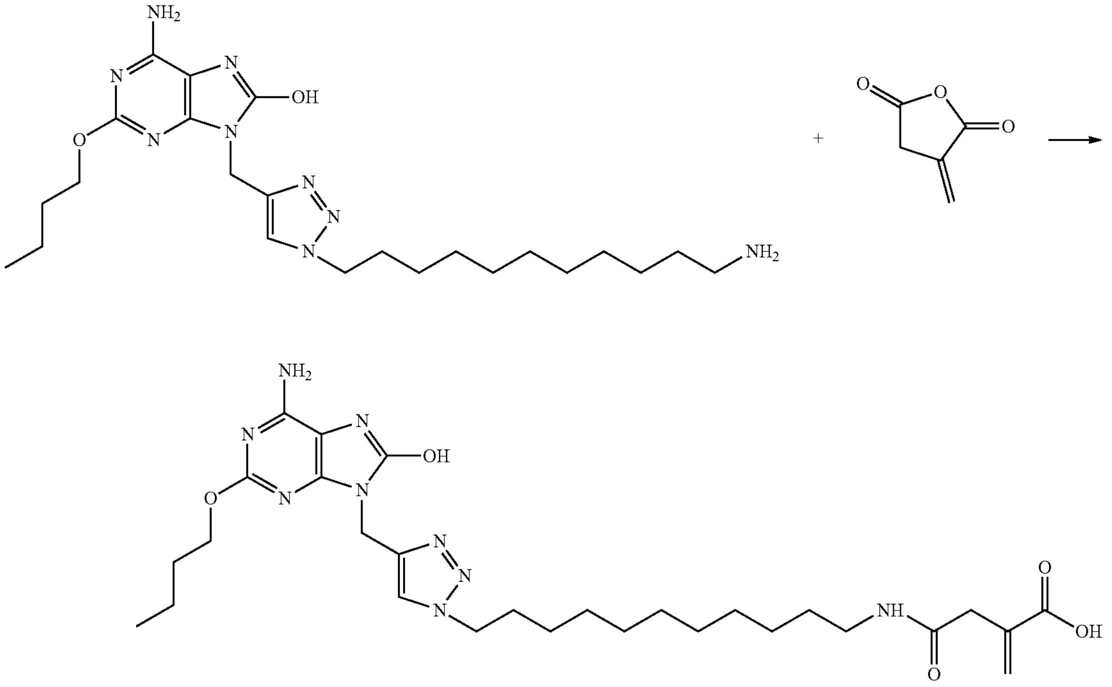

GY148

136 mg of compound GY100, 100 mg of 11-Azido-1-undecanamine, 20 mg of sodium L-ascorbate, and 10 mg of $CuSO_4$ were dissolved in 2 mL of DMSO+500 μL of $H_2O$, and reacted overnight at room temperature. The reaction was monitored by an LC-MS. When the reaction was completed 42 mg of itaconic anhydride was added, and stirred at room temperature for 3 hrs for next step reaction, which was monitored by the LC-MS. When the next step reaction was completed, a resulting reaction product was purified by HPLC, and 35 mg of compound GY148 in the form of a white solid having a yield of 11.5 wt. % was obtained. ESI-MS: m/z=586.2 $[M+H]^+$.

GY149

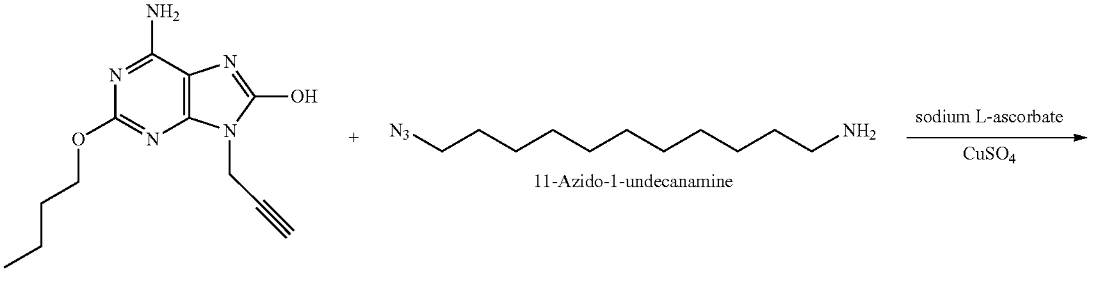

GY100

-continued

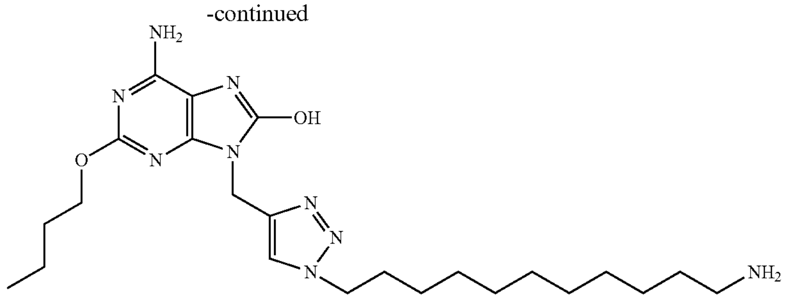

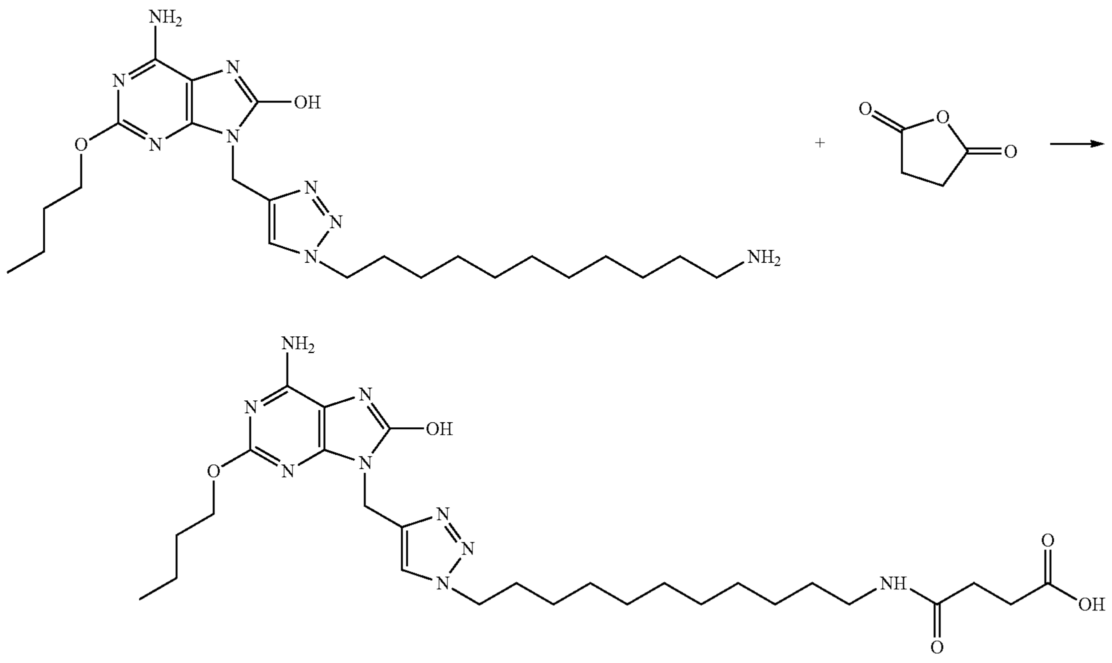

GY149

136 mg of compound GY100, 100 mg of 11-Azido-1-undecanamine, 20 mg of sodium L-ascorbate, and 10 mg of $CuSO_4$ were dissolved in 2 mL of DMSO+500 μL of $H_2O$, and reacted overnight at room temperature. The reaction was monitored by an LC-MC. When the reaction was completed, 38 mg of succinic anhydride was added and stirred at room temperature for 3 hrs for next step reaction, which was monitored by the LC-MS. When the reaction was completed, a resulting reaction product was purified by HPLC, and 45 mg of compound GY149 in the form of a white solid having a yield of 15.1 wt. % was obtained. ESI-MS: m/z=574.2 $[M+H]^+$.

GY150

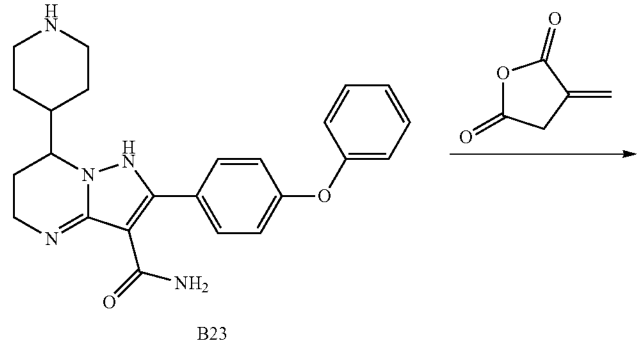

B23

-continued

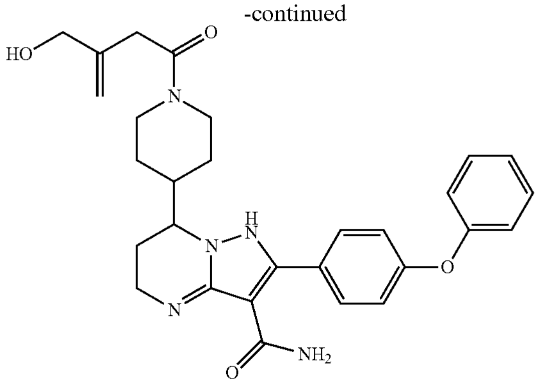

+

B24

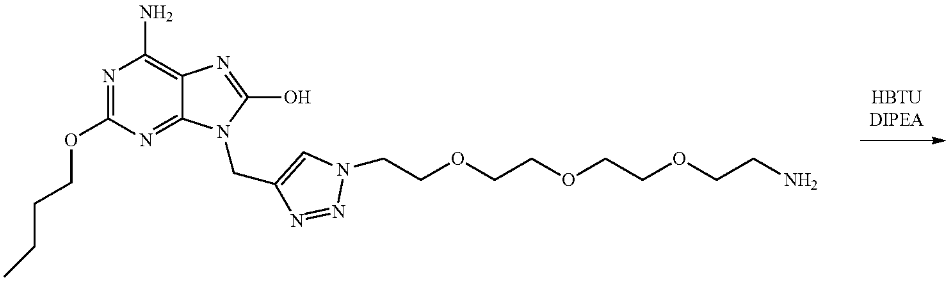

GY102

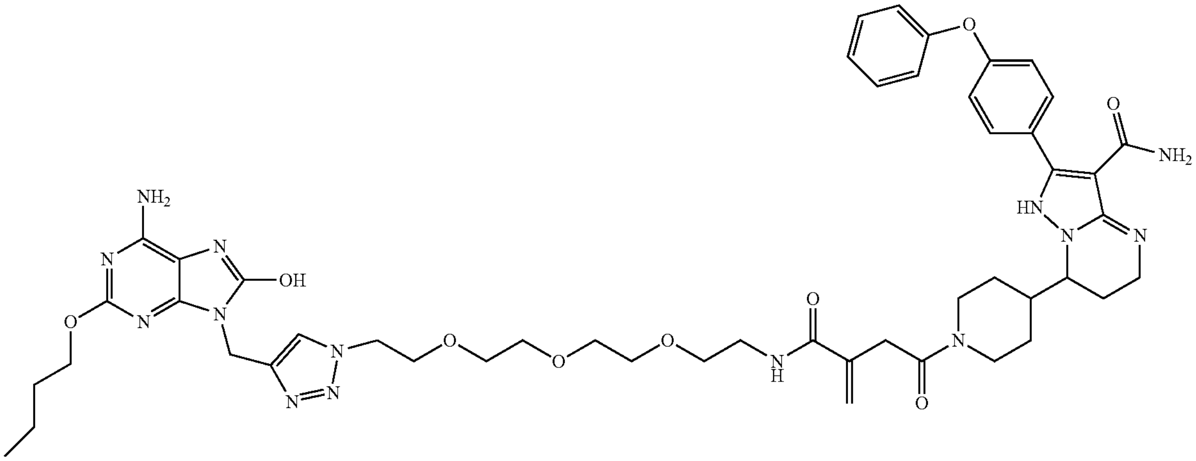

GY150

16.7 mg of B23 (Zanubrutinib intermediate in an S-configuration), 5.1 mg of itaconic anhydride, and 6.1 mg of triethylamine were dissolved in 1 mL of DMSO, and reacted at room temperature for 2 hrs. The reaction was monitored by TLC. When the reaction was completed, 19.2 mg of GY102, 18.2 mg of HBTU, and 10.3 mg of DIPEA were added for next step reaction for 4 hrs. A resulting reaction product was purified by HPLC, and lyophilized, such that 10.6 mg of compound GY150 in the form of a white solid having a yield of 26.7 wt. % was obtained. ESI-MS=992.1 $[M+H]^+$.

GY151

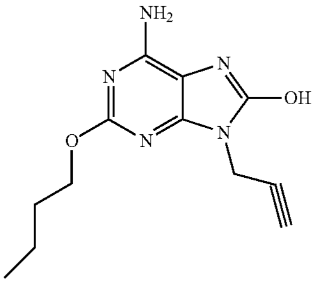

+

GY100

-continued

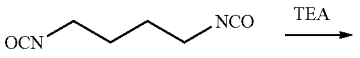

B25

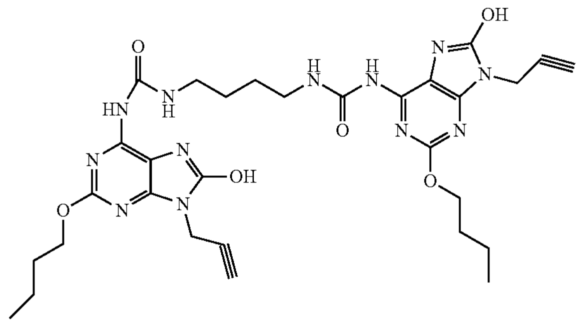

GY151

26.2 mg of compound GY100, 7 mg of B25, and 10.1 mg of triethylamine were dissolved in 1 mL of DMSO, and reacted at room temperature for 4 hrs. The reaction was monitored by a TLC. When the reaction was completed, a resulting reaction product was purified by an HPLC, and lyophilized, such that 15.3 mg of compound GY151 in the form of a white solid having a yield of 23.1 wt. % was obtained. ESI-MS=664.1 [M+H]+.

GY152

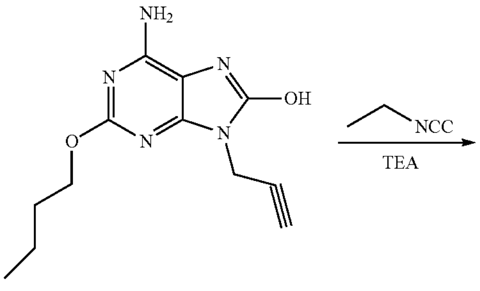

GY100

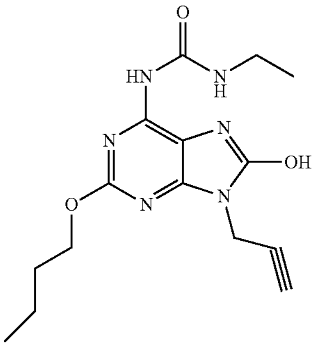

GY152

26.2 mg of compound GY100, 8.4 mg of isocyanate, and 10.1 mg of triethylamine were dissolved in 1 mL of DMSO, and reacted at room temperature for 4 hrs. The reaction was monitored by a TLC. When the reaction was completed, a resulting reaction product was purified by an HPLC, and lyophilized, such that 13.2 mg of compound GY152 in the form of a white solid having a yield of 39.6 wt. % was obtained. ESI-MS=333.1 [M+H]+.

GY153

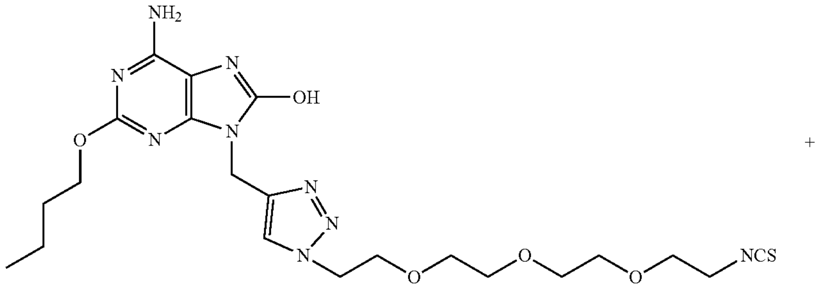

GY106

-continued

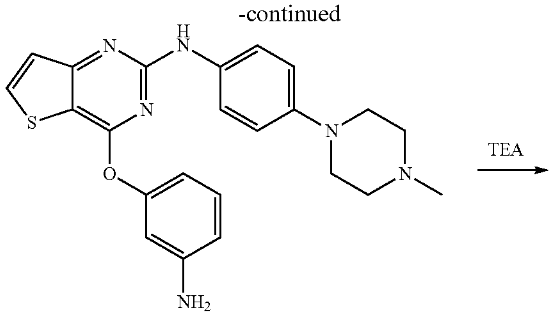

Olmutinib

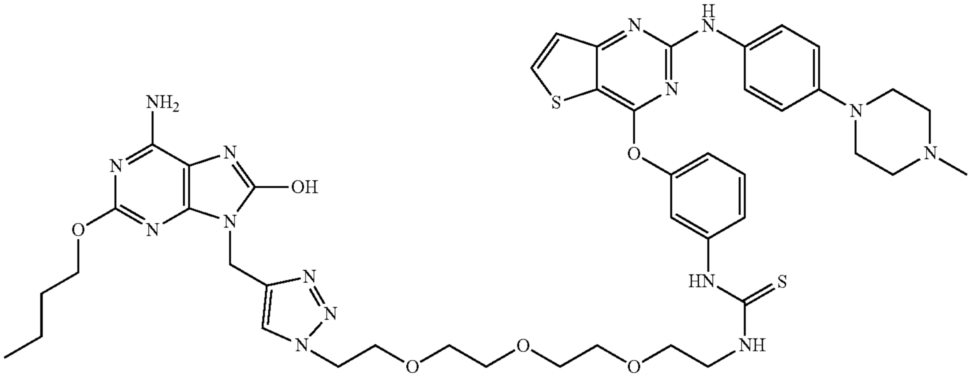

GY153

40 mg of compound GY106, 30 mg of an Olmutinib intermediate, and 20 μL of TEA were dissolved in 500 μL of DMSO, and reacted overnight at room temperature. The reaction was monitored by an LC-MS. When the reaction was completed, a resulting reaction product was purified by an HPLC, such that 8.3 mg of compound GY153 in the form of an of f-white solid having a yield of 12.5 wt. % was obtained. ESI-MS: m/z=954.1 $[M+H]^+$.

GY155

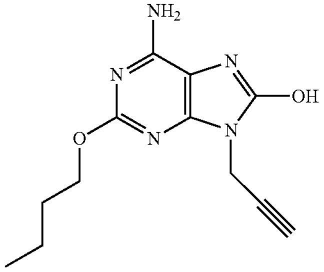

GY100

+

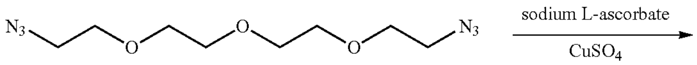

12a

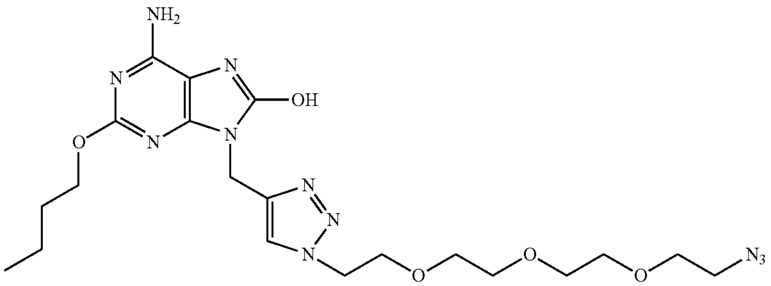

GY165

50 mg of compound GY100, 42 mg of 12a, 4 mg of sodium L-ascorbate, and 4 mg of $CuSO_4$ were dissolved in 500 μL of DMSO+100 μL of $H_2O$, reacted overnight at room temperature. The reaction was monitored by an LC-MC. When the reaction was completed, a resulting reaction product was purified by an HPLC, such that 25 mg of compound GY155 in the form of a white solid having a yield of 28.7 wt. % was obtained. ESI-MS: m/z=506.1 [M+H]

GY156

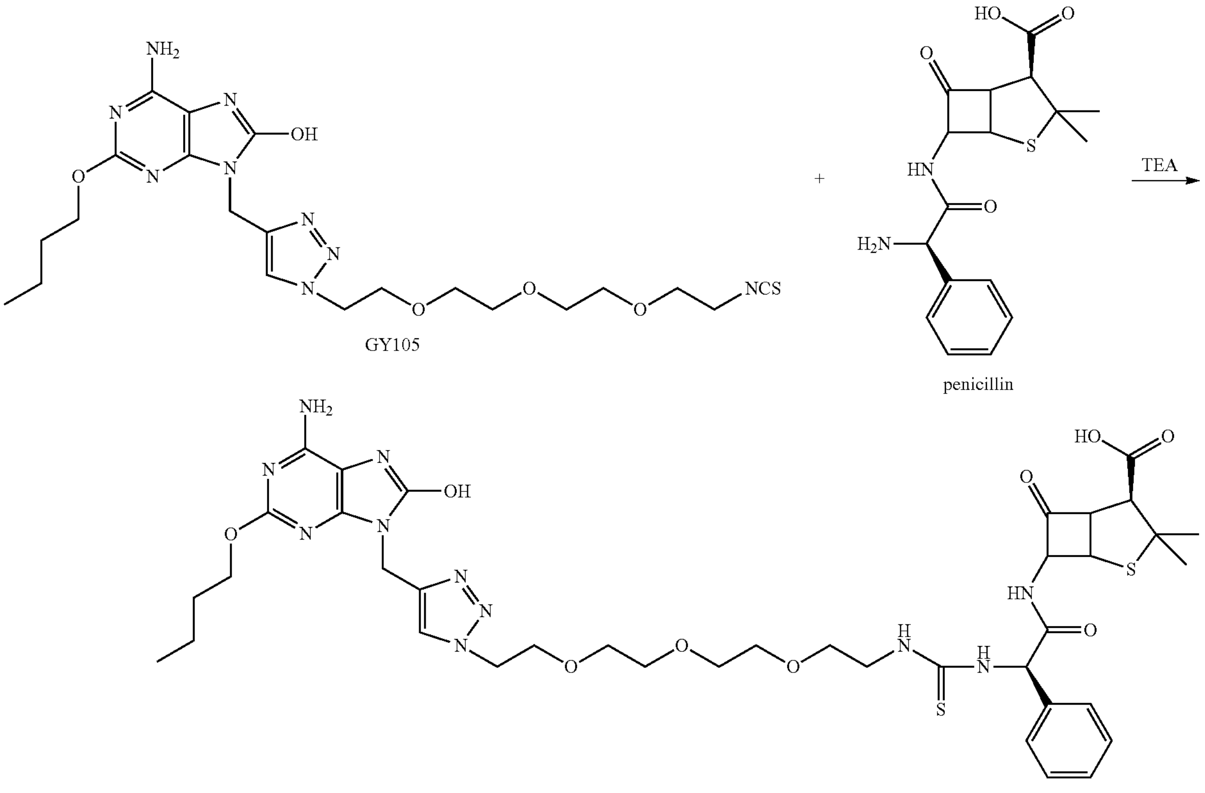

GY105 + penicillin → GY156

30 mg of compound GY106, 22 mg of penicillin, and 20 μL of TEA were dissolved in 500 μL of DMSO, and reacted overnight at room temperature. The reaction was monitored by an LC-MS. When the reaction was completed, a resulting reaction product was purified by an HPLC, such that 5 mg of compound GY156 in the form of a light yellow solid having a yield of 10 wt. % was obtained. ESI-MS: m/z=871.1 $[M+H]^+$.

GY157

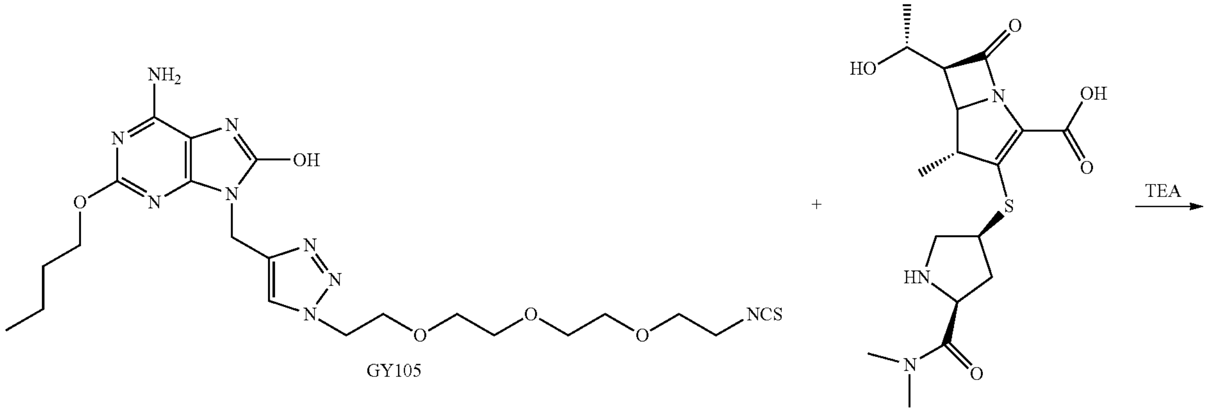

GY105 + Meropenem

-continued

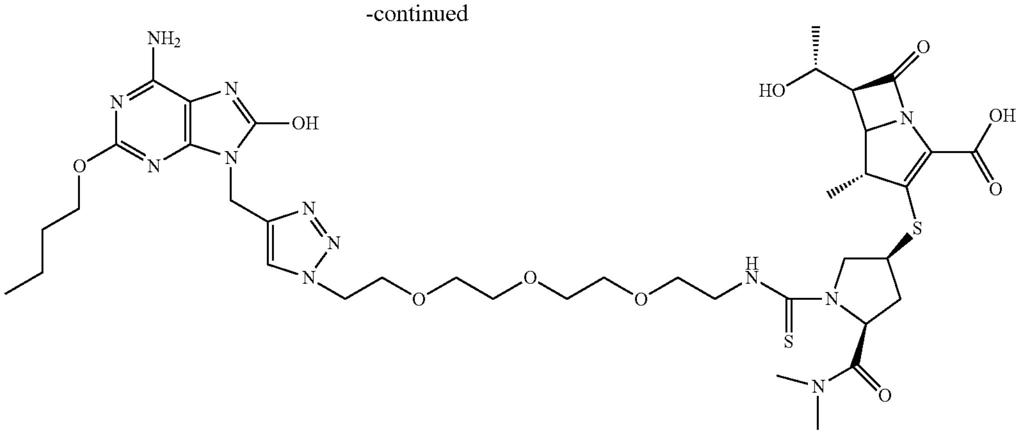

GY157

30 mg of compound GY106, 24 mg of Meropenem, and 20 μL of TEA were dissolved in 500 μL of DMSO, and reacted overnight at room temperature. The reaction was monitored by an LC-MS. When the reaction was completed, a resulting reaction product was purified by an HPLC, such that 8.5 mg of compound GY157 in the form of a light yellow solid having a yield of 16.3 wt. % was obtained. ESI-MS: m/z=905.1 $[M+H]^+$.

GY158

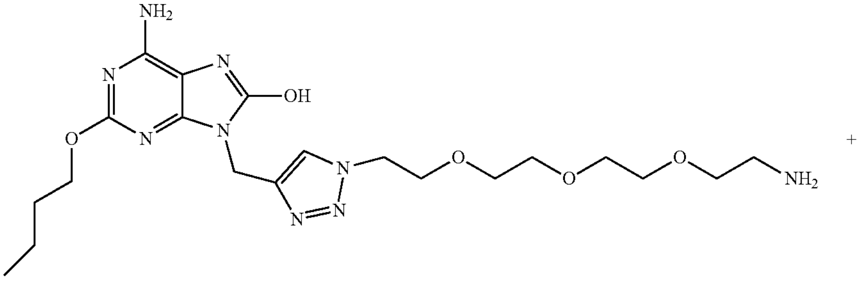

GY102

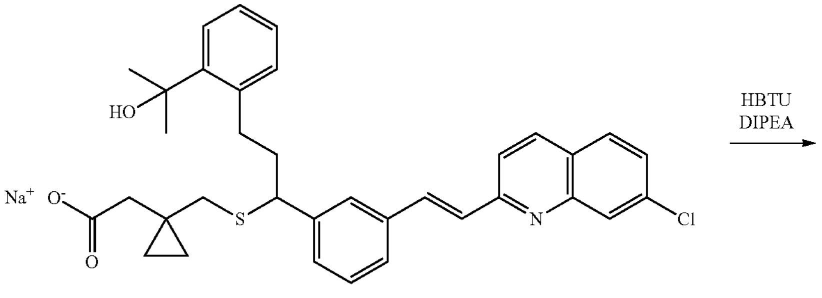

B26

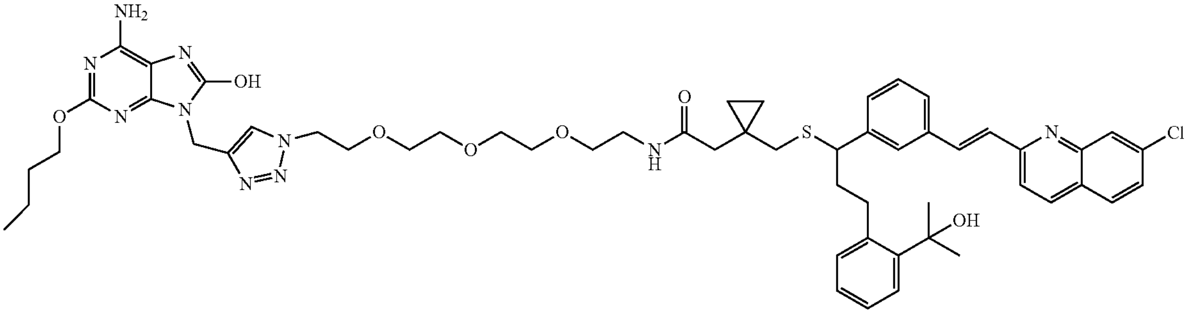

GY158

24 mg of compound GY102, 30.4 mg of b26 (montelukast sodium), 22.7 mg of HBTU, and 19.3 mg of DIPEA were dissolved in 1 mL of DMSO, and reacted at room temperature for 4 hrs. The reaction was monitored by a TLC. When the reaction was completed, a resulting reaction product was purified by an HPLC, and lyophilized, such that 15.5 mg of compound GY158 in the form of a white solid having a yield of 39.4 wt. % was obtained. ESI-MS=1048.1 [M+H]$^+$.

GY159

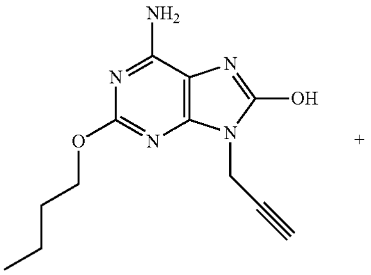

GY100

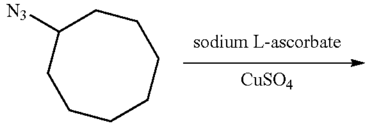

13a

-continued

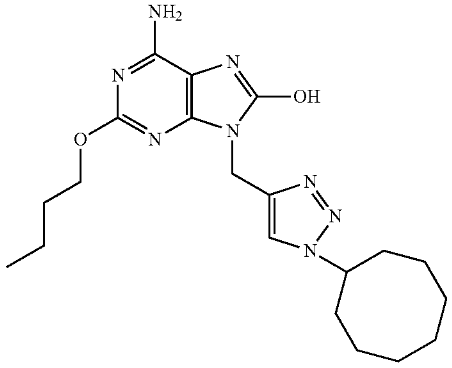

GY159

51 mg of compound GY100, 30 mg of 13a, 4 mg of sodium L-ascorbate, and 4 mg of $CuSO_4$ were dissolved in 500 μL of DMSO+100 μL of $H_2O$, and reacted overnight at room temperature. The reaction was monitored by an LC-MC. When the reaction was completed, a resulting reaction product was purified by HPLC, such that 20 mg of compound GY159 in the form of a white solid having a yield of 24.7 wt. % was obtained. ESI-MS: m/z=415.1 [M+H]

GY160

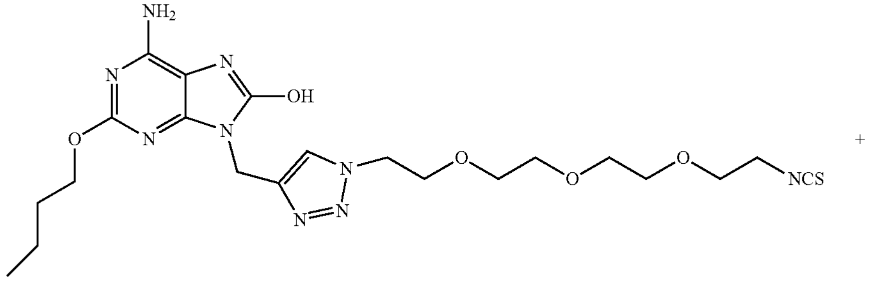

GY106

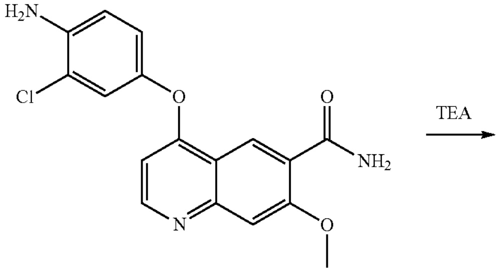

B27

-continued

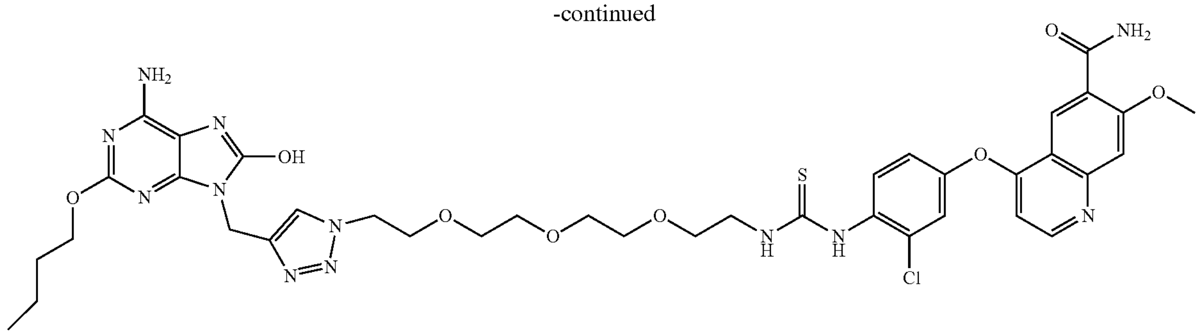

GY160

26 mg of compound GY106, 17.2 mg of B27 (lenvatinib intermediate), and 10.1 mg of triethylamine were dissolved in 1 mL of DMSO, and reacted at room temperature for 4 hrs. The reaction was monitored by a TLC. When the reaction was completed, a resulting reaction product was purified by an HPLC, and lyophilized, such that 18.2 mg of compound GY160 in the form of a white solid having a yield of 42.1 wt. % was obtained. ESI-MS=865.1 $[M+H]^+$.

GY161

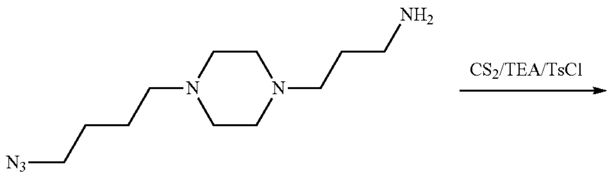

PIP-1

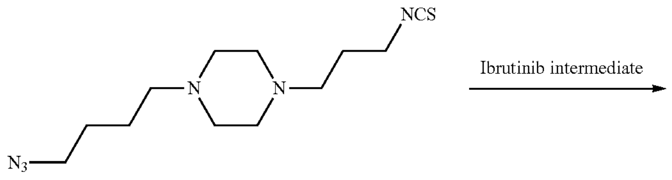

PIP-2

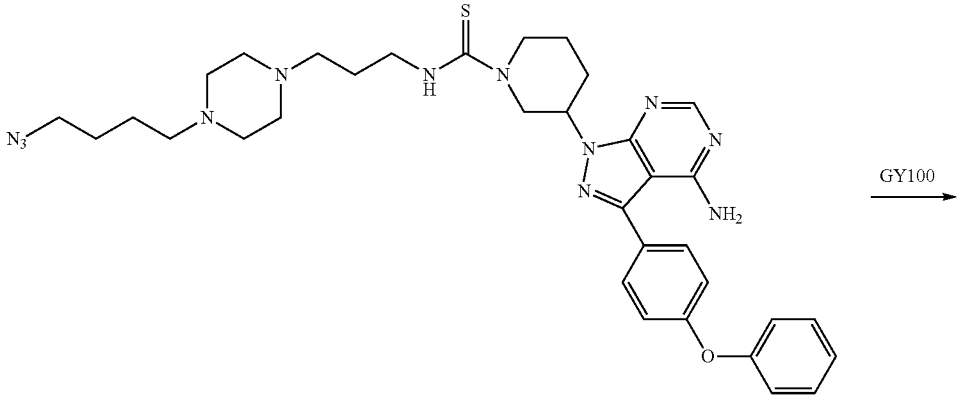

PIP-3

-continued

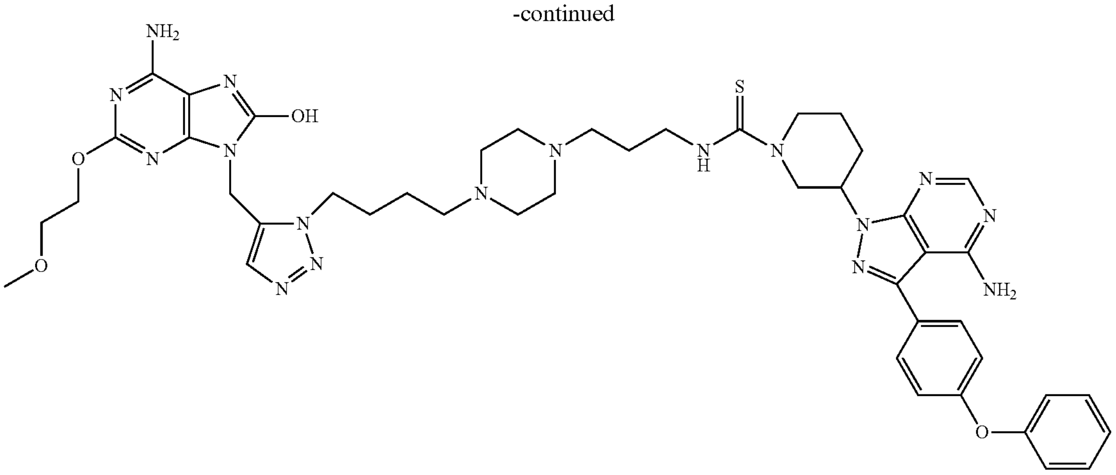

GY161

1) 100 mg of compound PIP-1, 95.2 mg of $CS_2$, and 174 μL of TEA were dissolved in 1 mL of DMF, and reacted overnight at room temperature. Thereafter, 87.2 mg of TsCl was added for reaction at room temperature for 5 hrs. The reaction was monitored by an LC-MS. When the reaction was completed, a resulting reaction product was purified by an HPLC, and 42 mg of compound PIP-2 having a yield of 36 wt. % was obtained. ESI-MS: m/z=283.1 $[M+H]^+$.
2) 40 mg of compound PIP-2 and 54 mg of Ibrutinib intermediate were dissolved in 2 mL of DMSO, 100 μL of TEA were then added, and stirred at room temperature for 12 hrs. When the reaction was completed, a resulting reaction product was purified by the HPLC to obtain 62 mg of compound PIP-3 having a yield of 66 wt. %.
3) 60 mg of compound PIP-3 and 25 mg of GY100 were dissolved in 60 μL of water+250 μL of DMSO, and 5 mg of sodium L-ascorbate and 5 mg of $CuSO_4$ were added for reaction at room temperature for 8 hrs. A resulting reaction product was purified by an HPLC to obtain 64 mg of compound GY161 in the form of a white solid having a yield of 77 wt. %. ESI-MS: m/z=931.2 $[M+H]^+$.

Second Synthesis Scheme for Synthesis of GY161 and Synthesis of GY178

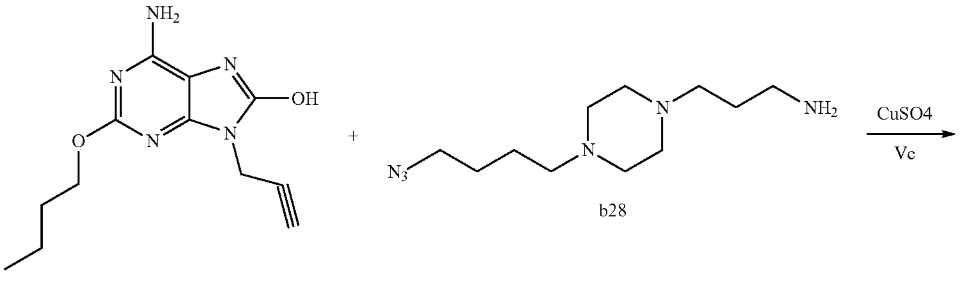

GY100 b28

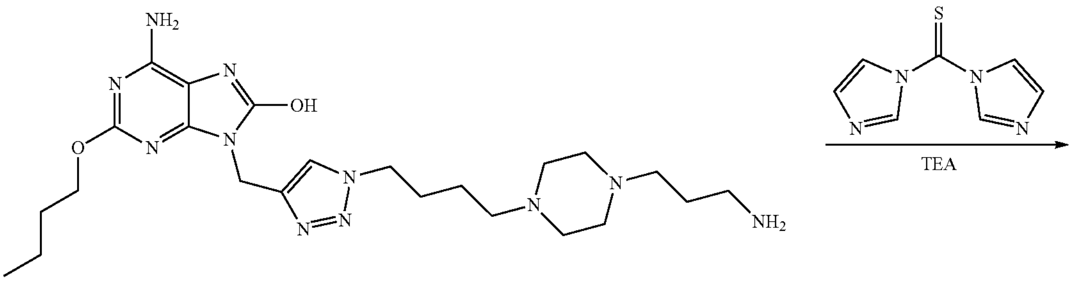

b29

-continued

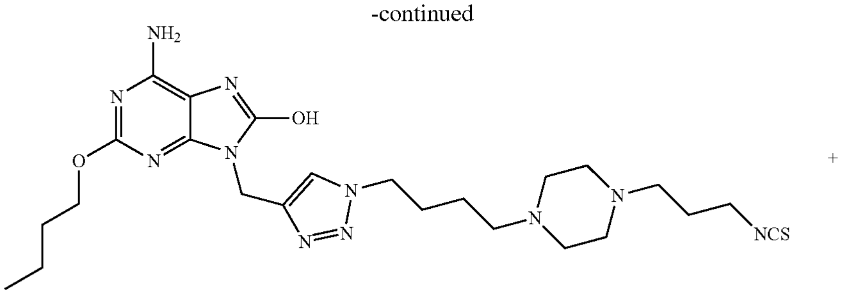

GY178

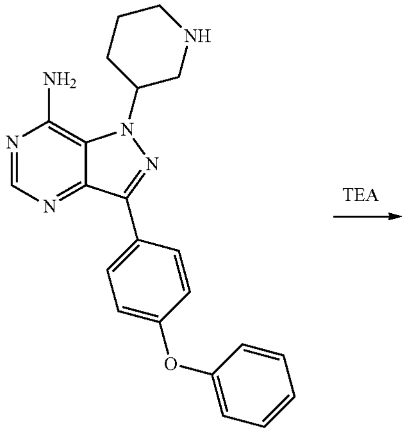

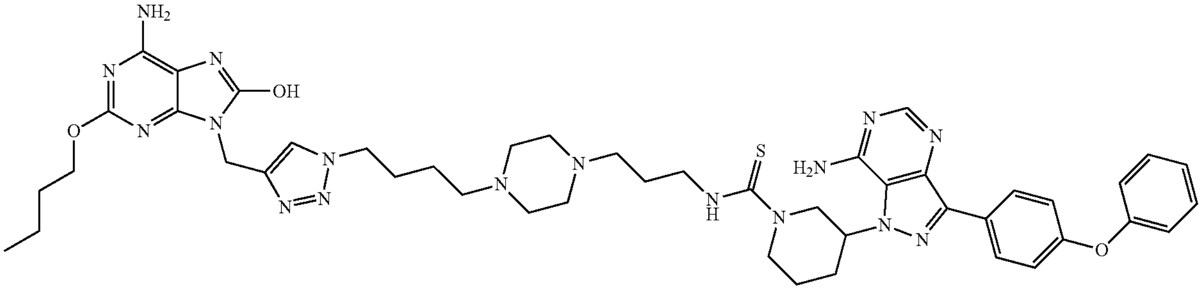

GY161

26.2 mg of GY100 and 24.1 mg of b28 were dissolved in 1 mL of a solvent (DMSO: $H_2O$=4:1), a catalytic amount of copper sulfate and sodium ascorbate were added, for carrying out reaction at room temperature for 2 hrs. After the reaction, a resulting reaction product was lyophilized and a crude b29 was obtained for use.

The obtained crude b29 was dissolved in DMSO, and 25.7 mg (1.5 eq) of thiocarbonyldiimidazole and 20.2 mg (2 eq) of trimethylamine were added, a resulting mixture was stirred at room temperature for 16 hrs. When the reaction was completed, a resulting product was lyophilized to obtain crude GY178, which was purified by an HPLC to obtain a pure GY178. The molecular weight of the pure GY178 measured by a mass spectrometry was ESI-MS: m/z=544.1.

The obtained pure GY178 was dissolved in DMSO, which was added with 38.6 mg of Ibrutinib intermediate, and stirred at room temperature for 4 hrs fore reaction. A resulting reaction product was purified by an HPLC, and lyophilized, such that 30.4 mg of GY161 in the form of white powder having a yield of 29.8 wt. % was obtained, ESI-MS: m/z=931.3.

GY162

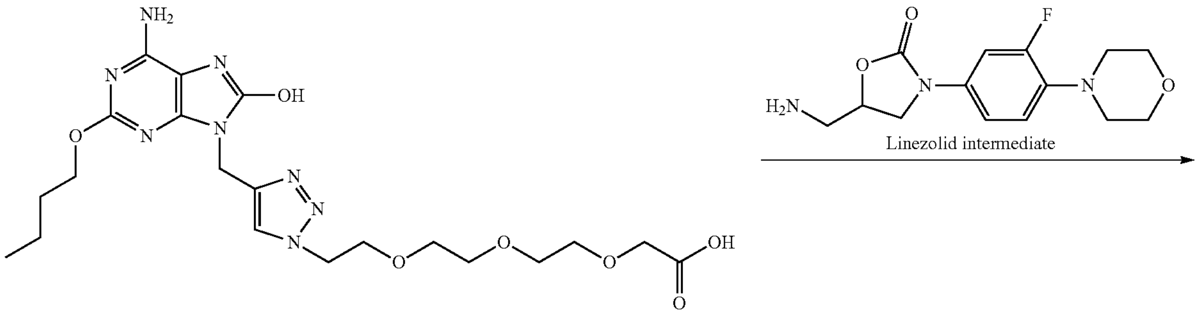

GY101

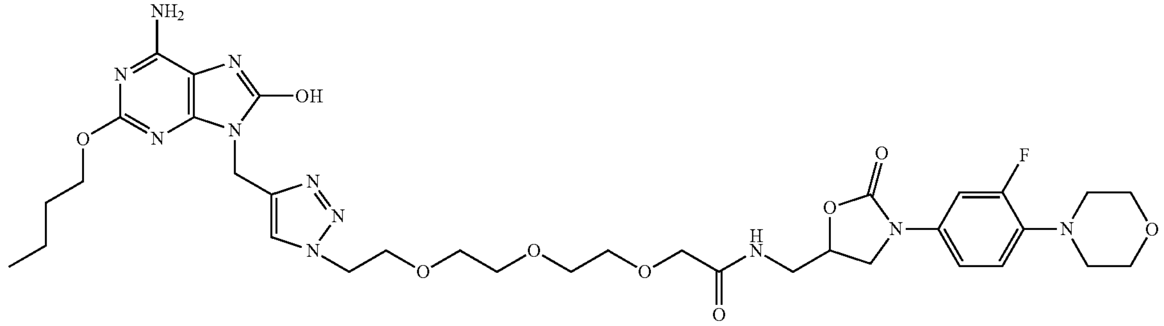

GY162

Compound GY101 and a Linezolid intermediate were mixed in a dry DMSO at a molar ratio of 1:1, and equimolar amounts of HOBT, EDC and DIPEA were added to the dry DMSO, and reacted overnight at room temperature. The reaction was monitored by an LC-MS. When the reaction was completed, a resulting reaction product was purified by an HPLC, such that the compound GY162 in the form of a white solid having a yield of 39.3 wt. % was obtained. ESI-MS: m/z=772.2 $[M+H]^+$.

GY163

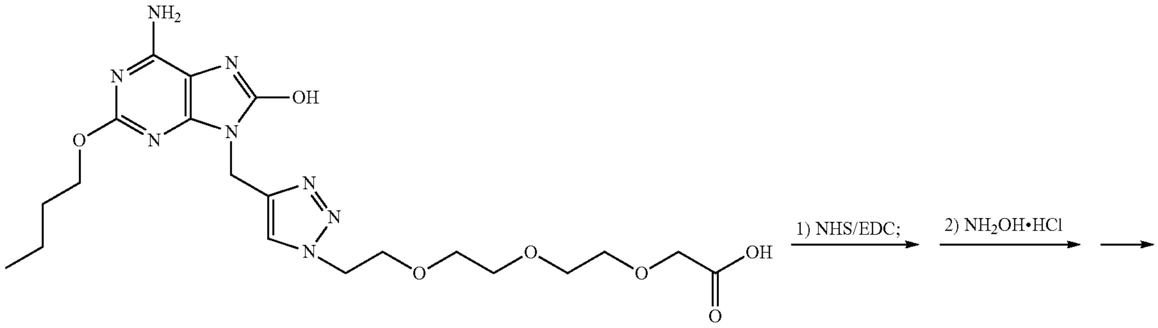

GY101

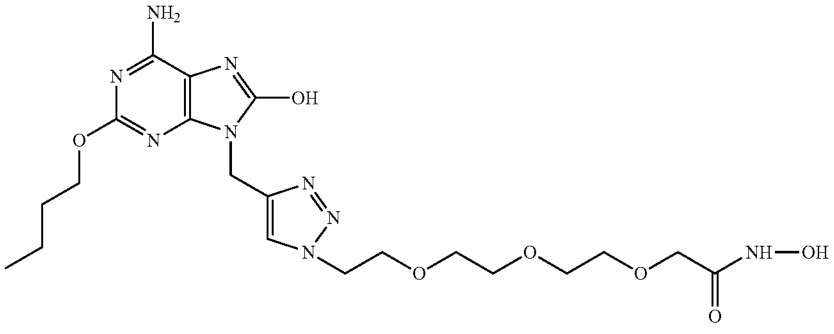

GY163

Compound GY101 was dissolved in an appropriate amount of a dry DMSO, equimolar amounts of NHS and EDC were added, and a resulting mixture was stirred at room temperature for 4 hrs. Then an equimolar amount of $NH_2OH$ and 2 times mole of TEA were added, and a reaction mixture was stirred overnight at room temperature. After the reaction was completed, the reaction mixture was added with an equal volume of water and mixed uniformly, purified by an HPLC, such that compound GY163 having a yield of 47 wt. % was obtained. ESI-MS: m/z=510.2 $[M+H]^+$.

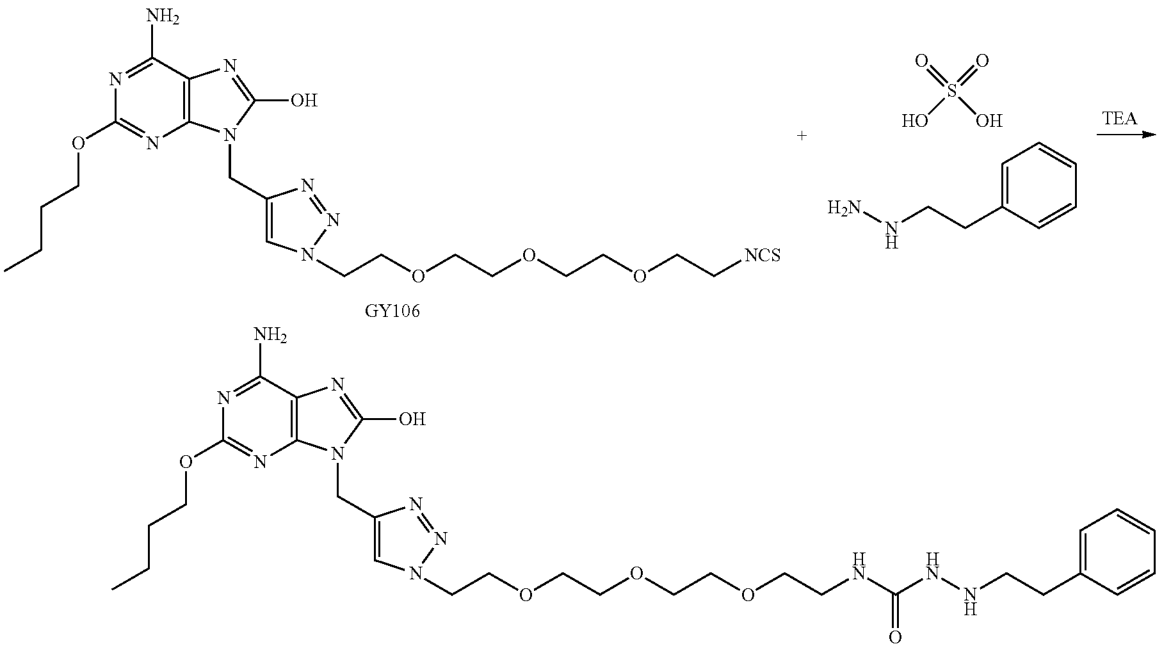

GY106

GY164

Compound GY106 and an equimolar amount of phenelzine sulfate were mixed and added into DMF, 2 times mole of TEA was then added, and stirred overnight at room temperature. After the reaction, an equal volume of water was added, and a resulting mixture was uniformly mixed, purified by HPLC, such that compound GY164 having a yield of 73 wt. % was obtained. ESI-MS: m/z=658.6 $[M+H]^+$.

GY165

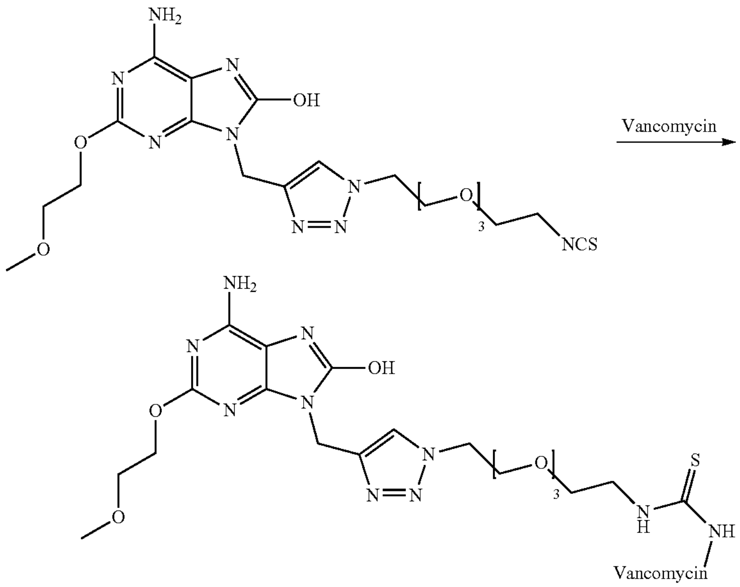

The synthesis scheme of compound GY165 was the same as that of compound GY164, and the yield of compound GY165 was 43 wt. %. ESI-MS: m/z=985/[M+H]$^+$(1/2).

GY166

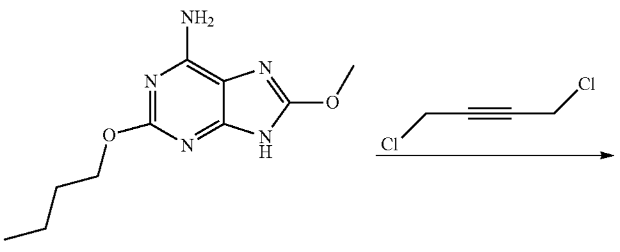

1a

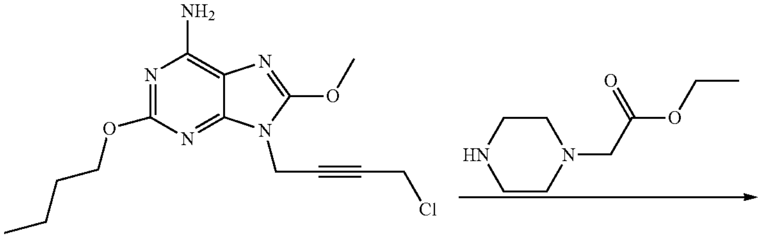

b29

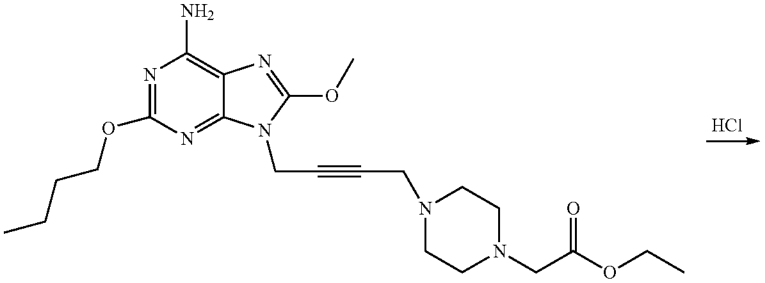

b30

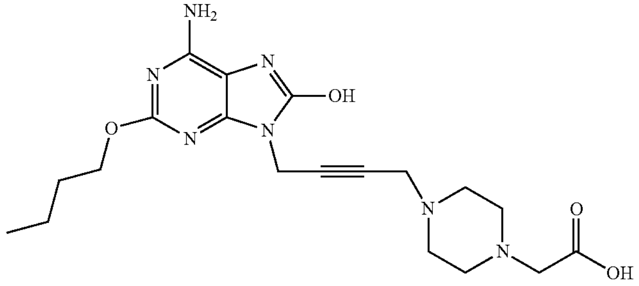

GY166

An appropriate amount of compound 1a was dissolved in an appropriate amount of DMF, an equal amount of $K_2CO_3$ and 1,4-dichlorobutyne was added, and heated at 40° C. and stirred for 6 hrs. Thereafter, equal amounts of $K_2CO_3$ and N-ethyl acetate piperazine were added to the reaction system. The reaction system was continued to be stirred for another 6 hrs, filtered to remove $K_2CO_3$, and evaporate under a reduced pressure for dryness, so as to obtain a crude compound b30. After that, the crude compound b30 was dissolved in a concentrated hydrochloric acid, stirred at room temperature, the reaction was monitored by an LC-MS. After the reaction, a resulting product was evaporated under a reduced pressure for dryness, and then dissolved with DMSO, and purified by HPLC, such that compound GY-166 having a yield of 32.4 wt. % was obtained. ESI-MS: m/z=418.4 [M+H]$^+$.

GY 167

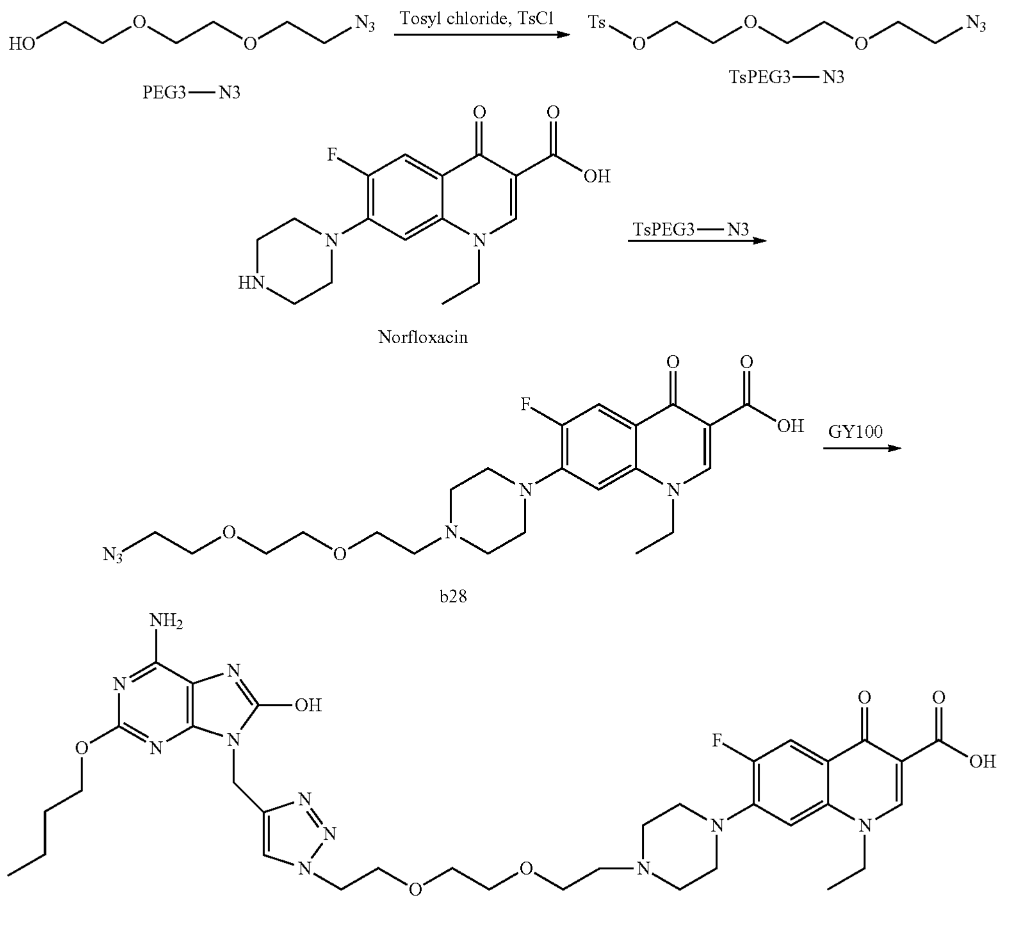

PEG3—N3

TsPEG3—N3

Norfloxacin b28

GY167

1 eq of PEG3-$N_3$ and 1.1 eq of TSCl were dissolved in an appropriate amount of a dry DMF, and stirred at room temperature for 6 hrs, to obtain TsPEG3-$N_3$. The obtained product was directly added to 1.1 eq of Norfloxacin, and stirred overnight at room temperature. After the reaction, an appropriate amount of water was added, so as to precipitate a product, the product was performed with suction filtration, and then dried to obtain compound b28. 1 eq of compound b28, 1.1 eq compound GY100, a small amount of sodium L-ascorbate, and small amount of $CuSO_4$ were dissolved in a solvent of DMSO: $H_2O$ (with a volume ratio of 4:1), and stirred overnight at room temperature. The completion of the reaction was detected by a mass spectrometry. A resulting reaction product was purified by an HPLC, such that a compound GY167 having a yield of 35 wt. % was obtained. ESI-MS: m/z=738.1 [M+H]$^+$.

GY168

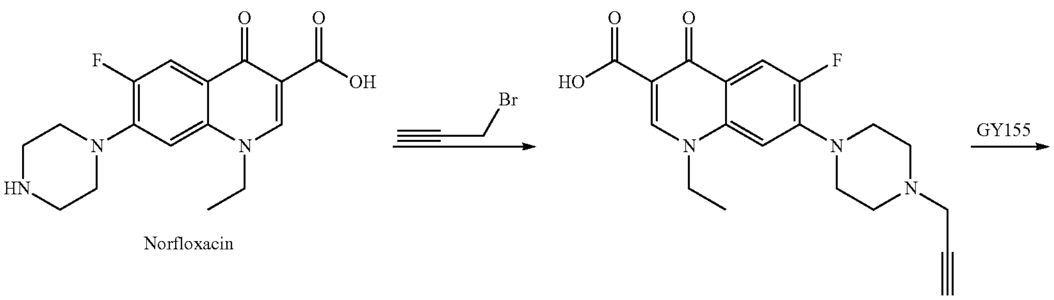

Norfloxacin

-continued

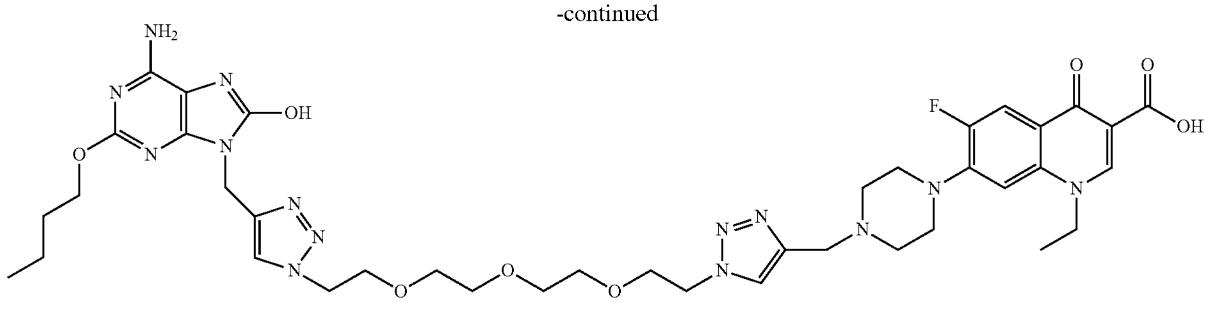

GY168

320 mg of Norfloxacin and 120 mg of 3-bromopropyne were dissolved in 5 mL of DMSO, and added with a trace amount of $K_2CO_3$, a resulting mixture was stirred at room temperature for 12 hrs until the reaction was completed. After that, 1 mL of water, 505 mg of compound GY155, a trace amount of sodium L-ascorbate, and a trace amount of copper sulfate were added to the mixture, which was continued to be stirred for reaction for hrs. A resulting reaction product was separated and purified by an HPLC, such that compound GY168 having a yield of 62 wt. % was obtained. ESI-MS: m/z=863.7 $[M+H]^+$.

GY169

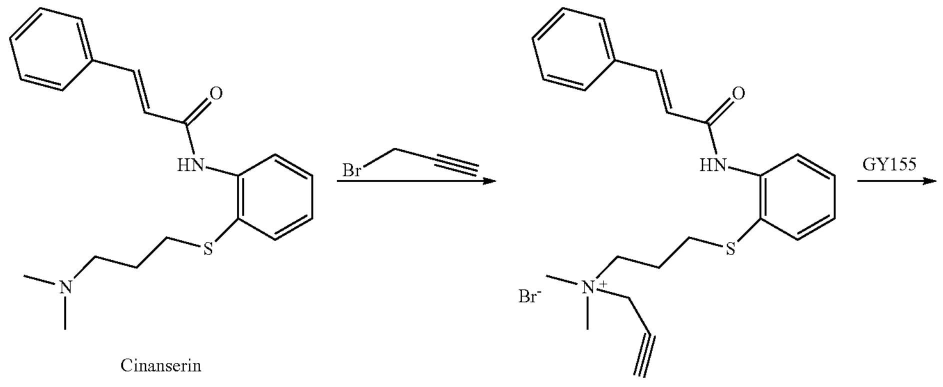

Cinanserin

Bromide

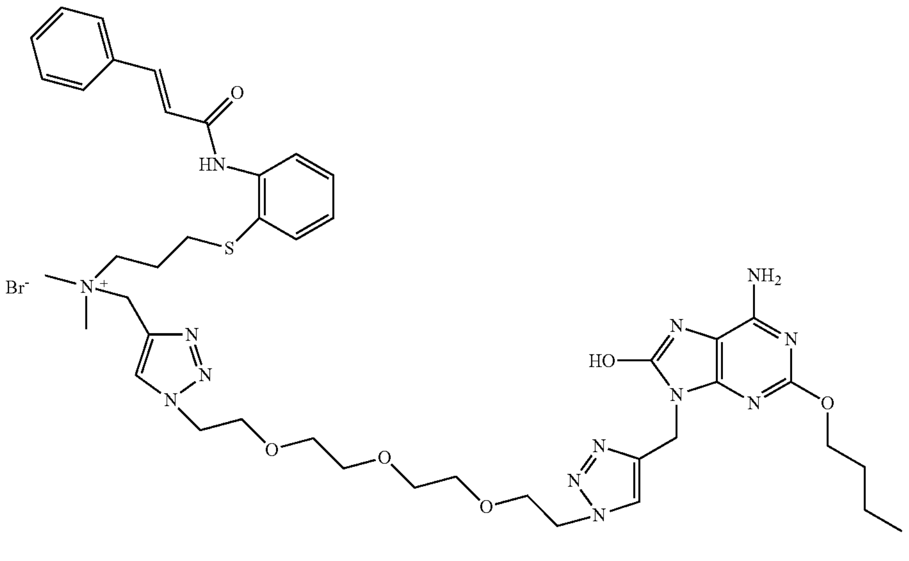

GY169

70 mg of cinnamon thiamine hydrochloride (Cinanserin) and 30 mg of $K_2CO_3$ were dissolved in 5 mL of DMF, an equimolar amount of 3-bromopropyne was added, a resulting mixture was stirred overnight at 40° C. After that, 1 mL of water, 95 mg of compound GY155, a trace amount of sodium L-ascorbate, and a trace amount of copper sulfate were added to a resulting reaction mixture, which was stirred for 12 hrs for reaction. A resulting reaction product was separated and purified by an HPLC, such that compound GY169 having a yield of 28 wt. % was obtained. ESI-MS: m/z=885.5 $[M+H]^+$.

GY170

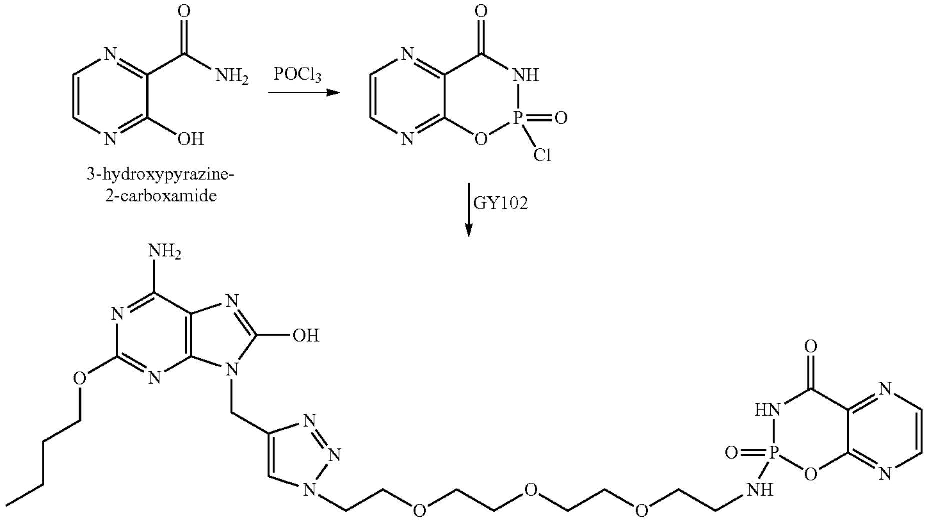

GY170

3-hydroxypyrazine-2-carboxamide was dissolved in dry chloroform, cooled to 0° C. and then added with an equimolar amount of phosphorus oxychloride, to enable a resulting mixture to react naturally under a dry and anhydrous condition for 12 hrs. After that, a solvent was evaporated under a reduced pressure, and a residue was dissolved in dry chloroform. 3 times mole of dry triethylamine, followed by an equimolar amount of compound GY102 was added to form a mixture. The mixture was stirred at room temperature for 12 hrs until the reaction was completed. Thereafter, a solvent was evaporated under a reduced pressure, and a residue was separated and purified by an HPLC, such that compound GY170 in the form of an of f-white solid having a total yield of 49 wt. % was obtained. ESI-MS: m/z=663.3 $[M+H]^+$.

GY171

Synthesis method of compound GY171 was the same as that of compound GY170 except that 3-hydroxypyrazine-2-carboxamide was replaced by 6-fluoro-3-hydroxypyrazine-2-carboxamide (Favipiravir), so as to obtain compound GY171. ESI-MS: m/z=681.6$[M+H]^+$.

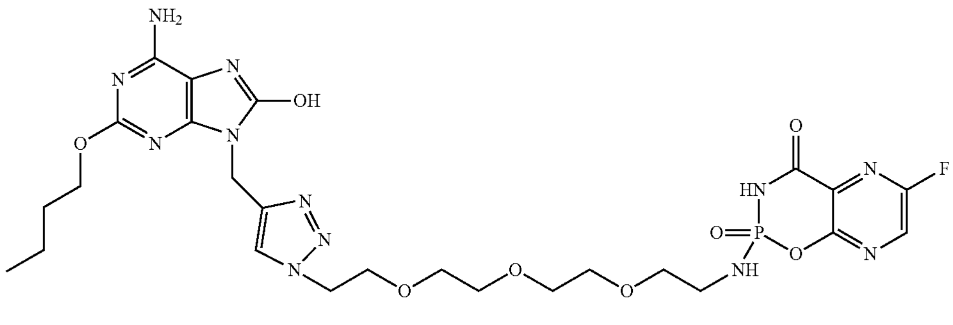

GY171

GY172
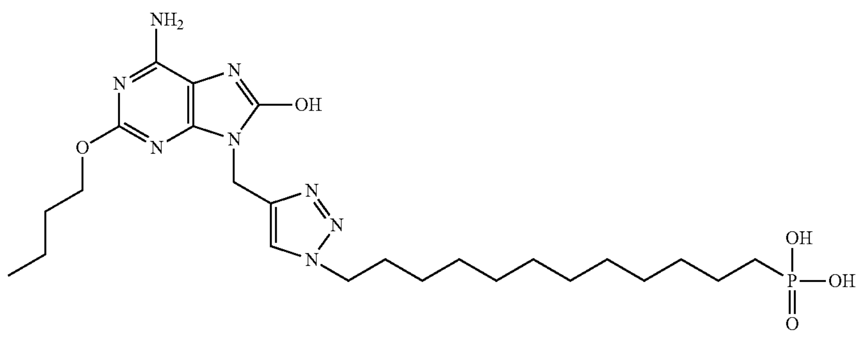
GY103
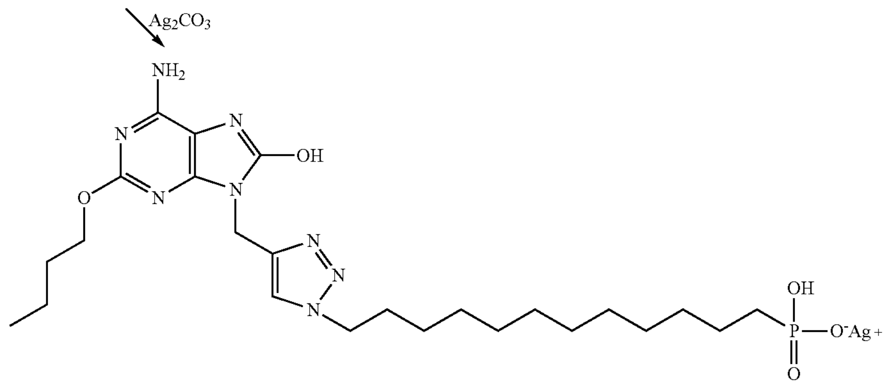
GY103-Ag
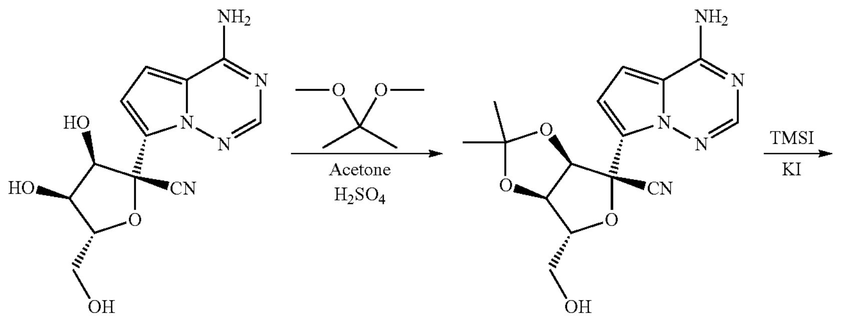
GS-441524
GS-441524-1
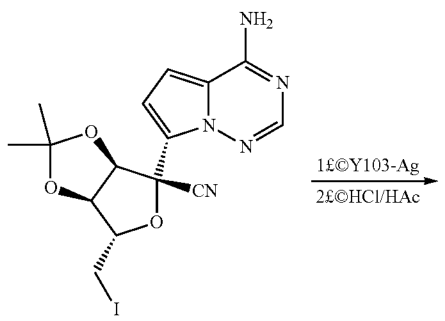
GS-441524-2

-continued

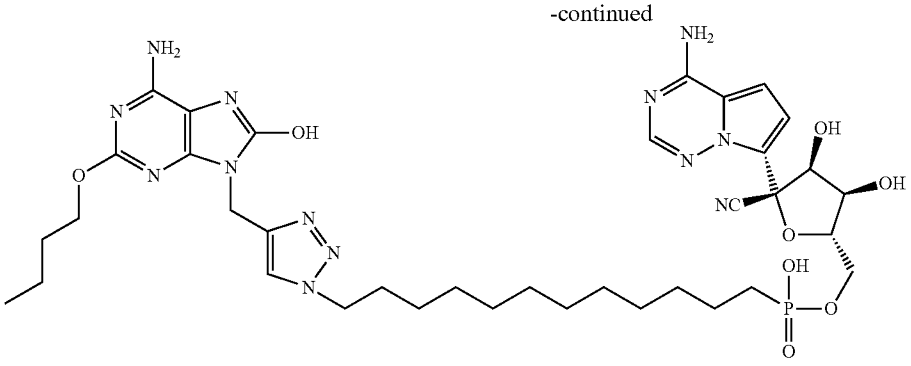

GY172

Under an anhydrous condition, 1 g of compound GS-441524 (Remdesivir prodrug), 0.5 g of 2,2-dimethoxy-propane, and 20 mL of acetone were mixed, stirred while cooling to 0° C. 1 mL of concentrated sulfuric acid in 5 mL of acetone solution was slowly dropped to a resulting solution. A process temperature was lower than 15° C. A resulting reaction mixture was continued to be stirred naturally for 10 hrs. After the reaction was complete, a saturated $Na_2CO_3$ solution was adopted to neutralize a pH value of the reaction solution to be 7. A solvent was removed by evaporation under a reduced pressure. And then a remaining solid was extracted by chloroform for three times. After that, chloroform was removed by evaporation under a reduced pressure, such that 0.6 g of compound GS-441524-1 was obtained. ESI-MS: m/z=332.3[M+H]$^+$.

0.5 g of compound GS-441524-1 was mixed with 20 mL of anhydrous acetonitrile, an equimolar amount of trimethylsilyl iodide and KI were added. A resulting mixture was stirred at room temperature for 1 hr, and reacted at 40° C. for 3 hrs. A solvent was evaporated under a reduced pressure to obtain a solid. The obtained solid was extracted 3 times with ethyl acetate, the extracts were combined, and a solvent was evaporated under a reduced pressure to obtain 0.33 g of compound GS-441524-2 in the form of a light yellow solid. ESI-MS: m/z=442.1[M+H]$^+$.

0.2 g of compound GS-441524-2 was added to 10 mL of acetonitrile, then 0.3 g of compound GY103-Ag was added. A resulting mixture was refluxed for 12 hrs in the dark, then cooled to room temperature, and filtered to obtain a clear filtrate. The filtrate was evaporated under a reduced pressure to remove a solvent. After that, a residue was dissolved in 10 mL of 1:1 mixture of THF and concentrated hydrochloric acid, and stirred at 60° C. for 1 hr, evaporated under a reduced pressure to remove a solvent, and a resulting residue was added with a small amount of pure water. Thereafter, a resulting product was separated and purified by an HPLC to obtain 0.12 g of compound GY172 in the form of an of f-white solid, ESI-MS: m/z=826.5[M+H]$^+$.

GY173 and GY174

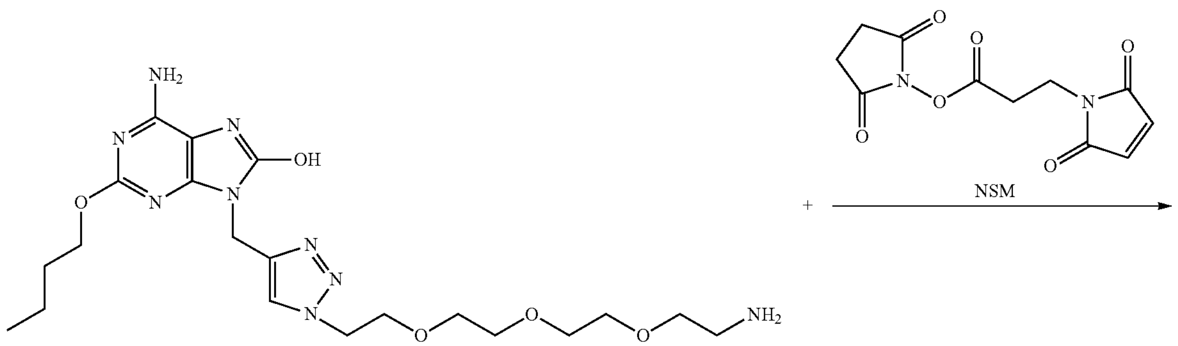

GY102

-continued

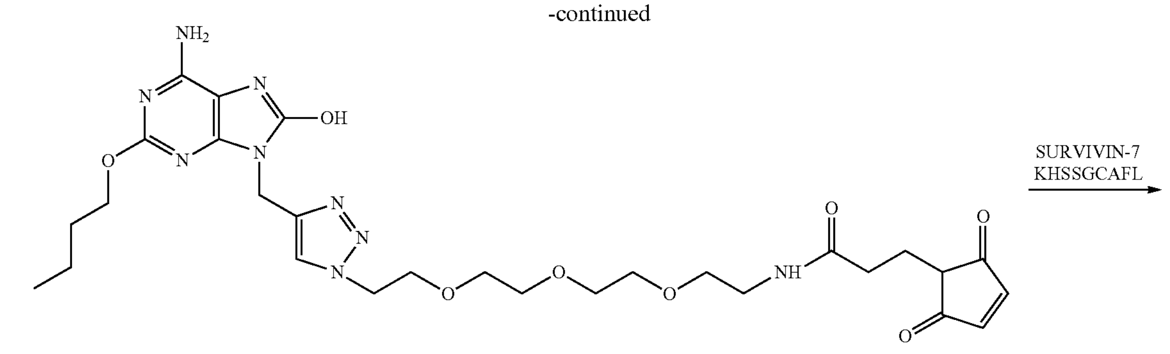

GY173

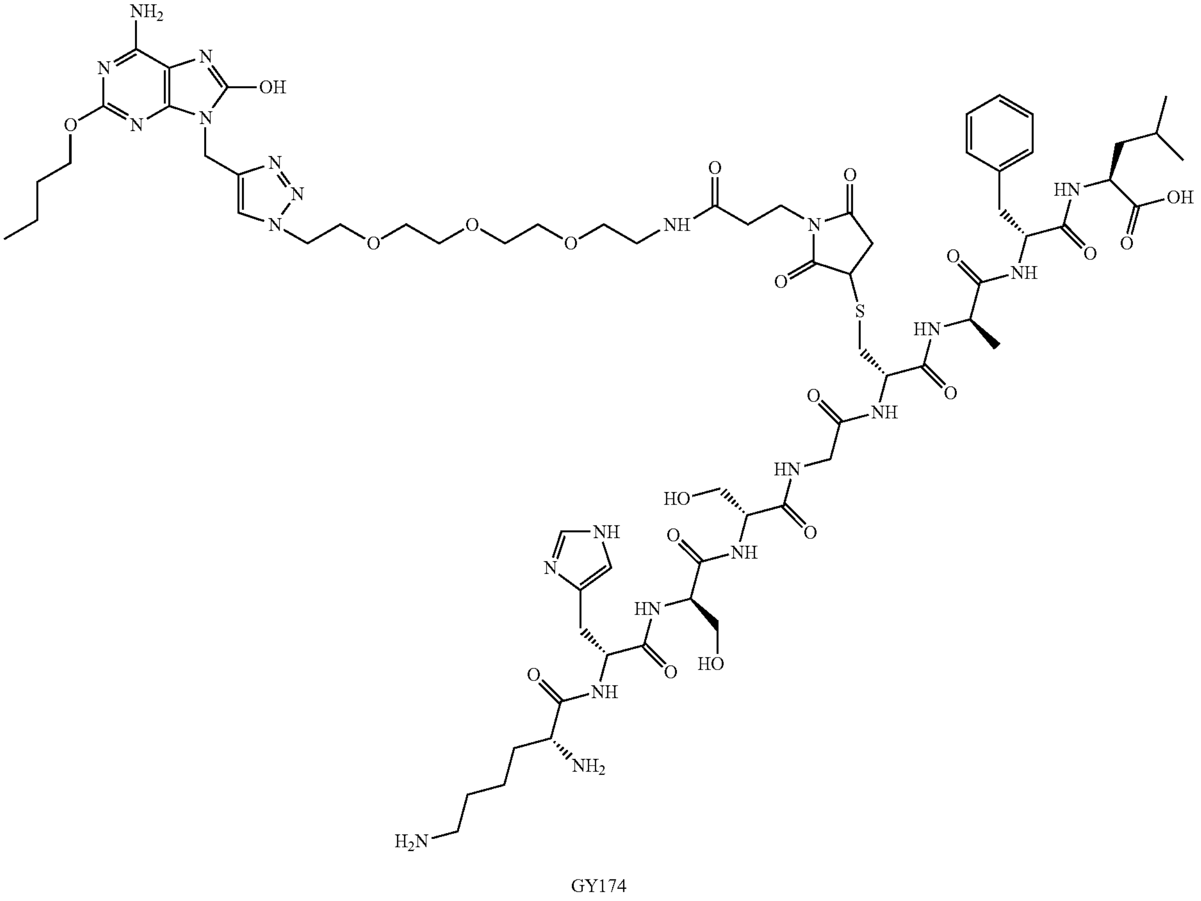

GY174

20 mg of compound GY102 and 12 mg of NSM were mixed into 1 mL of a dry DMSO solvent, a resulting mixture was stirred at 10° C. for reaction for 1 hr, then stirred at natural room temperature for reaction for 10 hrs. A resulting reaction solution was directly separated and purified by an HPLC, such that 6 mg of compound GY173 in the form of a white solid was obtained. ESI-MS: m/z=631.1[M+H]$^+$.

3.3 mg of compound GY173 and 5 mg of SURVIVIN-7 were mixed into 1 mL of DMSO. The resulting mixture was stirred at room temperature for 4 hrs. The reaction solution was directly separated and purified by an HPLC, such that 1.2 mg of compound GY174 having a yield of 14.6 wt. % was obtained. ESI-MS: m/z=790.7 (1/2) M$^+$.

GY175

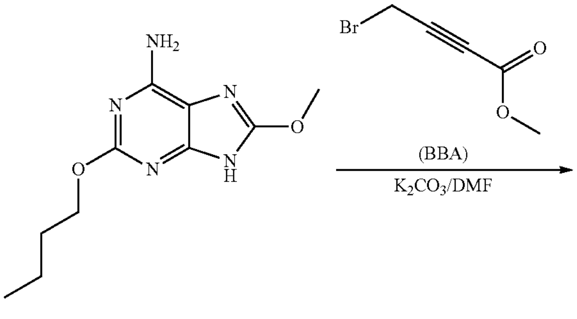

1a

-continued

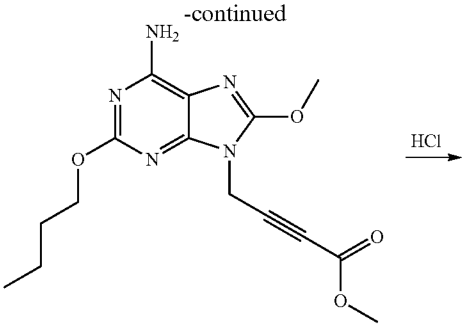

BBA-1a

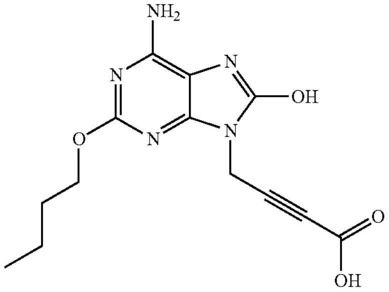

GY175

100 mg of compound 1a and 75 mg of methyl 4-bromobutynoate (BBA) was mixed into 5 mL of DMF, a small amount of $K_2CO_3$ was added, and a resulting mixture was stirred at room temperature for 12 hrs. A substantially completed consumption of the raw material was detected by a mass spectrometry. Solvent was removed by evaporation under a reduced pressure (60° C. below), and a residue (crude BBA-1a) was cooled at 5° C. 10 mL of concentrated hydrochloric acid was slowly added, and stirred overnight at room temperature. A resulting reaction product was evaporated under a reduced pressure (60° C. below) to remove a solvent, a residue was added with 5 mL of water, and NaCO3 was adopted to adjust the pH value to be 8. A resulting solution was directly separated and purified by HPLC, and then lyophilized, such that 72 mg of GY175 in the form of a colorless solid was obtained, ESI-MS=306.5 $[M+H]^+$.

GY176

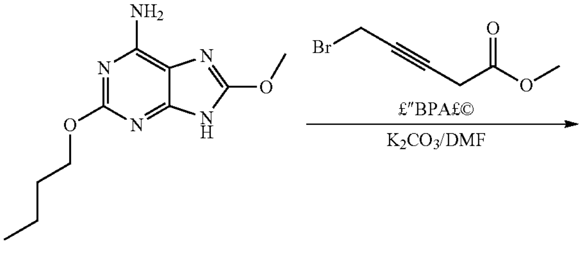

1a

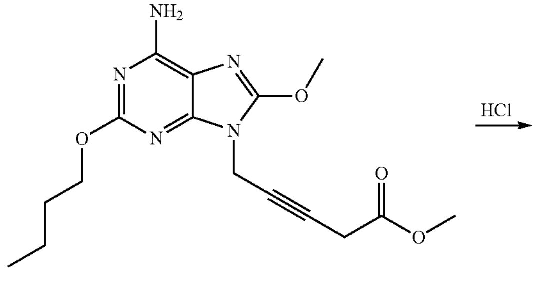

BPA-1a

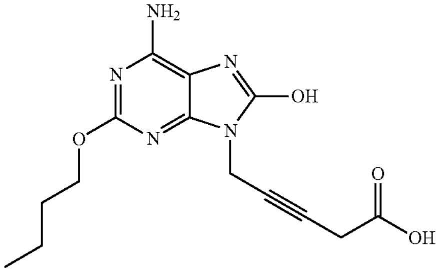

GY176

The synthesis method of GY176 was the same as that of GY175, except that BBA in the synthesis routine for compound GY175 was replaced by BPA, such that compound GY176 was obtained. ESI-MS=320.6$[M+H]^+$, in which, the synthesis raw material BPA was purchased from Wuxi Optec company.

GY179

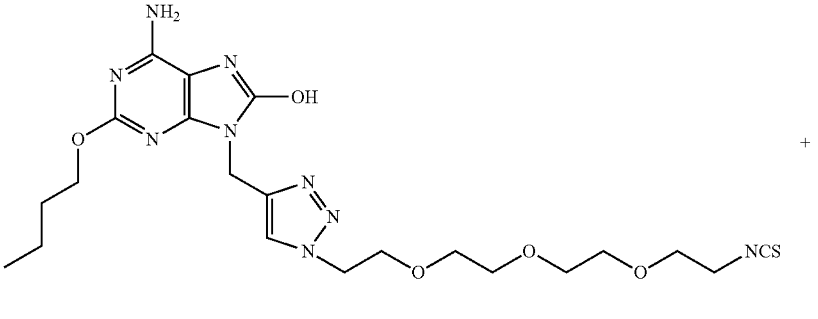

GY106

-continued

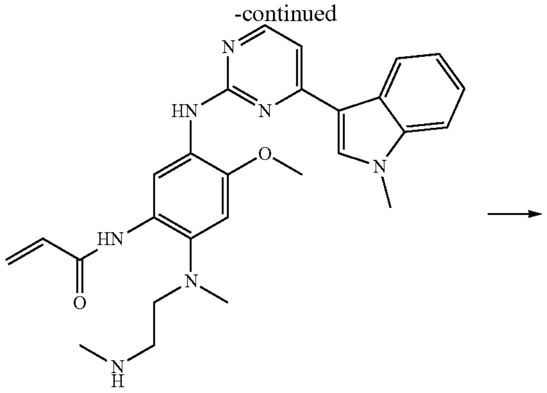

DeMe-9291

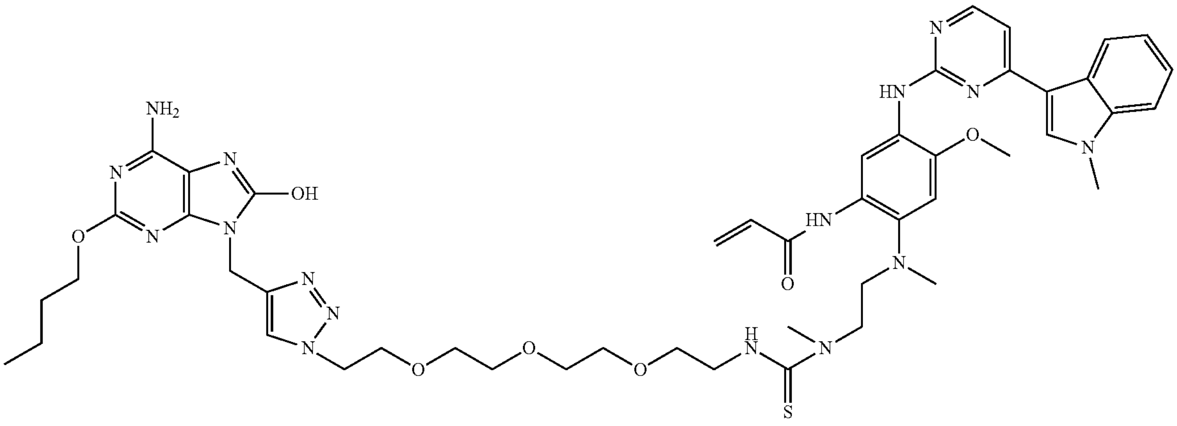

GY179

6 mg of GY106, 5 mg of DeMe-9291, and 2 μL of TEA were dissolved in 500 μL of DMSO, and reacted overnight at room temperature. The reaction was monitored by an LC-MS. When the reaction was completed, a resulting reaction product was purified by an HPLC, such that 2 mg of GY179 in the form of a yellow solid having a yield of 20 wt. % was obtained. ESI-MS: m/z=1007.1 $[M+H]^+$.

GY180

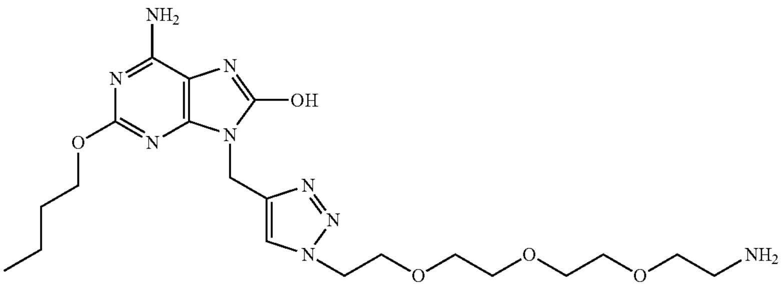

GY102

+

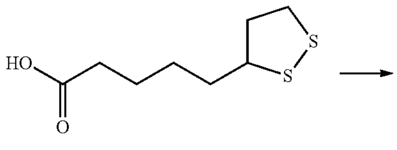

alpha-lipoic acid

-continued

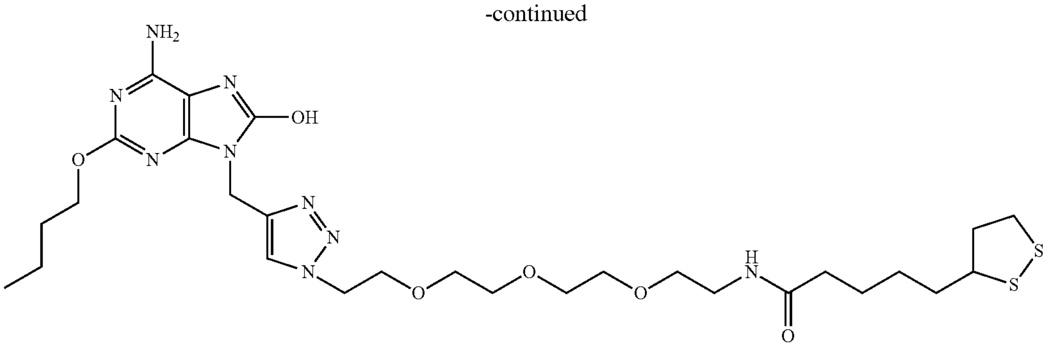

GY180

20 mg of GY102, 9.5 mg of alpha-lipoic acid, 5 mg of HBTU, a small amount of DMAP, and 10 μL of TEA were dissolved in 500 μL of DMSO, and reacted overnight at room temperature. The reaction was monitored by an LC-MS. When the reaction was completed, a resulting reaction product was purified by an HPLC, such that 4.5 mg of GY180 in the form of a white solid having a yield of 16.2 wt. %. ESI-MS: m/z=668.3 $[M+H]^+$.

GY181

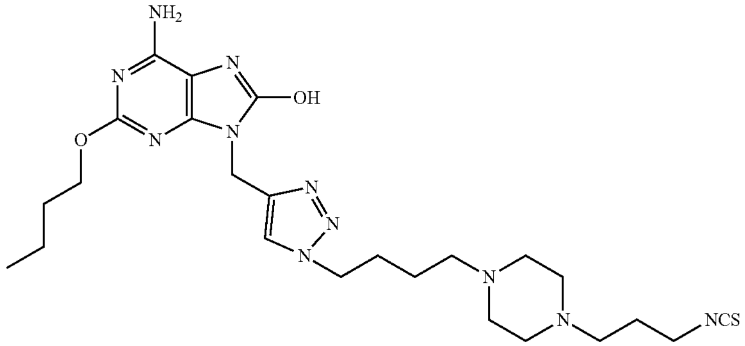

GY178

+

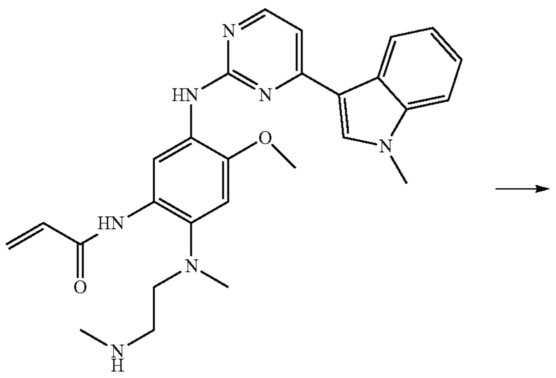

DeMe-9291

-continued

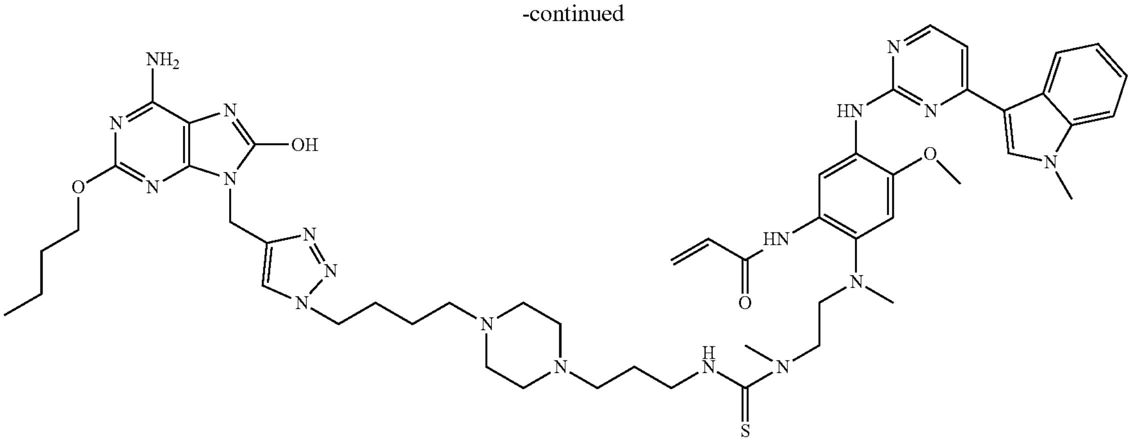

GY181

5 mg of GY178, 4.9 mg of DeMe-9291, and 5 μL of TEA were dissolved in 500 μL of DMSO, and reacted overnight at room temperature. The reaction was monitored by an LC-MS. When the reaction was completed, a resulting reaction product was purified by an HPLC, such that 1.6 mg of GY181 in the form of a yellow solid having a yield of 35.5 wt. % was obtained. ESI-MS: m/z=1029.5 [M+H]$^+$.

GY182

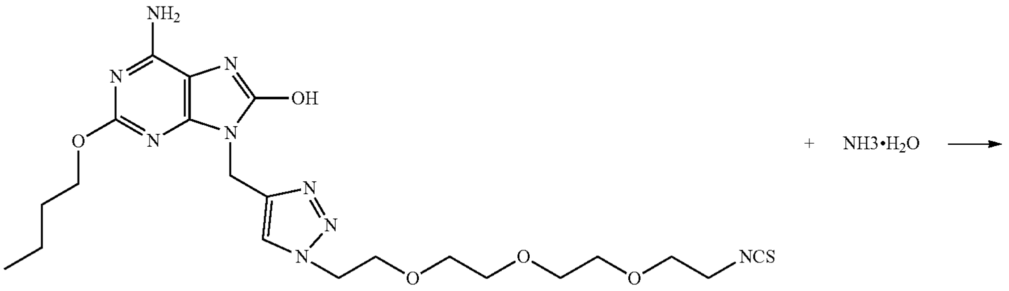

GY106

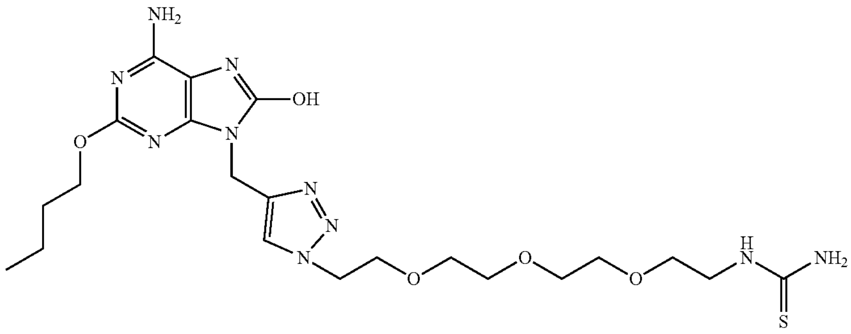

GY182

20 mg of GY106, 50 μL of concentrated ammonia, and 5 μL of TEA were dissolved in 500 μL of DMSO, and reacted at room temperature for 3 hrs. The reaction was monitored by an LC-MS. When the reaction was completed, a resulting reaction product was purified by an HPLC, such that 8 mg of GY182 in the form of a white solid having a yield of 36.4 wt. % was obtained. ESI-MS: m/z=539.2 [M+H]$^+$.

GY183
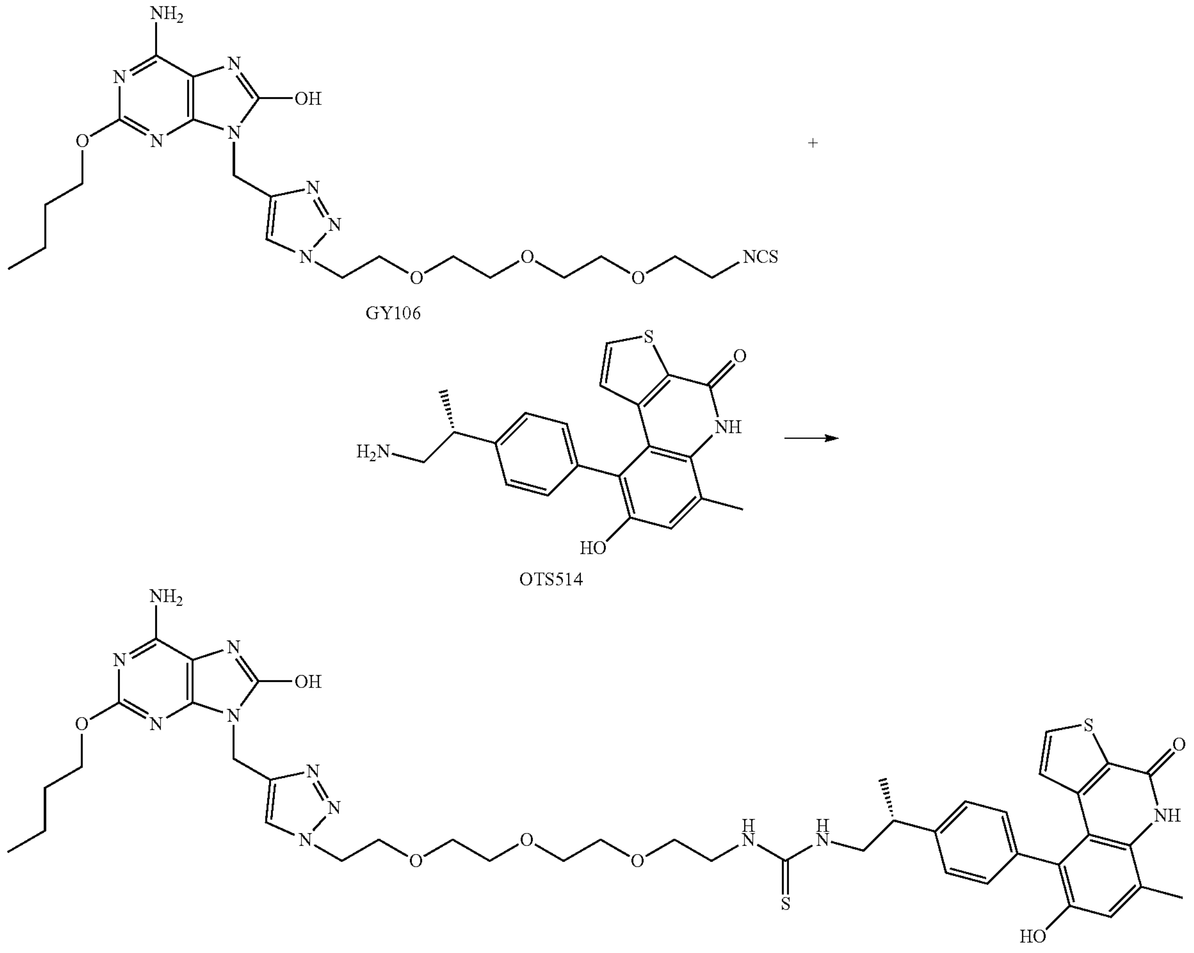
GY106
OTS514
GY183
20 mg of GY106, 15.4 mg of OTS514, and 10 μL of TEA were dissolved in 500 μL of DMSO, and reacted overnight at room temperature. The reaction was monitored by an LC-MS. When the reaction was completed, a resulting reaction product was purified by an HPLC, such that 5 mg of GY183 in the form of a white solid having a yield of 14.7 wt. % was obtained. ESI-MS: m/z=886.3 $[M+H]^+$.
GY184
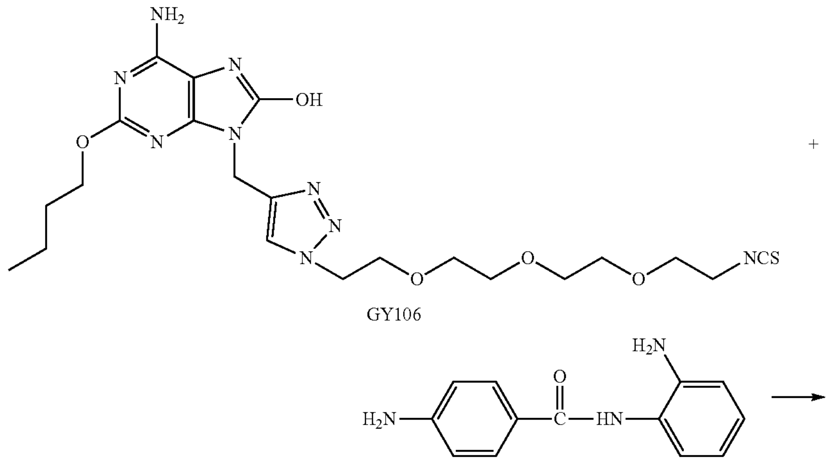
GY106
Dinalin -continued

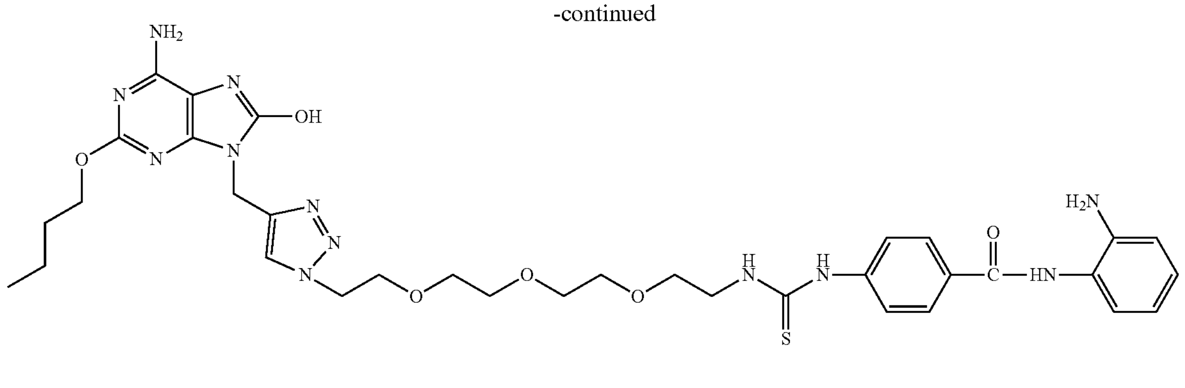

GY184

20 mg of GY106, 9.6 mg of Denali, and 10 μL of TEA were dissolved in 500 μL of DMSO, and reacted overnight at room temperature. The reaction was monitored by an LC-MS. When the reaction was completed, a resulting reaction product was purified by an HPLC, 6 mg of GY184 in the form of a white solid having a yield of 20.9 wt. % was obtained. ESI-MS: m/z=749.3 $[M+H]^+$.

GY185

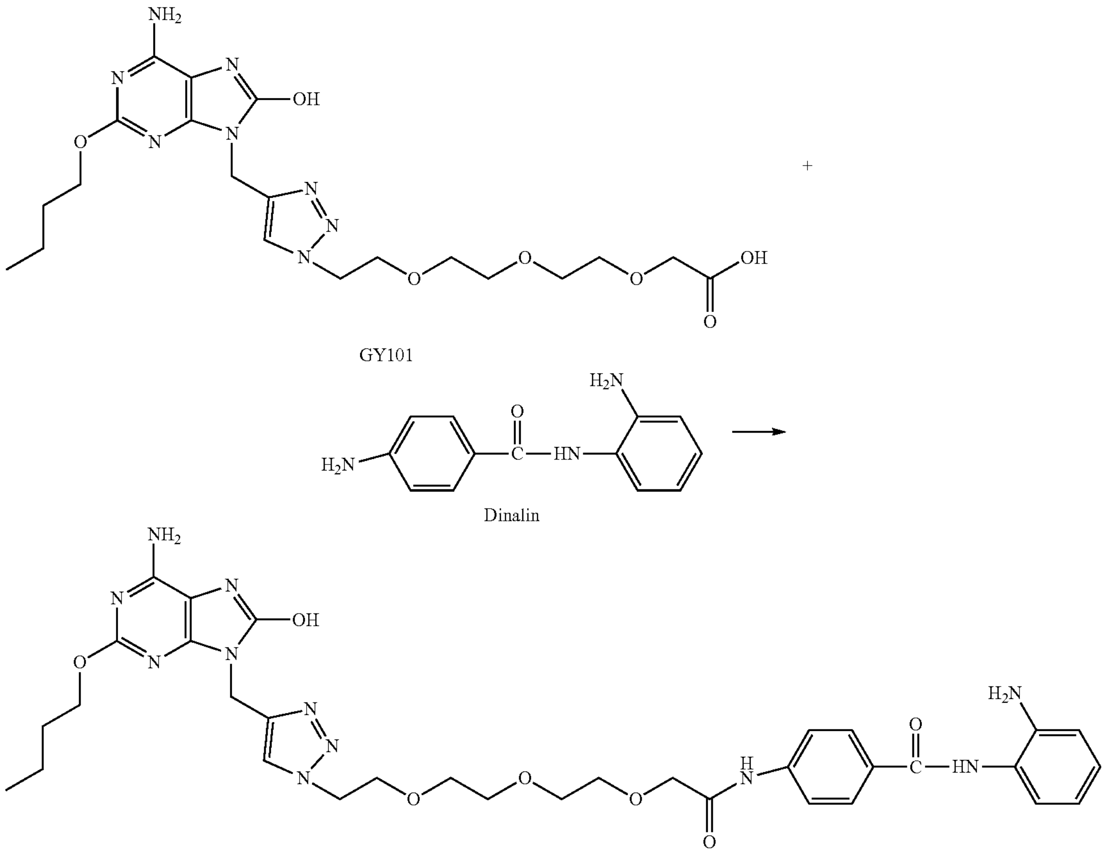

GY101

Dinalin

GY185

20 mg of GY101, 10 mg of Denali, 8 mg of HOBT, 10 mg of EDC, and 10 μL of DIPEA were dissolved in 500 μL of DMSO, and reacted overnight at room temperature. The reaction was monitored by an LC-MS. When the reaction was completed, a resulting reaction product was purified by an HPLC, such that 7.5 mg of in the form of a white solid having a yield of 26.4 wt. % was obtained. ESI-MS: m/z=704.3 $[M+H]^+$.

GY186

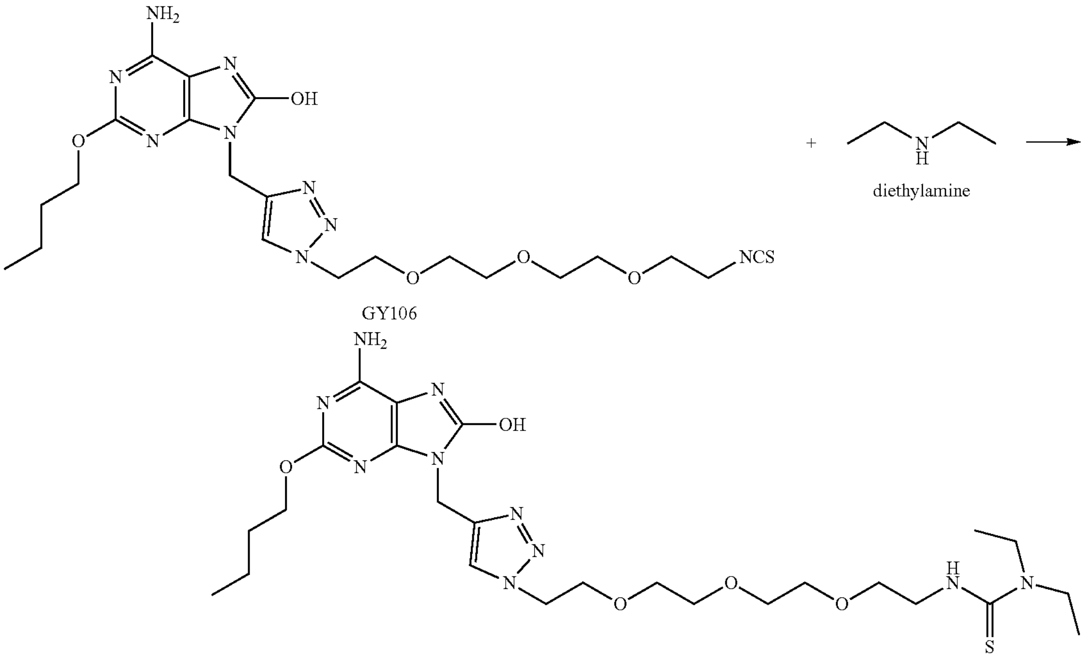

GY106 diethylamine

GY186

20 mg of GY106, 2.8 mg of diethylamine, and 10 μL of TEA were dissolved in 500 μL of DMSO, and reacted at room temperature for 5 hrs. The reaction was monitored by an LC-MS. When the reaction was completed, a resulting reaction product was purified by an HPLC, such that 10.6 mg of GY186 in the form of an of f-white solid having a yield of 46.5 wt. % was obtained. ESI-MS: m/z=595.1 $[M+H]^+$.

GY187

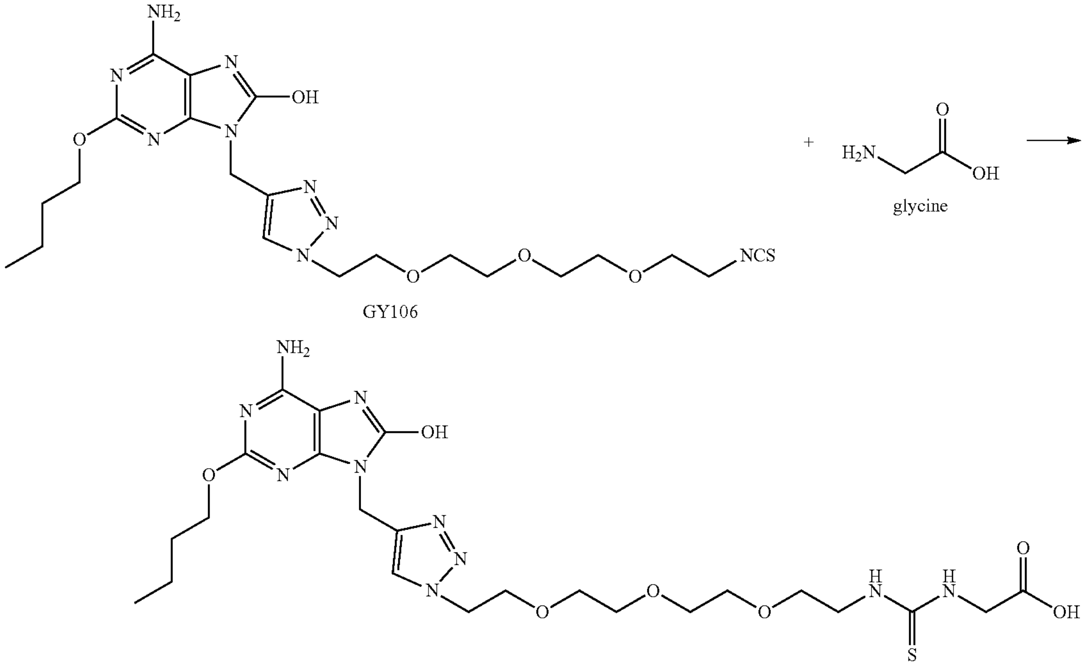

GY106 glycine

GY187

20 mg of GY106, 2.9 mg of glycine, and 10 μL of TEA were dissolved in 500 LL of DMSO, and reacted at room temperature for 5 hrs. The reaction was monitored by an LC-MS. When the reaction was completed, a resulting reaction product was purified by an HPLC, such that 10.6 mg of GY187 in the form of a white solid having a yield of 37.6 wt. % was obtained. ESI-MS: m/z=597.1 $[M+H]^+$.

SZU-194

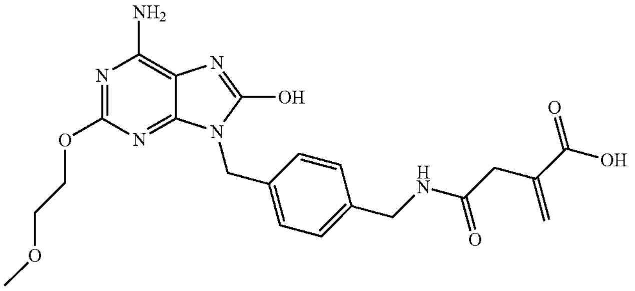

SZU-138

+

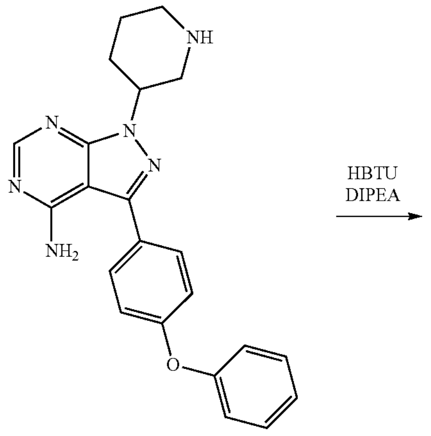

ibrutinib

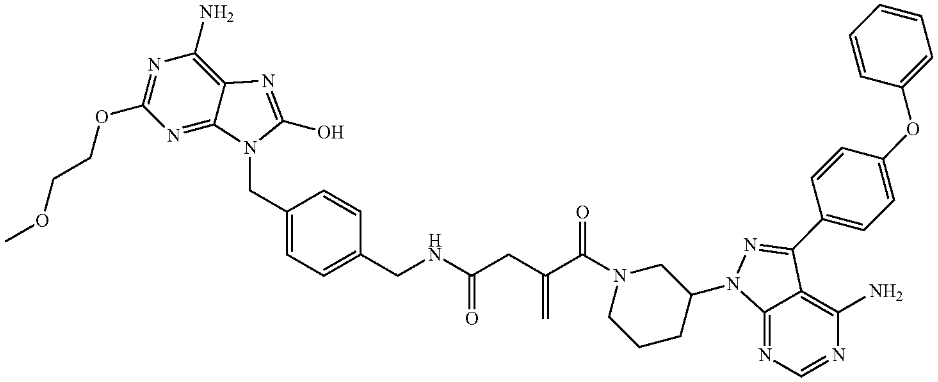

SZU-194

0.05 mole of compound SZU-138 and an equivalent amount of Ibrutinib intermediate were dissolved in 1 mL of DMSO, then 0.06 mole of HBTU and 0.12 mole of DIPEA was added. A resulting mixture was stirred at room temperature for 4 hrs. After that, a reaction product was purified by an HPLC, and lyophilized, such that compound SZU-194 in the form of a white powder having a yield of 23.2 wt. % was obtained. ESI-MS=824.3 $[M+H]^+$.

SZU-195

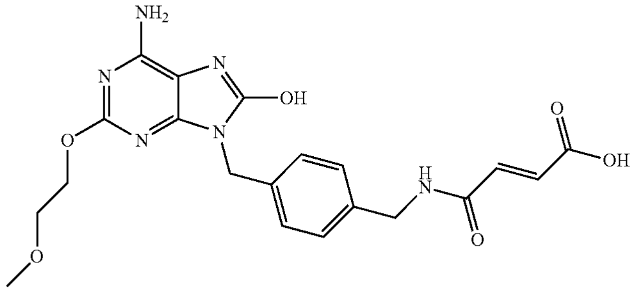

SZU-144

+

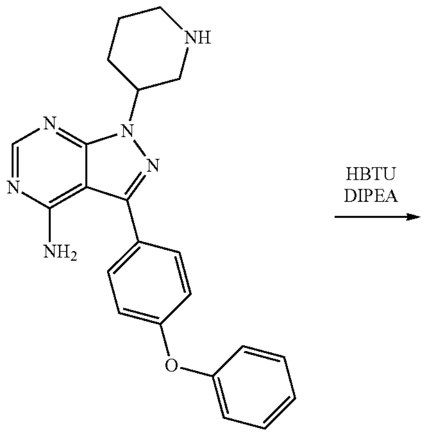

ibrutinib

-continued

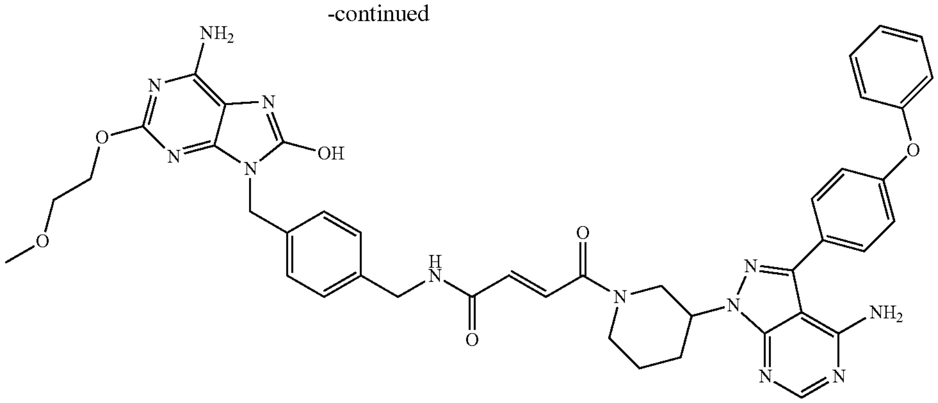

SZU-195

0.05 mole of compound SZU-144 and an equivalent amount of an Ibrutinib intermediate were dissolved in 1 mL of DMSO, and then 0.06 mole of HBTU and 0.12 mole of DIPEA were added. A resulting mixture was stirred at room temperature for 4 hrs. After that, a resulting reaction product was purified by an HPLC, and lyophilized, such that compound SZU-195 in the form of a white powder having a yield of 19.8 wt. % was obtained. ESI-MS=810.3 $[M+H]^+$.

SZU-213

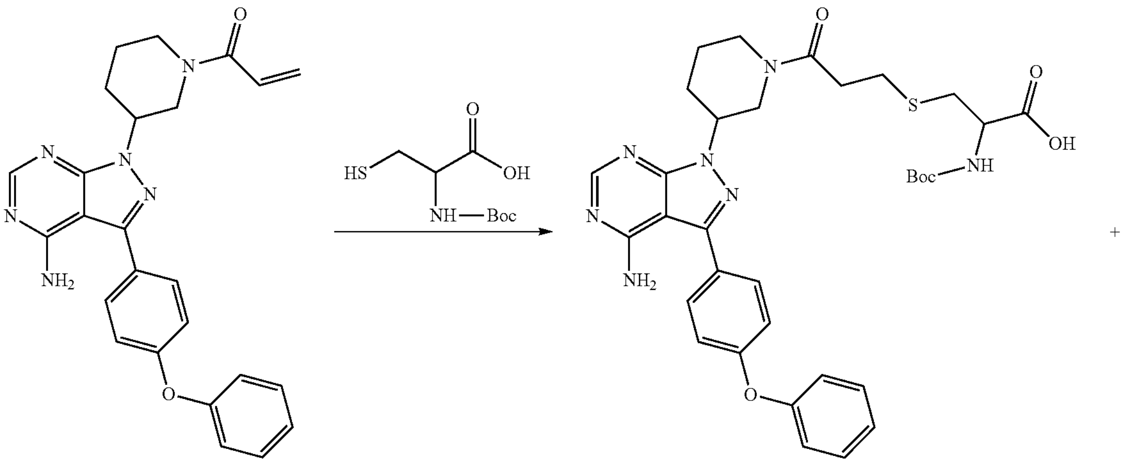

ibrutinib

IB-1

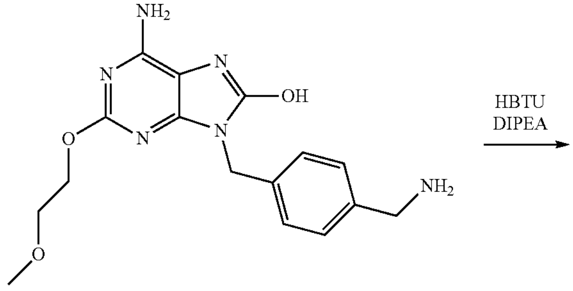

SZU-142

-continued

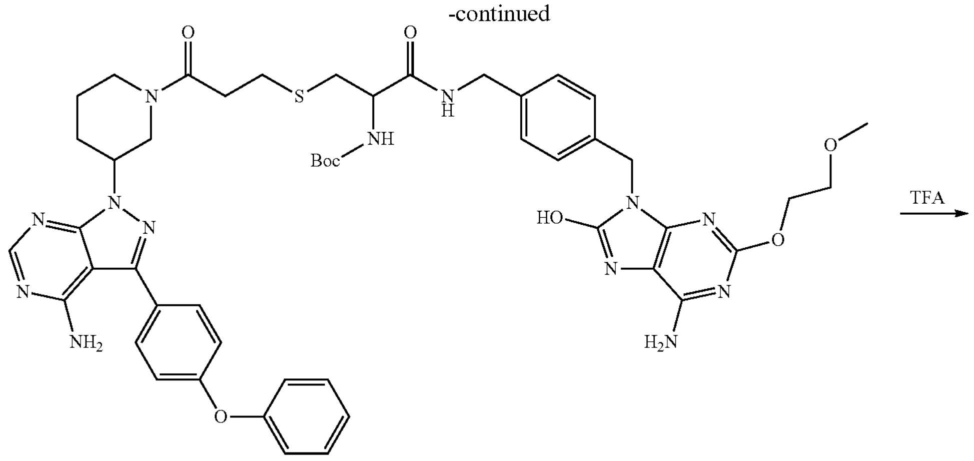

IB-2

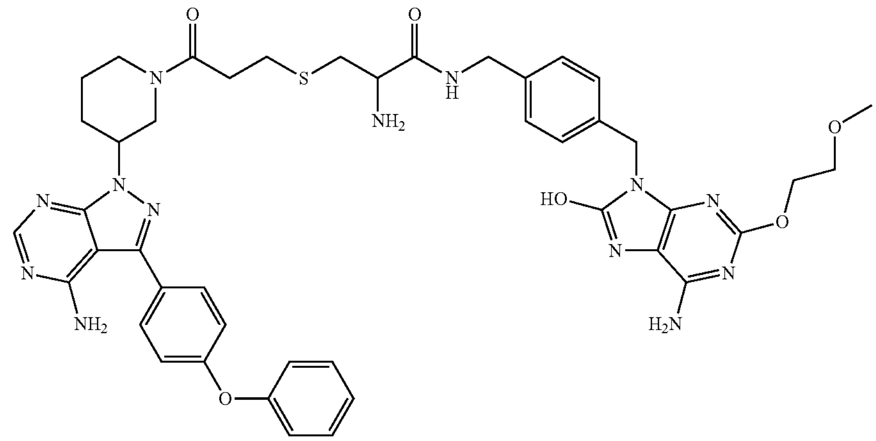

SZU-213

0.1 mole of Ibrutinib and an equivalent amount of N-boc protected cysteine were dissolved in 1 mL of DMSO, and then an equivalent amount of trimethylamine was added, a resulting mixture was stirred for 3 hrs. After that, water was added to separate out a precipitate. The precipitate was lyophilized to obtain a crude compound IB-1 for use.

0.05 mole of compound IB-1 and an equivalent amount of compound SZU-142 were dissolved in 1 mL of DMSO, and then added with 0.06 mole of HBTU and 0.12 mole of DIPEA. A resulting mixture was stirred at room temperature for 4 hrs, and lyophilized to obtain a crude compound IB-2. The crude compound IB-2 was dissolved in 1 mL of $CH_2Cl_2$, then added with 0.5 mL of TFA, and stirred at room temperature for 4 hrs. After reaction, a resulting reaction product was performed with rotary evaporation, a pH value thereof was adjusted to be neutral, then purified by an HPLC, such that compound SZU-213 in the form of a white power having a yield of 16.9 wt. % was obtained. ESI-MS=886.1 $[M+H]^+$.

SZU-215

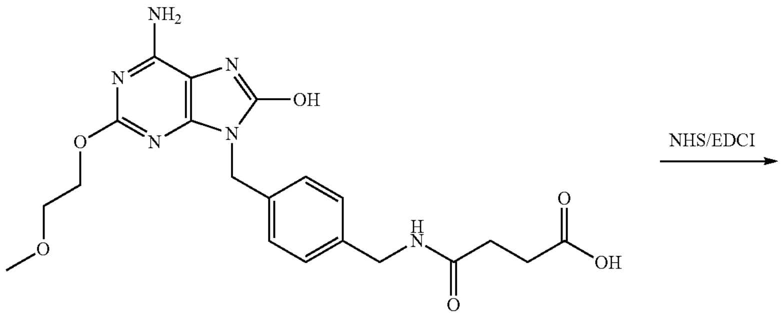

-continued

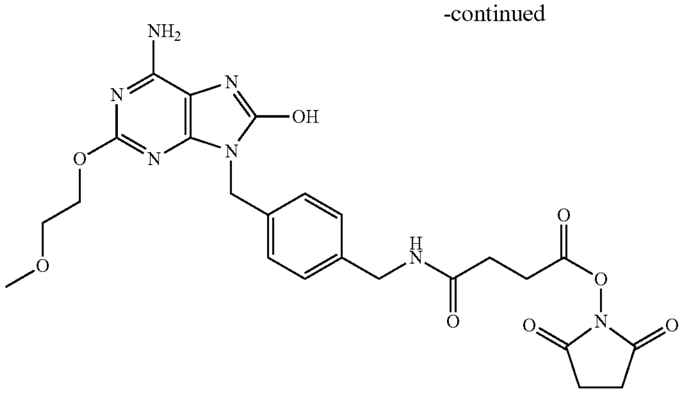

SZU-101-NHS

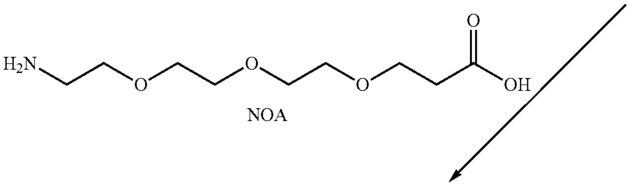

NOA

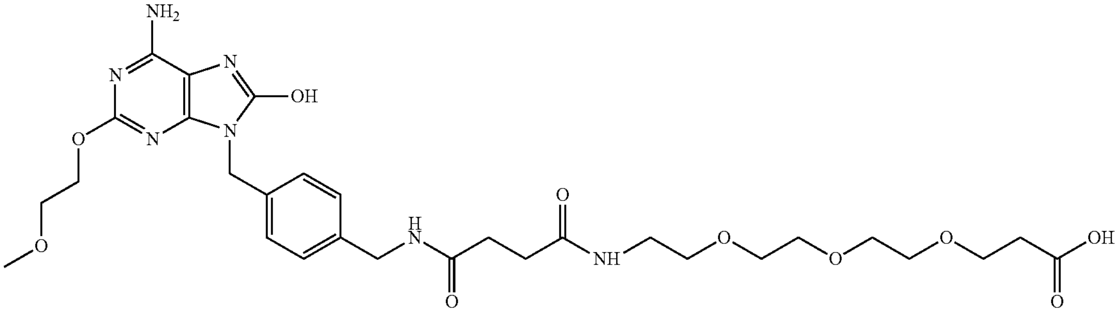

SZU-107

1 g of SZU-101, 310 mg of NHS, and 530 mg of EDCI were dissolved in 5 mL of anhydrous DMF, and stirred at room temperature for 2 hrs. The reaction was monitored by an LC-MS. When the reaction was completed, water was added to a resulting reaction mixture to precipitate a white solid, which was filtered and lyophilized, such that 800 mg of SZU-101-NHS in the form of a white solid was obtained.

200 mg of SZU-101-NHS and 89 mg of NOA were dissolved in 1 mL of anhydrous DMSO, and stirred at room temperature for 3 hrs. The reaction was monitored by the LC-MS. When the reaction was completed, a resulting reaction product was purified by an HPLC and lyophilized, such that 110 mg of SZU-107 in the form of a white solid was obtained. ESI-MS=648.31 $[M+H]^+$.

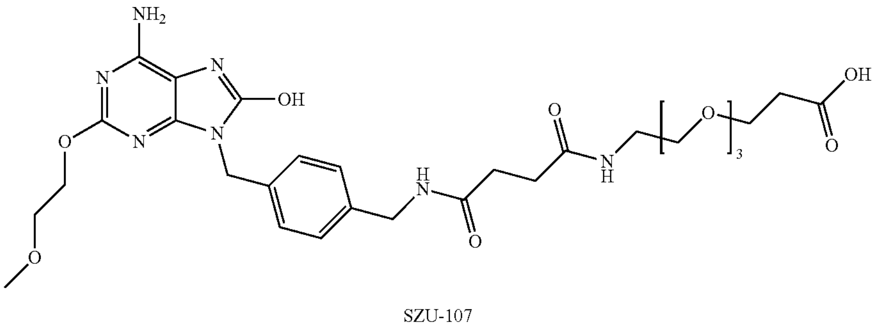

+

SZU-107

-continued

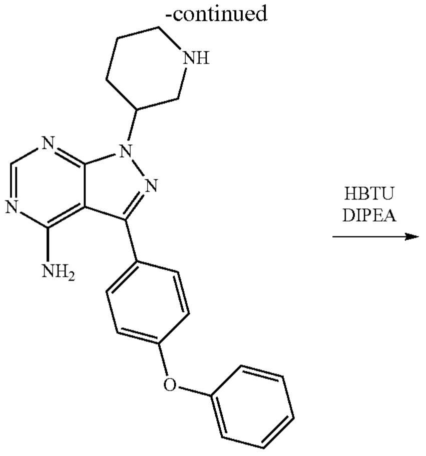

ibrutinib

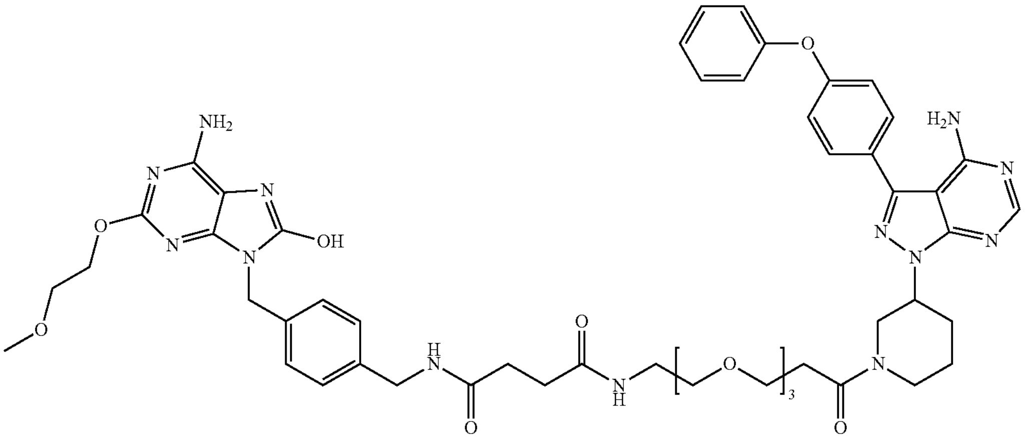

SZU-215

0.05 mole of compound SZU-107 and an equivalent amount of an Ibrutinib intermediate were dissolved in 1 mL of DMSO, added with 0.06 mole of HBTU and 0.12 mole of DIPEA, and then stirred at room temperature for 4 hrs. A resulting reaction product was purified by an HPLC, and lyophilized, such that compound SZU-215 in the form of a white powder having a yield of 26.3 wt. % was obtained. ESI-MS=1016.1 $[M+H]^+$.

SZU-251

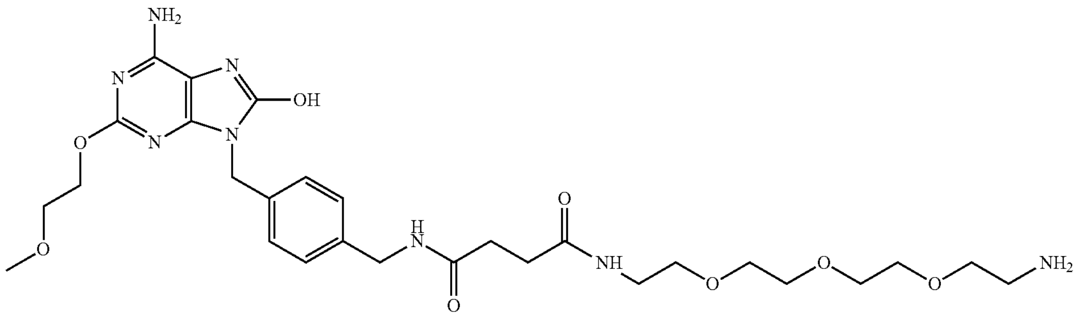

16a

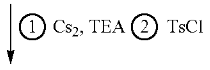

-continued

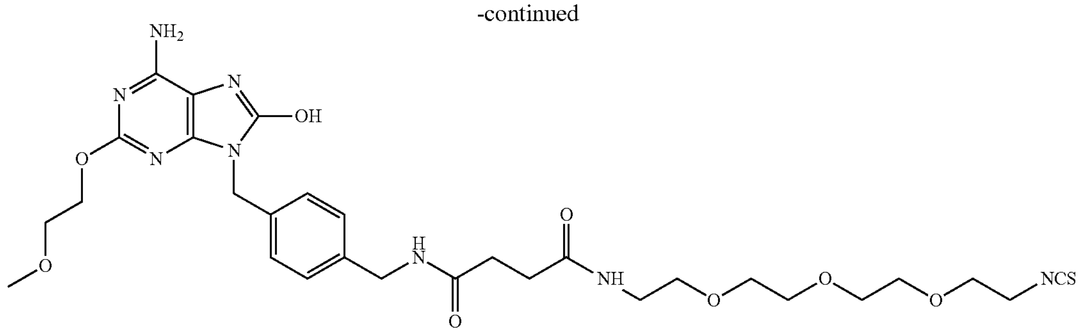

SZU-251

200 mg of compound 16a, 120 mg of $CS_2$, and 220 μL of TEA were dissolved in 1 mL of DMF, reacted overnight at room temperature. Thereafter, 110 mg of TsCl was added, and a reaction mixture continued to react at room temperature for 5 hrs. The reaction was monitored by an LC-MS. When the reaction was completed, a resulting reaction product was purified by an HPLC, such that 110 mg of compound SZU-251 in the form of a white solid having a yield of 40.4 wt. % was obtained. ESI-MS: m/z=660.2 $[M+H]^+$.

SZU-254

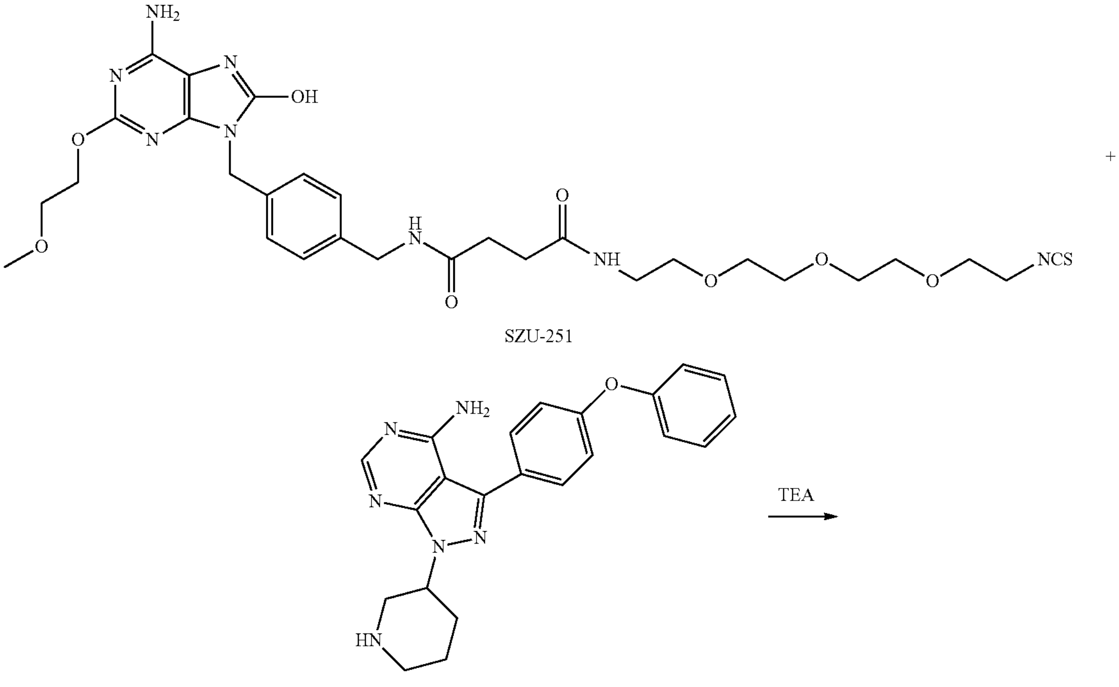

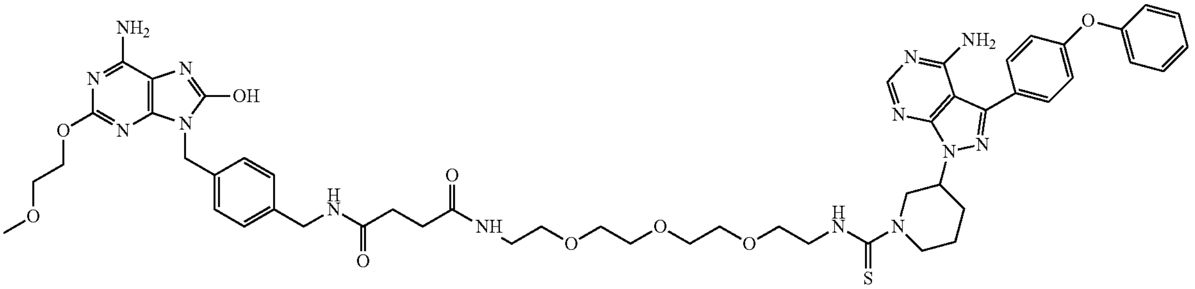

SZU-254

25 mg of compound SZU-251, 16 mg of Ibrutinib, and 10 μL of TEA were dissolved in 500 μL of DMSO, and reacted overnight at room temperature. The reaction was monitored by an LC-MS. When the reaction was completed, a resulting reaction product was purified by an HPLC, such that 10 mg of compound SZU-254 in the form of a white solid having a yield of 25.6 wt. % was obtained. ESI-MS: m/z=1046.5 $[M+H]^+$.

Synthesis of GY106-PD-L1 Antibody

Figure 14:
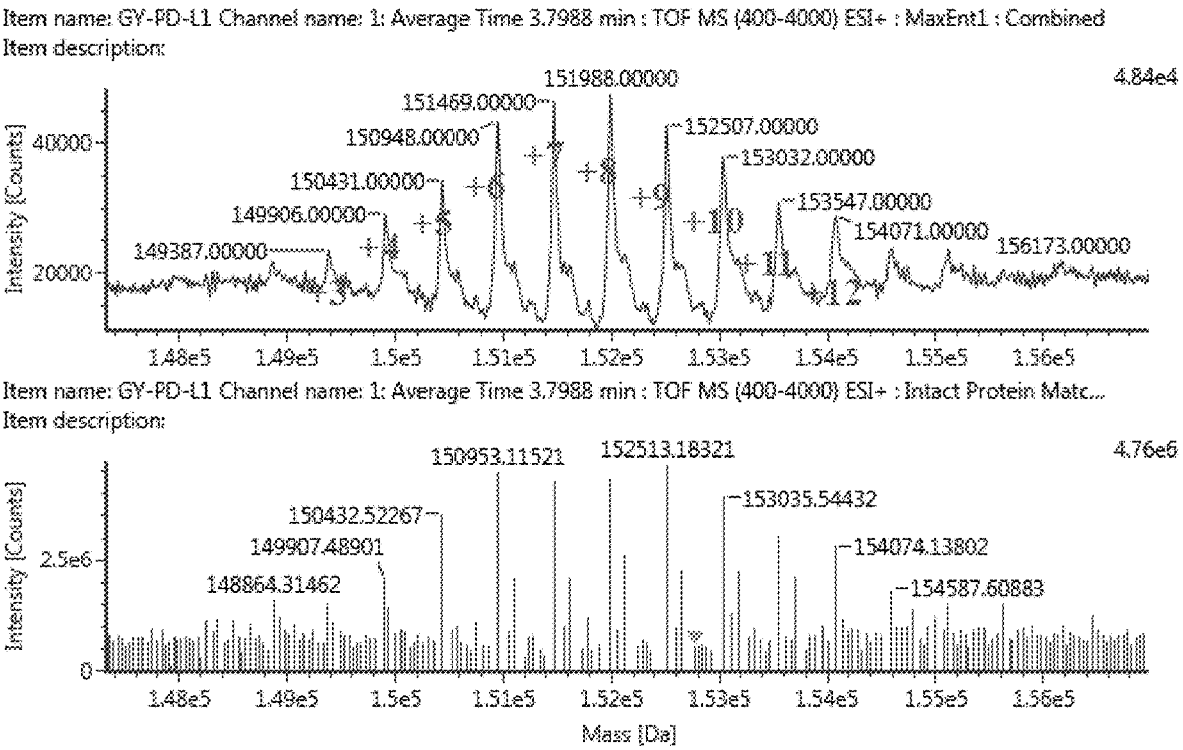
FIG. 14 shows determination of a coupling degree of GY106-PD-L1 by mass spectrometry (the molecular weight of an original naked anti-PD-L1 is 147825). The mass spectrometry confirmed that GY106-PD-1 had an average of 7.5 GY106 coupled thereto.
Figure 15:
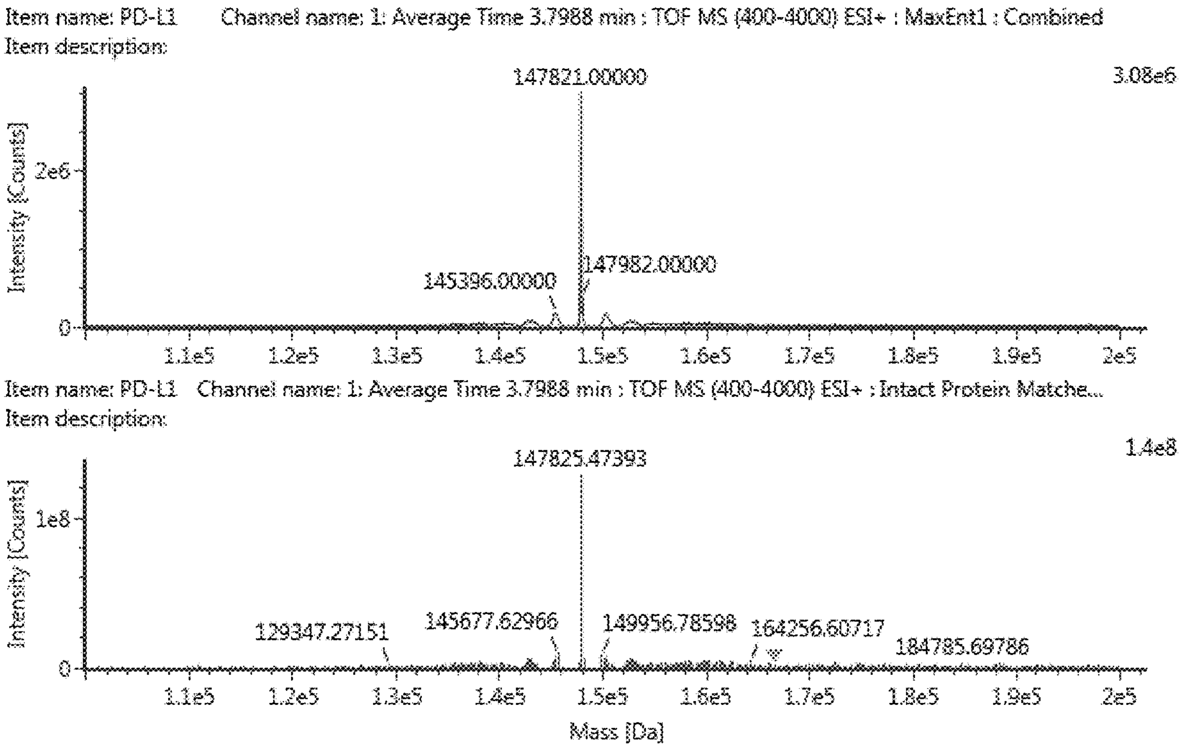
FIG. 15 shows determination of a mass spectrometric molecular weight of an original PD-L1 antibody.
Figure 16:
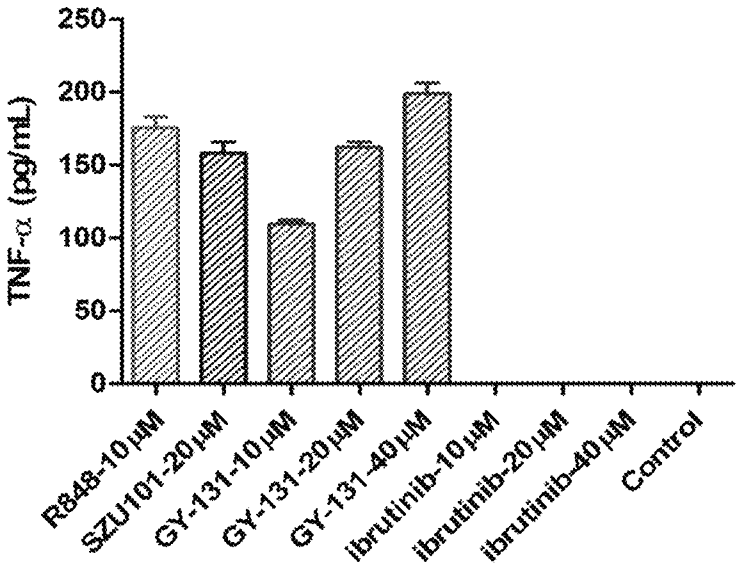
FIG. 16 shows the TNF-α cytokine production effect of GY131 on murine spleen cells.
Figure 17:
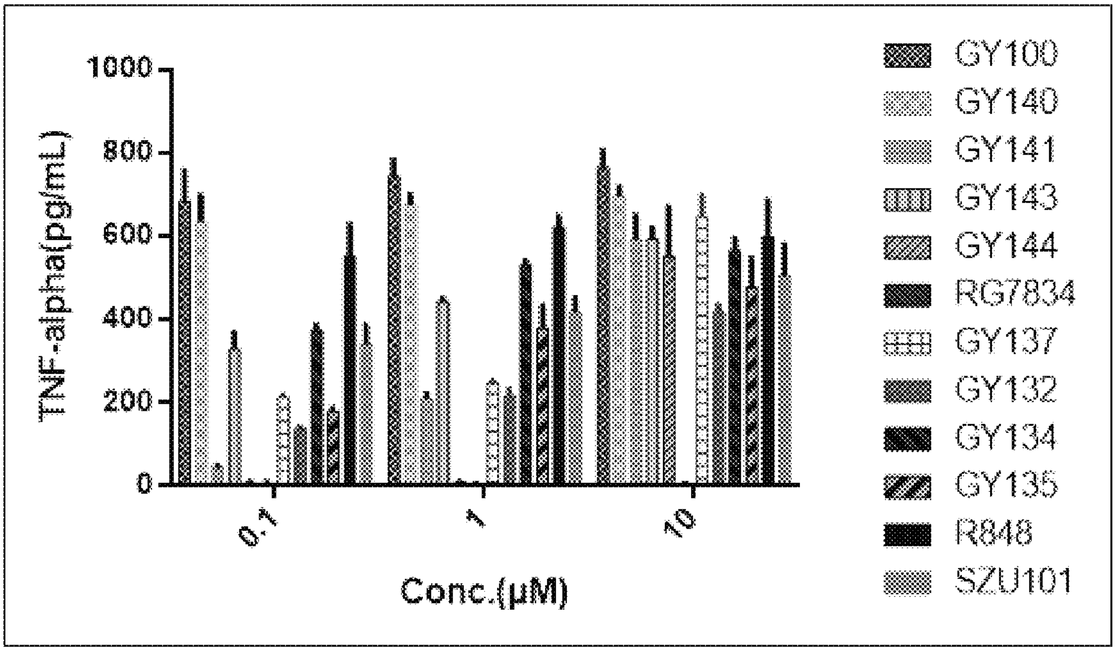
FIG. 17 shows the TNF-α cytokine production effect of a series of GY compounds on murine spleen cells.
Figure 18:
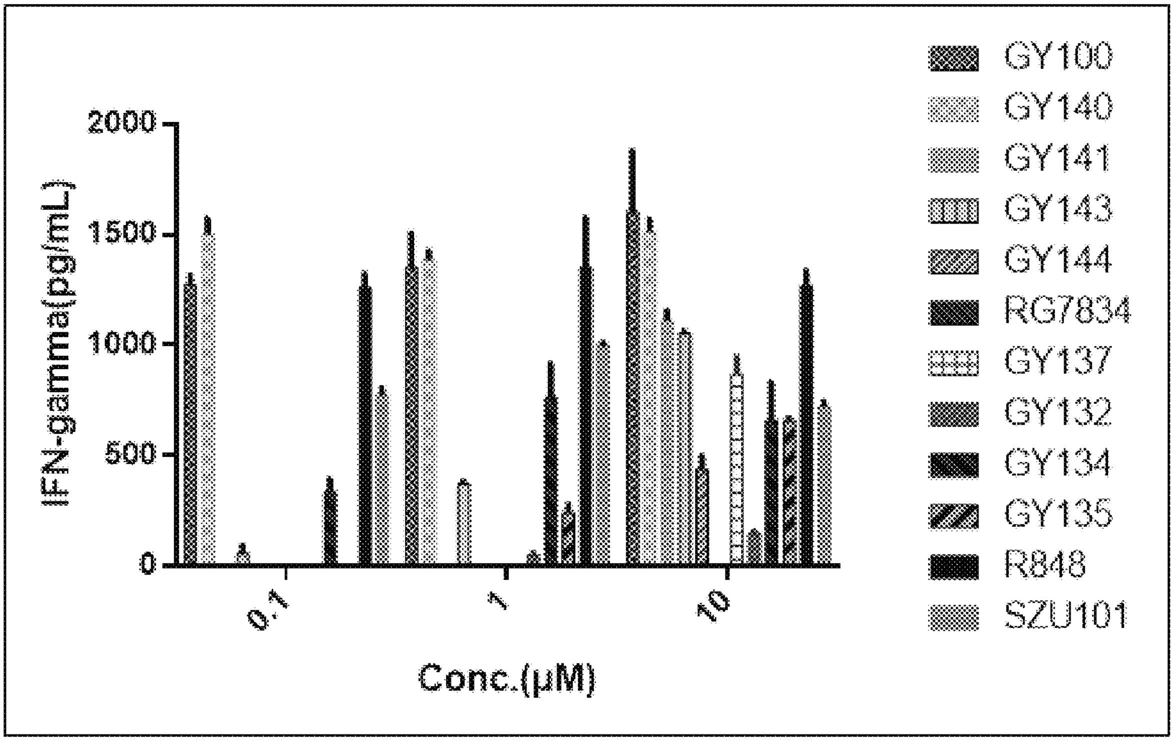
FIG. 18 shows the IFN-γ cytokine production effect of a series of GY compounds on murine spleen cells.
Figure 19:
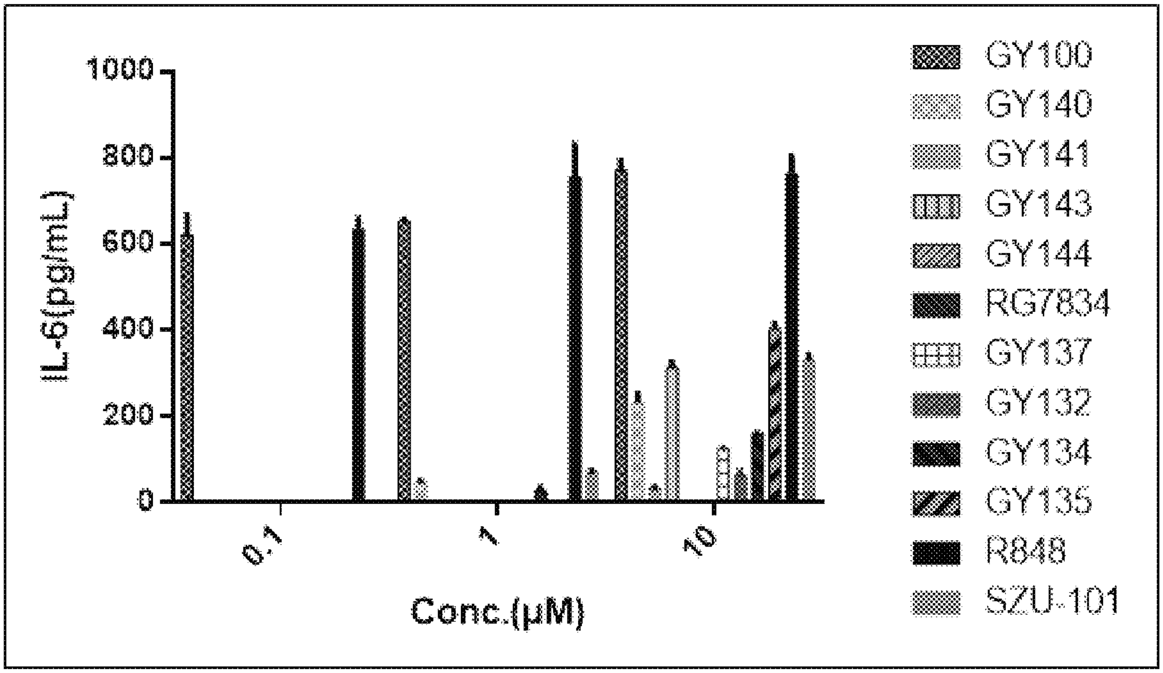
FIG. 19 shows the IL-6 cytokine production effect of a series of GY compounds on murine spleen cells.
Figure 20:
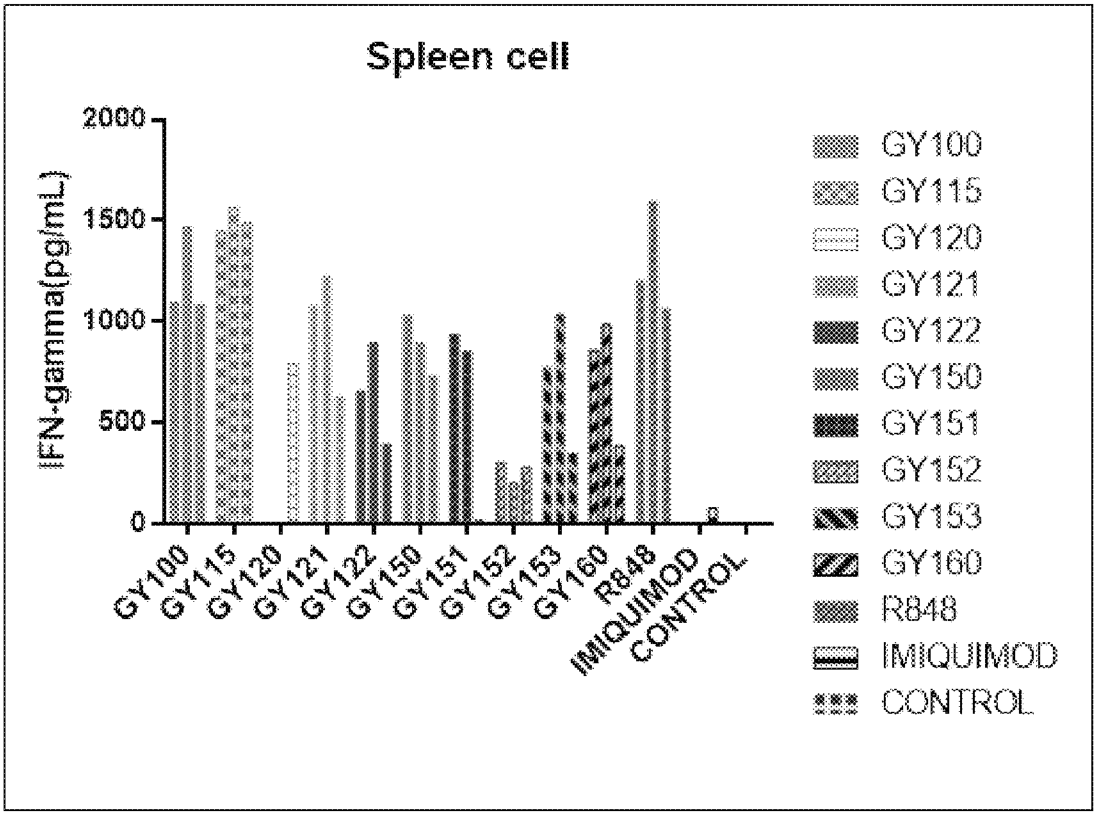
FIG. 20 shows the IFN-γ cytokine production effect of a series of GY compounds (0.1, 1, 10 μM) on murine spleen cells.
Figure 21:
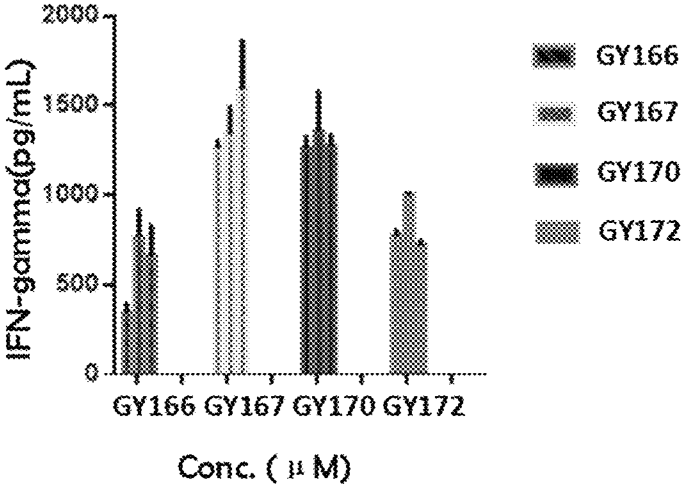
FIG. 21 shows the IFN-γ cytokine production effect of a series of GY compounds (0.1, 1, 10 μM) on murine spleen cells.

The synthesis method of GY106-PD-L1 antibody was the same as that of the GY106-PD-1 body. The mass spectrometry characterization is shown in FIGS. 14-15.

Synthesis of Peptide-54-GY106

Peptide-54 (54 amino acids, FZD7 epitope) has a sequence of APVCTVLDQAIPPCRSLCERARQGCEALMNKFGFQWPERLRCENFPVHGAGEIC (SEQ ID NO: 1) (purchased from Shanghai Nuoyou Biotechnology Co., Ltd.) and a molecular weight of 6048.98 g/mol.

Figure 22:
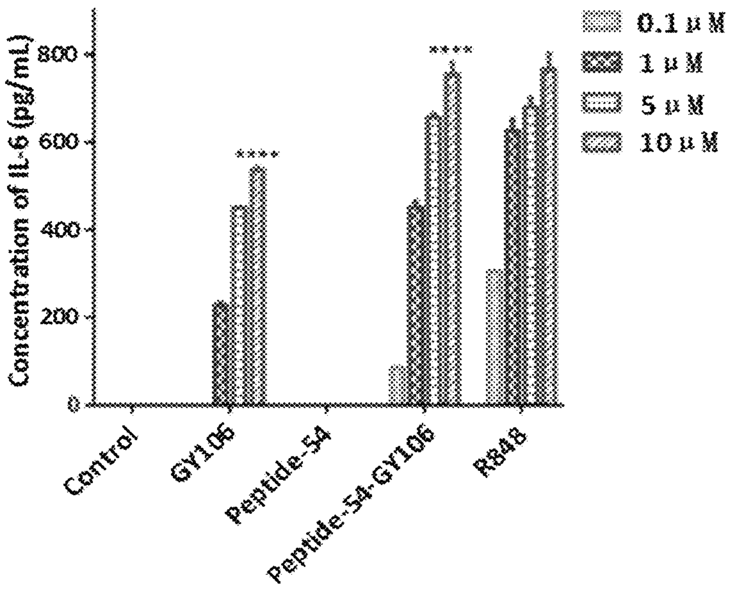
FIG. 22 shows the IL-6 cytokine induction effect of GY106 coupled with Peptide-54 on murine spleen lymphocytes.
Figure 23:
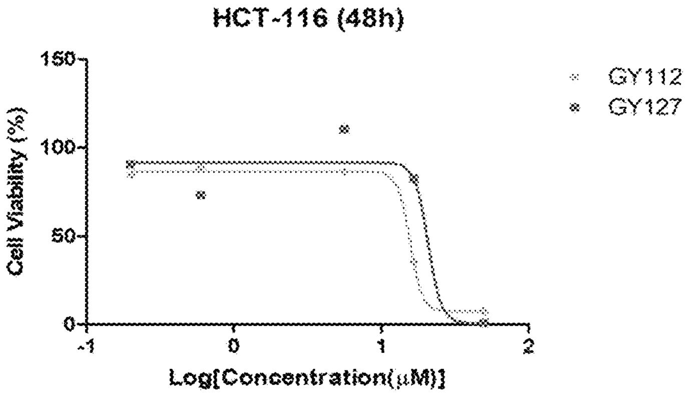
FIG. 23 shows the inhibitory effects of a series of GY compounds on human colon cancer HCT-116 cells.
Figure 24:
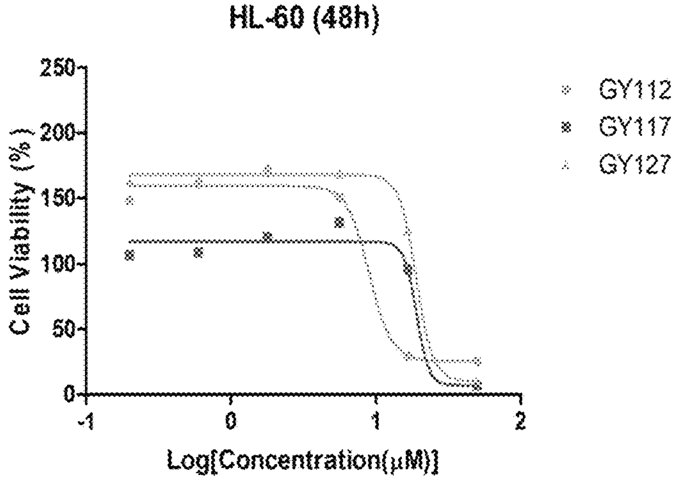
FIG. 24 shows the inhibitory effect of a series of GY compounds on human leukemia HL-60 cells.
Figure 25:
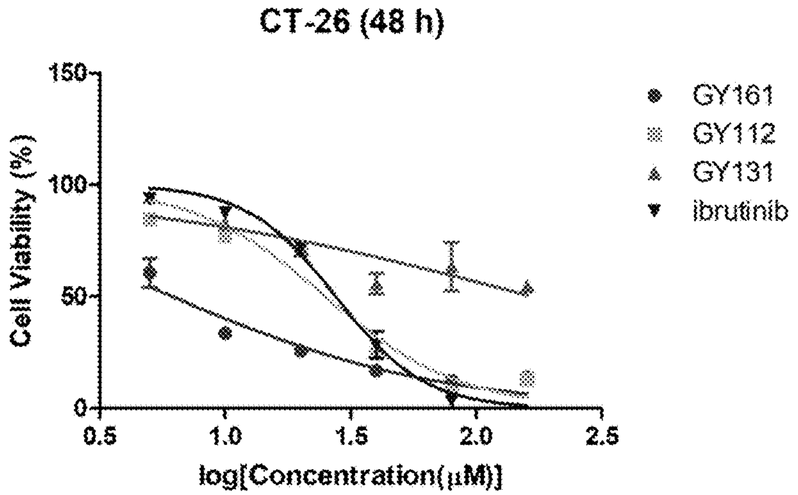
FIG. 25 shows the inhibitory effect of a series of GY compounds on murine colon cancer CT-26 cells.
Figure 26:
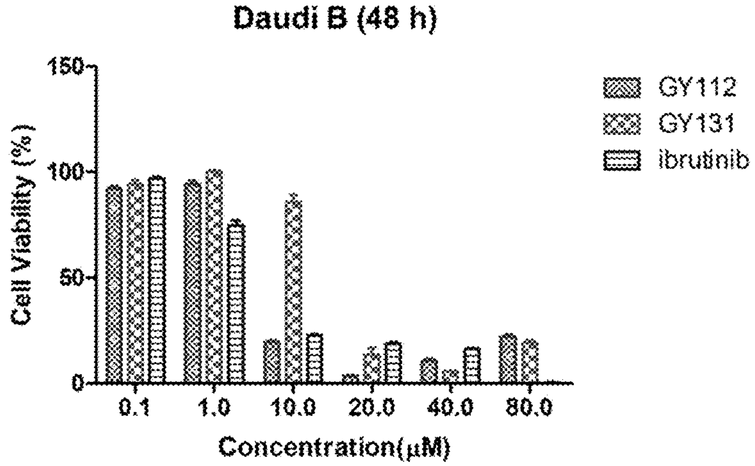
FIG. 26 shows the inhibitory effects of GY112 and GY131 on tumor cells (human lymphoma Daudi B cells).
Figure 27:
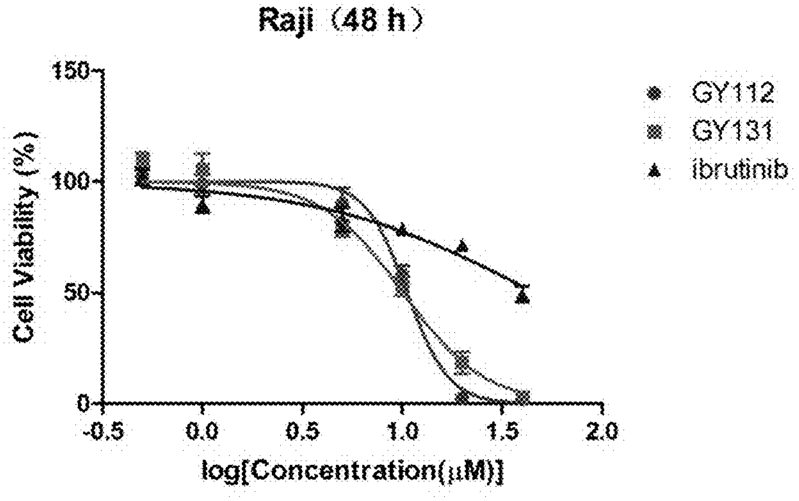
FIG. 27 shows the inhibitory effects of GY112 and GY131 on tumor cells (human lymphoma Raji cells).
Figure 28:
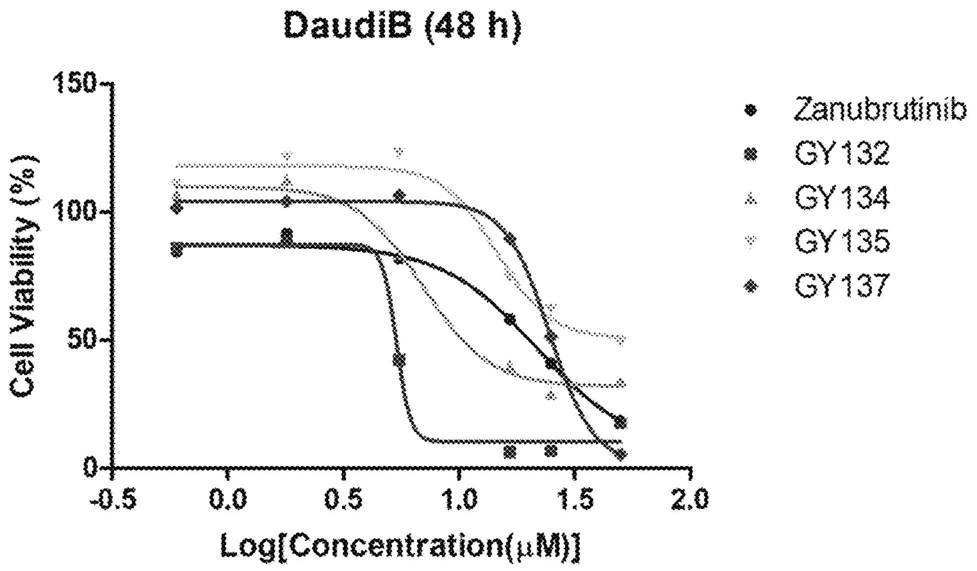
FIG. 28 shows the inhibitory effect of GY132, 134, 135, and 137 on tumor cells (human lymphoma Daudi B cells).
Figure 29:
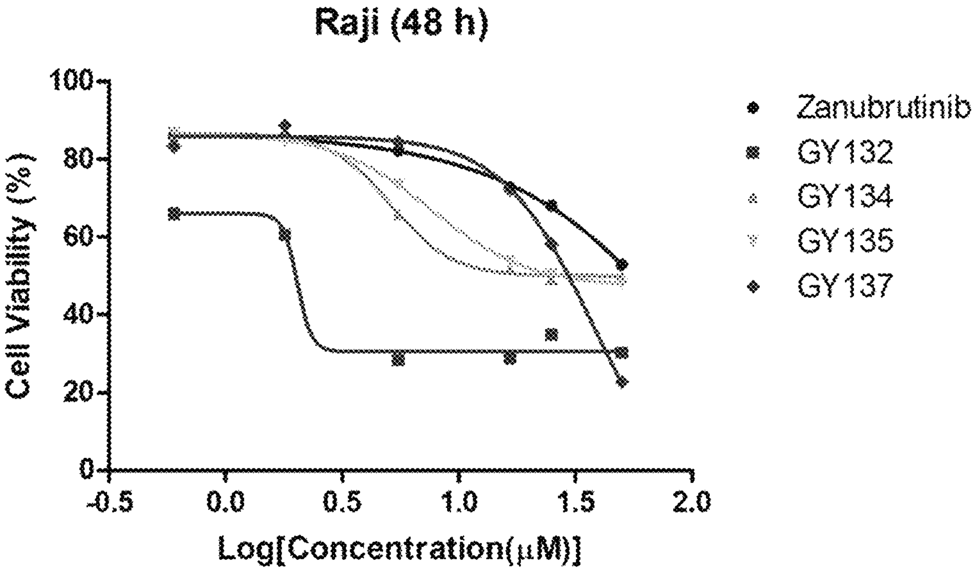
FIG. 29 shows the inhibitory effect of GY132, 134, 135, and 137 on tumor cells (human lymphoma Raji cells).
Figure 30A:
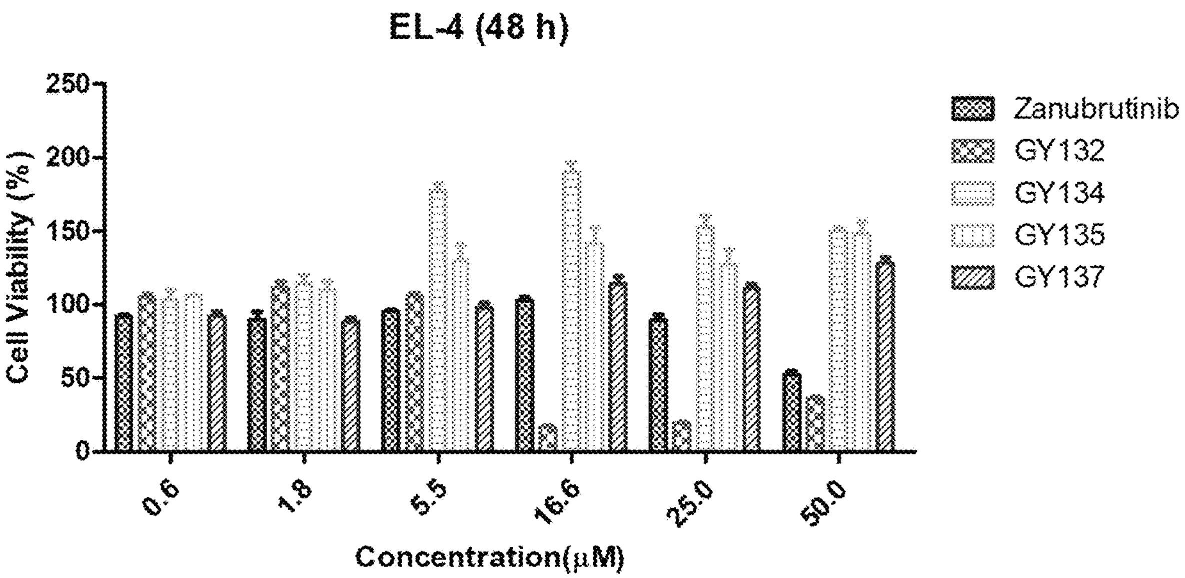
FIG. 30A, 30B shows the effect of GY132, 134, 135, and 137 on lymphoma EL-4 cells.
Figure 30B:
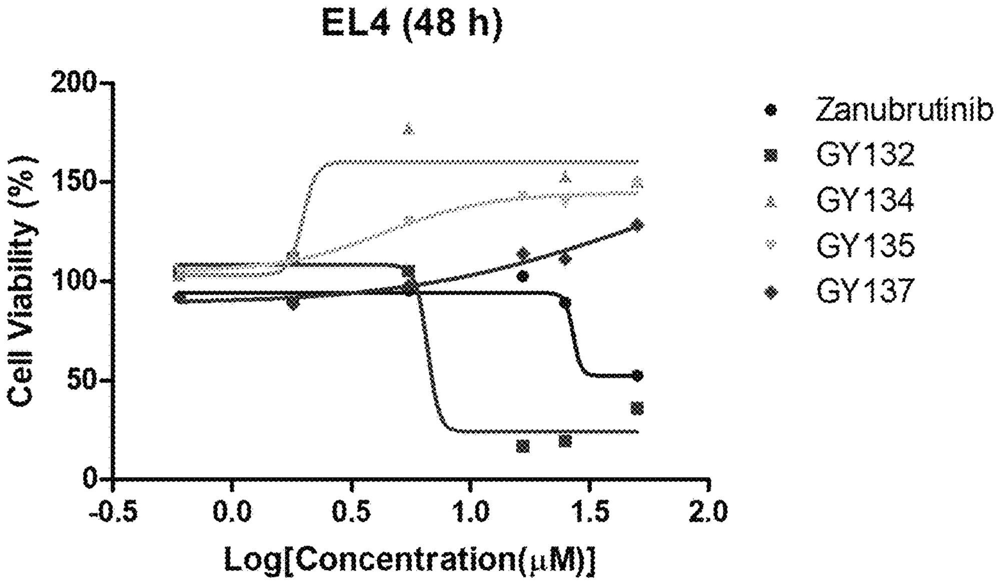
Figure 31A:
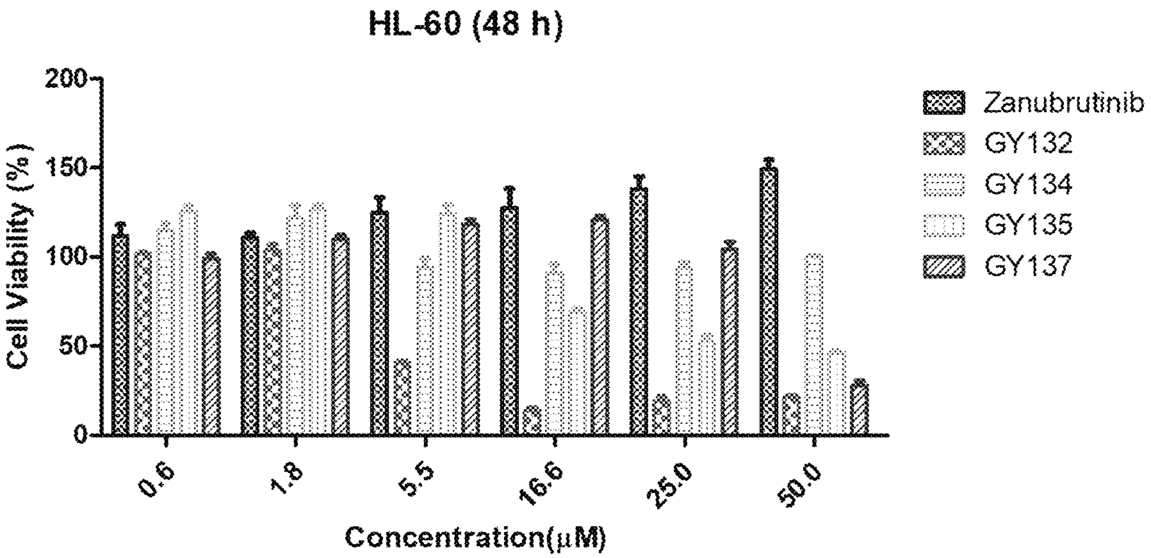
FIGS. 31A and 31B show the inhibitory effects of GY132, 134, 135, and 137 on myeloid leukemia HL-60 cells.
Figure 31B:
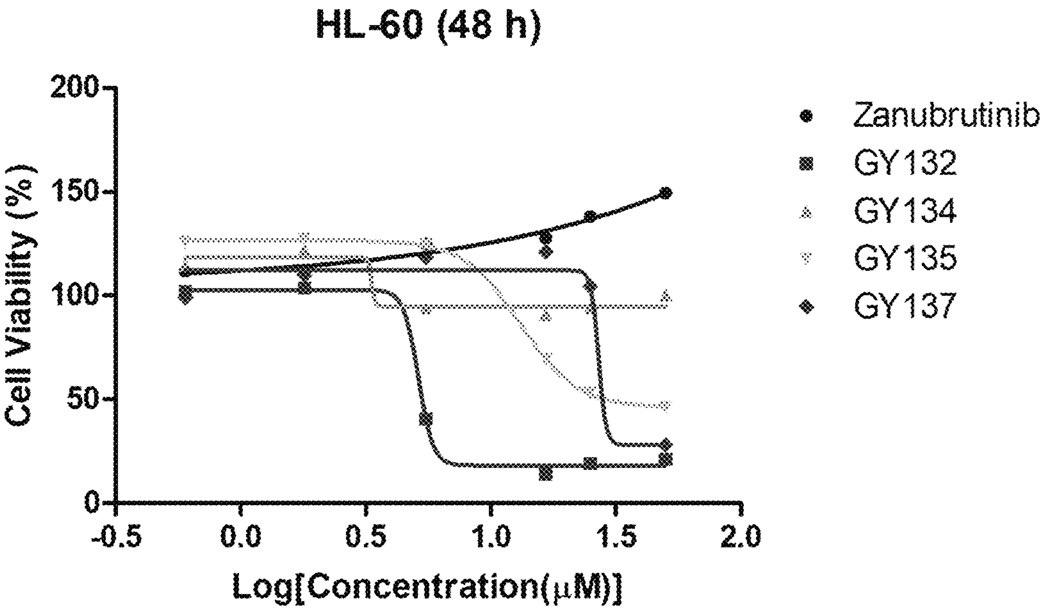
Figure 32:
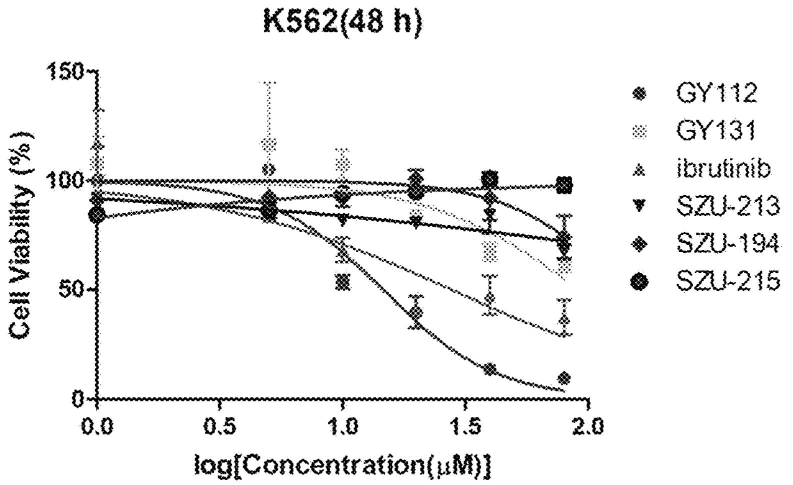
FIG. 32 shows the inhibitory effects of GY112 and GY131 on human leukemia K562 cells.
Figure 33:
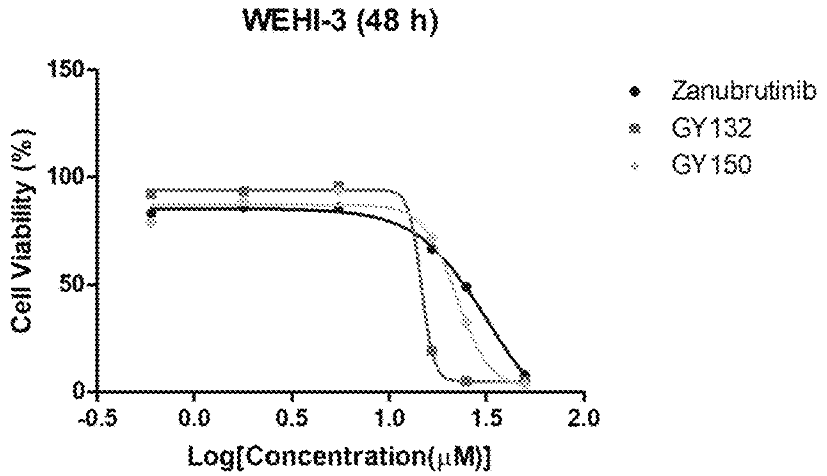
FIG. 33 shows the inhibitory effects of GY132, GY150, and Zanubrutinib on murine leukemia WEHI-3 cells.
Figure 34:
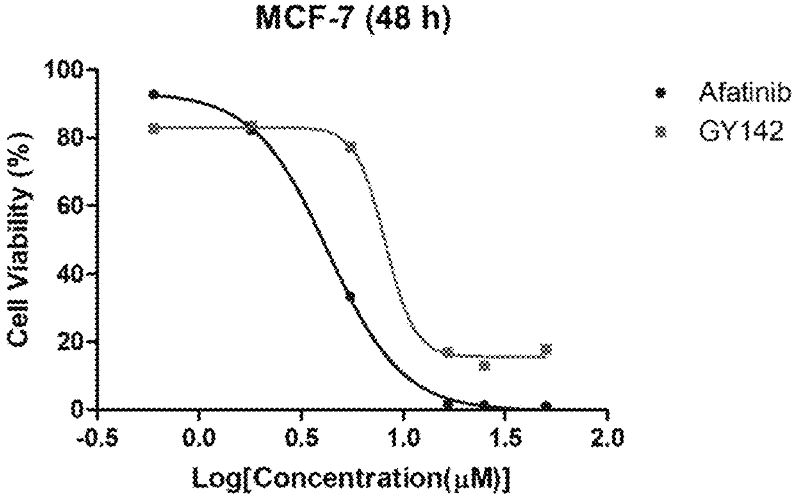
FIG. 34 shows the inhibitory effect of GY142 on human breast cancer MCF-7 cells.
Figure 35:
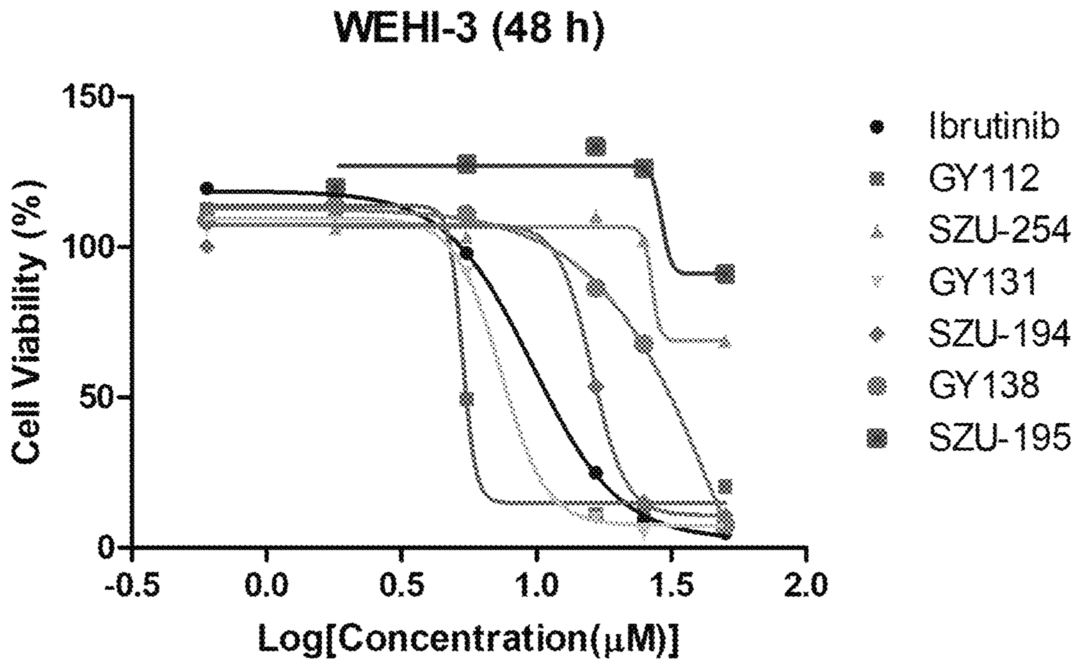
FIG. 35 shows the inhibitory effects of GY112, GY131, GY138, SZU-254, SZU-194, SZU-195, and Ibrutinib on murine leukemia WEHI-3 cells.
Figure 36:
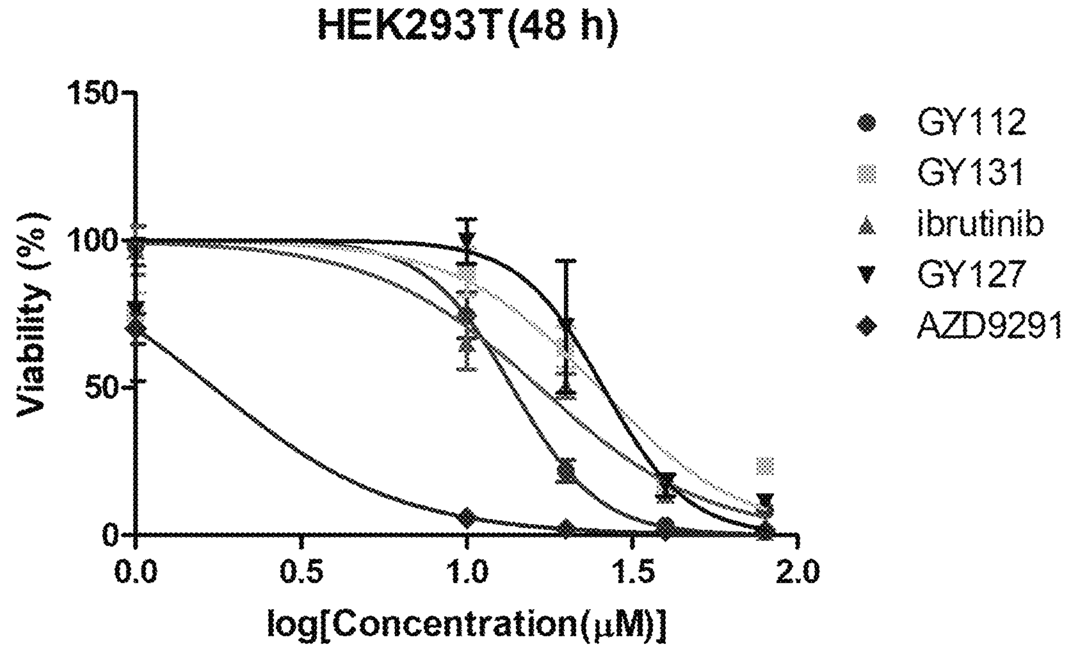
FIG. 36 shows the growth inhibitory effects of GY112, GY131, and GY127 on $HEK_{293}T$ cells.
Figure 37:
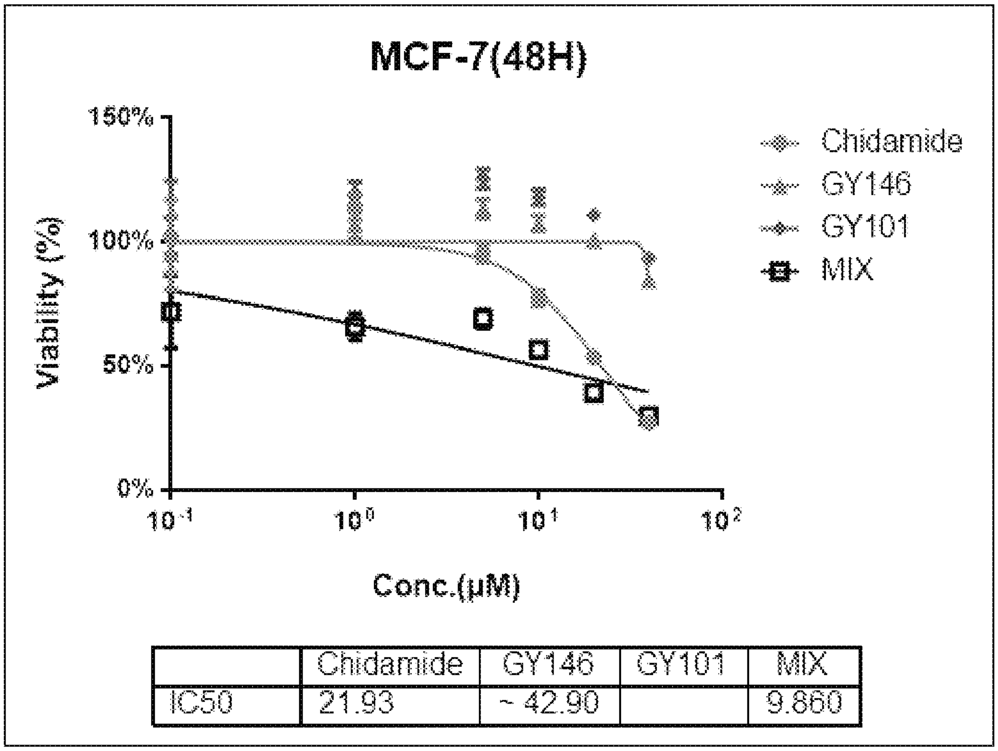
FIG. 37 shows the inhibitory effect of a combination of GY101 and Chidamide (1:1, MIX) on human breast cancer MCF-7 cells.
Figure 38:
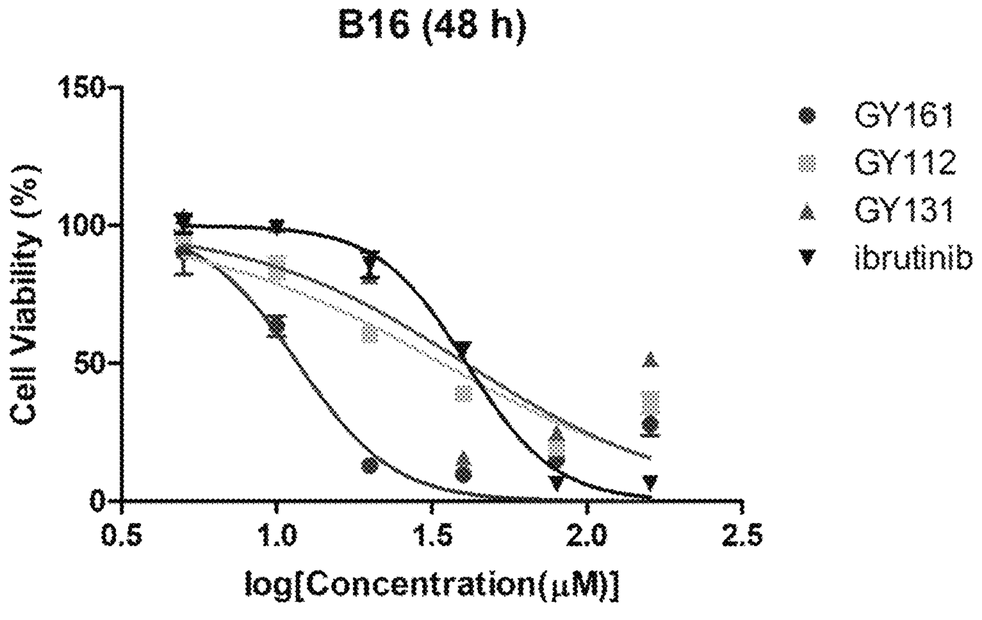
FIG. 38 shows the inhibitory effects of GY161, GY112, GY131, and Ibrutinib on black melanoma B16 cells.
Figure 39:
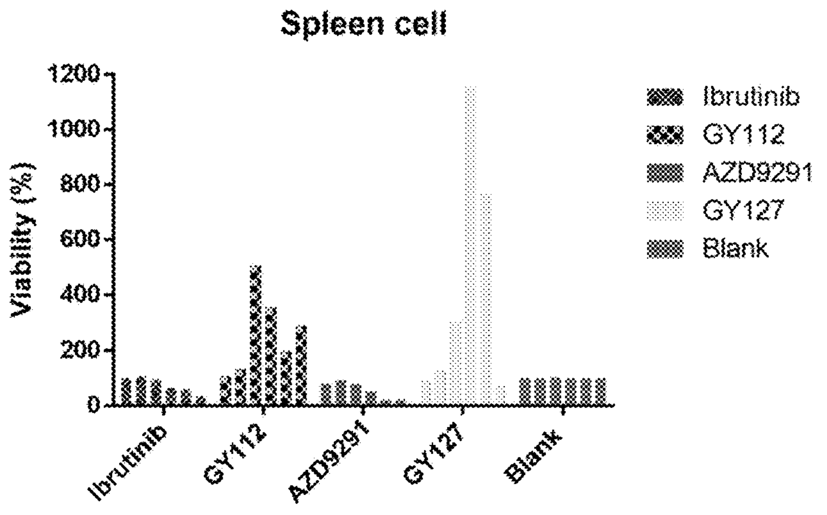
FIG. 39 shows the effect of GY112 and GY127 on the in vitro amplification of murine spleen lymphocytes for 24 hrs (concentration range 0, 0.1, 1, 10, 20, 40 μM, where Blank is an untreated control group).
Figure 40:
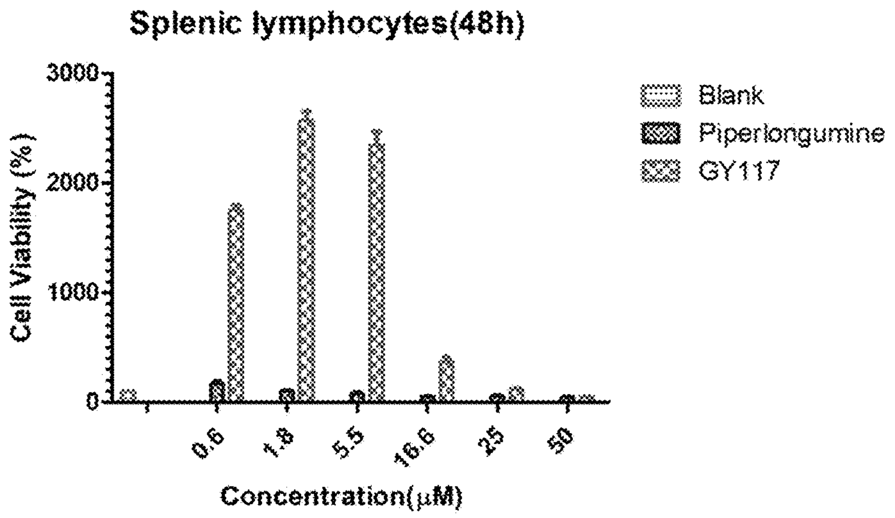
FIG. 40 shows the effect of GY117 on the in vitro amplification of murine spleen immune cells (Blank is an untreated control group).
Figure 41:
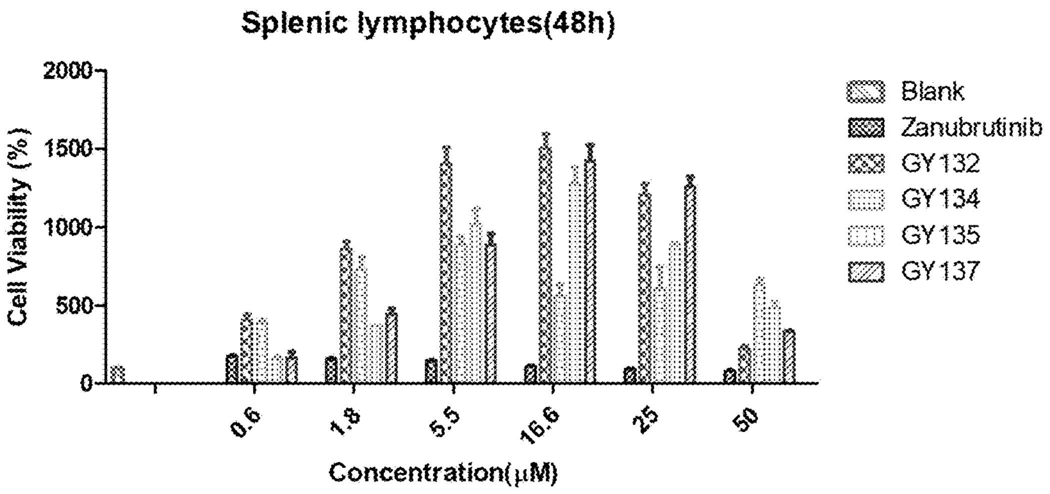
FIG. 41 shows the effect of GY132, 134, 135, and 137 on the in vitro amplification of murine spleen immune cells (Blank is an untreated control group).

2 times mole of compound GY-106 and 1 time mole of Peptide-54 were dissolved in an appropriate amount of DMSO, and 26 times mole of triethylamine were added. A resulting mixture was shaken for reaction at 10-15° C. for 3 hrs, then lyophilized to obtain a peptide-54-GY106. A yield thereof was 100 wt. %. A molecular weight of the product is identified by mass spectrometry: 7091 (coupling degree 2) (biological activity is shown in FIG. 22).

EXAMPLES

Example 1 Detection of TLR7 Activation by a Series of GY Compounds or Drugs (HEK-Blue™ Detection HEK-Blue™hTLR7 cells (purchased from InvivoGen) in a logarithmic growth phase were taken, with a growth medium (Gibco, C11995500BT, Invivo Gen, ant-nr) discarded. The cells were gently rinsed twice by an appropriate amount of 37° C. PBS (Hyclone, SH30256.01), a rinsed PBS was discarded. Thereafter, the cells were added with 2-5 mL of 37° C. PBS, incubated for 1 to 2 minutes, and then scraped by a cell scraper and gently pipetted to be dispersed into a single cell suspension. A hemocytometer was adopted to count the cells and a cell concentration was calculated. After that, a HEK-Blue™ Detection solution (purchased from Invivo Gen) was adopted to adjust the cell concentration of the cell suspension to $2.5\times10^4$/180 μL per well for cell plating on a 96-well cell culture plate. The HEK-Blue™hTLR7 cells were stimulated according to the designed series of GY compound or drug concentrations (0.01 μM, 0.1 μM, 1 μM, 5 μM, 15 μM, and 30 μM), with 3 replicate wells for each concentration, and were incubated at 37° C., 5% carbon dioxide for 6-16 hrs. After the incubation, the absorbance value was read at 650 nm with a full-wavelength microplate reader (BioTek-Epoch), as listed in Table 2.

TABLE 2

EC50 values of detection (HEK-Blue ™ Detection) of TLR7 activation by various Series of GY compounds.

| Compounds | GY100 | GY101 | GY102 | GY103 | GY106 | GY109 | GY135 | GY145 | GY161 |
|---|---|---|---|---|---|---|---|---|---|
| TLR7(EC50/μM) | 2.25 | 0.003 | 0.79 | 0.86 | 0.08 | 0.65 | 9.07 | 0.29 | 3.86 |
| Compounds | GY112 | GY117 | GY126 | GY127 | GY131 | GY132 | GY127 | GY134 | GY137 |
| TLR7(EC50/μM) | 2.65 | 0.22 | 0.92 | 1.06 | 4.97 | 5.42 | 1.06 | 1.991 | 2.918 |

| Compounds | GY109 | GY110 | GY112 | GY113 | GY114 | GY126 |
|---|---|---|---|---|---|---|
| TLR7(EC50/μM) | 0.65 | 3.175 | 2.65 | 1.871 | 1.978 | 0.92 |

Relative induction=(average OD value of experimental group−average OD value of negative control group)/average OD value of negative control group.

Specific details for the above method may be referred to https:

//www.invivogen.com/hek-blue-htlr7; https://www.invivogen.com/sites/default/files/invivogen/products/files/hek_blue_htlr7_tds.pdf.

It can be seen that the series of GY compounds in Table 2 are activators for the TLR7 receptor pathway.

Example 2 Experiments on Immune Cell Inflammatory Factor Activation by a Series of GY Compounds The stimulating effect of a series of GY compounds or drugs on murine spleen lymphocytes was detected by ELISA.

2-1. Obtaining of Murine Spleen Lymphocytes 6-week-old Balb/c mice were sacrificed by cervical dislocation, spleens were taken under aseptic conditions. A 1 mL sterile syringe and a 200 mesh cell strainer were adopted to quickly grind and disperse the spleen into individual cells in 4 mL of a murine lymphocyte separation solution (Dakko's, 7211011). A resulting cell homogenate was transferred to a 15 mL centrifuge tube, then 1 mL of a RPMI 1640 medium (Hyclone, SH30809.01) was slowly added. Spleen lymphocytes were separated by a density gradient centrifugation method (800×g, 30 min), washed, red blood cells therein were lysed, such that a dispersed spleen lymphocyte suspension was obtained. Cells were counted by a hemocytometer, to calculate the cell concentration. A RPMI 1640 complete medium was adopted to adjust the cell suspension to a concentration of $1\times10^6$/ml/well, and the cells were then plated on a 24-well cell culture plate (Corning, 3524).

2-2. Drug Stimulation

Murine spleen lymphocytes were stimulated according to the gradient concentrations of the series of GY compounds or drugs, and incubated in a 37° C., 5% carbon dioxide incubator for 24 hrs.

2-3. ELISA test (1) Coating: a Capture antibody (primary antibody, purchased from Invitrogen) was diluted with a 1×Coating Buffer (coating buffer, purchased from Invitrogen) to a recommended concentration, and 100 μL of a resulting diluted solution was added to each well of a 96-well microtiter plate, the plate was sealed with a sealing film at 4° C. overnight.

(2) Washing: a liquid in each well was discarded, then 300 μL of a PBST working solution was added to each well and kept for 1 min, thereafter, the liquid therein was discarded. The washing process was repeated 3 times.

(3) Blocking: 200 μL of a blocking solution was added to each well. The plate was sealed with a sealing film, and placed on a shaker and incubated at room temperature for 1 hr, then washed and patted to be dry.

(4) Sample incubation: a sample was collected and centrifuged to collect a supernatant. Standards, samples, negative controls, and blank controls were provided in the 96-well microtiter plate, and each concentration or sample were provided with 2 replicates. 100 μL of a standard or sample was added to each well, thereafter, the plate was sealed with a sealing film, incubated on a shaker at room temperature for 1 hr or overnight at 4° C., then washed and pated to be dry.

(5) Secondary antibody incubation: the detection antibody (secondary antibody, purchased from Invitrogen) was diluted to a recommended concentration with a dilution buffer, 100 μL of a secondary antibody was added to each well. After being sealed with a sealing film, the plate was incubated on a shaker at room temperature for 1 hr, then washed and patted to be dry.

(6) Avidin-HRP incubation: Avidin-HRP (horseradish peroxidase marker, purchased from Invitrogen) was diluted to the recommended concentration with a dilution buffer, 100 μL of Avidin-HRP was added to each well. After being sealed with a sealing film, the plate was placed on a shaker and incubated at room temperature for 30 mins, washed 5-7 times by the process of step 2), and patted to be dry.

(7) TMB color development: 100 μL of a TMB color development solution (purchased from Invitrogen) was added to each well, for carrying out reaction for 15 mins at room temperature in the dark.

(8) Stopping reaction: 50 μL of 1M $H_2SO_4$ solution was added to each well.

(9) Reading an absorbance value by a microplate reader: the OD value at 450 nm wavelength was read. A standard curve and a parameter nonlinear regression equation were drawn, and a sample concentration was calculated according to the obtained formula. As shown in Table 3.

TABLE 3

EC50 values of cytokine stimulating activity of a series of GY compounds on mouse immune cells.

| | Compounds EC50 (μM) | | | | | | | |
|---|---|---|---|---|---|---|---|---|
| | R848 | Imiquimod | GY100 | GY101 | GY102 | GY103 | GY104 | GY106 |
| TNF-alpha | <0.001 | 8.354 | <0.001 | 0.007 | 1.439 | 2.62 | 34.73 | <0.001 |
| IFN-gamma | 0.056 | No fit | 0.104 | 0.122 | 1.07 | 3.341 | No fit | 2.83 |
| IL-6 | <0.001 | 8.303 | <0.001 | 1.047 | 0.637 | 1.506 | 27.67 | <0.001 |

| | Compounds EC50 (μM) | | | | | | |
|---|---|---|---|---|---|---|---|
| | GY109 | GY132 | GY127 | GY112 | GY161 | GY163 | GY164 |
| TNF-alpha | 0.153 | 2.153 | 0.248 | 0.914 | 0.011 | 0.058 | 0.001 |
| IFN-gamma | 0.983 | No fit | 0.753 | 8.296 | 1.532 | 7.86 | 0.010 |
| IL-6 | 0.653 | No fit | 0.083 | 0.3144 | 0.006 | 1.1 | 5.93 |

It is seen that the series of GY compounds as listed in Table 3 has the immune regulation activity by stimulating immune cell factors.

Example 3 Detection of Growth Inhibitory Effect or Amplification Effect of a Series of GY Compounds or Drugs on Cells by CCK8 Method Murine breast cancer 4T1 cells (Kailian Biotech, KG338) in a logarithmic growth phase were selected and washed with PBS, digested with 0.25% trypsin (including EDTA), stopped digestion with a DMEM complete medium, then centrifuged, and resuspended to form a suspension of 4T1 single cells. Cells were counted using a hemocytometer and a cell concentration was calculated. A DMEM complete medium was used to adjust the cell suspension to a target concentration, and thereafter, the cells were plated on a 96-well cell culture plate according to $4\times10^3$/100 μL per well. After adherering to the wall, the 4T1 cells were stimulated according to the designed concentration gradients of the series of GY compounds or drugs, with each concentration being provided with 3 replicate holes. The 96-well cell culture plate with 4T1 cells seeded and dosing was placed in the cell incubator, and incubated at 37° C., 5% carbon dioxide for 24 hrs (or 36, 72 hrs). After the incubation time was over, 10 μL of CCK8 reagent was added to each well and incubated for 1-2 hrs at 37° C. A full-wavelength microplate reader was adopted to test an OD value at 450 nm wavelength.

(as Shown in Table 4)

CCK8 calculation formula is as follows:

Cell survival rate (100%)=$(As-A_c)/(A_c-A_b)\times100\%$

As: Absorbance of wells containing cells, CCK8 solution, and drug solution

Ac: Absorbance of wells containing cells and CCK8 solution, and no drug solution Ab: Absorbance of wells containing CCK8 solution, no cells, and no drug solution

TABLE 4

IC50 values of the inhibitory activities of a series of GY compounds on tumor cell growth

| | Cancer cells | | | | | | | | | | | | |
|---|---|---|---|---|---|---|---|---|---|---|---|---|---|
| Compounds | K562 | HL60 | 4T1 | CT26 | A549 | MB231 | Daudi B | Raji | WEHI-3 | HEK-293T | LLC | HCT-116 | B16 |
| GY104 | | | | | 17.09 | | | | | | | | |
| GY112 | 14.63 | 9.75 | 1.45 | 25.02 | 16.79 | | 8.73 | 10.61 | 5.31 | 13.77 | 18.82 | 15.66 | 34.14 |
| GY117 | | 18.98 | | | | | | | | | | | |
| GY118 | | 15.11 | 14.66 | | 16.55 | 5.80 | | | | | | | |
| GY127 | 17.77 | 19.07 | 17.28 | 16.93 | 23.24 | | | | | 25.97 | 15.27 | 20.77 | |
| GY131 | 92.14 | 92.14 | 2.86 | 165.9 | | | 14.09 | 10.41 | 7.38 | 25.07 | | | 40.68 |
| GY132 | | 5.13 | | | | | 5.36 | 2.03 | 14.69 | | | | |
| GY134 | | | | | | | 6.99 | 5.12 | | | | | |
| GY135 | | 13.14 | | | | | 14.56 | 7.60 | | | | | |
| GY137 | | 26.98 | | | | | 24.64 | 37.23 | | | | | |
| GY138 | | | | | | | | | 47.59 | | | | |
| GY150 | | | | | | | | | 22.26 | | | | |
| GY161 | | | 0.78 | 6.15 | | | 11.82 | 16.07 | | | | | 11.72 |

Note:
IC50 (μM)

Cell growth inhibition rate (%)=1−((OD value of experimental group−OD value of blank group)/(OD value of control group−OD value of blank group)×100%).

The series of GY compounds in the present application coupled with the targeted drug have the dual-functional effect of immune activation and targeted inhibition of specific targets. On the basis of inducing immune cells to produce immune cell factors, such series of GY compounds have different growth inhibition effects for different tumor cells.

The series of GY compounds in the present application coupled with the targeted drug has the effect of amplifying immune cells.

The multifunctional immune targeted compound formed by the immune agonist coupled with the targeted drug described in the present application has both the effect of activating immune cells and the effect of inhibiting the growth of cancer cells. For the coupling product of the same original drug, although the coupling site completely maintains the functional group and structure of the original drug, the inhibitory function of cancer cells is maintained or changed. The level of effect on the same or different cells under standard experimental conditions (such as the CCK8 method) has unexpected effects.

For example, for the derivative coupled with Ibrutinib, a series of GY conjugate and a series of SZU conjugate produced significantly different unexpected effects in K562 cells and leukemia WEHI-3 cells.

The compounds involved in the present application also have unexpected effects on immune cells activation. For example, based on the same immune agonist GY109 as a precursor agonist, the resulting conjugates GY132, GY137, GY131 and GY133 all show different immune activation effects. These effects vary according to different coupling compounds. Although the rules are worthy of in-depth mechanism research, the present application provides a practical technique and example for creating such characteristic compounds.

In summary, in the present application, a potent TLR7 agonist, that is, an alkynyl derivative of purine GY100, is accidentally discovered. Based on this discovery, a series of immune agonists containing a five-membered heterocycle having three nitrogens are synthesized. Through further exploration and optimization, a series of novel immune agonists are obtained. These novel immune agonists not only have good immune activation effects, but also can be coupled with other targeted compounds and drugs to produce a new generation of dual-function immune targeted agonists. On the basis of maintaining or strengthening the original targeting effect, this series of novel immune agonists are also incorporated with immune activation effect, and can amplify the number of immune cells as well. These series of novel multifunctional immune targeted compounds are directed to new directions for immunotargeted drugs. It has been known that the major side effect of many classic anticancer drugs or the targeted drugs is immunosuppression, and viral infections reduce lymphocytes. The multifunctional immune targeted compounds of the present application have the above-mentioned beneficial effects, and have important values in anti-tumor and anti-viral aspects.

REFERENCES

1. Blasius, A. L. & Beutler, B. Intracellular toll-like receptors. *Immunity* 2010, 32, 305-315.
2. Huju Chi et al. Anti-tumor Activity of Toll-Like Receptor 7 Agonists. *Front Pharmacol.* 2017 May 31; 8: 304. doi: 10.3389/fphar.2017.00304.

What is claimed is:

1. A compound having a structure represented by Formula I:

Formula I

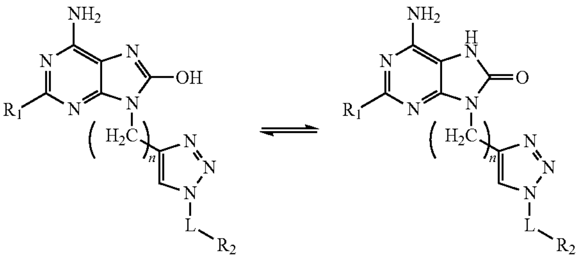

wherein $R_1$ represents any one of the following alkoxy groups and alkylamino groups:

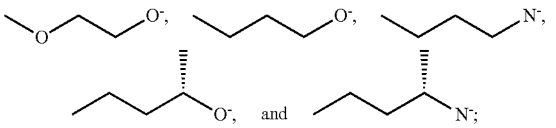

and

L represents a connection chain, and the connection chain comprises any one of a polyethylene glycol chain, an alkyl chain, and a heterocyclic chain;

n represents an integer between 1 and 20;

$R_2$ represents a functional group or a functional carrier;

the functional group comprises at least one of a carboxyl group, a phosphate group, an amino group, an isothiocyano group, an isocyanate group, a thiourea group, an azide group, an unsaturated double bond, and an unsaturated triple bond; or consists of at least one of a targeted drug or a precursor thereof, a protein, a polypeptide, an antibody, a virus, a bacteria, and a cell; and the functional carrier comprises: a biocompatible material capable of binding the Formula I, a carrier capable of binding the Formula I, a biocompatible material capable of supporting the Formula I, and a carrier capable of supporting the Formula I.

2. The compound of claim 1, wherein a target protein of the targeted drug is at least one selected from the group consisting of: EGFR and a tyrosine kinase thereof, VEGFR and a tyrosine kinase thereof, VEGF, FGFR, HER2, HER3, HER4, NTRK, ROS1, ALK, BRD4, HDAC, KRAS, BRAF, BTK, PARP, BRCA, MEK, MET, NYC, TOPK, EZH2, BCMA, PI3K, PDGFR, FLT3, TOX, PD-L1, PD-1, CTLA-4, LAG3, TIM3, Siglec-15, TIGIT, TROP2, OX40, mTOR, BCL2, CD40, CD47, CD122, CD160, CD3, CD19, CD20, CD38, MUC1, MUC16, CDK4/6, TGFβ, HIF-1α/2α, PSGL-1, SURVIVIN, Frizzled-7, SLC4A7, CCR4, CCR5, CXCR4, CXCR5, CCL12, CXCL1, CXCL8, CXCL10, carbonic anhydrase IX, a virus subunit protein and a T and/or B cell epitope peptide thereof, and a T and/or B cell epitope peptide of a bacterial subunit protein.

3. The compound of claim 1, wherein the targeted drug is at least one of an antibacterial drug, a precursor of the antibacterial drug, an antiviral drug, and a precursor of the antiviral drug.

4. The compound of claim 1, wherein the targeted drug is at least one selected from TQB3804, AMG510, Mavorixafor, TAK-220, TAK-779, Osimertinib, Ibrutinib, Zanubrutinib, JQ1, Norfloxacin, a conservative or variant protein of SARS-CoV and an epitope peptide thereof, a conservative or variant protein of SARS-CoV-2 and an epitope peptide thereof, and an RNA polymerase inhibitor.

5. The compound of claim 1, wherein the compound is selected from the group consisting of:

GY101 having a structural formula of

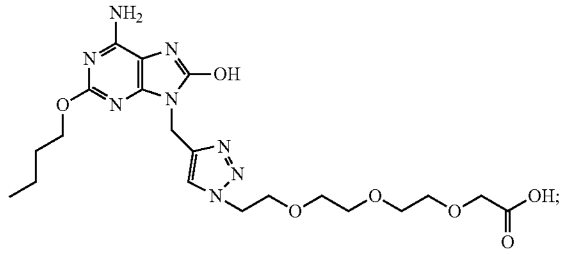 [SMILES: CCCCOc1nc(N)c2nc(O)n(Cc3cn(CCOCCOCCOCC(=O)O)nn3)c2n1]

GY102 having a structural formula of

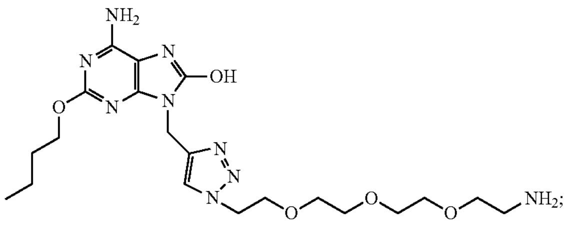 [SMILES: CCCCOc1nc(N)c2nc(O)n(Cc3cn(CCOCCOCCOCCN)nn3)c2n1]

GY103 having a structural formula of
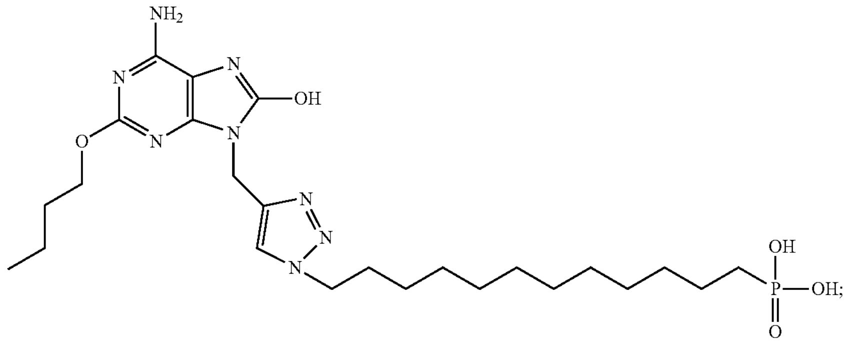 [SMILES: CCCCOc1nc(N)c2nc(O)n(Cc3cn(CCCCCCCCCCCCP(=O)(O)O)nn3)c2n1]
GY105 having a structural formula of
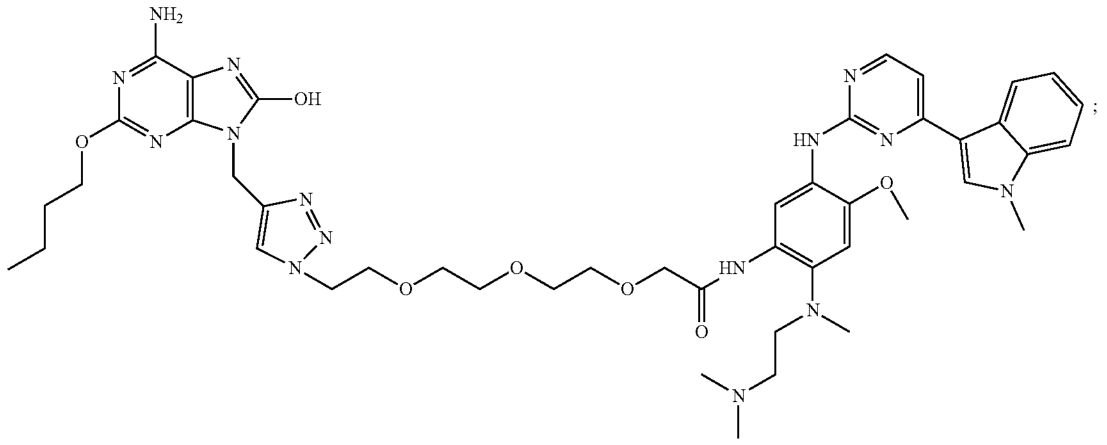 [SMILES: CCCCOc1nc(N)c2nc(O)n(Cc3cn(CCOCCOCCOCC(=O)Nc4cc(Nc5nccc(-c6cn(C)c7ccccc67)n5)c(OC)cc4N(C)CCN(C)C)nn3)c2n1]
GY106 having a structural formula of
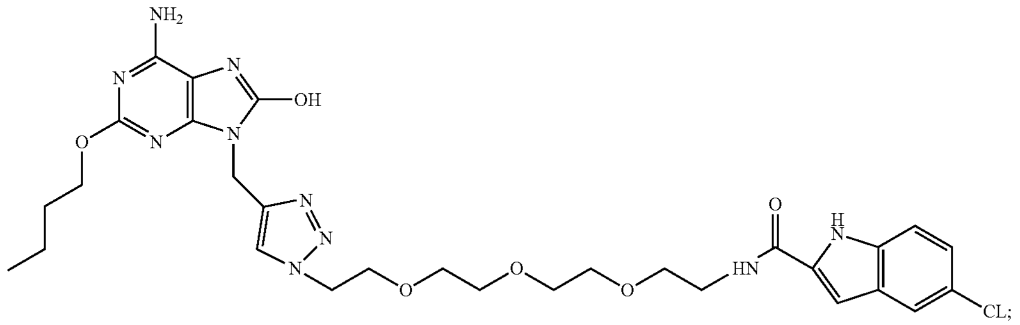

GY107 having a structural formula of
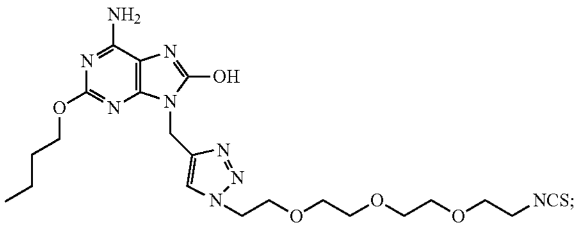
GY106 having a structural formula of
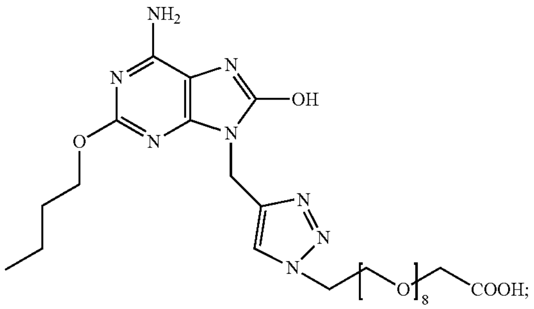
GY108 having a structural formula of
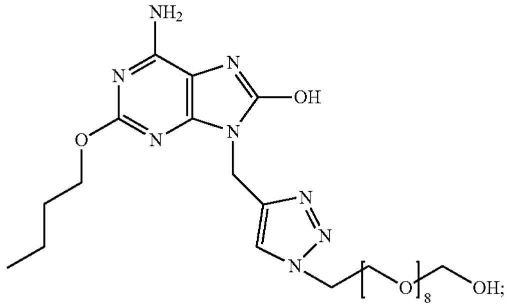
GY109 having a structural formula of
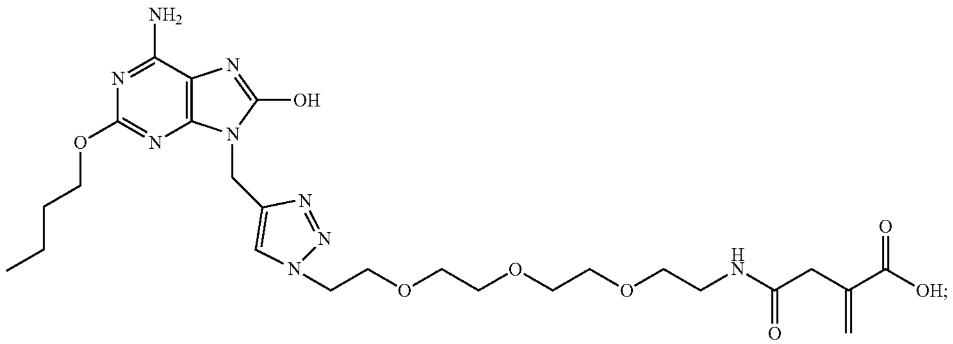 [SMILES: C=C(CC(=O)NCCOCCOCCOCCn1cc(Cn2c(O)nc3c(N)nc(OCCCC)nc32)nn1)C(=O)O]
GY1110 having a structural formula of
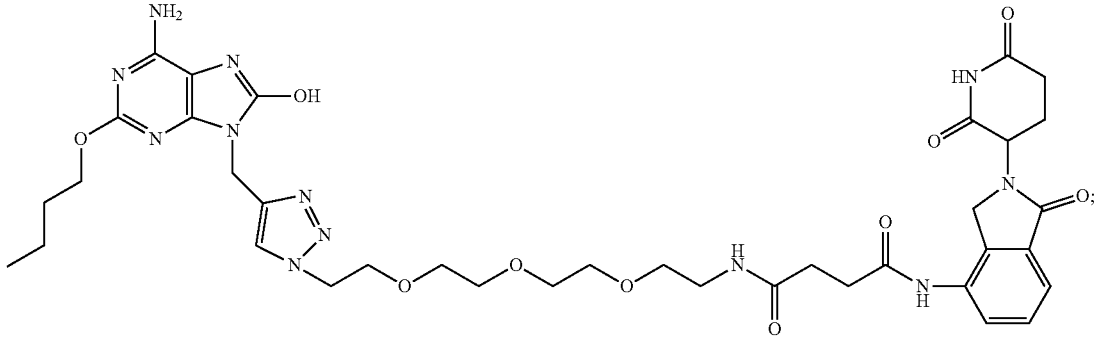 [SMILES: CCCCOc1nc(N)c2nc(O)n(Cc3cn(CCOCCOCCOCCNC(=O)CCC(=O)Nc4cccc5c4CN(C4CCC(=O)NC4=O)C5=O)nn3)c2n1]

GY111 having a structural formula of
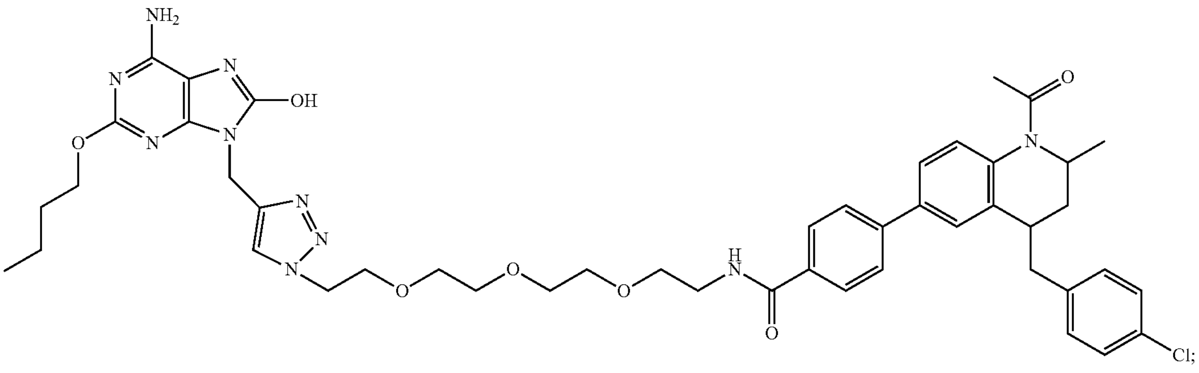 [SMILES: CCCCOc1nc(N)c2nc(O)n(Cc3cn(CCOCCOCCOCCNC(=O)c4ccc(-c5ccc6c(c5)C(Cc5ccc(Cl)cc5)CC(C)N6C(C)=O)cc4)nn3)c2n1]
GY112 having a structural formula of
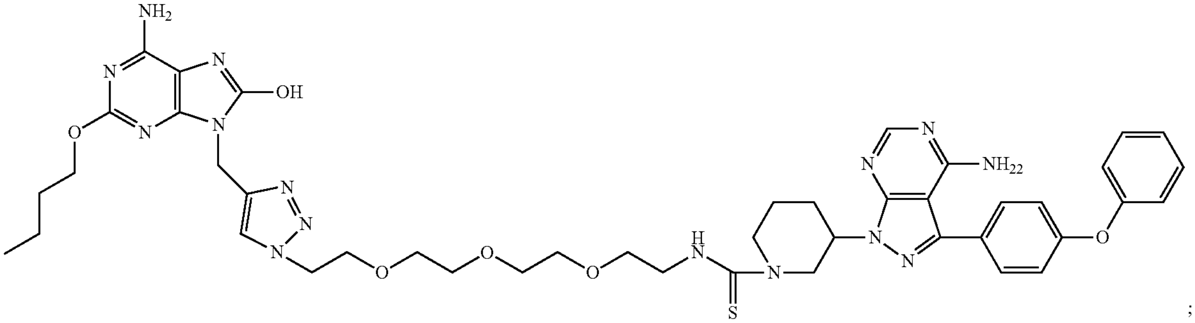
;
GY113 having a structural formula of
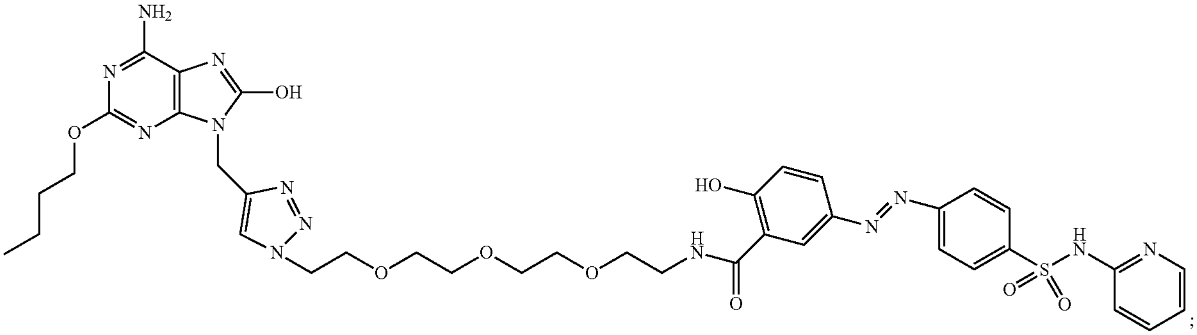 [SMILES: CCCCOc1nc(N)c2nc(O)n(Cc3cn(CCOCCOCCOCCNC(=O)c4cc(/N=N/c5ccc(S(=O)(=O)Nc6ccccn6)cc5)ccc4O)nn3)c2n1]
;
GY114 having a structural formula of
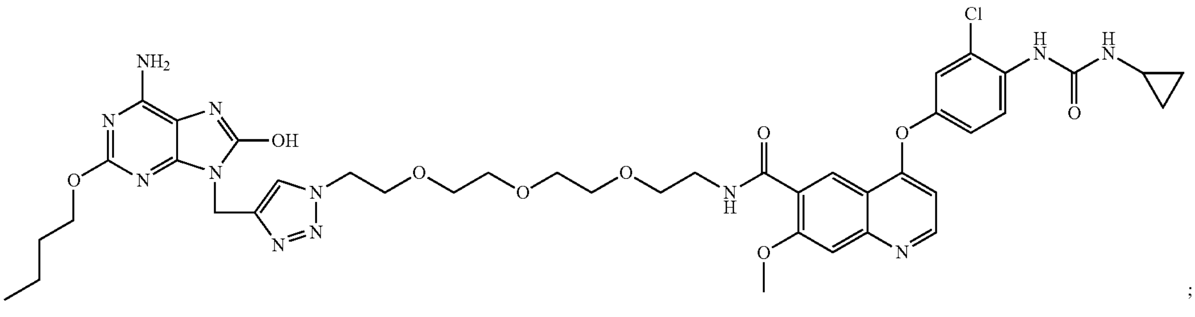 [SMILES: CCCCOc1nc(N)c2nc(O)n(Cc3cn(CCOCCOCCOCCNC(=O)c4cc5c(Oc6ccc(NC(=O)NC7CC7)c(Cl)c6)ccnc5cc4OC)nn3)c2n1]
;

GY116 having a structural formula of
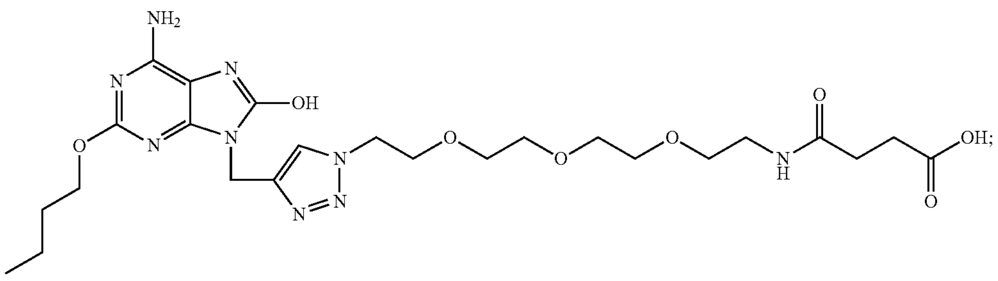 [SMILES: CCCCOc1nc(N)c2nc(O)n(Cc3cn(CCOCCOCCOCCNC(=O)CCC(=O)O)nn3)c2n1]
GY117 having a structural formula of
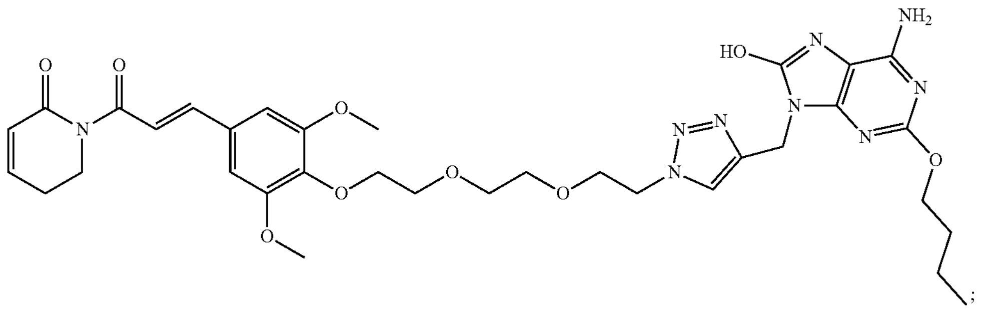 [SMILES: CCCCOc1nc(N)c2nc(O)n(Cc3cn(CCOCCOCCOc4c(OC)cc(/C=C/C(=O)N5CCC=CC5=O)cc4OC)nn3)c2n1]
GY118 having a structural formula of a
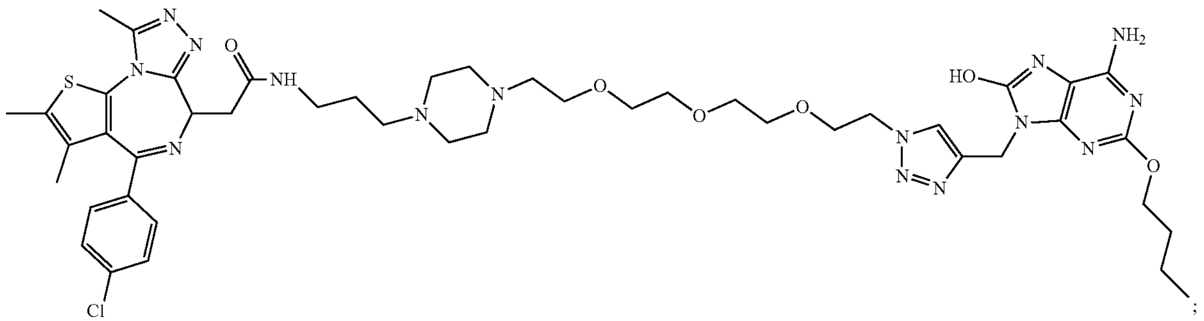 [SMILES: CCCCOc1nc(N)c2nc(O)n(Cc3cn(CCOCCOCCOCCN4CCN(CCCNC(=O)CC5N=C(c6ccc(Cl)cc6)c6c(sc(C)c6C)-n6c(C)nnc65)CC4)nn3)c2n1]
GY119 having a structural formula of a
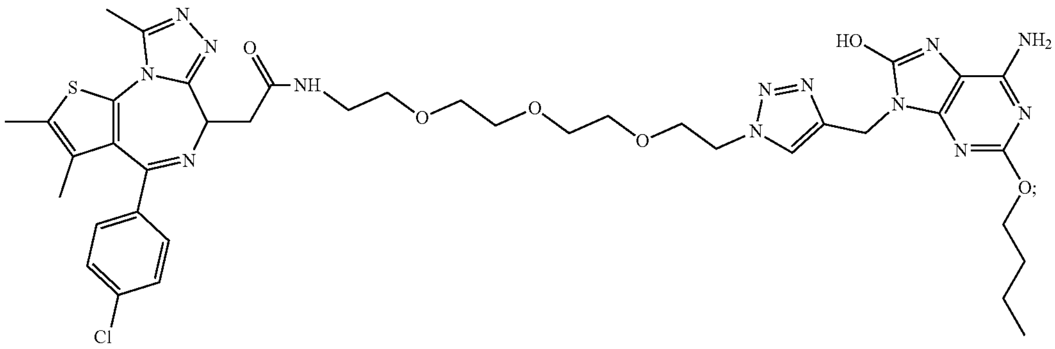 [SMILES: CCCCOc1nc(N)c2nc(O)n(Cc3cn(CCOCCOCCOCCNC(=O)CC4N=C(c5ccc(Cl)cc5)c5c(sc(C)c5C)-n5c(C)nnc54)nn3)c2n1]

GY126 having a structural formula of
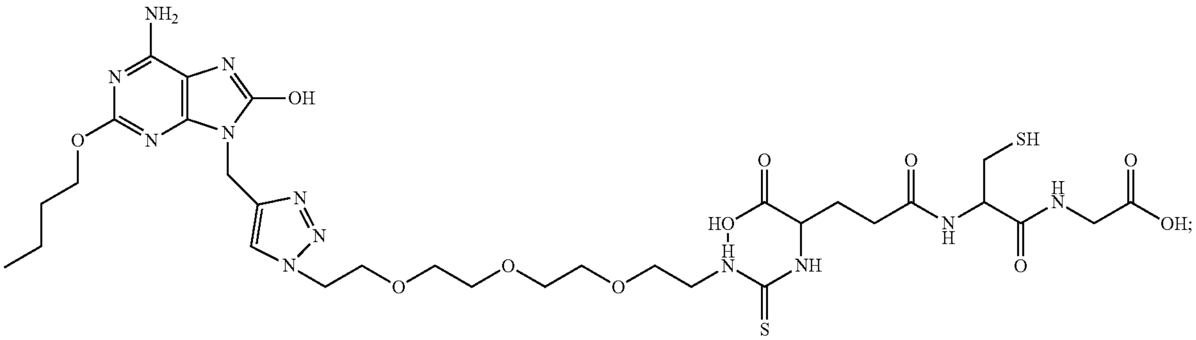
GY127 having a structural formula of
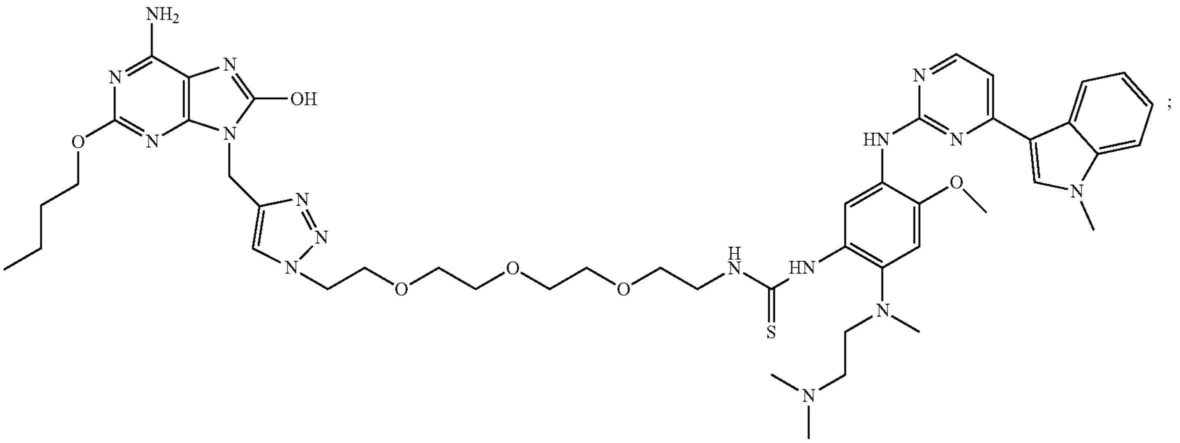 [SMILES: CCCCOc1nc(N)c2nc(O)n(Cc3cn(CCOCCOCCOCCNC(=S)Nc4cc(Nc5nccc(-c6cn(C)c7ccccc67)n5)c(OC)cc4N(C)CCN(C)C)nn3)c2n1]
GY131 having a structural formula of
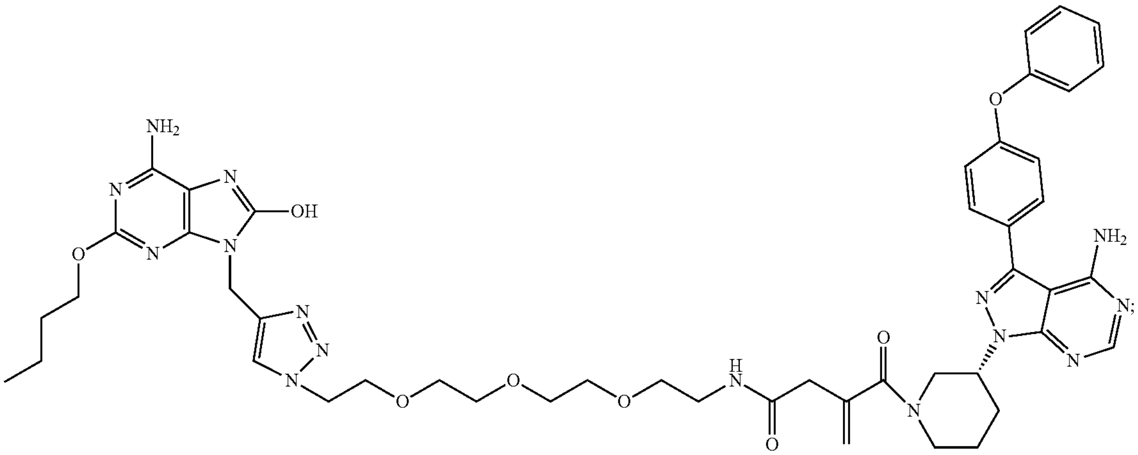 [SMILES: C=C(CC(=O)NCCOCCOCCOCCn1cc(Cn2c(O)nc3c(N)nc(OCCCC)nc32)nn1)C(=O)N1CCC[C@@H](n2nc(-c3ccc(Oc4ccccc4)cc3)c3c(N)ncnc32)C1]

GY1132 having a structural formula of
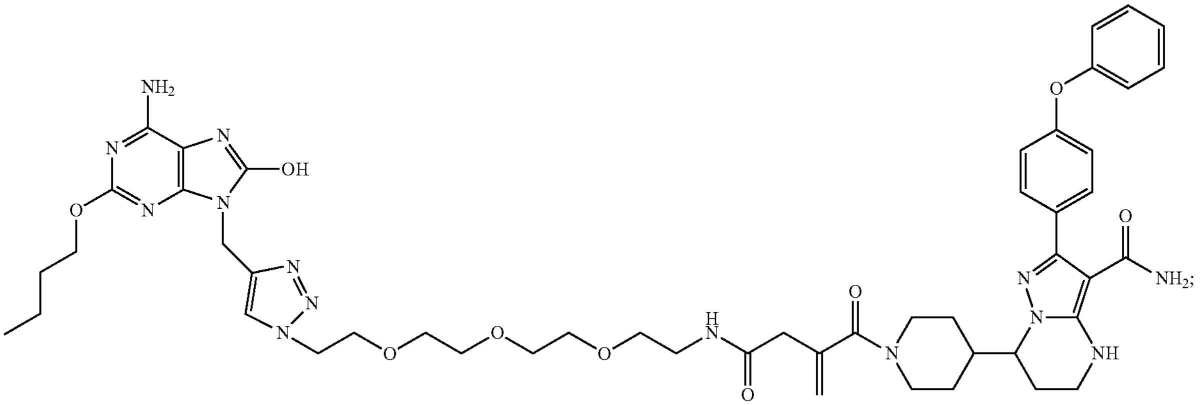 [SMILES: C=C(CC(=O)NCCOCCOCCOCCn1cc(Cn2c(O)nc3c(N)nc(OCCCC)nc32)nn1)C(=O)N1CCC(C2CCNc3c(C(N)=O)c(-c4ccc(Oc5ccccc5)cc4)nn32)CC1]
GY133 having a structural formula of
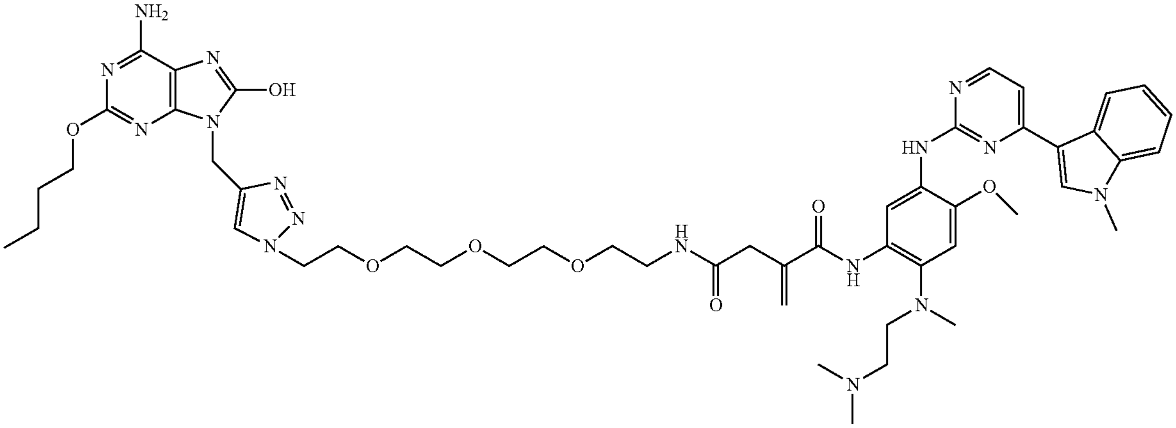
;
GY134 having a structural formula of
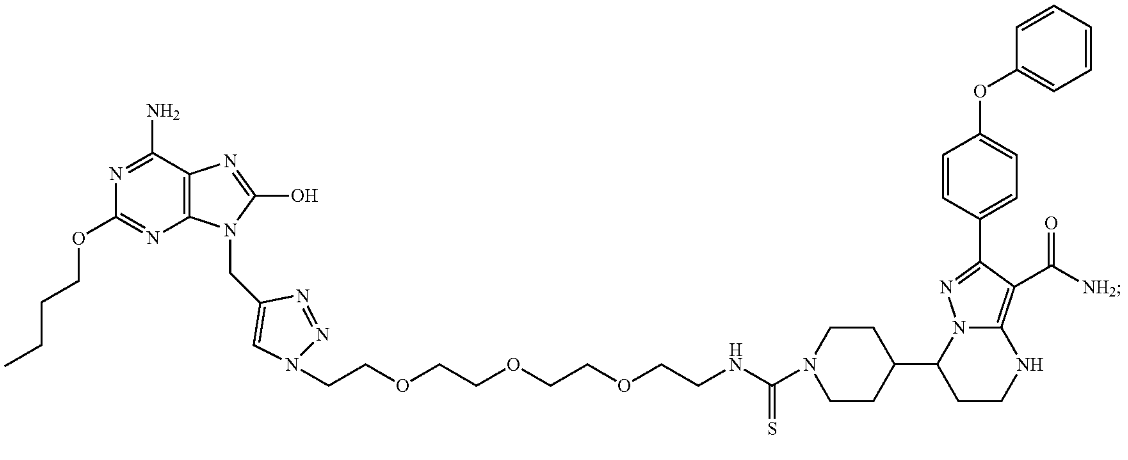 [SMILES: CCCCOc1nc(N)c2nc(O)n(Cc3cn(CCOCCOCCOCCNC(=S)N4CCC(C5CCNc6c(C(N)=O)c(-c7ccc(Oc8ccccc8)cc7)nn65)CC4)nn3)c2n1]

GY135 having a structural formula of
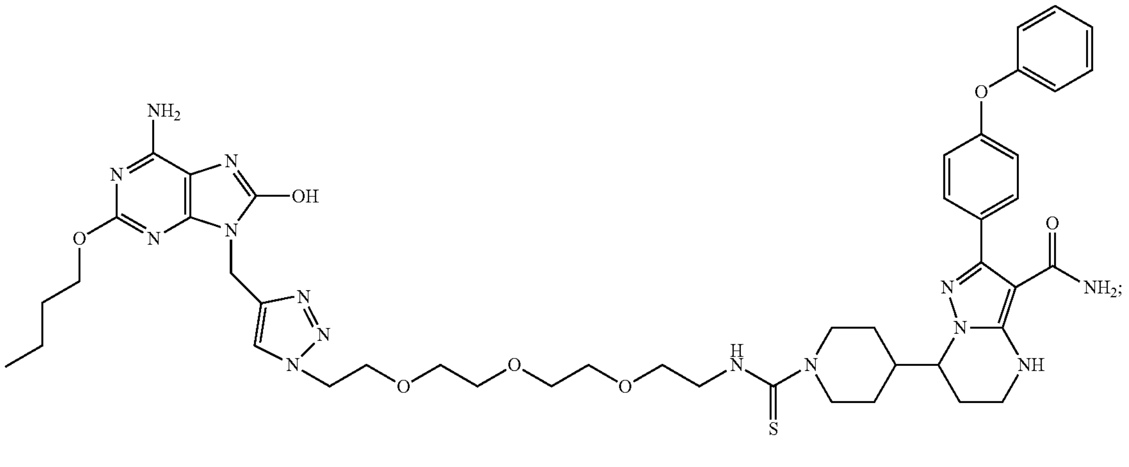 [SMILES: CCCCOc1nc(N)c2nc(O)n(Cc3cn(CCOCCOCCOCCNC(=S)N4CCC(C5CCNc6c(C(N)=O)c(-c7ccc(Oc8ccccc8)cc7)nn65)CC4)nn3)c2n1]
GY136 having a structural formula of
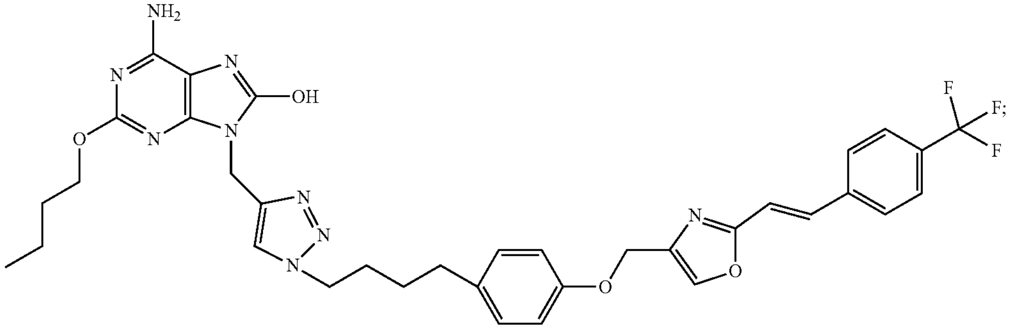 [SMILES: CCCCOc1nc(N)c2nc(O)n(Cc3cn(CCCCc4ccc(OCc5coc(/C=C/c6ccc(C(F)(F)F)cc6)n5)cc4)nn3)c2n1]
GY137 having a structural formula of
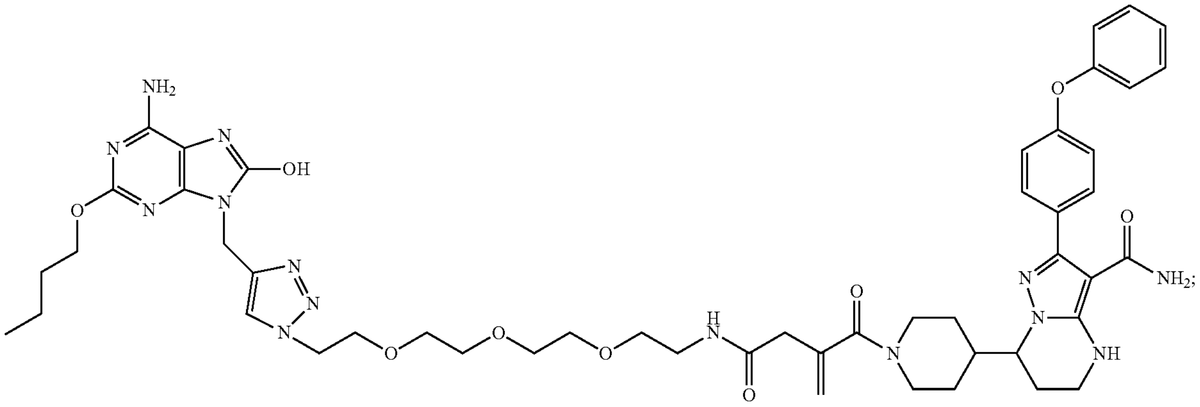 [SMILES: C=C(CC(=O)NCCOCCOCCOCCn1cc(Cn2c(O)nc3c(N)nc(OCCCC)nc32)nn1)C(=O)N1CCC(C2CCNc3c(C(N)=O)c(-c4ccc(Oc5ccccc5)cc4)nn32)CC1]

GY138 having a structural formula of
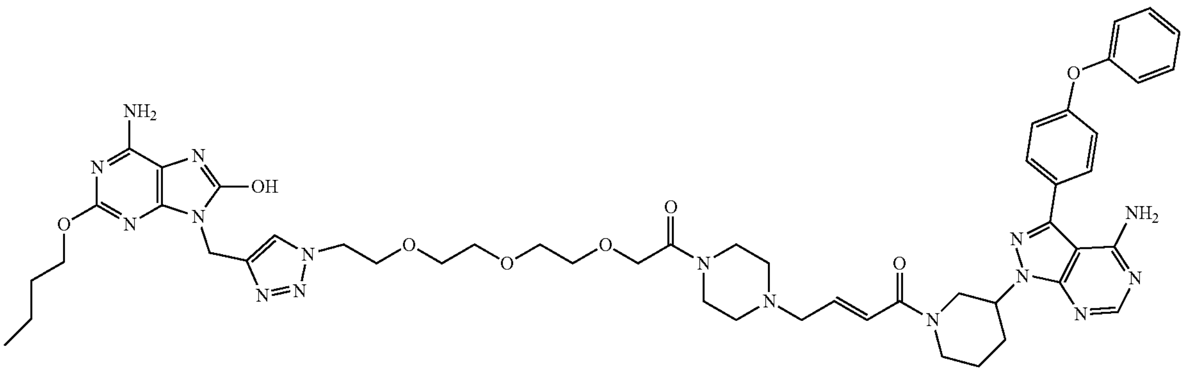
;
GY139 having a structural formula of
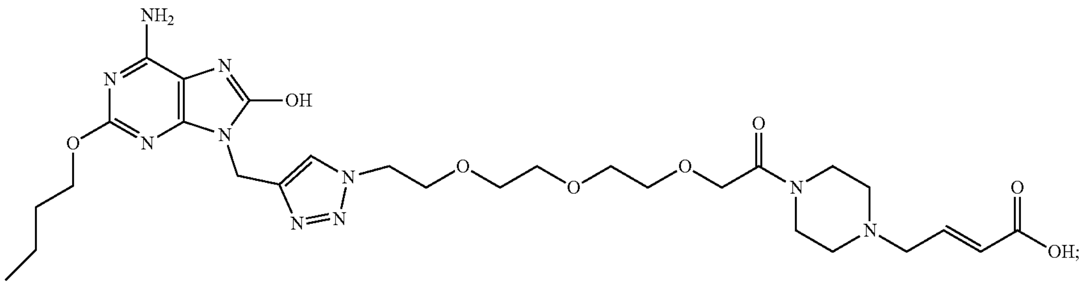 [SMILES: CCCCOc1nc(N)c2nc(O)n(Cc3cn(CCOCCOCCOCC(=O)N4CCN(C/C=C/C(=O)O)CC4)nn3)c2n1]
GY140 having a structural formula of
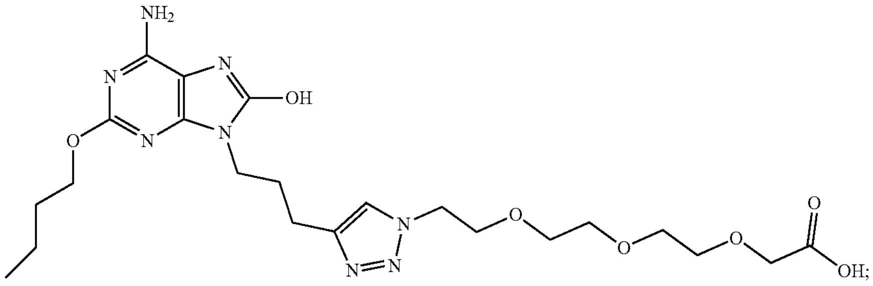 [SMILES: CCCCOc1nc(N)c2nc(O)n(CCCc3cn(CCOCCOCCOCC(=O)O)nn3)c2n1]
GY141 having a structural formula of
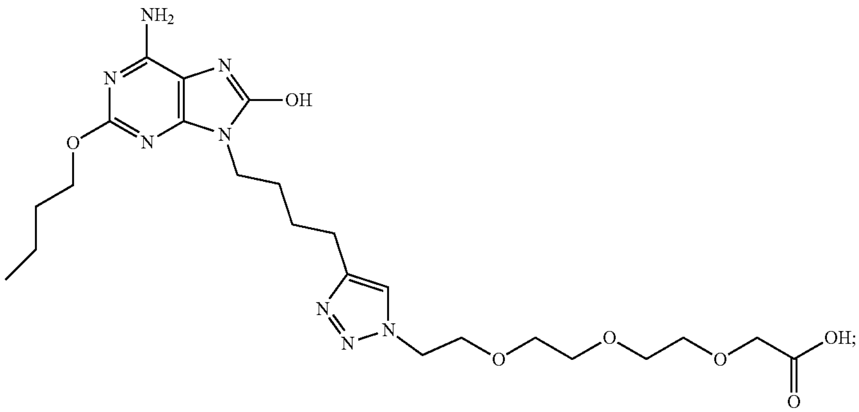 [SMILES: CCCCOc1nc(N)c2nc(O)n(CCCCc3cn(CCOCCOCCOCC(=O)O)nn3)c2n1]

GY142 having a structural formula of
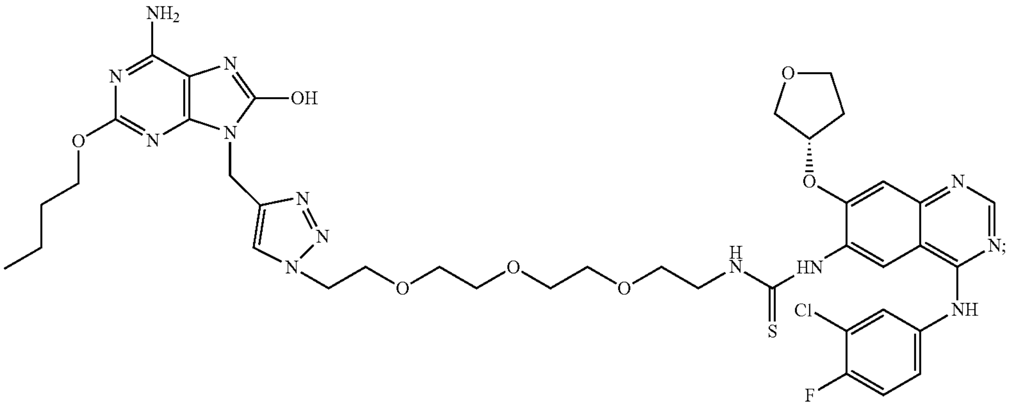 [SMILES: CCCCOc1nc(N)c2nc(O)n(Cc3cn(CCOCCOCCOCCNC(=S)Nc4cc5c(Nc6ccc(F)c(Cl)c6)ncnc5cc4O[C@H]4CCOC4)nn3)c2n1]
GY143 having a structural formula of
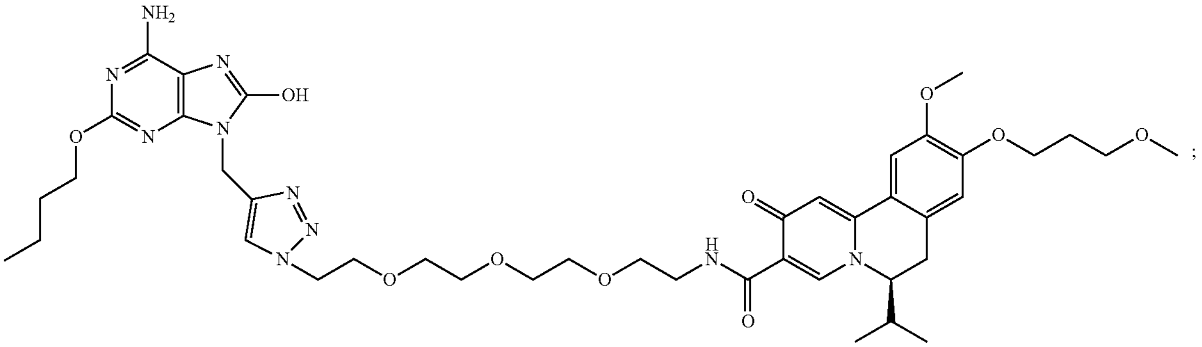 [SMILES: CCCCOc1nc(N)c2nc(O)n(Cc3cn(CCOCCOCCOCCNC(=O)c4cn5c(cc4=O)-c4cc(OC)c(OCCCOC)cc4C[C@H]5C(C)C)nn3)c2n1]
GY144 having a structural formula of
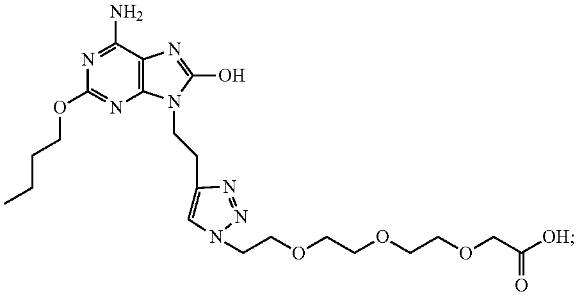 [SMILES: CCCCOc1nc(N)c2nc(O)n(CCc3cn(CCOCCOCCOCC(=O)O)nn3)c2n1]
GY145 having a structural formula of
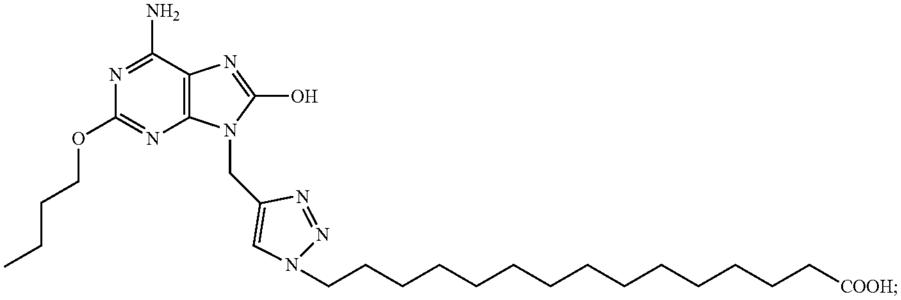 [SMILES: CCCCOc1nc(N)c2nc(O)n(Cc3cn(CCCCCCCCCCCCCCC(=O)O)nn3)c2n1]

GY146 having a structural formula of
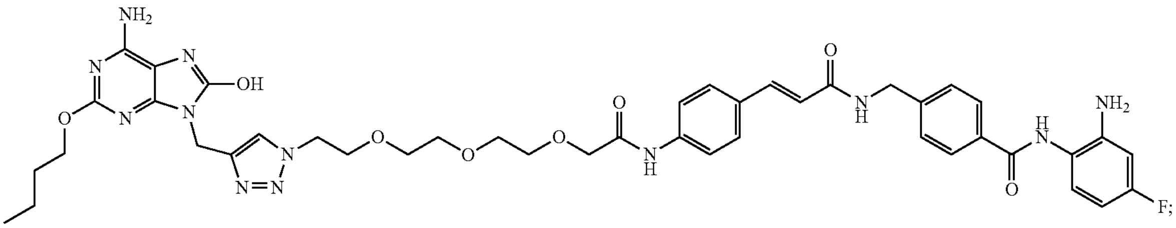 [SMILES: CCCCOc1nc(N)c2nc(O)n(Cc3cn(CCOCCOCCOCC(=O)Nc4ccc(/C=C/C(=O)NCc5ccc(C(=O)Nc6ccc(F)cc6N)cc5)cc4)nn3)c2n1]
GY147 having a structural formula of
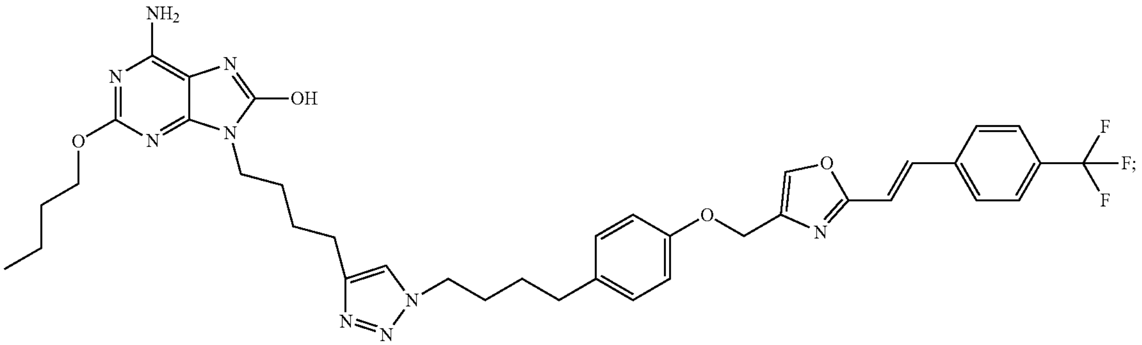 [SMILES: CCCCOc1nc(N)c2nc(O)n(CCCCc3cn(CCCCc4ccc(OCc5coc(/C=C/c6ccc(C(F)(F)F)cc6)n5)cc4)nn3)c2n1]
GY148 having a structural formula of
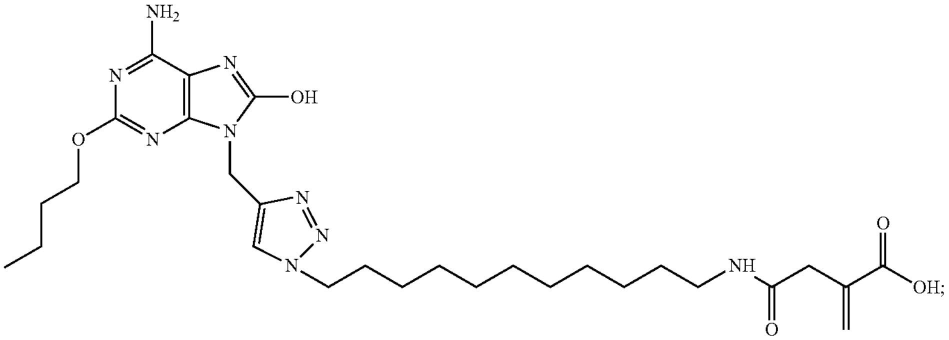 [SMILES: C=C(CC(=O)NCCCCCCCCCCCn1cc(Cn2c(O)nc3c(N)nc(OCCCC)nc32)nn1)C(=O)O]
GY149 having a structural formula of
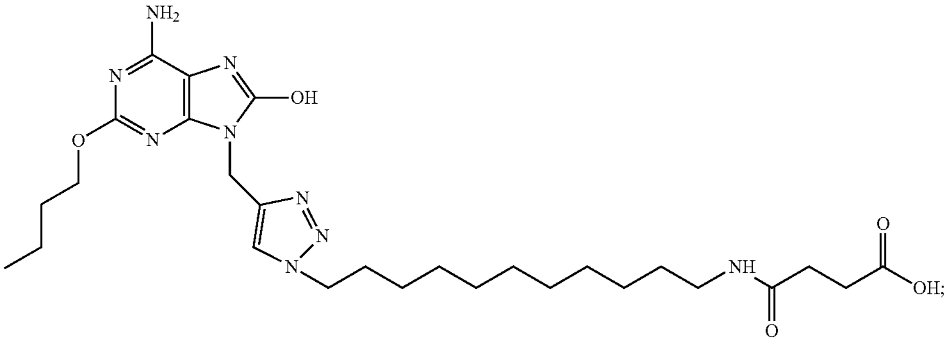 [SMILES: CCCCOc1nc(N)c2nc(O)n(Cc3cn(CCCCCCCCCCCNC(=O)CCC(=O)O)nn3)c2n1]

GY150 having a structural formula of
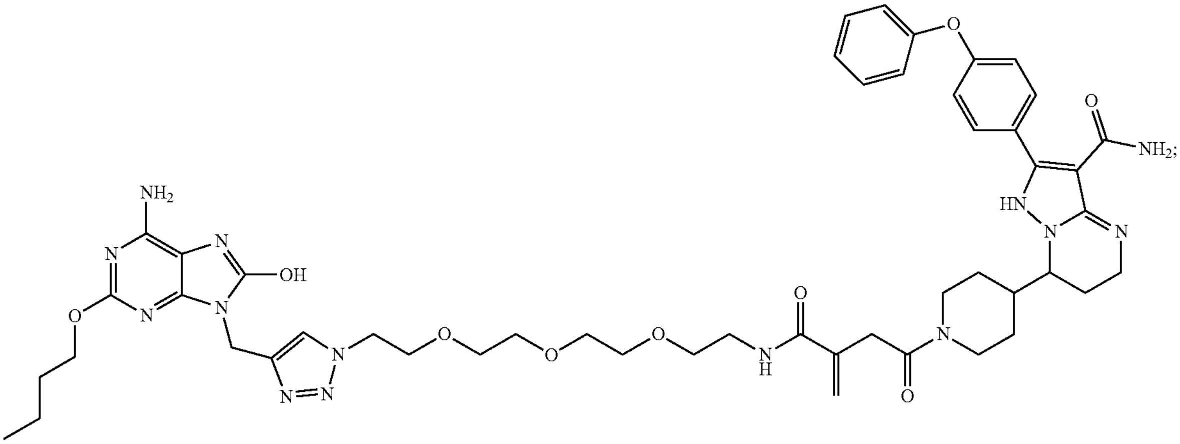 [SMILES: C=C(CC(=O)N1CCC(C2CCN=C3C(C(N)=O)=C(c4ccc(Oc5ccccc5)cc4)NN32)CC1)C(=O)NCCOCCOCCOCCn1cc(Cn2c(O)nc3c(N)nc(OCCCC)nc32)nn1]
GY153 having a structural formula of
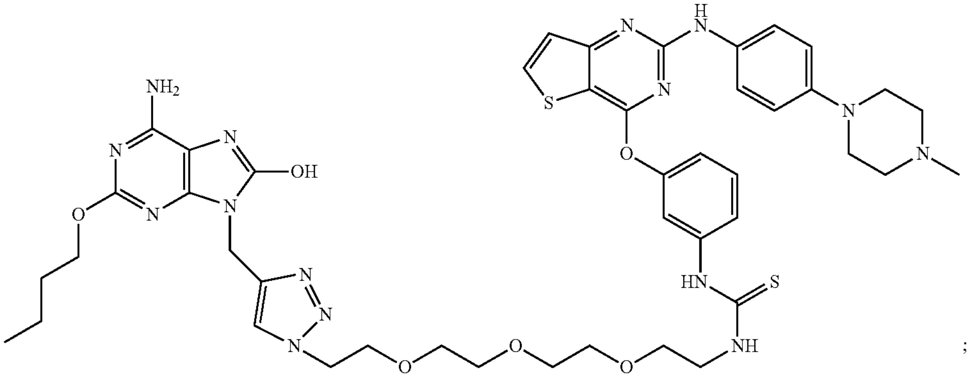 [SMILES: CCCCOc1nc(N)c2nc(O)n(Cc3cn(CCOCCOCCOCCNC(=S)Nc4cccc(Oc5nc(Nc6ccc(N7CCN(C)CC7)cc6)nc6ccsc56)c4)nn3)c2n1]
;
GY155 having a structural formula of
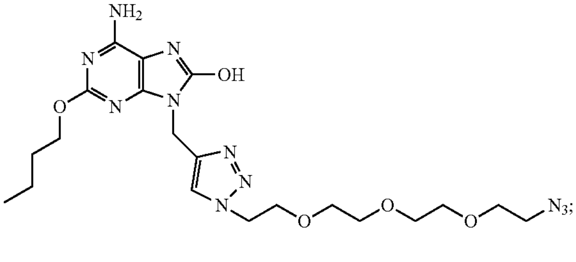 [SMILES: CCCCOc1nc(N)c2nc(O)n(Cc3cn(CCOCCOCCOCCN=[N+]=[N-])nn3)c2n1]
;

GY156 having a structural formula of
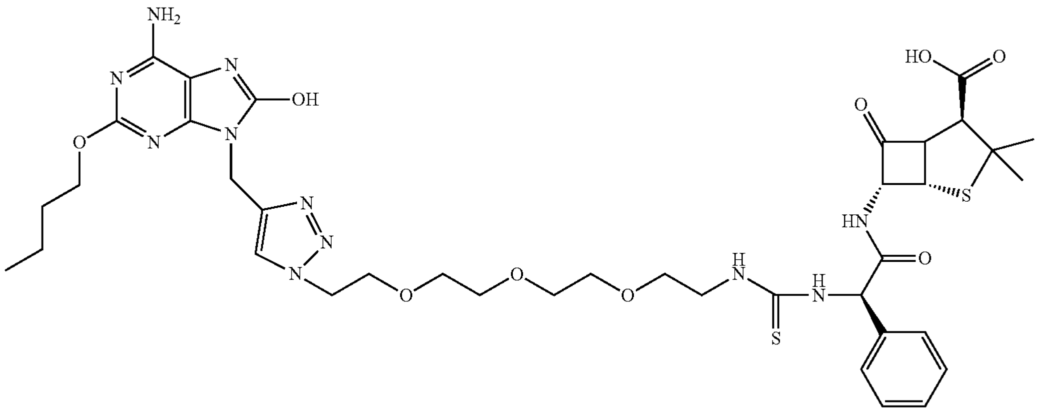
;
GY157 having a structural formula of
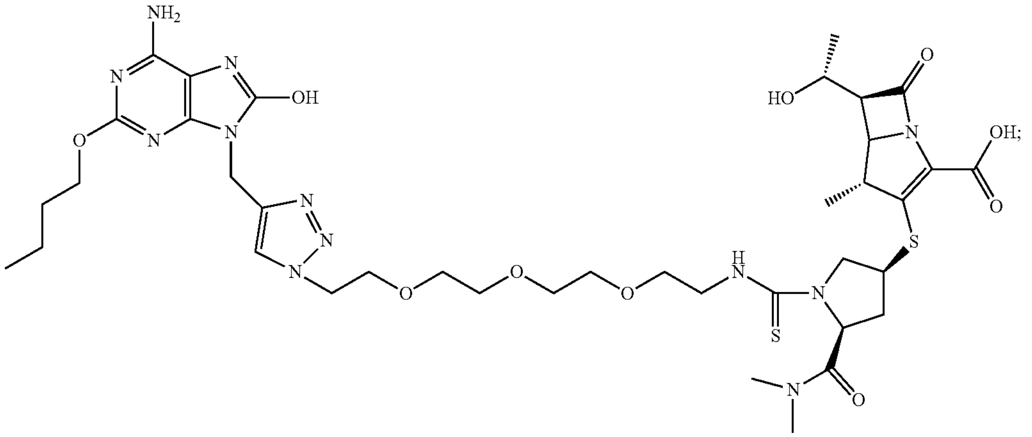
GY158 having a structural formula of
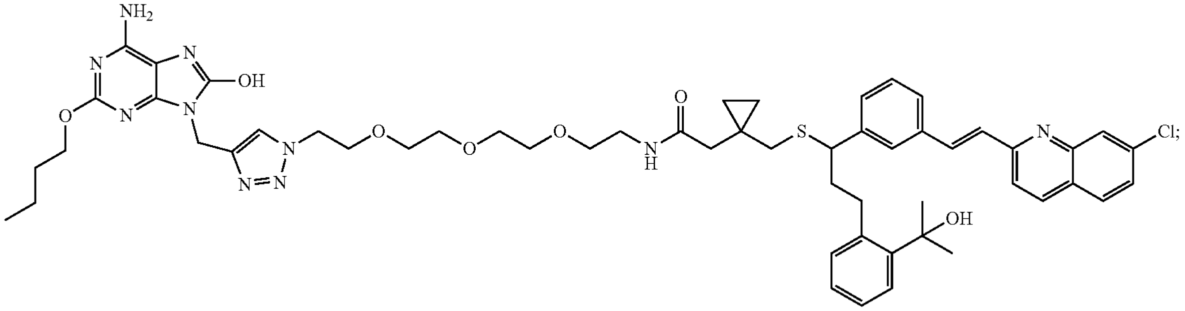 [SMILES: CCCCOc1nc(N)c2nc(O)n(Cc3cn(CCOCCOCCOCCNC(=O)CC4(CSC(CCc5ccccc5C(C)(C)O)c5cccc(/C=C/c6ccc7ccc(Cl)cc7n6)c5)CC4)nn3)c2n1]

GY160 having a structural formula of
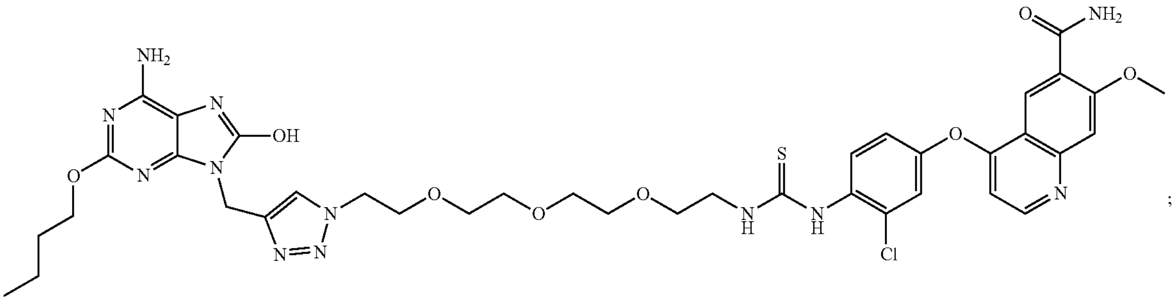 [SMILES: CCCCOc1nc(N)c2nc(O)n(Cc3cn(CCOCCOCCOCCNC(=S)Nc4ccc(Oc5ccnc6cc(OC)c(C(N)=O)cc56)cc4Cl)nn3)c2n1]
;
GY161 having a structural formula of
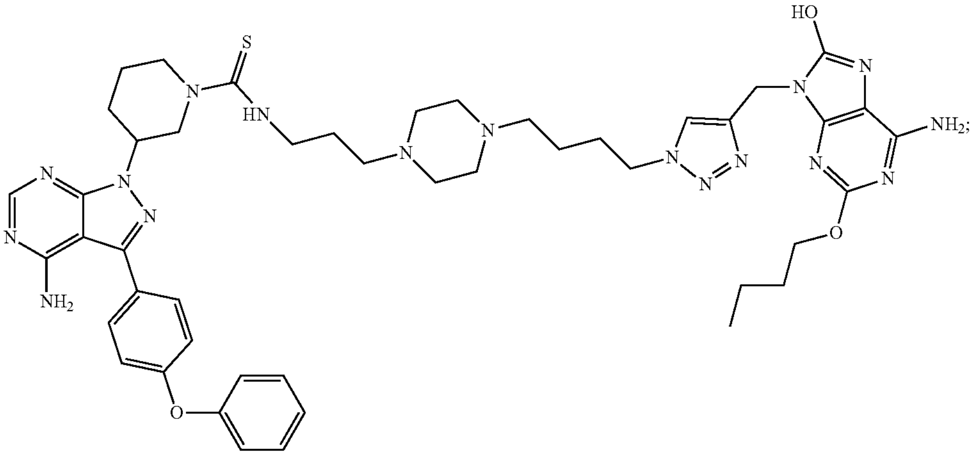 [SMILES: CCCCOc1nc(N)c2nc(O)n(Cc3cn(CCCCN4CCN(CCCNC(=S)N5CCCC(n6nc(-c7ccc(Oc8ccccc8)cc7)c7c(N)ncnc76)C5)CC4)nn3)c2n1]
GY162 having a structural formula of
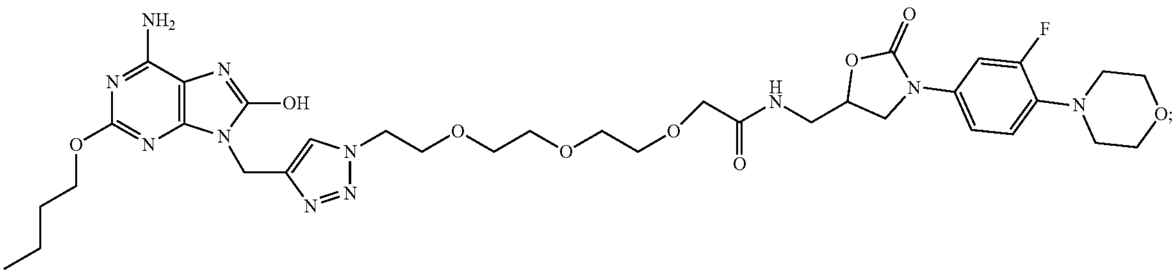 [SMILES: CCCCOc1nc(N)c2nc(O)n(Cc3cn(CCOCCOCCOCC(=O)NCC4CN(c5ccc(N6CCOCC6)c(F)c5)C(=O)O4)nn3)c2n1]
GY163 having a structural formula of
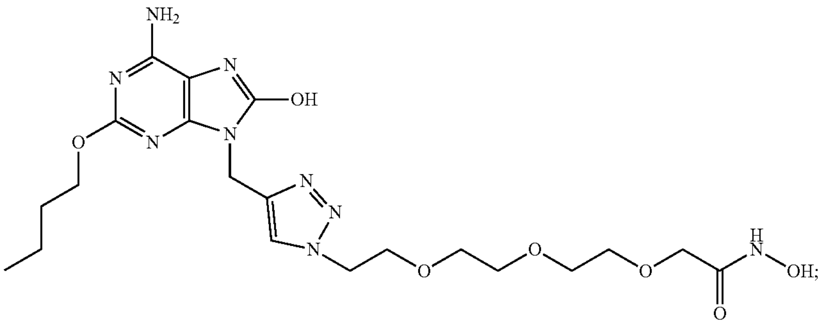 [SMILES: CCCCOc1nc(N)c2nc(O)n(Cc3cn(CCOCCOCCOCC(=O)NO)nn3)c2n1]

GY164 having a structural formula of
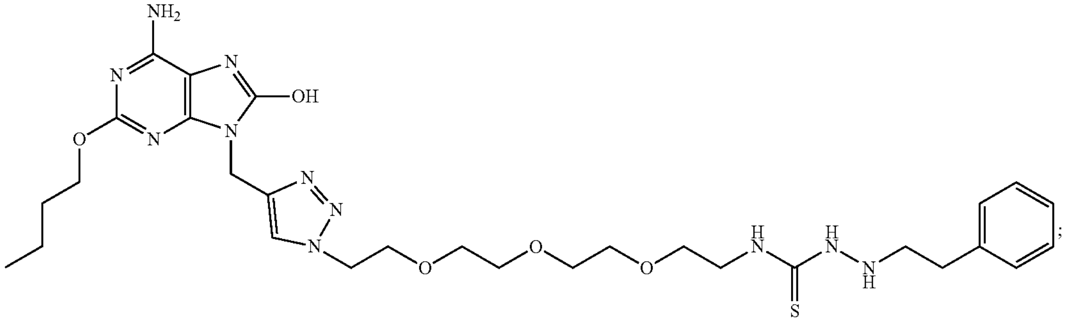 [SMILES: CCCCOc1nc(N)c2nc(O)n(Cc3cn(CCOCCOCCOCCNC(=S)NNCCc4ccccc4)nn3)c2n1]
;
GY165 having a structural formula of
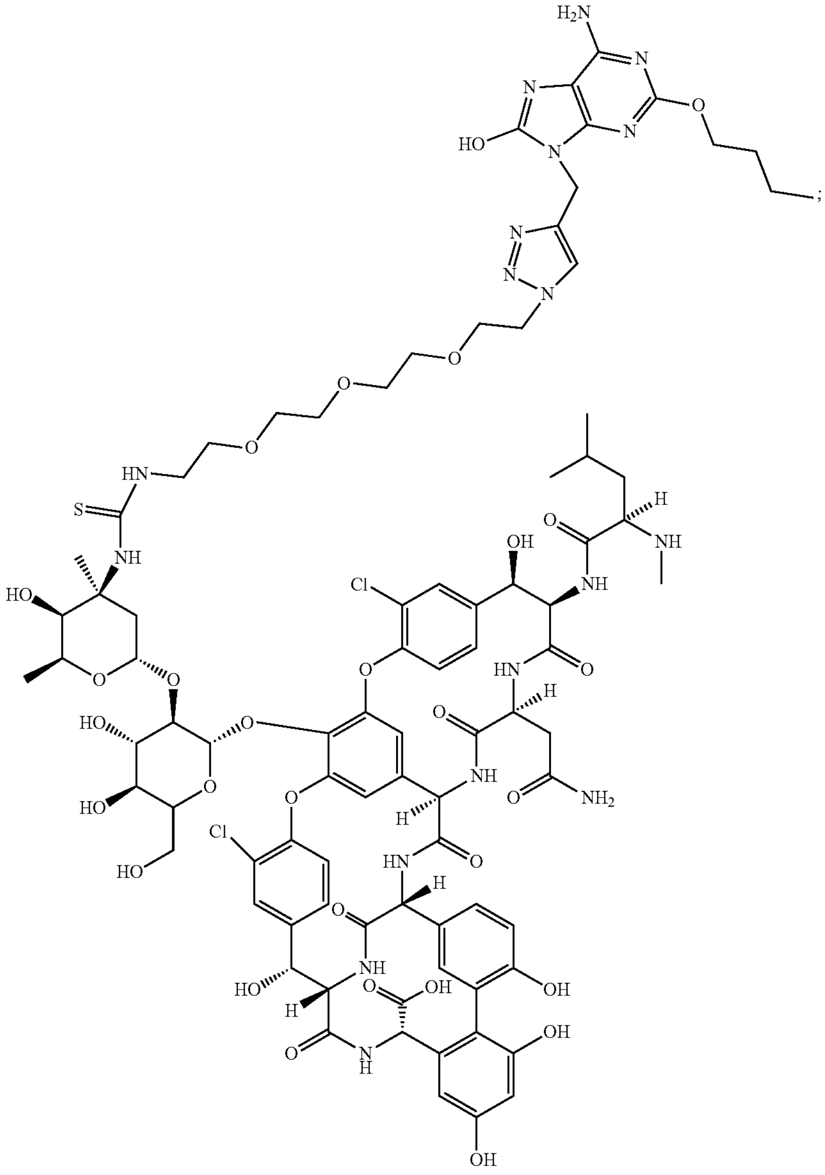 [SMILES: CCCCOc1nc(N)c2nc(O)n(Cc3cn(CCOCCOCCOCCNC(=S)N[C@@]4(C)C[C@H](O[C@H]5[C@H](Oc6c7cc8cc6Oc6ccc(cc6Cl)[C@@H](O)[C@@H](NC(=O)[C@@H](CC(C)C)NC)C(=O)N[C@@H](CC(N)=O)C(=O)N[C@H]8C(=O)N[C@H]6C(=O)N[C@H](C(=O)N[C@H](C(=O)O)c8cc(O)cc(O)c8-c8cc6ccc8O)[C@H](O)c6ccc(c(Cl)c6)O7)OC(CO)[C@@H](O)[C@@H]5O)O[C@@H](C)[C@H]4O)nn3)c2n1]
;

GY167 having a structural formula of
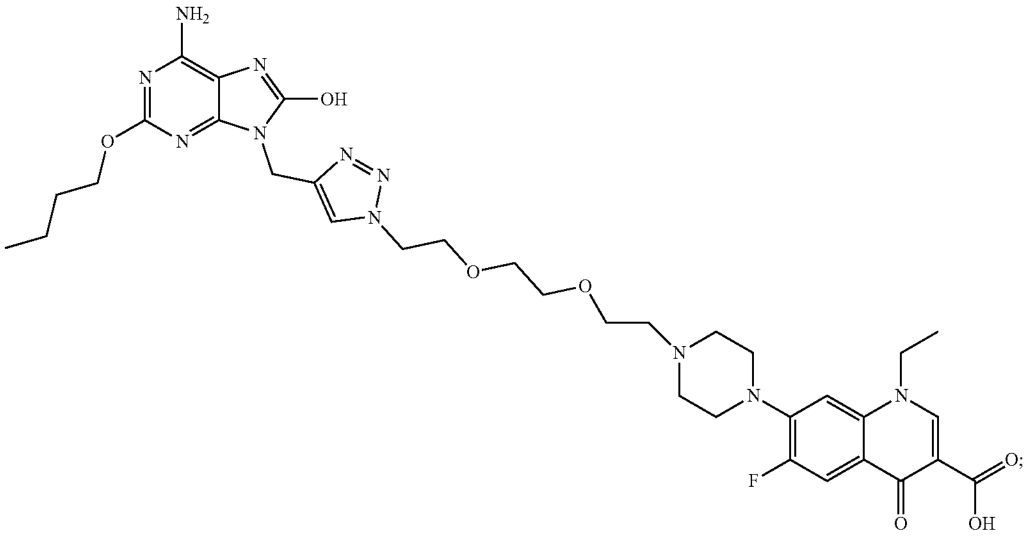 [SMILES: CCCCOc1nc(N)c2nc(O)n(Cc3cn(CCOCCOCCN4CCN(c5cc6c(cc5F)c(=O)c(C(=O)O)cn6CC)CC4)nn3)c2n1]
GY168 having a structural formula of
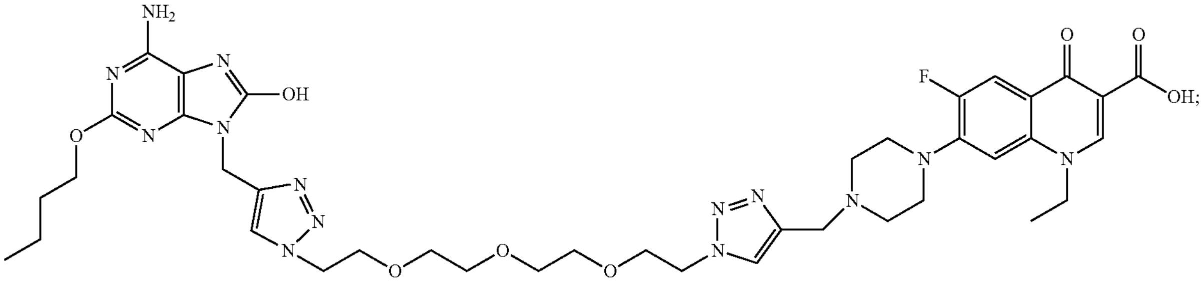 [SMILES: CCCCOc1nc(N)c2nc(O)n(Cc3cn(CCOCCOCCOCCn4cc(CN5CCN(c6cc7c(cc6F)c(=O)c(C(=O)O)cn7CC)CC5)nn4)nn3)c2n1]
GY169 having a structural formula of
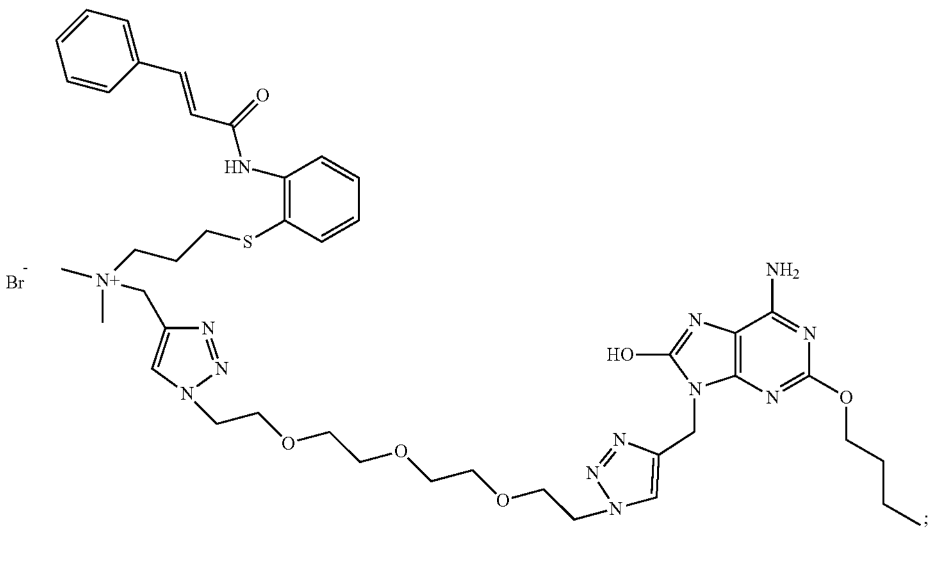 [SMILES: Br ; CCCCOc1nc(N)c2nc(O)n(Cc3cn(CCOCCOCCOCCn4cc(C[N+](C)(C)CCCSc5ccccc5NC(=O)/C=C/c5ccccc5)nn4)nn3)c2n1]

GY170 having a structural formula of
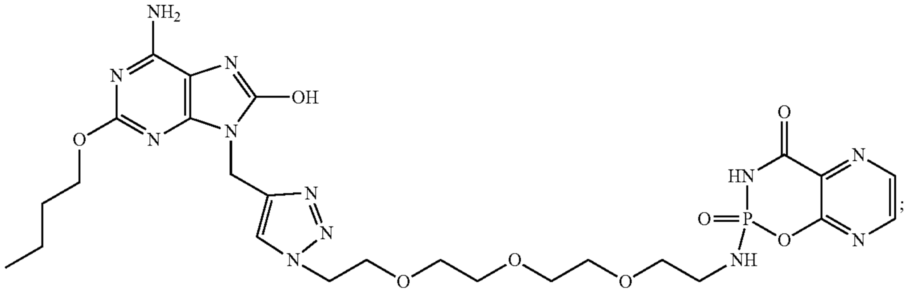 [SMILES: CCCCOc1nc(N)c2nc(O)n(Cc3cn(CCOCCOCCOCCNP4(=O)NC(=O)c5nccnc5O4)nn3)c2n1]
GY171 having a structural formula of
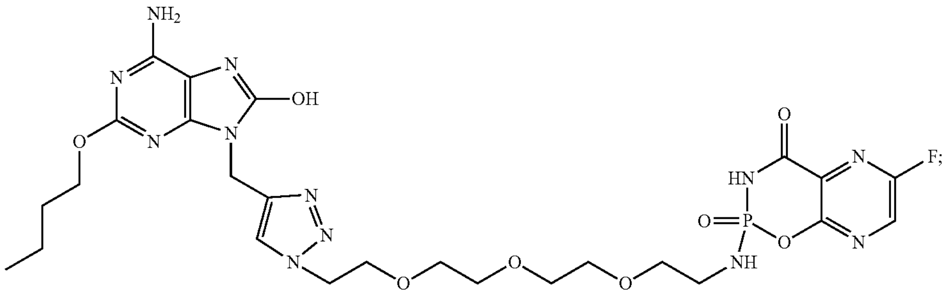 [SMILES: CCCCOc1nc(N)c2nc(O)n(Cc3cn(CCOCCOCCOCCNP4(=O)NC(=O)c5nc(F)cnc5O4)nn3)c2n1]
GY172 having a structural formula of
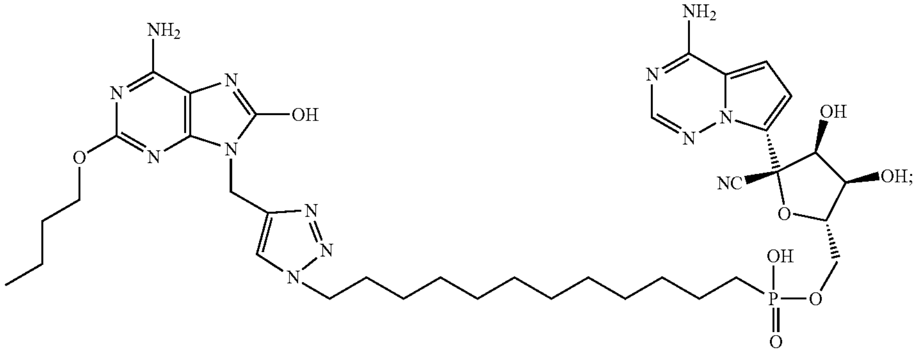
GY173 having a structural formula of
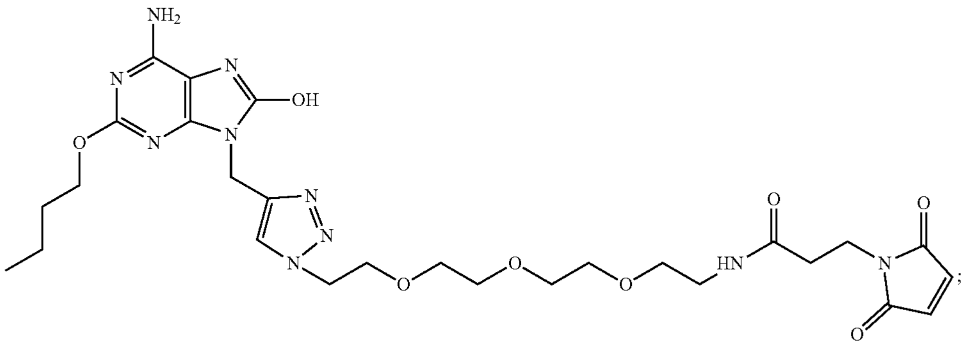 [SMILES: CCCCOc1nc(N)c2nc(O)n(Cc3cn(CCOCCOCCOCCNC(=O)CCN4C(=O)C=CC4=O)nn3)c2n1]

GY174 having a structural formula of
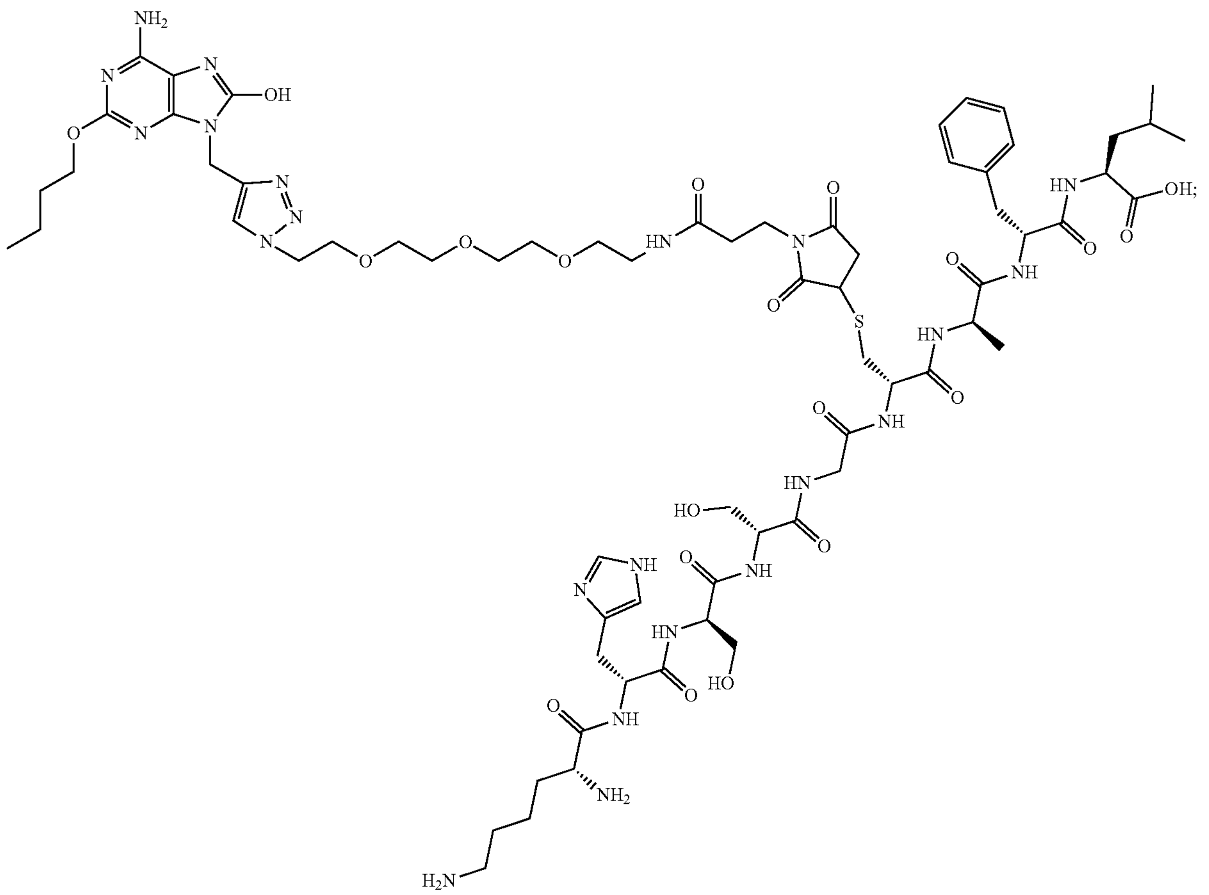 [SMILES: CCCCOc1nc(N)c2nc(O)n(Cc3cn(CCOCCOCCOCCNC(=O)CCN4C(=O)CC(SC[C@@H](NC(=O)CNC(=O)[C@@H](CO)NC(=O)[C@@H](CO)NC(=O)[C@@H](Cc5c[nH]cn5)NC(=O)[C@H](N)CCCCN)C(=O)N[C@H](C)C(=O)N[C@H](Cc5ccccc5)C(=O)N[C@@H](CC(C)C)C(=O)O)C4=O)nn3)c2n1]
GY178 having a structural formula of
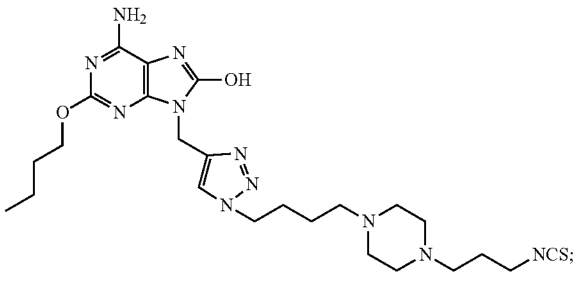

GY179 having a structural formula of
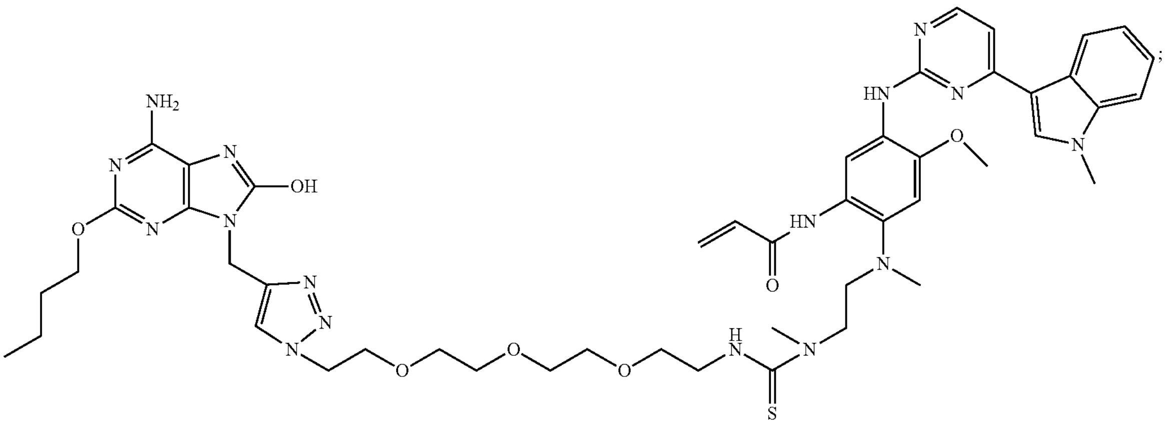 [SMILES: C=CC(=O)Nc1cc(Nc2nccc(-c3cn(C)c4ccccc34)n2)c(OC)cc1N(C)CCN(C)C(=S)NCCOCCOCCOCCn1cc(Cn2c(O)nc3c(N)nc(OCCCC)nc32)nn1]
GY180 having a structural formula of
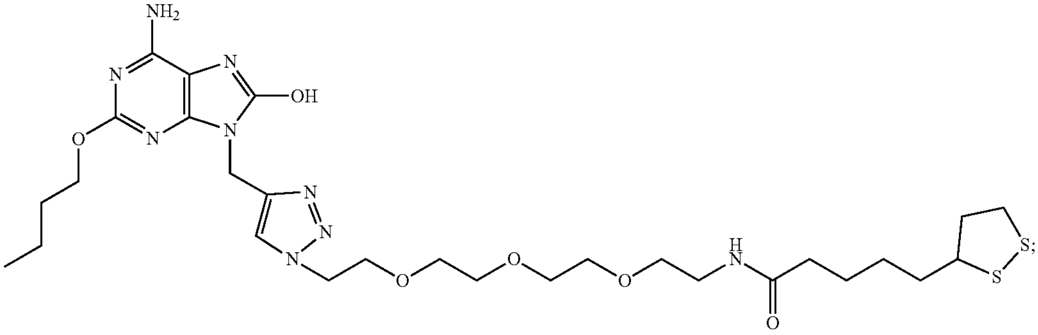 [SMILES: CCCCOc1nc(N)c2nc(O)n(Cc3cn(CCOCCOCCOCCNC(=O)CCCCC4CCSS4)nn3)c2n1]
GY181 having a structural formula of
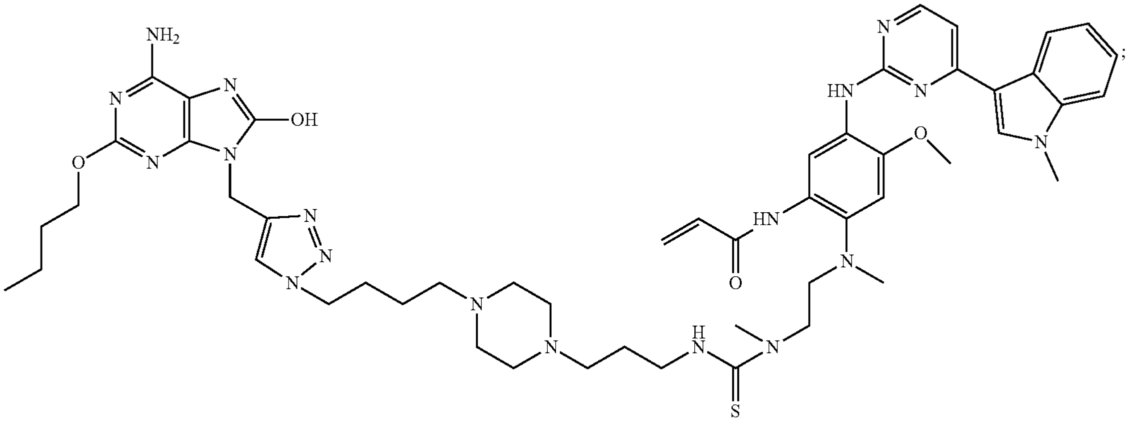 [SMILES: C=CC(=O)Nc1cc(Nc2nccc(-c3cn(C)c4ccccc34)n2)c(OC)cc1N(C)CCN(C)C(=S)NCCCN1CCN(CCCCn2cc(Cn3c(O)nc4c(N)nc(OCCCC)nc43)nn2)CC1]

GY182 having a structural formula of
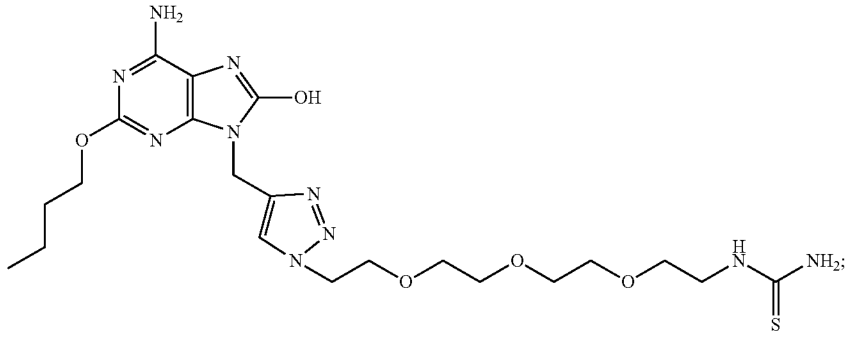 [SMILES: CCCCOc1nc(N)c2nc(O)n(Cc3cn(CCOCCOCCOCCNC(N)=S)nn3)c2n1]
GY183 having a structural formula of
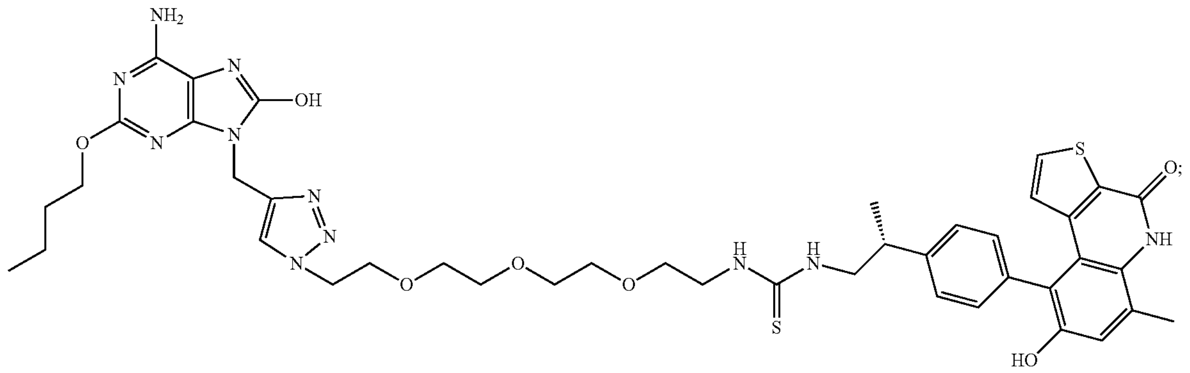 [SMILES: CCCCOc1nc(N)c2nc(O)n(Cc3cn(CCOCCOCCOCCNC(=S)NC[C@H](C)c4ccc(-c5c(O)cc(C)c6[nH]c(=O)c7sccc7c56)cc4)nn3)c2n1]
GY184 having a structural formula of
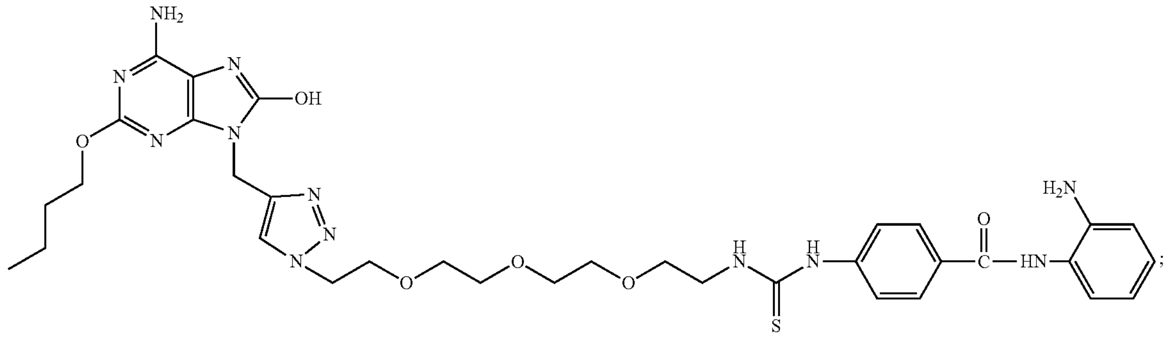 [SMILES: CCCCOc1nc(N)c2nc(O)n(Cc3cn(CCOCCOCCOCCNC(=S)Nc4ccc(C(=O)Nc5ccccc5N)cc4)nn3)c2n1]

GY185 having a structural formula of
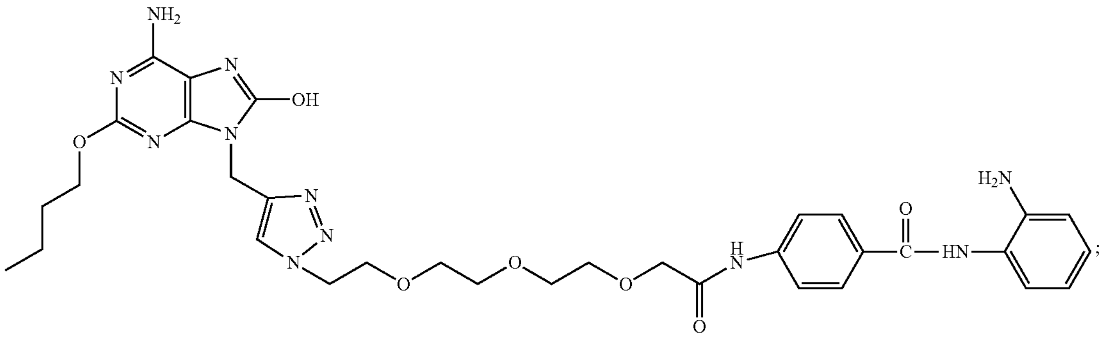 [SMILES: CCCCOc1nc(N)c2nc(O)n(Cc3cn(CCOCCOCCOCC(=O)Nc4ccc(C(=O)Nc5ccccc5N)cc4)nn3)c2n1]
GY186 having a structural formula of
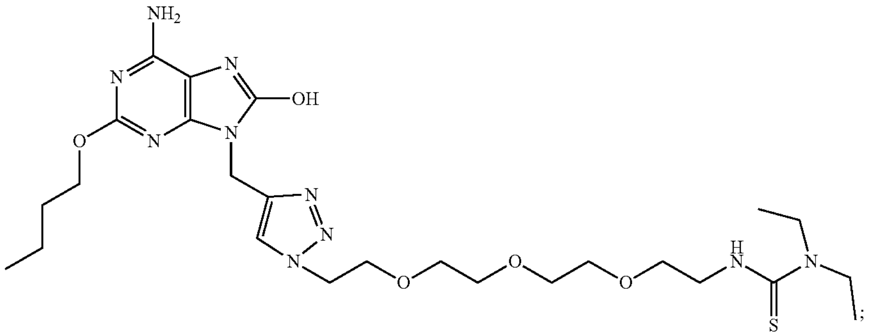 [SMILES: CCCCOc1nc(N)c2nc(O)n(Cc3cn(CCOCCOCCOCCNC(=S)N(CC)CC)nn3)c2n1]
GY187 having a structural formula of
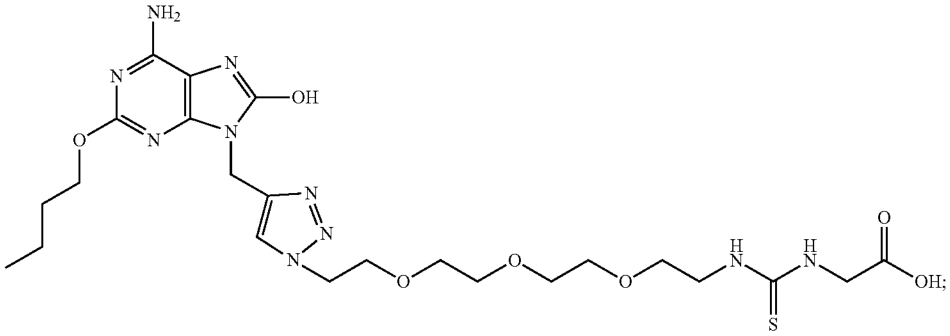 [SMILES: CCCCOc1nc(N)c2nc(O)n(Cc3cn(CCOCCOCCOCCNC(=S)NCC(=O)O)nn3)c2n1]

GY189 having a structural formula of
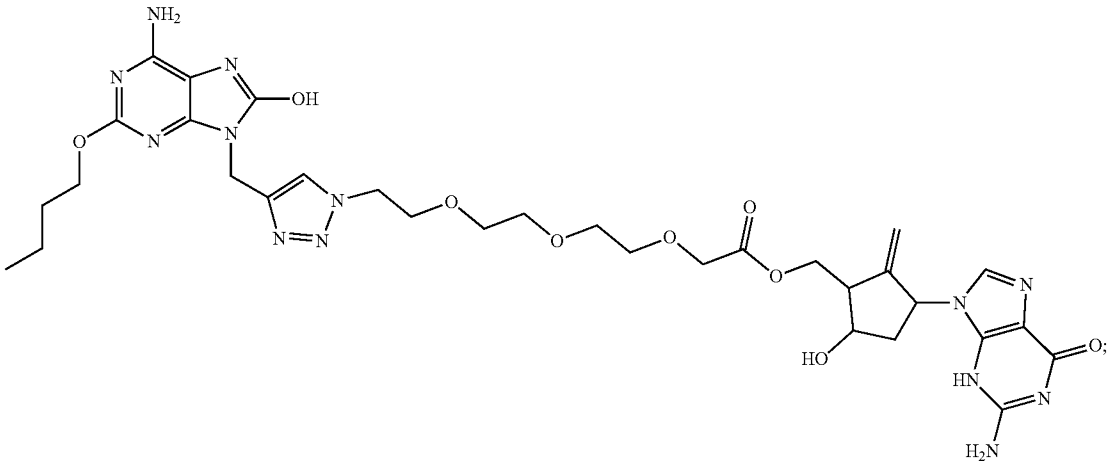 [SMILES: C=C1C(COC(=O)COCCOCCOCCn2cc(Cn3c(O)nc4c(N)nc(OCCCC)nc43)nn2)C(O)CC1n1cnc2c(=O)nc(N)[nH]c21]
GY190 having a structural formula of
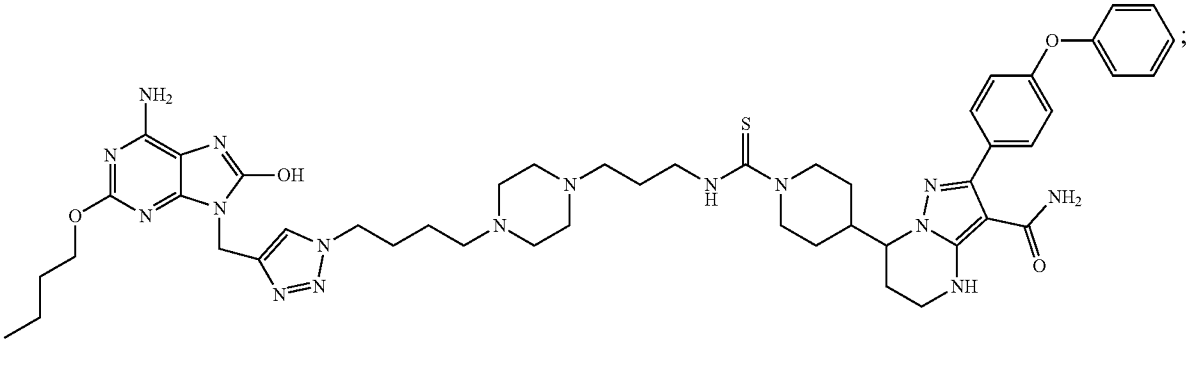 [SMILES: CCCCOc1nc(N)c2nc(O)n(Cc3cn(CCCCN4CCN(CCCNC(=S)N5CCC(C6CCNc7c(C(N)=O)c(-c8ccc(Oc9ccccc9)cc8)nn76)CC5)CC4)nn3)c2n1]
GY191 having a structural formula of
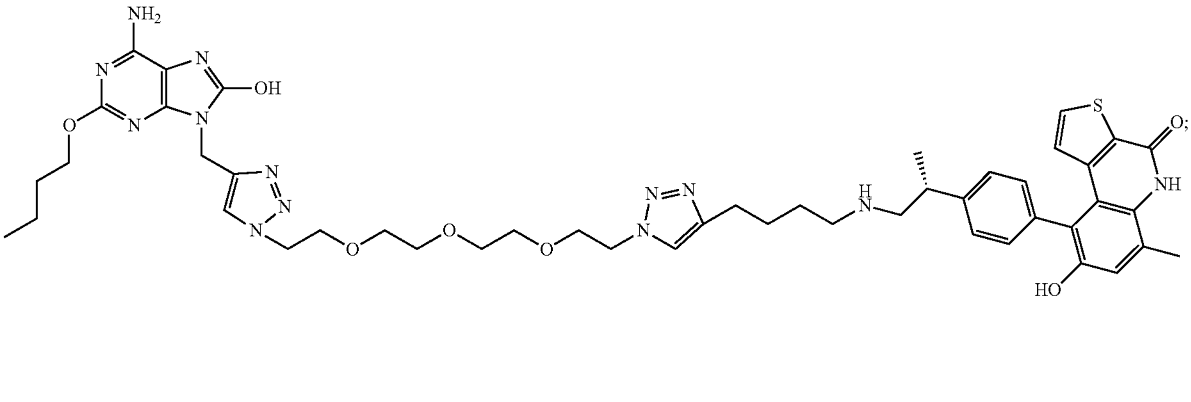 [SMILES: CCCCOc1nc(N)c2nc(O)n(Cc3cn(CCOCCOCCOCCn4cc(CCCCNC[C@H](C)c5ccc(-c6c(O)cc(C)c7[nH]c(=O)c8sccc8c67)cc5)nn4)nn3)c2n1]

GY192 having a structural formula of
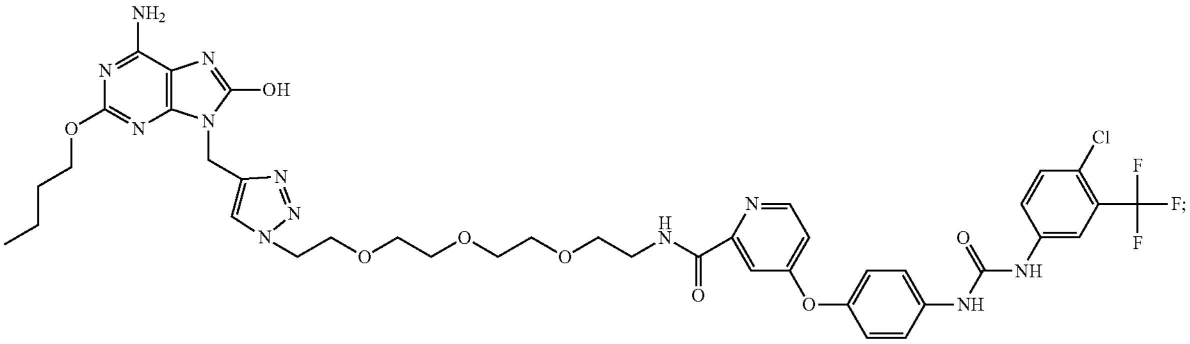 [SMILES: CCCCOc1nc(N)c2nc(O)n(Cc3cn(CCOCCOCCOCCNC(=O)c4cc(Oc5ccc(NC(=O)Nc6ccc(Cl)c(C(F)(F)F)c6)cc5)ccn4)nn3)c2n1]
GY193 having a structural formula of
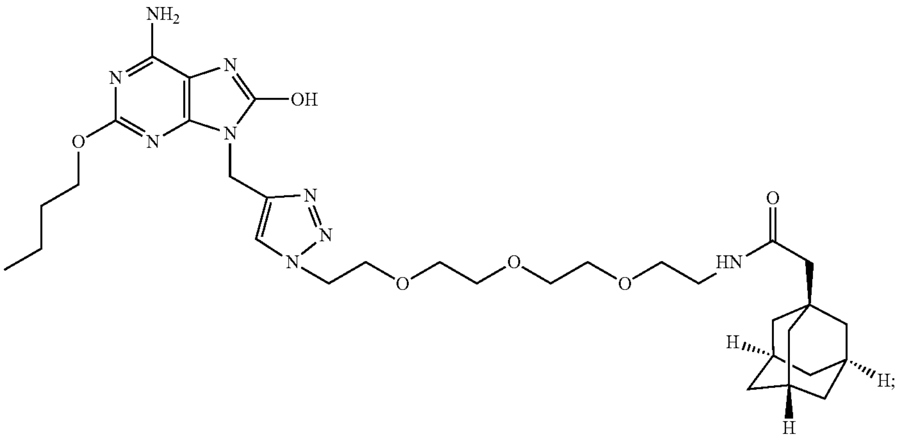
GY196 having a structural formula of
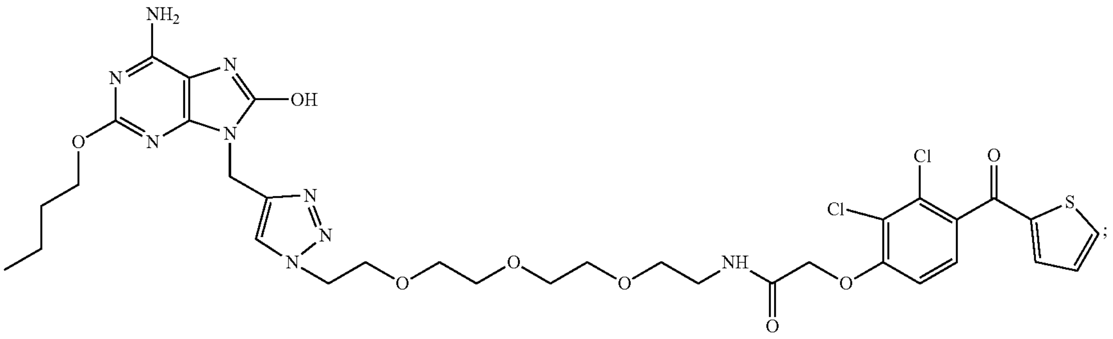 [SMILES: CCCCOc1nc(N)c2nc(O)n(Cc3cn(CCOCCOCCOCCNC(=O)COc4ccc(C(=O)c5cccs5)c(Cl)c4Cl)nn3)c2n1]

GY197 having a structural formula of
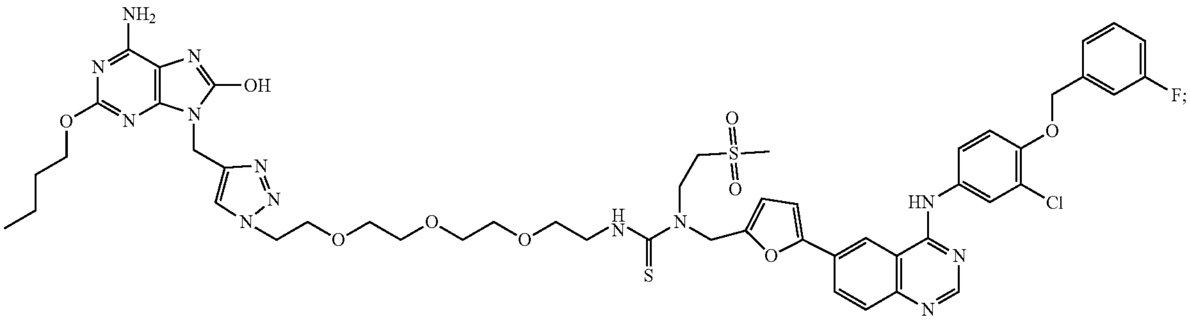 [SMILES: CCCCOc1nc(N)c2nc(O)n(Cc3cn(CCOCCOCCOCCNC(=S)N(CCS(C)(=O)=O)Cc4ccc(-c5ccc6ncnc(Nc7ccc(OCc8cccc(F)c8)c(Cl)c7)c6c5)o4)nn3)c2n1]
GY198 having a structural formula of
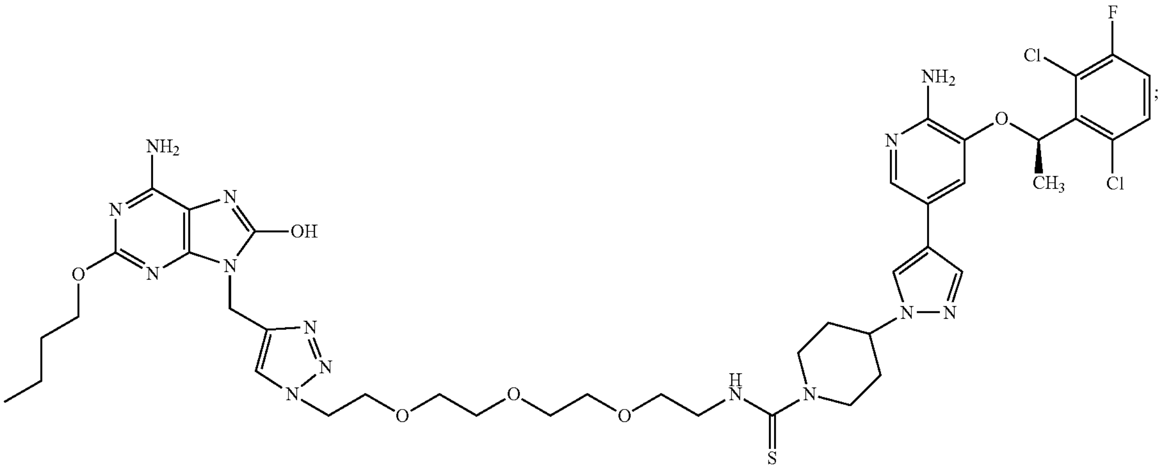 [SMILES: CCCCOc1nc(N)c2nc(O)n(Cc3cn(CCOCCOCCOCCNC(=S)N4CCC(n5cc(-c6cnc(N)c(O[C@H](C)c7c(Cl)ccc(F)c7Cl)c6)cn5)CC4)nn3)c2n1]
GY199 having a structural formula of
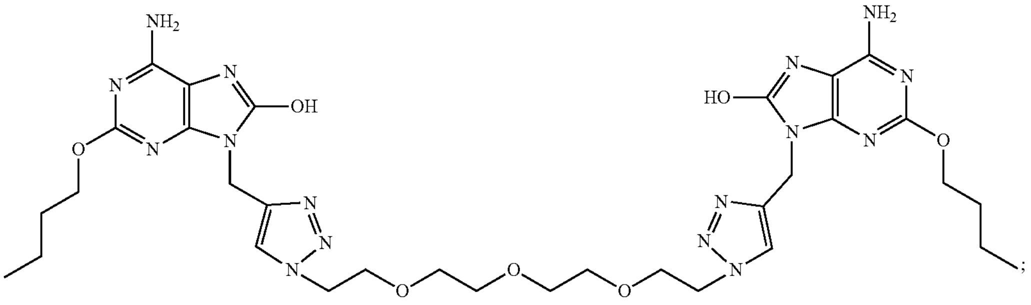 [SMILES: CCCCOc1nc(N)c2nc(O)n(Cc3cn(CCOCCOCCOCCn4cc(Cn5c(O)nc6c(N)nc(OCCCC)nc65)nn4)nn3)c2n1]

GY200 having a structural formula of
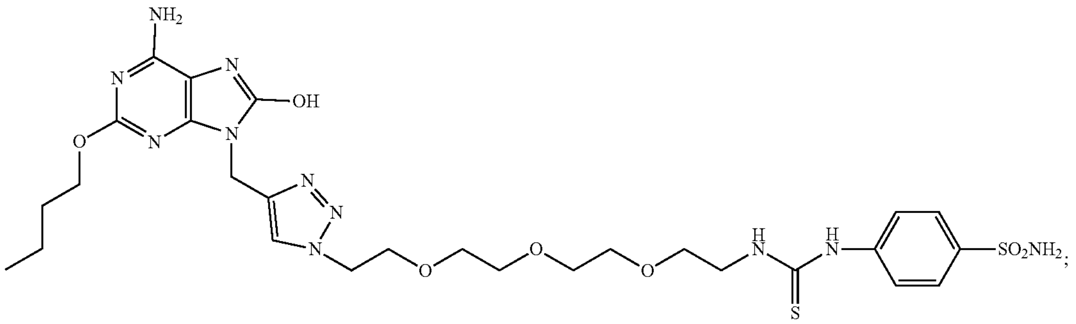 [SMILES: CCCCOc1nc(N)c2nc(O)n(Cc3cn(CCOCCOCCOCCNC(=S)Nc4ccc(S(N)(=O)=O)cc4)nn3)c2n1]
GY201 having a structural formula of
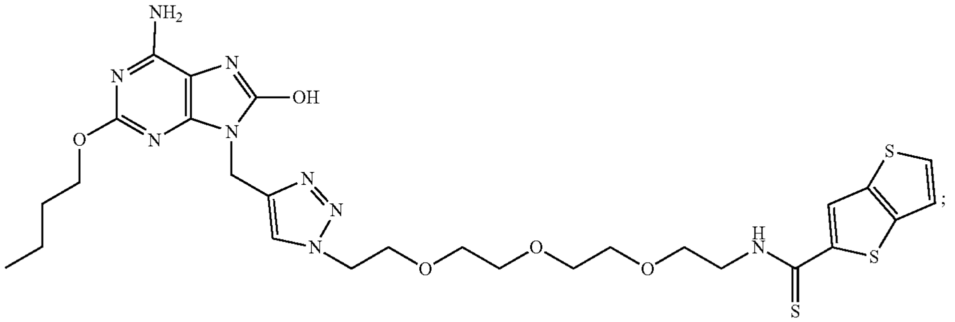 [SMILES: CCCCOc1nc(N)c2nc(O)n(Cc3cn(CCOCCOCCOCCNC(=S)c4cc5sccc5s4)nn3)c2n1]
GY202 having a structural formula of
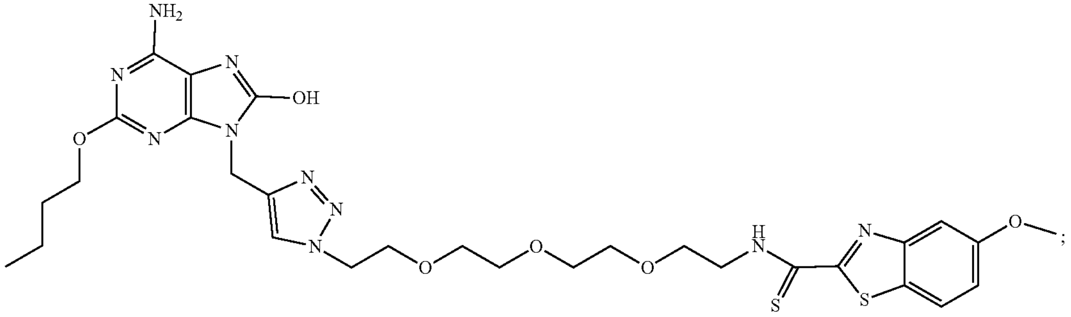 [SMILES: CCCCOc1nc(N)c2nc(O)n(Cc3cn(CCOCCOCCOCCNC(=S)c4nc5cc(OC)ccc5s4)nn3)c2n1]
GY203 having a structural formula of
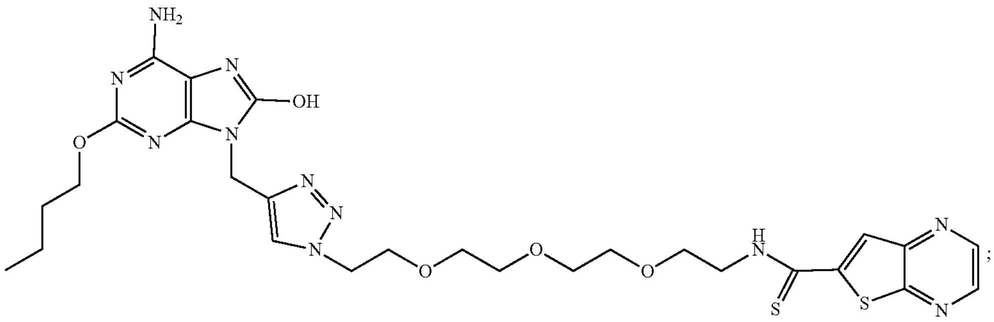 [SMILES: CCCCOc1nc(N)c2nc(O)n(Cc3cn(CCOCCOCCOCCNC(=S)c4cc5nccnc5s4)nn3)c2n1]

a conjugate of Peptide-54 and the GY106;

a conjugate of PD-1 antibody and the GY106; and a conjugate of PD-L1 antibody and the GY106.

6. The compound of claim 1, wherein an enantiomer of the compound or a salt of the compound is configured to be used in preparation of an immunomodulatory drug and/or an immunotargeted drug.

7. The compound of claim 1, wherein an enantiomer of the compound or a salt of the compound is configured to be used in preparation of a drug for activating and/or amplifying immune cells.

8. The compound of claim 1, wherein an enantiomer of the compound or a salt of the compound is configured to be used in preparation of an anti-tumor drug, an antiviral drug, or a drug for targeted protein clearance.

9. The compound of claim 1, wherein a conjugate of an enantiomer of the compound or a salt of the compound with at least one of an antibody, a protein, a polypeptide, and a cell is configured to be used in preparation of a vaccine and/or an immunotargeted drug.

10. A pharmaceutical preparation, comprising the compound of claim 1 and/or an enantiomer of the compound of claim 1 and/or a slk-salt of the compound of claim 1.

11. The pharmaceutical preparation of claim 10, wherein the pharmaceutical preparation is an immune agonist.

12. The pharmaceutical preparation of claim 10, wherein the pharmaceutical preparation is in the form of a solid preparation, a liquid preparation, or a spray preparation.

13. The pharmaceutical preparation of claim 10, wherein the pharmaceutical preparation is a covalent and/or complex formed by at least one of the compound, the enantiomer thereof, and the salt thereof with a carrier.

14. An immune agonist compound, being selected from the group consisting of:

SZU-194, having a structural formula of

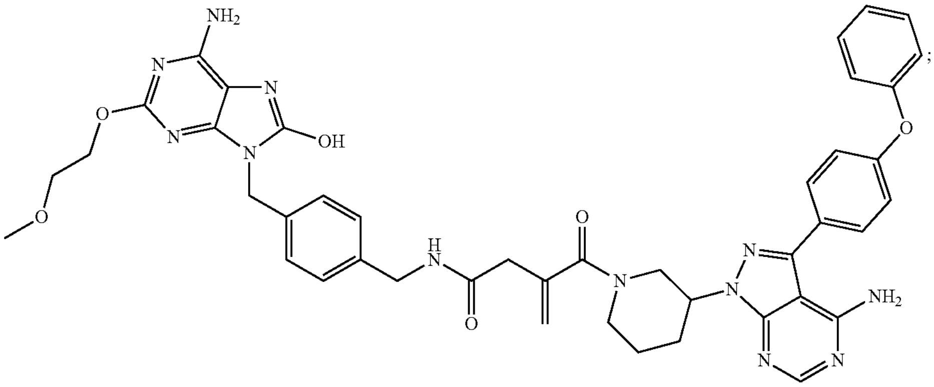 [SMILES: C=C(CC(=O)NCc1ccc(Cn2c(O)nc3c(N)nc(OCCOC)nc32)cc1)C(=O)N1CCCC(n2nc(-c3ccc(Oc4ccccc4)cc3)c3c(N)ncnc32)C1]

;

SZU-195, having a structural formula of

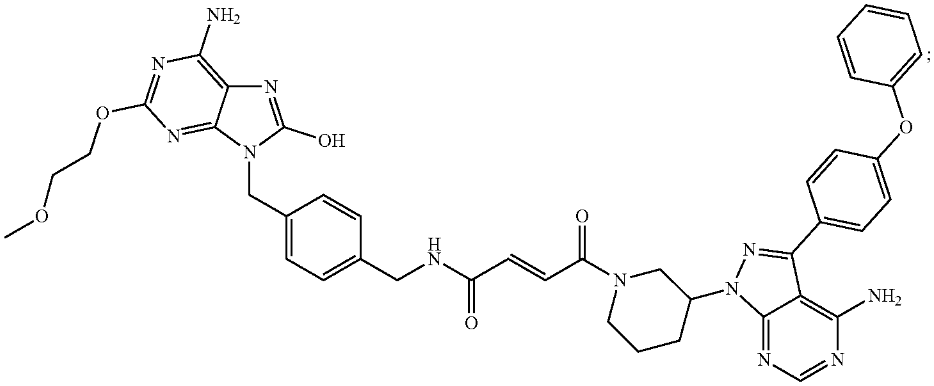 [SMILES: COCCOc1nc(N)c2nc(O)n(Cc3ccc(CNC(=O)/C=C/C(=O)N4CCCC(n5nc(-c6ccc(Oc7ccccc7)cc6)c6c(N)ncnc65)C4)cc3)c2n1]

;

SZU-213, having a structural formula of
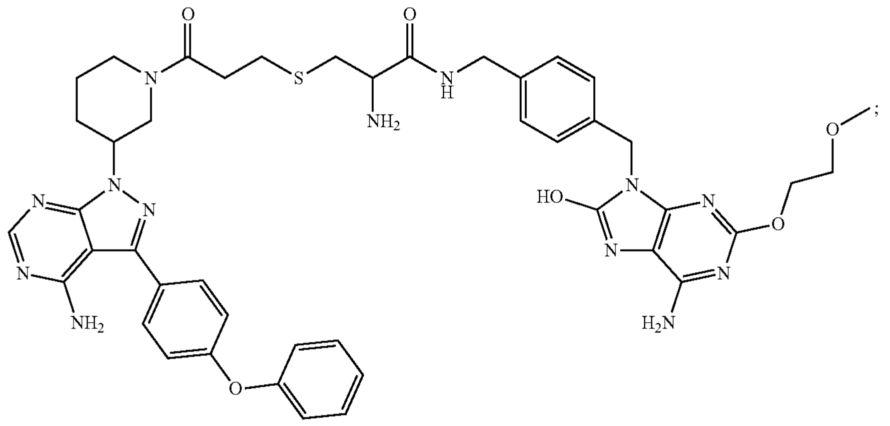 [SMILES: COCCOc1nc(N)c2nc(O)n(Cc3ccc(CNC(=O)C(N)CSCCC(=O)N4CCCC(n5nc(-c6ccc(Oc7ccccc7)cc6)c6c(N)ncnc65)C4)cc3)c2n1]
SZU-215, having a structural formula of
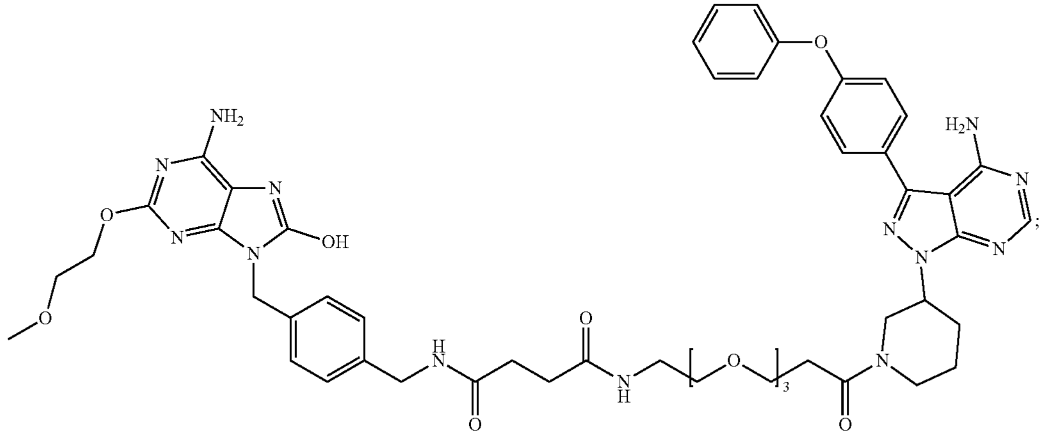
SZU-251, having a structural formula of
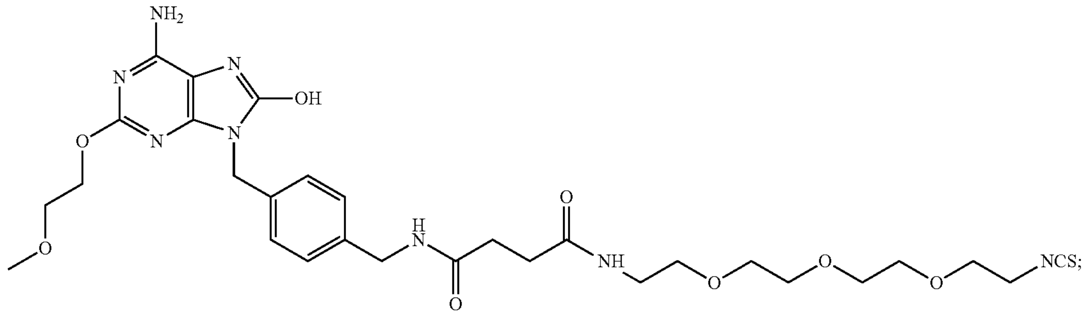

SZU-254, having a structural formula of

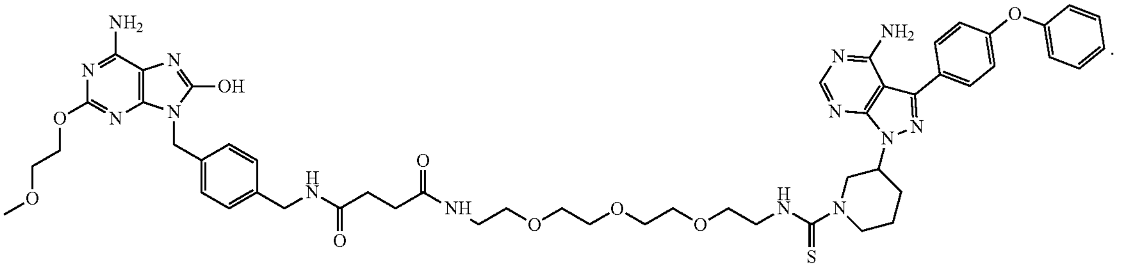 [SMILES: COCCOc1nc(N)c2nc(O)n(Cc3ccc(CNC(=O)CCC(=O)NCCOCCOCCOCCNC(=S)N4CCCC(n5nc(-c6ccc(Oc7ccccc7)cc6)c6c(N)ncnc65)C4)cc3)c2n1]

15. A starting compound of a compound having a structure represented by Formula I:

Formula I

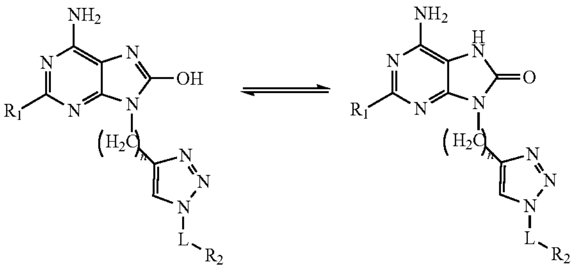

wherein $R_1$ represents any on of the following alkoxy groups and alkylamino groups:

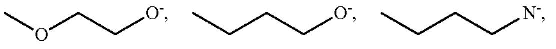

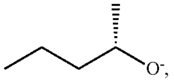

and

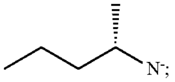

L represents a gonnegtion chain, and the gonnegtion chain comprises any one of a polyethylene glycol chain, an alkyl chain, and a heterocylic chain;

n represents an integer between 1 and 20;

$R_2$ represents a functional group or a functional carrier;

the functional group comprises at least one of a carboxyl group, a phosphate group, an amino group, an isothiocyano group, an isocyanate group, a thiourea group, an azide group, an unsaturated double bond, and an unsaturated triple bond; or consists of at least one of a targeted drug or a precursor thereof, a protein, a polypeptide, an antibody, a virus, a bacteria, and a cell;

the functional carrier comprises: a biocompatible material capable of binding the Formula I, a carrier capable of binding the Formula I, a biocompatible material capable of supporting the Formula I, and a carrier capable of supporting the Formula I; and the starting compound is one selected from the group consisting of the following compounds:

GY100, having a structural formula of

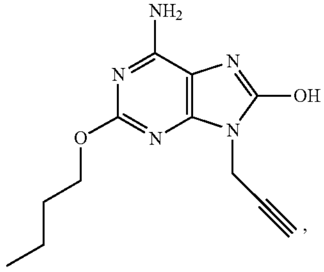 [SMILES: C#CCn1c(O)nc2c(N)nc(OCCCC)nc21]

GY115, which is an alkynyl-containing compound derived from GY100 and has a structural formula of

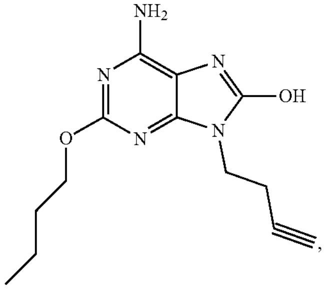 [SMILES: C#CCCn1c(O)nc2c(N)nc(OCCCC)nc21]

GY121, which is an alkynl-containing compound derived from GY100 and has a structural formula of

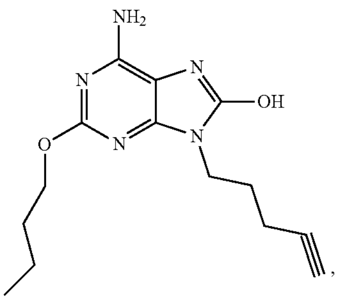 [SMILES: C#CCCCn1c(O)nc2c(N)nc(OCCCC)nc21]

and

GY122, which is an alkynyl-containing compound derived from GY100 and has a structural formula of

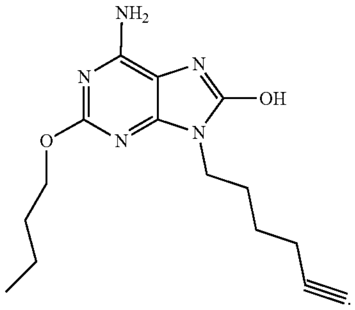 [SMILES: C#CCCCCn1c(O)nc2c(N)nc(OCCCC)nc21]
* * * * *